(12) United States Patent
Wei et al.

(10) Patent No.: US 11,976,054 B2
(45) Date of Patent: May 7, 2024

(54) AMIDE DERIVATIVE AND PREPARATION METHOD THEREFORE AND USE THEREOF IN MEDICINE

(71) Applicant: Chengdu Baiyu Pharmaceutical Co., Ltd., Sichuan (CN)

(72) Inventors: Yonggang Wei, Sichuan (CN); Hongzhu Chu, Sichuan (CN); Yue Gao, Sichuan (CN); Lingfeng Xiong, Sichuan (CN); Guizhuan Su, Sichuan (CN); Meiwei Wang, Sichuan (CN); Yi Sun, Sichuan (CN)

(73) Assignee: Chengdu Baiyu Pharmaceutical Co., Ltd. (CN)

( * ) Notice: Subject to any disclaimer, the term of this patent is extended or adjusted under 35 U.S.C. 154(b) by 0 days.

(21) Appl. No.: 17/776,513

(22) PCT Filed: Nov. 12, 2020

(86) PCT No.: PCT/CN2020/128446
§ 371 (c)(1),
(2) Date: May 12, 2022

(87) PCT Pub. No.: WO2021/093820
PCT Pub. Date: May 20, 2021

(65) Prior Publication Data
US 2022/0411392 A1    Dec. 29, 2022

(30) Foreign Application Priority Data

Nov. 12, 2019 (CN) .......................... 201911103612.2
Apr. 23, 2020 (CN) .......................... 202010326231.7
Jul. 15, 2020 (CN) .......................... 202010679491.2

(51) Int. Cl.
| | | |
|---|---|---|
| C07D 307/64 | (2006.01) |
| C07D 277/36 | (2006.01) |
| C07D 333/34 | (2006.01) |
| C07D 405/12 | (2006.01) |
| C07D 409/04 | (2006.01) |

(52) U.S. Cl.
CPC ......... *C07D 307/64* (2013.01); *C07D 277/36* (2013.01); *C07D 333/34* (2013.01); *C07D 405/12* (2013.01); *C07D 409/04* (2013.01)

(58) Field of Classification Search
None
See application file for complete search history.

(56) References Cited

U.S. PATENT DOCUMENTS

| | | |
|---|---|---|
| 2018/0044287 A1 | 2/2018 | O'Neill et al. |
| 2021/0253596 A1 | 8/2021 | McBride et al. |
| 2021/0395268 A1 | 12/2021 | Stafford et al. |

FOREIGN PATENT DOCUMENTS

| | | |
|---|---|---|
| AU | 2017416068 A1 | 10/2019 |
| CA | 3114918 A1 | 5/2020 |
| CN | 107428696 A | 12/2017 |
| CN | 108017559 A | 5/2018 |
| CN | 110366549 A | 10/2019 |
| EP | 0098569 A2 | 1/1984 |
| EP | 4059930 A1 | 9/2022 |
| WO | 2019023147 A1 | 1/2019 |
| WO | 2019034686 A1 | 2/2019 |
| WO | 2019034690 A1 | 2/2019 |
| WO | 2019079119 A1 | 4/2019 |
| WO | 2020010118 A1 | 1/2020 |
| WO | 2020018970 A1 | 1/2020 |
| WO | 2020018975 A1 | 1/2020 |
| WO | 2020102096 A1 | 5/2020 |

OTHER PUBLICATIONS

He, H et al., "Research Advance of NLRP3 Inflammasome Inhibitor", "Journal of University of Science and Technology of China", Oct. 2018, pp. 801-809, vol. 48, No. 10, Hefei, China. (English Abstract Only).
International Search Report for PCT Application No. PCT/CN2020/128446 dated Feb. 10, 2021, 5 pages.
None. "STNext, RigistryGenBank Database" 1337025-70-3(ED Oct. 18, 2011), 1337249-90-7(ED Oct. 18, 2011), 1337250-16-4(ED Oct. 18, 2011), 1337658-13-5(ED Oct. 19, 2011), 1369821-96-4(ED Apr. 18, 2012), 1369851-98-8(ED Apr. 18, 2012), 1780692-44-5(ED Jun. 15, 2015), 172528-59-5(ED Jan. 24, 1996), 2167902-25-0(ED Jan. 2, 2018), 1337188-39-2(ED Oct. 18, 2011), 1337603-60-7(EDOct. 19, 2011), 2111859-86-8(ED Aug. 10, 2017), Jan. 2, 2018 (Jan. 2, 2018), pp. 1-5.
Search Report dated Jan. 26, 2022 from the Office Action for Chinese Application No. 2020112650114 dated Jan. 30, 2022, 4 pgs. (see pp. 8-10, categorizing the cited references).
Substantive Examination Examiner's Report for Appication No. PI2022002366, dated Mar. 21, 2023, 1 page.

*Primary Examiner* — Samantha L Shterengarts
(74) *Attorney, Agent, or Firm* — Lerner David LLP

(57) ABSTRACT

The present invention relates to an amide derivative and use thereof in medicine, and specifically to an amide derivative shown as general formula (I) or a stereoisomer, solvate, metabolite, deuteride, prodrug, pharmaceutically acceptable salt or cocrystal thereof, a pharmaceutical composition containing the same, and use of the compound or the composition disclosed herein in preparing an NLRP3 inhibitor.

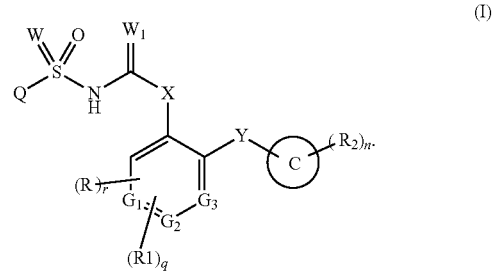

20 Claims, No Drawings

AMIDE DERIVATIVE AND PREPARATION METHOD THEREFORE AND USE THEREOF IN MEDICINE

CROSS-REFERENCE TO RELATED APPLICATION

The present application is a U.S. national entry, filed under 35 U.S.C. § 371 of International Patent Application No. PCT/CN2020/128446, filed on Nov. 12, 2020, which claims the priority of the following China Patent Applications 201911103612.2, filed on Nov. 12, 2019; 202010326231.7, filed on Apr. 23, 2020 and 202010679491.2, filed on Jul. 15, 2020, the disclosure of which are hereby incorporated by reference herein in its entirety.

TECHNICAL FIELD

The present invention relates to an amide derivative shown as general formula (I) or a stereoisomer, solvate, prodrug, metabolite, deuteride, pharmaceutically acceptable salt or cocrystal thereof, a pharmaceutical composition thereof, and use thereof in preparing an NLRP3 inhibitor.

BACKGROUND

NOD-like receptors (NLRs) of the nucleotide-binding oligomerization domain (NOD) are a type of pattern recognition receptors (PRRs) in cytoplasm of mammalian cells, and they play an important role in innate immune response. NLRs are a group of cytoplasmic proteins with signal transduction function and are widely involved in inflammatory response of organisms. The NLR family is composed of NOD, NALP (NLRP), CIITA (NLRA), and IPAF (NLRC), where NLRP and NLRC subfamilies are the two major types of NLRs, and NLRP can be classified as inflammasomes such as NLRP1, NLRP3, NLRP6, NLRP7 and NLRP12. The NLRP3 inflammasome is a multi-protein complex composed of NLRP3 protein itself, caspase-1 and apoptosis-associated speck-like protein containing CARD (ASC), and it is capable of recognizing various pathogenic microorganisms and stress-related endogenous signal molecules. Activation of classical NLRP3 inflammasome is initiated by a combined stimulation of two signals. The first signal activates the TLR4 (toll-like receptor4) signaling pathway, promotes the translocation into nucleus of nuclear transcription factor κB, and induces production of precursors such as IL-1β and IL-18. The second signal promotes NLRP3/ASC/pro-caspase-1 complex formation; namely, NLRP3 aggregates with apoptosis-associated speck-like protein containing a CARD (ASC) when activated, ASC then interacts with cysteine protease caspase-1 to form a complex called inflammasome, the precursor form of caspase (pro-caspase-1) self-cleaves into an activated form (Wen, H., Miao, E. A. & Ting, J. P, Mechanisms of NOD-like receptor-associated inflammasome activation, *Immunity,* 39, 432-441 (2013)), and activated caspase-1 cleaves the precursor forms of pro-inflammatory cytokines IL-1β and IL-18 to allow them to be converted into the active forms of IL-1β and IL-18 and released to the outside of the cells, thus recruiting inflammatory cells for aggregation and amplifying the inflammatory response. The ASC speck-like protein can also recruit and activate caspase-8, then cleave the precursor forms of IL-1β and IL-18 to convert them into mature forms and thus trigger pyroptosis. Activation of non-classical NLRP3 inflammasomes is independent of activation of TLR4 signaling pathway, and it is initiated through direct recognition of intracellular LPS by caspase-11, thereby facilitating activation and release of Gasdermin D to mediate cell death (Lamkanfi, M. & Dixit, V. M. Mechanisms and functions of inflammasomes, *Cell,* 157, 1013-1022 (2014)).

Abnormal activation of NLRP3 inflammasomes is closely related to the occurrence process of various inflammatory diseases, including hereditary CAPS diseases (Muckle-Wells syndrome (MWS), familial cold autoinflammatory syndrome, and neonatal-onset multisystem inflammatory disease), Alzheimer's disease, Parkinson disease, nonalcoholic fatty liver, atherosclerosis, asthma, nephropathy, enteritis, tumor, gout, neurodegenerative disease, diabetes, obesity, etc.

Currently available medicines for treating NLRP3-related diseases include: anakinra, a recombinant IL-1 receptor antagonist; canakinumab, an IL-1β-neutralizing antibody; and rilonacept, a soluble IL-1 receptor trapping agent, which are all biological products. Some NLRP3 small molecule inhibitors have been reported in recent years, such as glibenclamide, parthenolide, 3,4-methylenedioxy-β-nitrostyrene. However, the above drugs or small molecules still have such problems as low specificity or poor activity. Therefore, there is a need to develop a new generation of small molecule NLRP3 inhibitor with high specificity and activity for treating autoimmune diseases caused by NLRP3 mutation.

SUMMARY

The present invention relates to a new amide derivative or all stereoisomers, solvates, metabolites, deuterides, pharmaceutically acceptable salts, cocrystals or prodrugs thereof, a pharmaceutical composition thereof, and use thereof in preparing an NLRP3 inhibitor. One or more embodiments of the present invention relate to a compound shown as general formula (I) or all stereoisomers, solvates, prodrugs, metabolites, deuterides, pharmaceutically acceptable salts or cocrystals thereof:

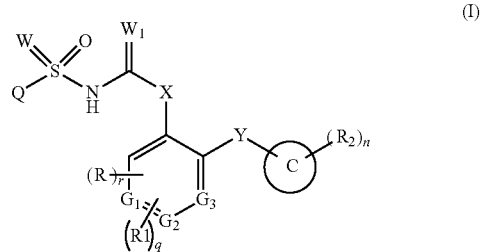

wherein,
Q is selected from 6-10 membered aryl and 5-10 membered heteroaryl, wherein the heteroaryl contains 1 to 3 heteroatoms selected from N, O and S, and the aryl or heteroaryl is optionally substituted with 0 to 4 $R^{q0}$;
$R^{q0}$ are the same or different and are each independently selected from $C_{1-6}$ alkyl, $C_{1-6}$ alkoxy, $C_{2-6}$ alkenyl, $C_{2-6}$ alkynyl, halogen, OH, cyano, nitro, —$NH_2$, $C_{3-8}$ cycloalkyl, $C_{3-8}$ heterocycloalkyl, $C_{6-10}$ aryl, $C_{5-10}$ heteroaryl, —C(=O)$C_{1-6}$ alkyl, —C(=O)O$C_{1-6}$ alkyl, —OC(=O)$C_{1-6}$ alkyl, —C(=O)O$C_{3-8}$ cycloalkyl, —OC(=O)$C_{3-8}$ cycloalkyl, —OC(=O)$C_{3-8}$ heterocycloalkyl, —C(=O)O$C_{3-8}$ heterocycloalkyl, —C(=O)$C_{6-10}$ aryl, —C(=O)O$C_{6-10}$ aryl, —OC(=O)$C_{6-10}$ aryl, —C(=O)C$_{5-10}$ heteroaryl, —C(=O)OC$_{5-10}$ heteroaryl, —OC(=O)C$_{5-10}$ heteroaryl, —NHC$_{1-6}$ alkyl, —N(C$_{1-6}$ alkyl)$_2$, —NHC(=O)C$_{1-6}$ alkyl, —NHC(=O)(C$_{1-6}$ alkyl)$_2$, —NHC(=O)C$_{6-10}$ aryl, —NHC(=O)C$_{5-10}$ heteroaryl, —NHC(=O)C$_{3-8}$ heterocycloalkyl, —NHC(=O)C$_{3-8}$ cycloalkyl, —NHC(=O)C$_{1-6}$ alkyl, —NHC(=O)C$_{2-6}$ alkynyl, —NHC(=O)C$_{2-6}$ alkenyl, —NH(C=NR$^{q1}$)NR$^{q2}$R$^{q3}$, —C(=O)NR$^{q4}$R$^{q5}$, —SH, —SC$_{1-6}$ alkyl, —S(=O)C$_{1-6}$ alkyl, —S(=O)$_2$C$_{1-6}$ alkyl and —S(=O)$_2$NR$^{q2}$R$^{q3}$, wherein the heterocycloalkyl or heteroaryl contains 1 to 3 heteroatoms selected from N, O and S, and the alkyl, alkoxy, NH$_2$, alkenyl, alkynyl, heterocycloalkyl, cycloalkyl, aryl or heteroaryl is optionally further substituted with 1 or more substituents selected from deuterium, OH, halogen, cyano, =O, C$_{1-6}$ alkyl, C$_{1-6}$ alkoxy, C$_{2-6}$ alkenyl, C$_{2-6}$ alkynyl, —NR$^{q4}$R$^{q5}$, =NR$^{q6}$, —C(=O)OC$_{1-6}$ alkyl, —OC(=O)C$_{1-6}$ alkyl, —C(=O)NR$^{q4}$R$^{q5}$, C$_{3-8}$ cycloalkyl, C$_{3-8}$ heterocycloalkyl, C$_{6-10}$ aryl, C$_{5-10}$ heteroaryl, —C(=O)OC$_{6-10}$ aryl, —OC(=O)C$_{6-10}$ aryl, —OC(=O)C$_{5-10}$ heteroaryl, —C(=O)OC$_{5-10}$ heteroaryl, —OC(=O)C$_{3-8}$ heterocycloalkyl, —C(=O)OC$_{3-8}$ heterocycloalkyl, —OC(=O)C$_{3-8}$ cycloalkyl, —C(=O)OC$_{3-8}$ cycloalkyl, —NHC(=O)C$_{3-8}$ heterocycloalkyl, —NHC(=O)C$_{6-10}$ aryl, —NHC(=O)C$_{5-10}$ heteroaryl, —NHC(=O)C$_{3-8}$ cycloalkyl, —NHC(=O)C$_{3-8}$ heterocycloalkyl, —NHC(=O)C$_{2-6}$ alkenyl and —NHC(=O)C$_{2-6}$ alkynyl, wherein the substituent C$_{1-6}$ alkyl, C$_{1-6}$ alkoxy, C$_{2-6}$ alkenyl, C$_{2-6}$ alkynyl, C$_{3-8}$ cycloalkyl, C$_{3-8}$ heterocycloalkyl, C$_{6-10}$ aryl, C$_{5-10}$ heteroaryl, —NHC(=O)C$_{6-10}$ aryl, —NHC(=O)C$_{5-10}$ heteroaryl, —NHC(=O)C$_{3-8}$ heterocycloalkyl or —NHC(=O)C$_{3-8}$ cycloalkyl is optionally further substituted with 1 to 3 substituents selected from OH, halogen, C$_{1-6}$ alkyl, C$_{1-6}$ alkoxy, —NR$^{q4}$R$^{q5}$ and =O; or at least one pair of R$^{q0}$ and an atom to which they are attached form a 4-10 membered carbocycle or a 5-10 membered heterocycle, wherein the heterocycle contains 1 to 2 heteroatoms selected from N, O and S, the carbocycle or heterocycle is optionally further substituted with 1 or more substituents selected from OH, halogen, C$_{1-6}$ alkyl, C$_{1-6}$ alkoxy, C$_{2-6}$ alkenyl, C$_{2-6}$ alkynyl, —NR$^{q4}$R$^{q5}$, =NR$^{q6}$, —C(=O)OC$_{1-6}$ alkyl and —C(=O)NR$^{q4}$R$^{q5}$, and the C$_{1-6}$ alkyl or C$_{1-6}$ alkoxy is optionally further substituted with a substituent selected from OH, halogen, =O, —NR$^{q4}$R$^{q5}$, =NR$^{q6}$, —C(=O)OC$_{1-6}$ alkyl, C$_{3-8}$ cycloalkyl, C$_{3-8}$ heterocycloalkyl, C$_{6-10}$ aryl, C$_{5-10}$ heteroaryl and —C(=O)NR$^{q4}$R$^{q5}$;

R$^{q1}$ is selected from C$_{1-6}$ alkyl, C$_{1-6}$ alkoxy and C$_{6-10}$ aryl;
R$^{q2}$ and R$^{q3}$ are selected from H and C$_{1-6}$ alkyl;
R$^{q4}$ and R$^{q5}$ are selected from H, C$_{1-6}$ alkyl, —NH(C=NR$^{q1}$)NR$^{q2}$R$^{q3}$, —S(=O)$_2$NR$^{q2}$R$^{q3}$, —C(=O)R$^{q1}$ and —C(=O)NR$^{q2}$R$^{q3}$, wherein the C$_{1-6}$ alkyl is optionally further substituted with 1 or more substituents selected from OH, halogen, C$_{1-6}$ alkyl, C$_{1-6}$ alkoxy, C$_{6-10}$ aryl, C$_{5-10}$ heteroaryl, C$_{3-8}$ cycloalkyl and C$_{3-8}$ heterocycloalkyl; or R$^{q4}$ and R$^{q5}$ form a 3-8 membered heterocycle with an N atom, the heterocycle containing 1 to 3 heteroatoms selected from N, O and S;
R$^{q6}$ is C$_{1-6}$ alkyl;
W is selected from O and NHR$_a$;
W$_1$ is O;
R$_a$ is selected from H, cyano, hydroxy, C$_{1-6}$ alkyl and C$_{1-6}$ alkoxy;
X is NH;
Y is CR$_b$R$_c$;
R$_b$ and R$_c$ are each independently selected from H, C$_{1-6}$ alkyl and 3-10 membered carbocyclyl, wherein the C$_{1-6}$ alkyl is optionally further substituted with 1 to 4 substituents selected from F, Cl, Br, I, C$_{1-6}$ alkyl, C$_{1-6}$ alkoxy, 3-10 membered carbocyclyl and 3-10 membered heterocyclyl, the heterocyclyl optionally containing 1 to 3 heteroatoms selected from N, O and S; or
R$_b$ and R$_c$ form a double bond;
R and R$_1$ are each independently selected from deuterium, H, F, Cl, Br, I, CN, NH$_2$, OH, C$_{1-6}$ alkyl, C$_{1-6}$ alkoxy, C$_{2-6}$ alkenyl, C$_{2-6}$ alkynyl, —(C=O)—C$_{1-6}$ alkyl, —(C=O)O—C$_{1-6}$ alkyl, —O(C=O)—C$_{1-6}$ alkyl, —O(C=O)-3-10 membered carbocyclyl, —O(C=O)-3-10 membered heterocyclyl, —(C=O)O-3-10 membered carbocyclyl, —O(C=O)O—C$_{1-6}$ alkyl, 3-10 membered carbocyclyl, 4-10 membered heterocyclyl, —NHC$_{1-6}$ alkyl, —N(C$_{1-6}$ alkyl)$_2$ and (C=O)NR$_{a1}$R$_{a2}$, wherein the heterocyclyl contains 1 to 3 heteroatoms selected from N, O and S, and the alkyl, alkenyl, alkoxy, carbocycle or heterocycle is optionally further substituted with 1 to 4 substituents selected from OH, F, Cl, Br, I, CN, NR$_{a1}$R$_{a2}$, =O, C$_{1-6}$ alkyl, C$_{1-6}$ alkoxy, C$_{1-6}$ haloalkyl, C$_{1-6}$ haloalkoxy, —(C=O)—C$_{1-6}$ alkyl, —(C=O)O—C$_{1-6}$ alkyl, —O(C=O)—C$_{1-6}$ alkyl, —(C=O)O-3-10 membered carbocyclyl, —O(C=O)-3-10 membered carbocyclyl, —O(C=O)-3-10 membered heterocyclyl, —O(C=O)O—C$_{1-6}$ alkyl, 3-10 membered carbocyclyl, 5-10-membered heterocyclyl, —NHCOC$_{1-6}$ alkyl, —NH(C=O)-3-10 membered carbocyclyl, —NH(C=O)-3-10 membered heterocyclyl and —(C=O)NR$_{a1}$R$_{a2}$; or
R and R$_1$, together with an atom to which they are attached, form a 4-8 membered ring, wherein the 4-8 membered ring contains 0 to 4 heteroatoms selected from N, O and S, and is optionally further substituted with 0 to 4 substituents selected from H, F, Cl, Br, I, OH, —NR$_{a1}$R$_{a2}$, =O, C$_{1-6}$ alkyl, C$_{1-6}$ alkoxy, C$_{2-6}$ alkenyl, C$_{2-6}$ alkynyl, —(C=O)OC$_{1-6}$ alkyl, 3-10 membered carbocyclyl and 5-10 membered heterocyclyl;
C is 3-10 membered cycloalkyl;
R$_2$ is selected from H, F, Cl, Br, I, OH, —NR$_{a1}$R$_{a2}$, C$_{1-6}$ alkyl, C$_{2-6}$ alkenyl, C$_{2-6}$ alkynyl and C$_{1-6}$ alkoxy;
G1, G2 and G3 are each independently selected from N and CH;
q and r are selected from 0, 1 and 2;
n is selected from 0, 1, 2 and 3.

One or more embodiments of the present invention provide a compound shown as general formula (II) or a stereoisomer, hydrate, metabolite, deuteride, solvate, pharmaceutically acceptable salt or cocrystal thereof:

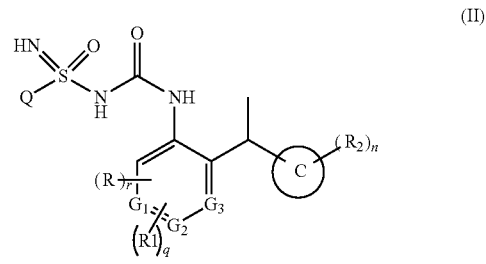

(II)

wherein,
Q, R, R₁, R₂, C, G1, G2, G3, r, q and n are defined in the same way as in general formula (I).

One or more embodiments of the present invention provide a compound shown as general formula (II-1) or a stereoisomer, hydrate, metabolite, deuteride, solvate, pharmaceutically acceptable salt or cocrystal thereof:

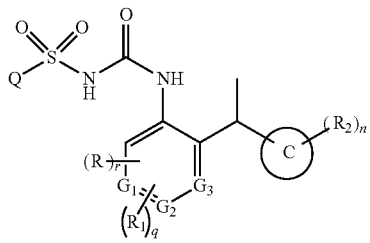

(II-1)

wherein,
Q, R, R₁, R₂, C, G1, G2, G3, r, q and n are defined in the same way as in general formula (I).

One or more embodiments of the present invention provide a compound shown as general formula (II-2) or a stereoisomer, solvate, metabolite, deuteride, prodrug, pharmaceutically acceptable salt or cocrystal thereof:

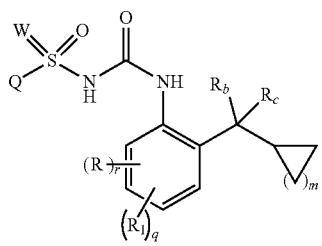

(II-2)

wherein, Q, W, R, R₁, $R_b$, $R_c$, r and q are defined in the same way as in general formula (I);
m is selected from 1, 2 and 3.

One or more embodiments of the present invention provide a compound shown as general formula (III) or a stereoisomer, hydrate, metabolite, deuteride, solvate, pharmaceutically acceptable salt or cocrystal thereof:

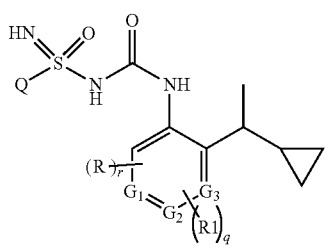

(III)

wherein, Q, R, R₁, G1, G2, G3, r an q are defined in the same way as in general formula (I).

One or more embodiments of the present invention provide a compound shown as general formula (III-1) or a stereoisomer, hydrate, metabolite, deuteride, solvate, pharmaceutically acceptable salt or cocrystal thereof:

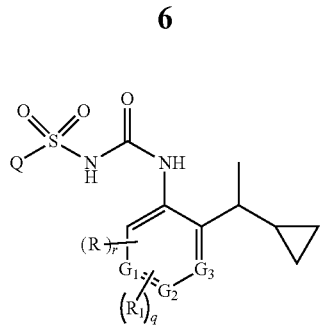

(III-1)

wherein, Q, R, R₁, G1, G2, G3, r and q are defined in the same way as in general formula (I).

One or more embodiments of the present invention provide a compound shown as general formula (III) or (III-1) or a stereoisomer, hydrate, metabolite, deuteride, solvate, pharmaceutically acceptable salt or cocrystal thereof, wherein:

Q is selected from 5 membered heteroaryl, wherein the heteroaryl contains 1 to 3 heteroatoms selected from N, O and S, and the aryl or heteroaryl is optionally substituted with 0 to 4 $R^{q0}$;

$R^{q0}$ are the same or different and are each independently selected from $C_{1-4}$ alkyl, halogen, OH, cyano, —NH₂, $C_{2-4}$ alkenyl, $C_{3-6}$ cycloalkyl, $C_{3-6}$ heterocycloalkyl, —NHC$_{1-4}$ alkyl and —N(C$_{1-4}$ alkyl)₂, wherein the heterocycloalkyl contains 1 to 3 heteroatoms selected from N and O, and the alkyl, heterocycloalkyl and cycloalkyl are optionally further substituted with 1 or more substituents selected from deuterium, OH, halogen, cyano, $C_{1-4}$ alkyl and —NR$^{q4}$R$^{q5}$;

$R^{q4}$ and $R^{q5}$ are selected from H and $C_{1-4}$ alkyl;

W is selected from O and NH;

R and R₁ are each independently selected from deuterium, H, F, CN, OH, $C_{1-6}$ alkyl and 4-6 membered heterocyclyl, wherein the heterocyclyl contains 1 to 3 heteroatoms selected from N and O, and the alkyl or heterocycle is optionally further substituted with 1 to 4 substituents selected from OH, F, CN and $C_{1-6}$ alkoxy; or R and R₁, together with an atom to which they are attached, form a 4-5 membered ring;

G1, G2 and G3 are each independently selected from CH;

q and r are selected from 0, 1 and 2.

One or more embodiments of the present invention provide a compound shown as general formula (IV) or a stereoisomer, solvate, metabolite, deuteride, prodrug, pharmaceutically acceptable salt or cocrystal thereof:

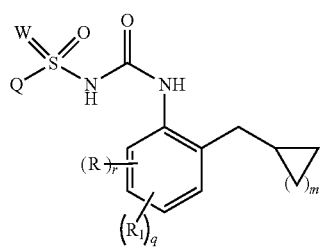

(IV)

wherein, Q, W, R, R₁, r and q are defined in the same way as in general formula (I);
m is selected from 1, 2 and 3.

One or more embodiments of the present invention provide a compound shown as general formula (IV) or a stereoisomer, solvate, metabolite, deuteride, prodrug, pharmaceutically acceptable salt or cocrystal thereof, wherein:

Q is selected from 5 membered heteroaryl, wherein the heteroaryl contains 1 to 3 heteroatoms selected from N, O and S, and the aryl or heteroaryl is optionally substituted with 0 to 4 $R^{q0}$;

$R^{q0}$ are the same or different and are each independently selected from $C_{1-4}$ alkyl, halogen, OH, cyano, —$NH_2$, $C_{2-4}$ alkenyl, $C_{3-6}$ cycloalkyl, $C_{3-6}$ heterocycloalkyl, —$NHC_{1-4}$ alkyl and —$N(C_{1-4}$ alkyl$)_2$, wherein the heterocycloalkyl contains 1 to 3 heteroatoms selected from N and O, and the alkyl, heterocycloalkyl and cycloalkyl are optionally further substituted with 1 or more substituents selected from deuterium, OH, halogen, cyano, $C_{1-4}$ alkyl and —$NR^{q4}R^{q5}$;

$R^{q4}$ and $R^{q5}$ are selected from H and $C_{1-4}$ alkyl;

W is selected from O and NH;

R and $R_1$ are each independently selected from deuterium, H, F, CN, OH, $C_{1-6}$ alkyl and 4-6 membered heterocyclyl, wherein the heterocyclyl contains 1 to 3 heteroatoms selected from N and O, and the alkyl or heterocycle is optionally further substituted with 1 to 4 substituents selected from OH, F, CN and $C_{1-6}$ alkoxy; or R and $R_1$, together with an atom to which they are attached, form a 4 membered ring or 5 membered ring;

q and r are selected from 0, 1 and 2;

m is selected from 1, 2 and 3.

One or more embodiments of the present invention provide a compound shown as general formula (V) or a stereoisomer, solvate, metabolite, deuteride, prodrug, pharmaceutically acceptable salt or cocrystal thereof:

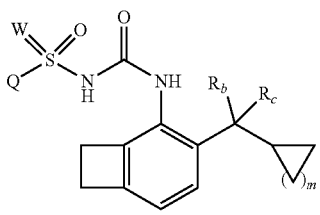

(V)

wherein, Q, W, $R_b$ and $R_c$ are defined in the same way as in general formula (I);

m is selected from 1, 2 and 3.

One or more embodiments of the present invention provide a compound shown as general formula (V) or a stereoisomer, solvate, metabolite, deuteride, prodrug, pharmaceutically acceptable salt or cocrystal thereof, wherein:

Q is selected from 5 membered heteroaryl, wherein the heteroaryl contains 1 to 3 heteroatoms selected from N, O and S, and the aryl or heteroaryl is optionally substituted with 0 to 4 $R^{q0}$;

$R^q$ are the same or different and are each independently selected from $C_{1-4}$ alkyl, halogen, OH, cyano, —$NH_2$, $C_{2-4}$ alkenyl, $C_{3-6}$ cycloalkyl, $C_{3-6}$ heterocycloalkyl, —$NHC_{1-4}$ alkyl and —$N(C_{1-4}$ alkyl$)_2$, wherein the heterocycloalkyl contains 1 to 3 heteroatoms selected from N and O, and the alkyl, heterocycloalkyl and cycloalkyl are optionally further substituted with 1 or more substituents selected from deuterium, OH, halogen, cyano, $C_{1-4}$ alkyl and —$NR^{q4}R^{q5}$;

$R^{q4}$ and $R^q$ are selected from H and $C_{1-4}$ alkyl;

W is selected from O and NH;

$R_b$ and $R_c$ are each independently selected from H, $C_{1-4}$ alkyl and 3-5 membered carbocyclyl, wherein the 3-5 membered carbocyclyl is preferably a 3 membered, 4 membered or 5 membered cycloalkyl;

q and r are selected from 0, 1 and 2;

m is selected from 1, 2 and 3.

One or more embodiments of the present invention provide a compound shown as general formula (VI) or a stereoisomer, solvate, metabolite, deuteride, prodrug, pharmaceutically acceptable salt or cocrystal thereof:

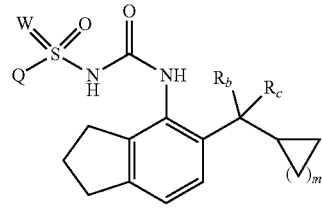

(VI)

wherein, Q, W, $R_b$ and $R_c$ are defined in the same way as in general formula (I);

m is selected from 1, 2 and 3.

One or more embodiments of the present invention provide a compound shown as (VI) or a stereoisomer, solvate, metabolite, deuteride, prodrug, pharmaceutically acceptable salt or cocrystal thereof, wherein:

Q is selected from 5 membered heteroaryl, wherein the heteroaryl contains 1 to 3 heteroatoms selected from N, O and S, and the aryl or heteroaryl is optionally substituted with 0 to 4 $R^{q0}$; $R^{q0}$ are the same or different and are each independently selected from $C_{1-4}$ alkyl, halogen, OH, cyano, —$NH_2$, $C_{2-4}$ alkenyl, $C_{3-6}$ cycloalkyl, $C_{3-6}$ heterocycloalkyl, —$NHC_{1-4}$ alkyl and —$N(C_{1-4}$ alkyl$)_2$, wherein the heterocycloalkyl contains 1 to 3 heteroatoms selected from N and O, and the alkyl, heterocycloalkyl and cycloalkyl are optionally further substituted with 1 or more substituents selected from deuterium, OH, halogen, cyano, $C_{1-4}$ alkyl and —$NR^{q4}R^{q5}$;

$R^{q4}$ and $R^{q5}$ are selected from H and $C_{1-4}$ alkyl;

W is selected from O and NH;

$R_b$ and $R_c$ are each independently selected from H, $C_{1-4}$ alkyl and 3-5 membered carbocyclyl, wherein the 3-5 membered carbocyclyl is preferably a 3 membered, 4 membered or 5 membered cycloalkyl;

q and r are selected from 0, 1 and 2;

m is selected from 1, 2 and 3.

One or more embodiments of the present invention provide a compound shown as general formula (I), (II), (II-1), (II-2), (III), (III-1), (IV), (V) or (VI) or a stereoisomer, hydrate, metabolite, deuteride, solvate, pharmaceutically acceptable salt or cocrystal thereof, wherein:

Q is selected from

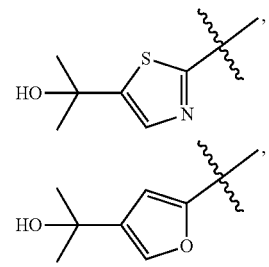

-continued
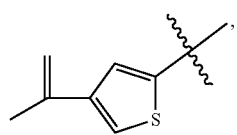
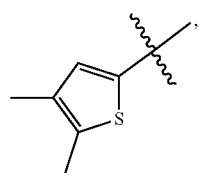
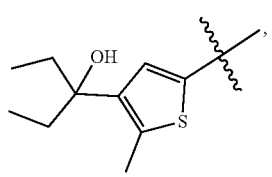
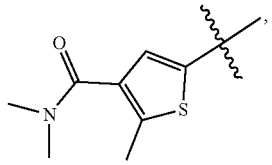
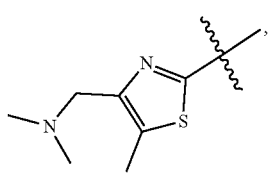
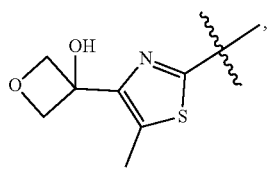
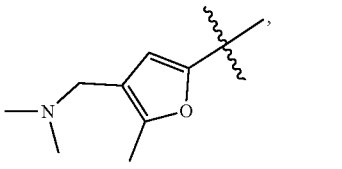
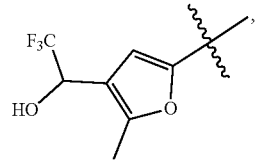, and
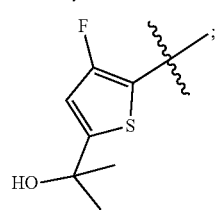;
-continued
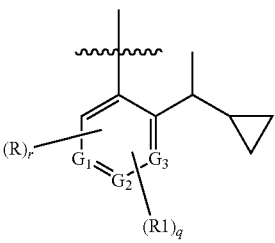
is selected from
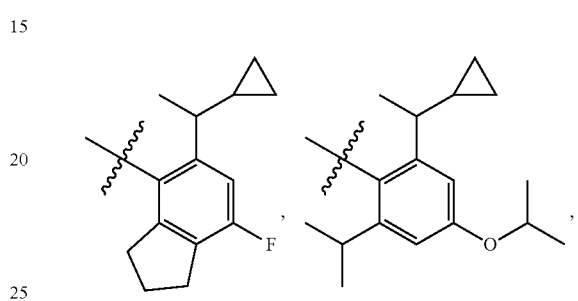
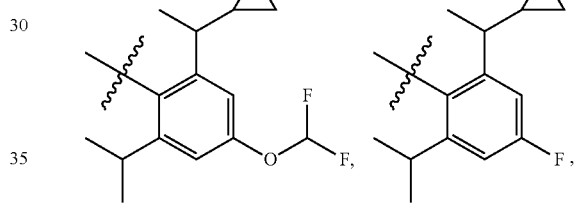
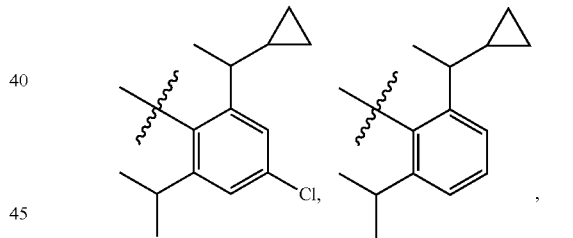
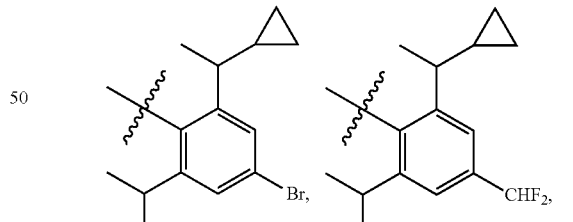
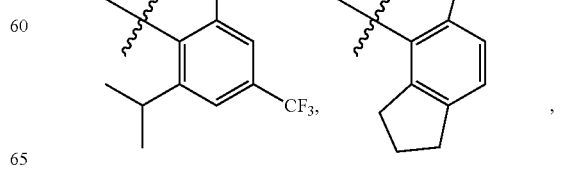

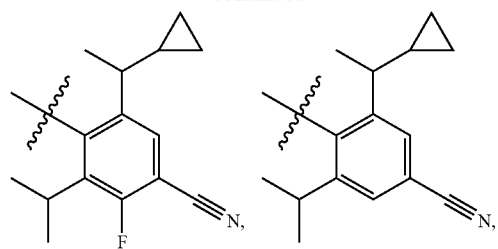
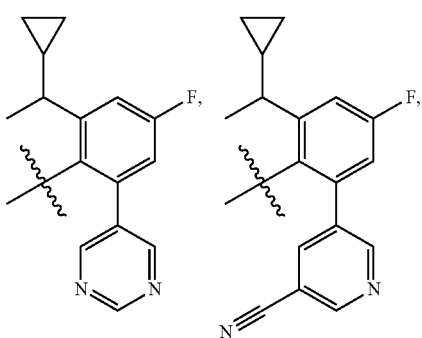
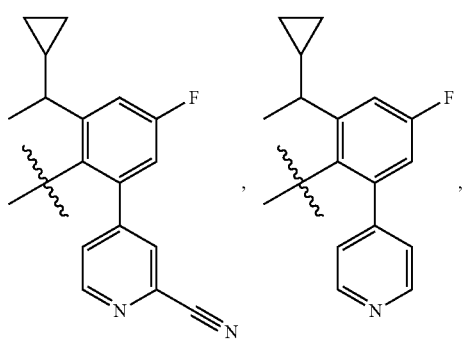
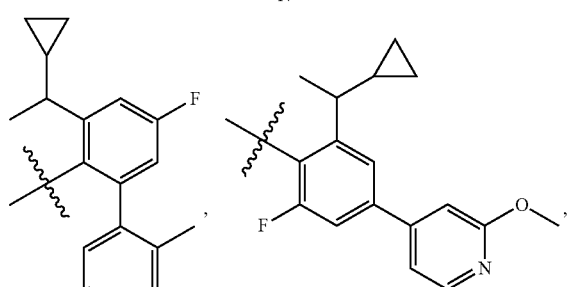
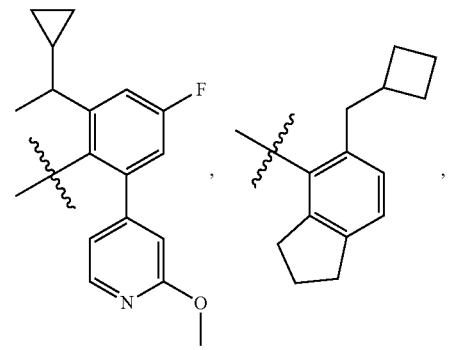
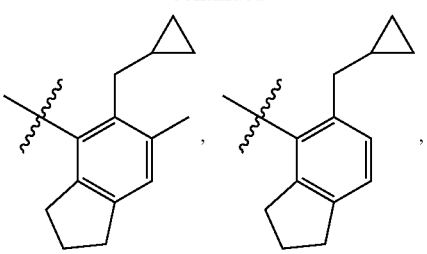
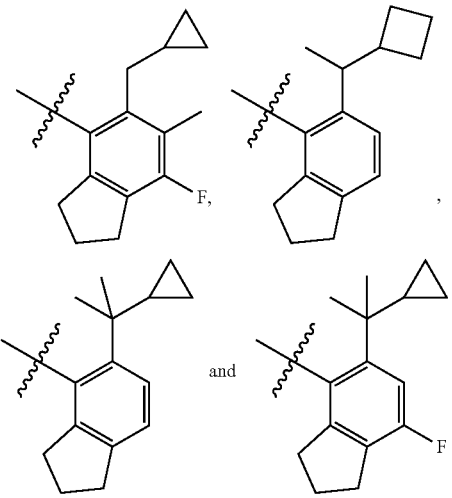
The compound provided in one or more embodiments of the present invention is selected from, but is not limited to, the following structures:
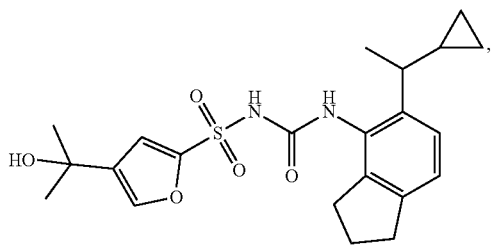
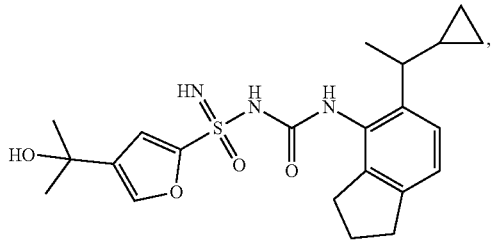
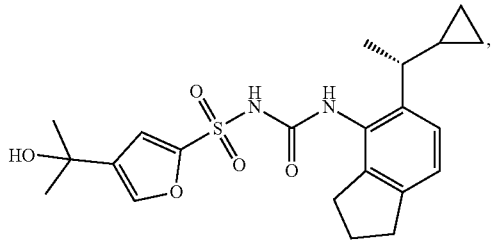

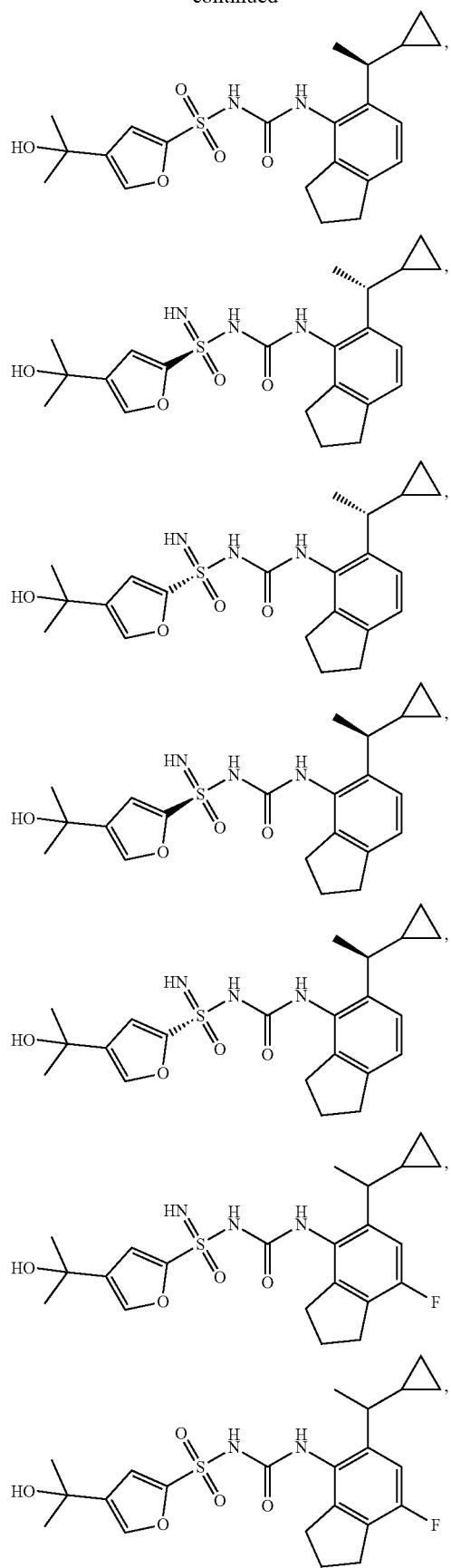
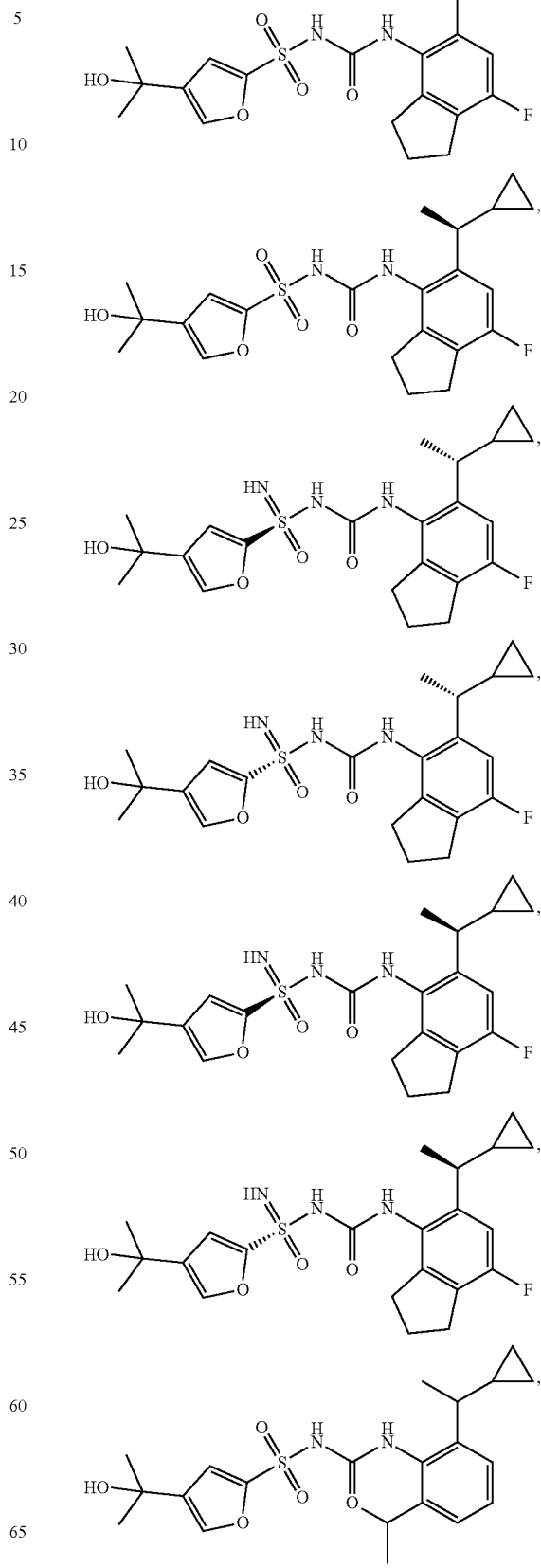

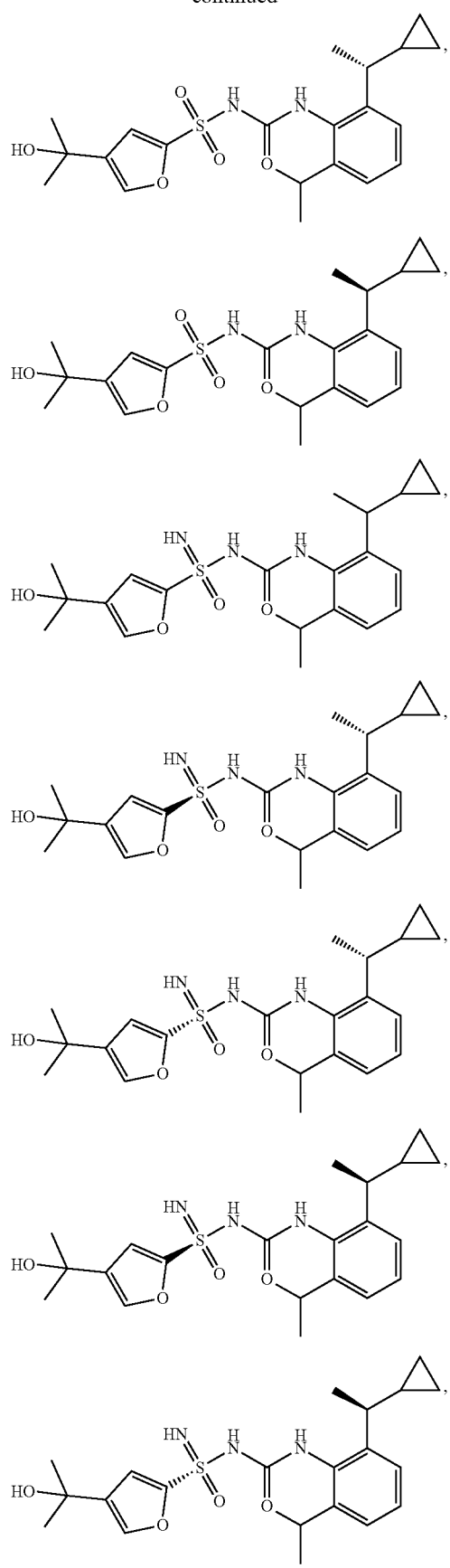
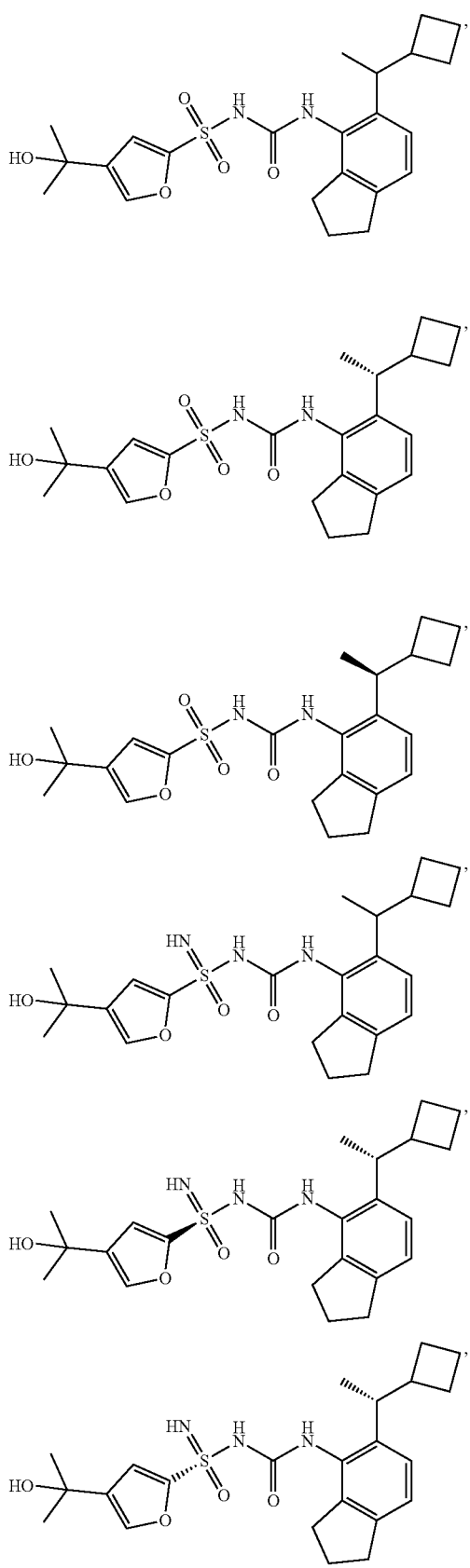

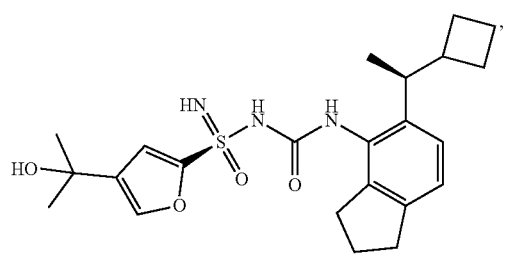
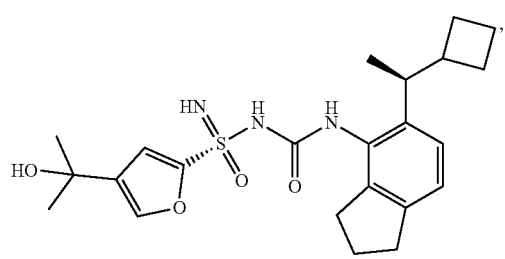
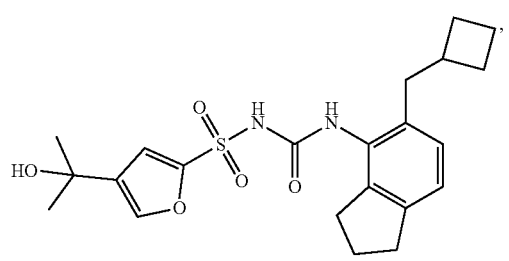
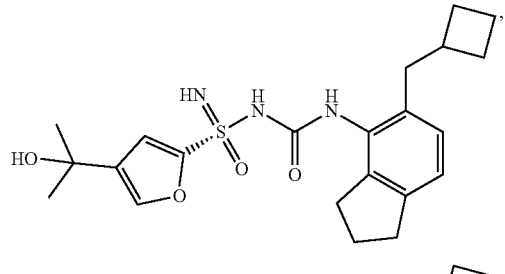
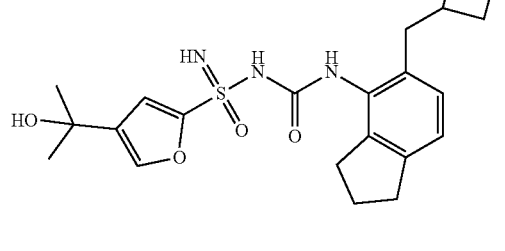
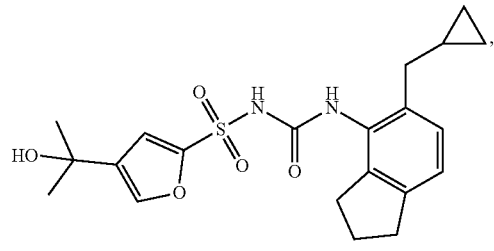
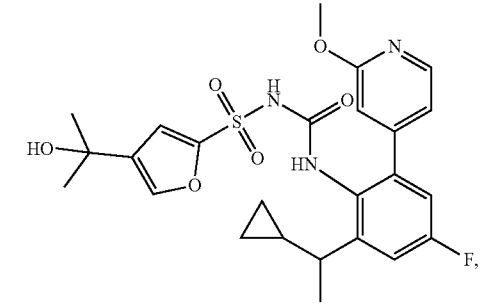
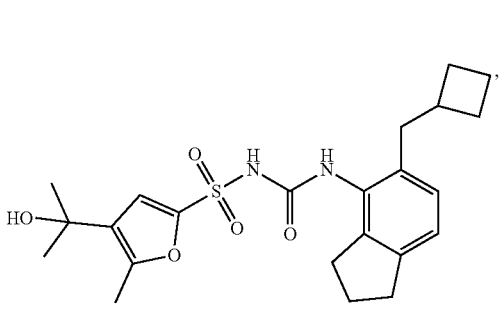
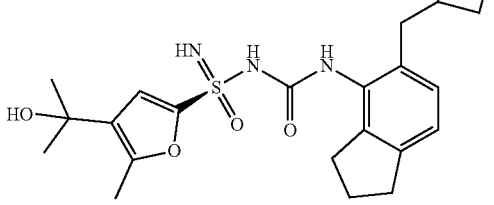
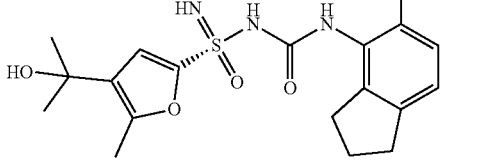
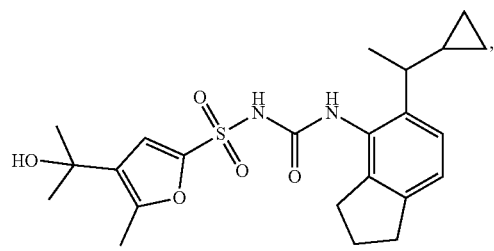

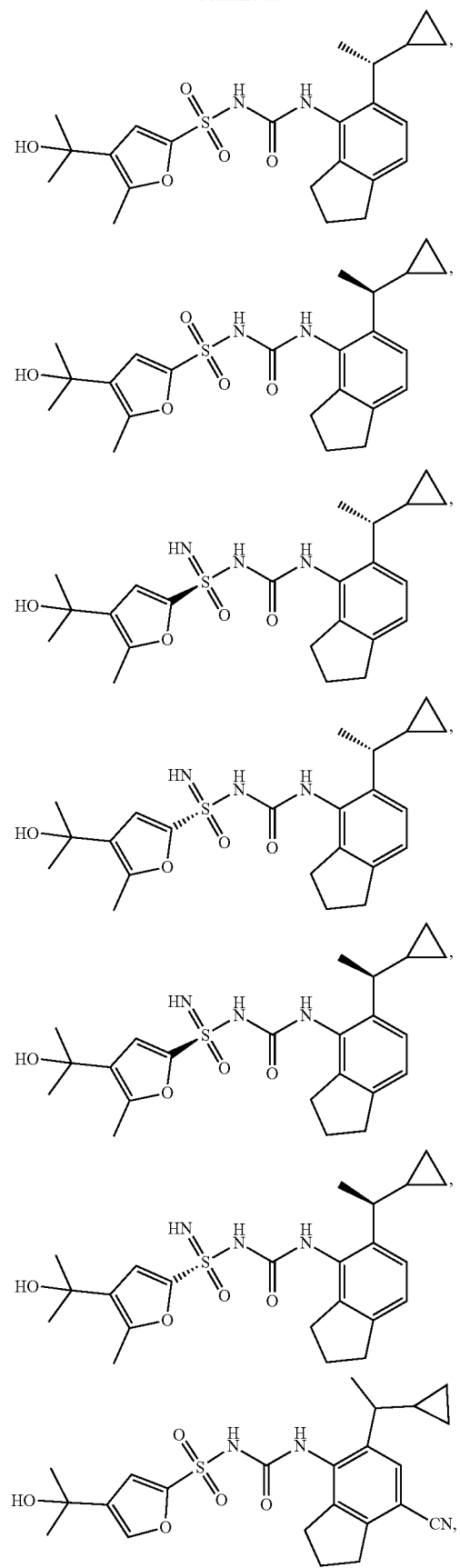
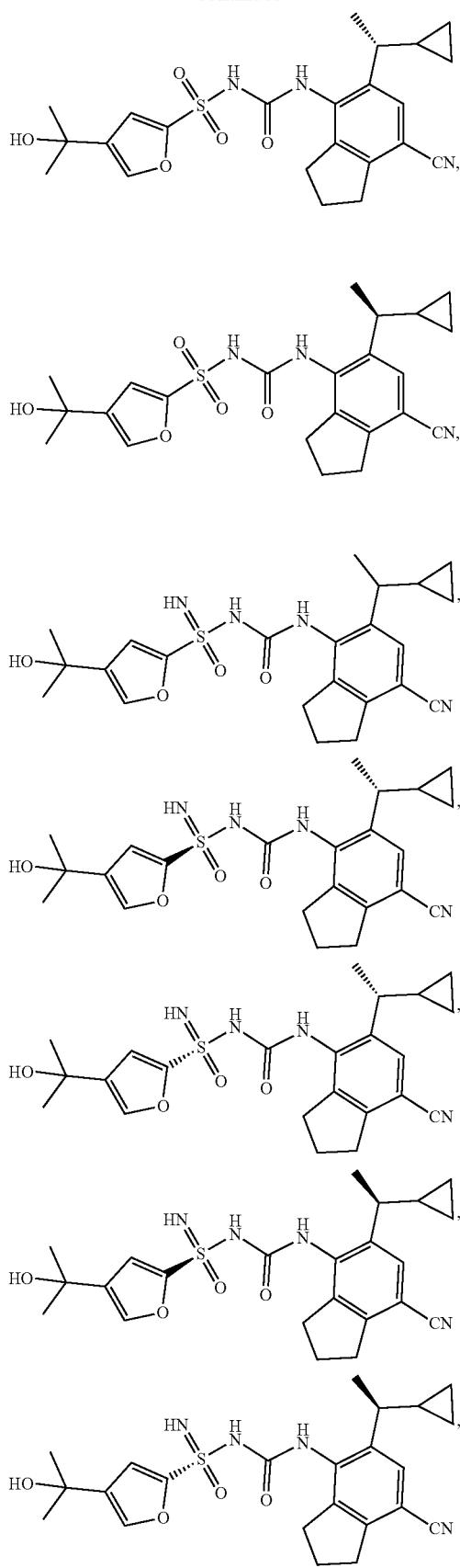

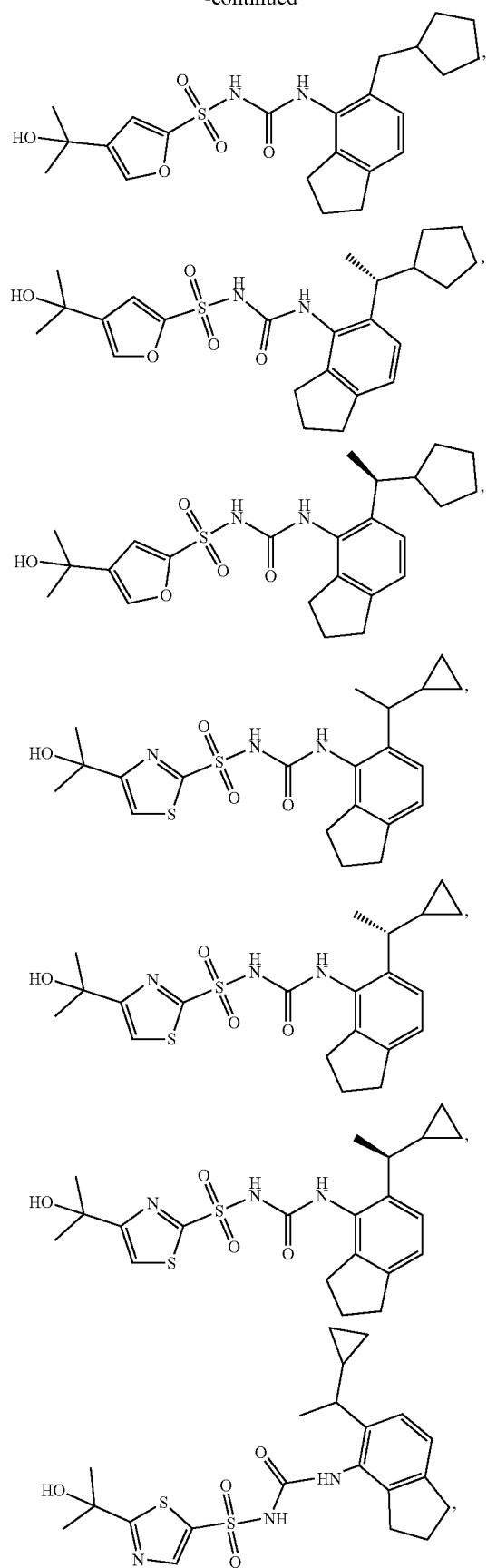
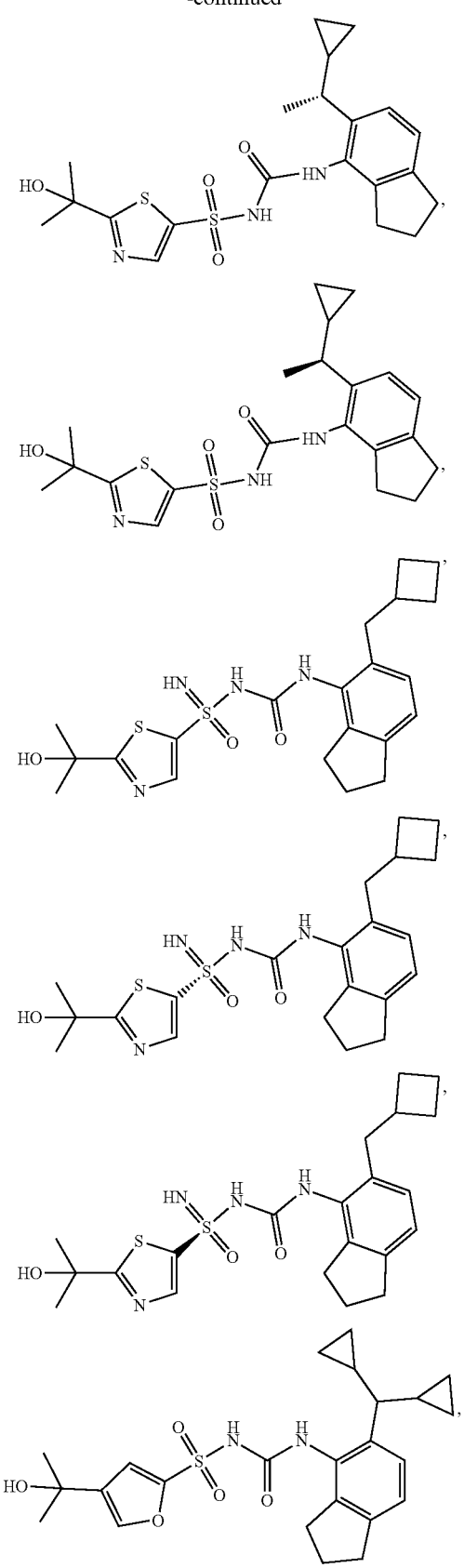

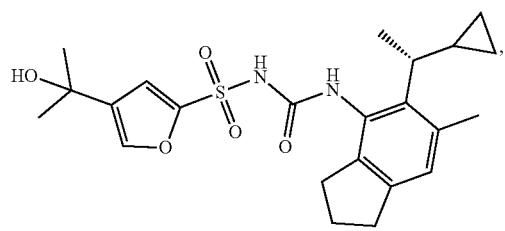
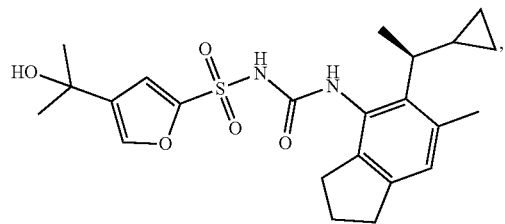
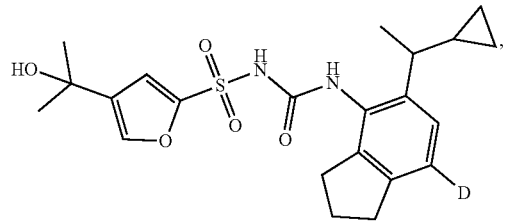
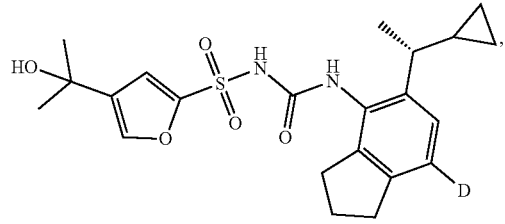
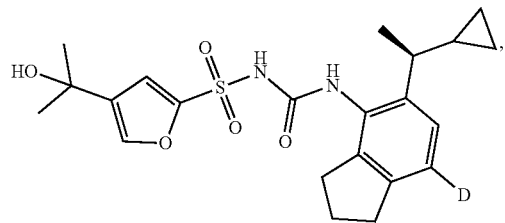
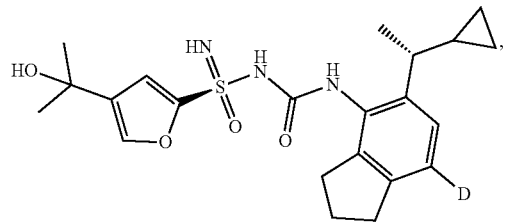
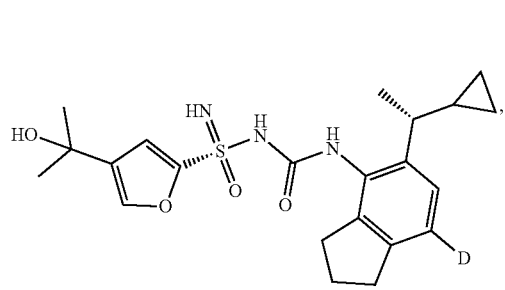
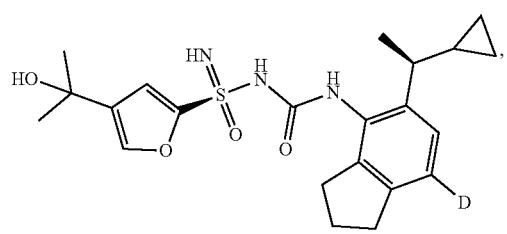
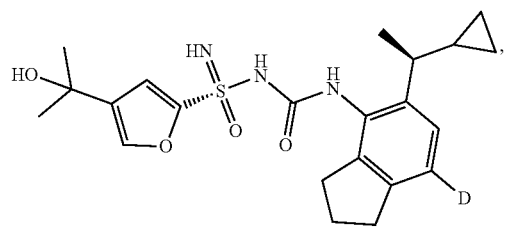
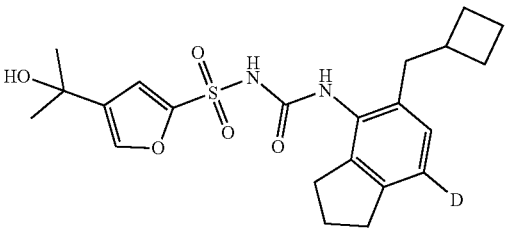
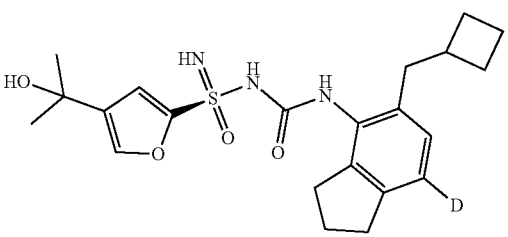
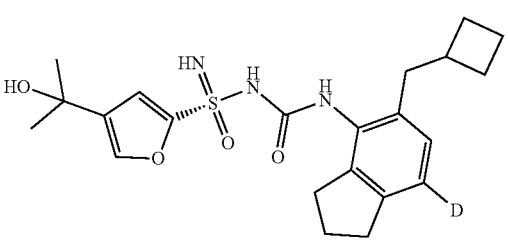
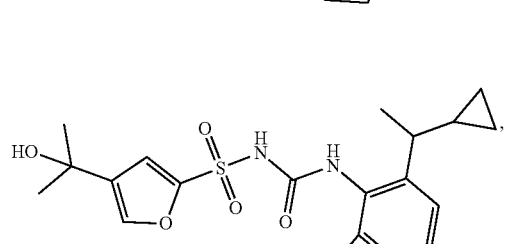
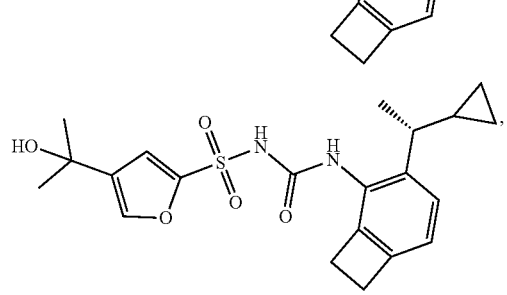

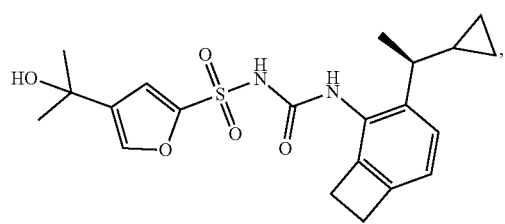
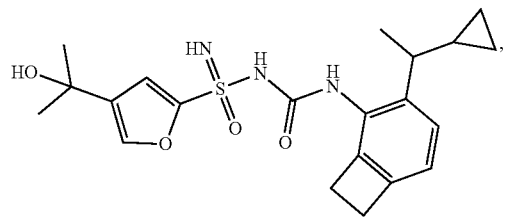
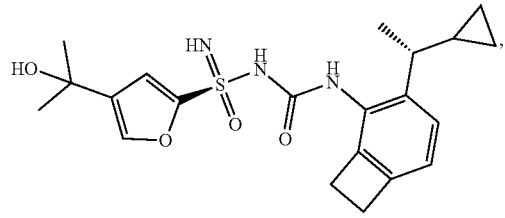
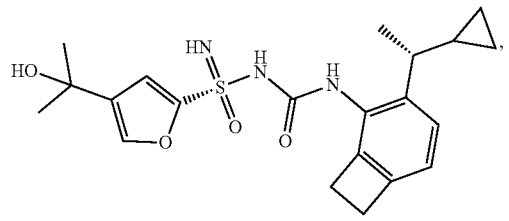
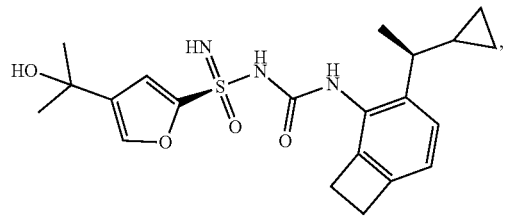
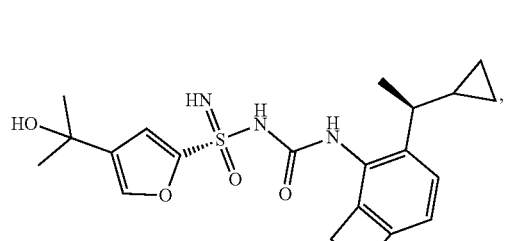
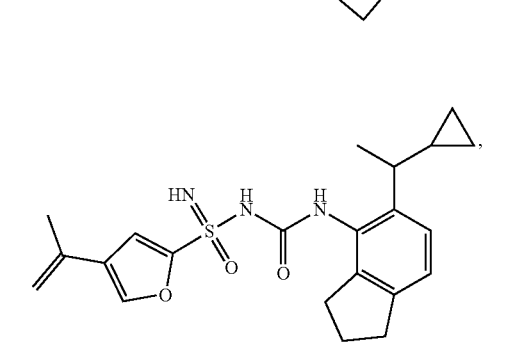
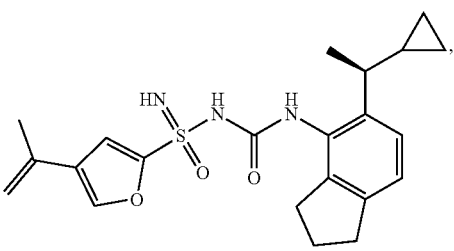
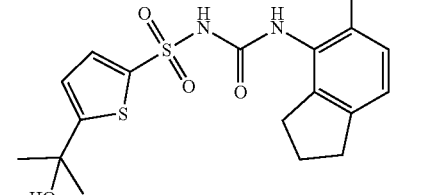
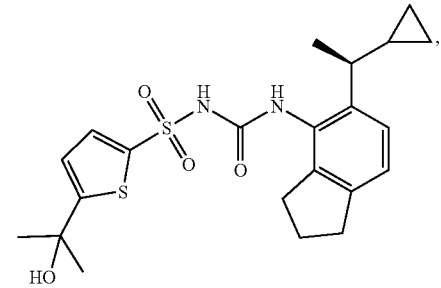
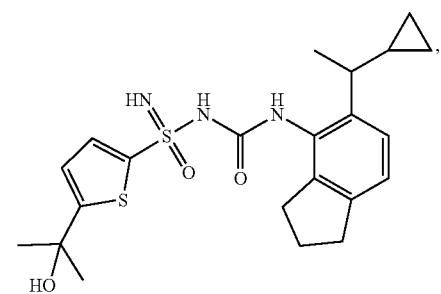
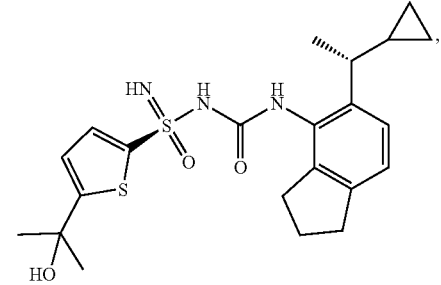
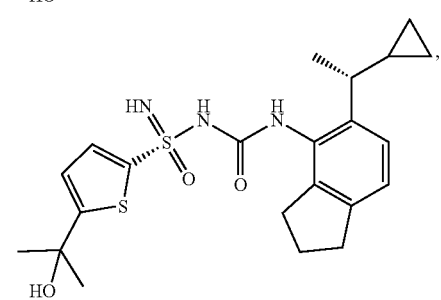

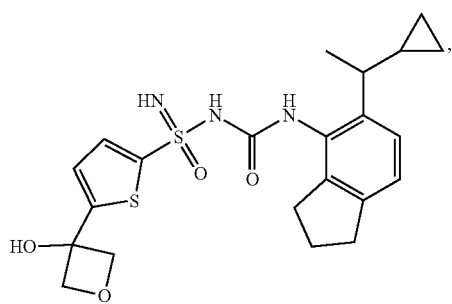
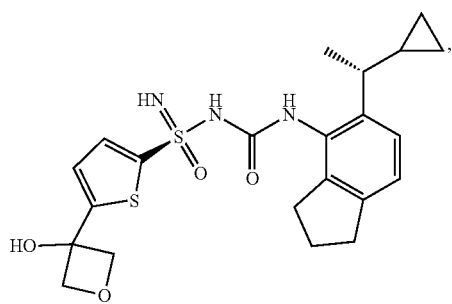
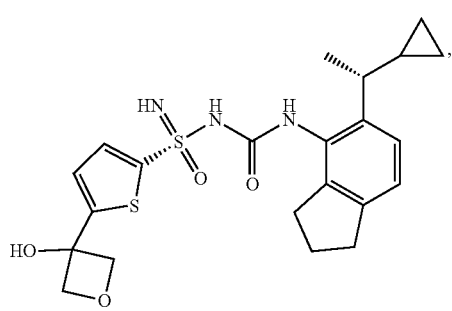
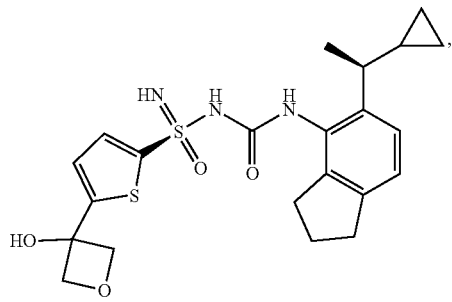
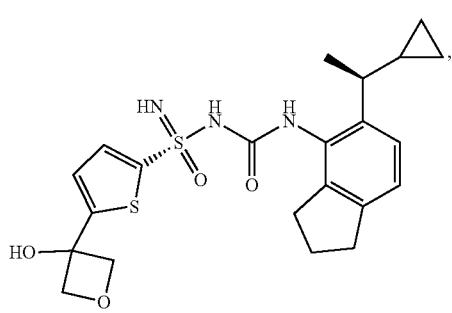
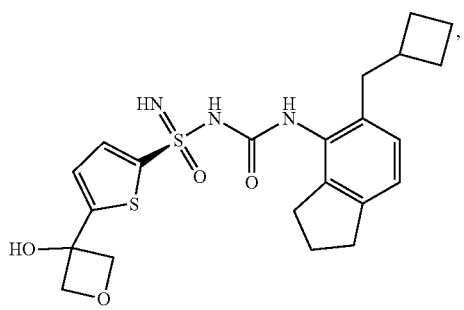
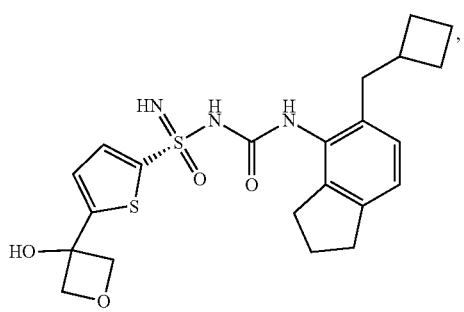
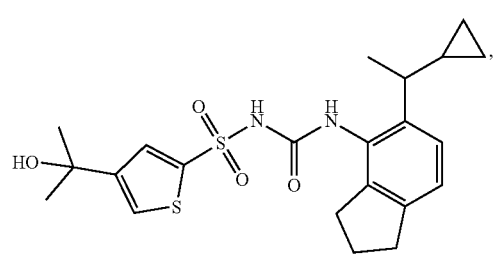
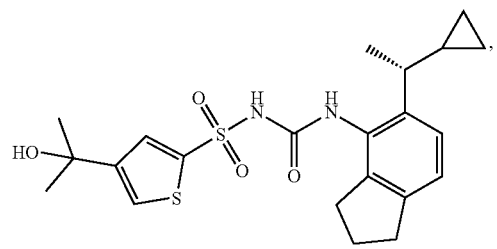
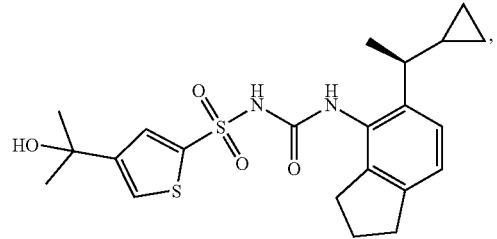
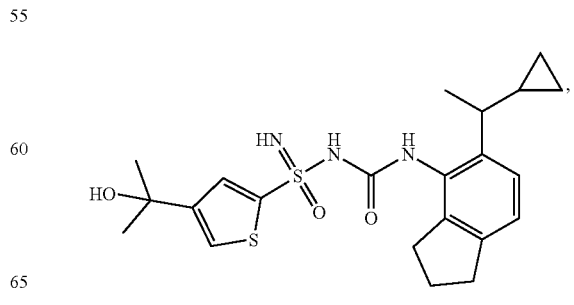

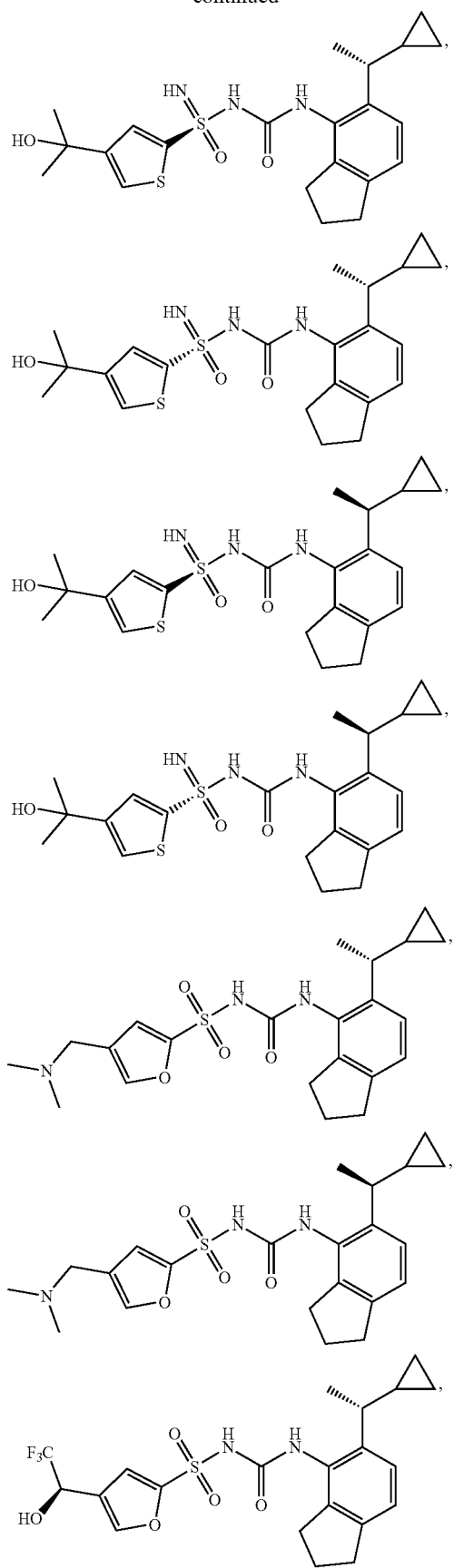
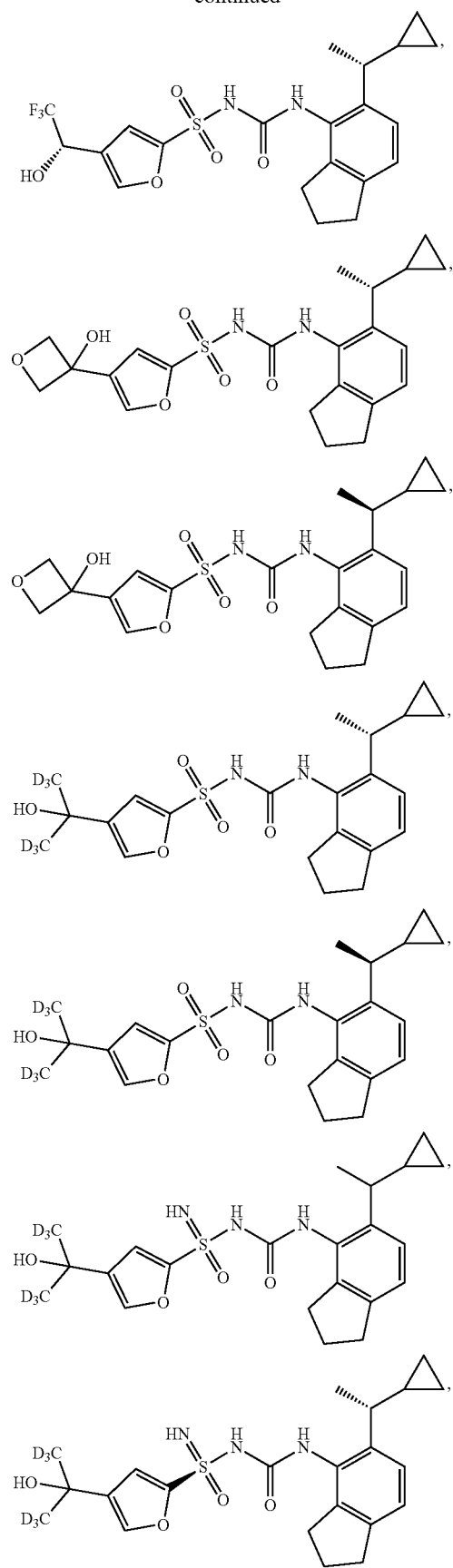

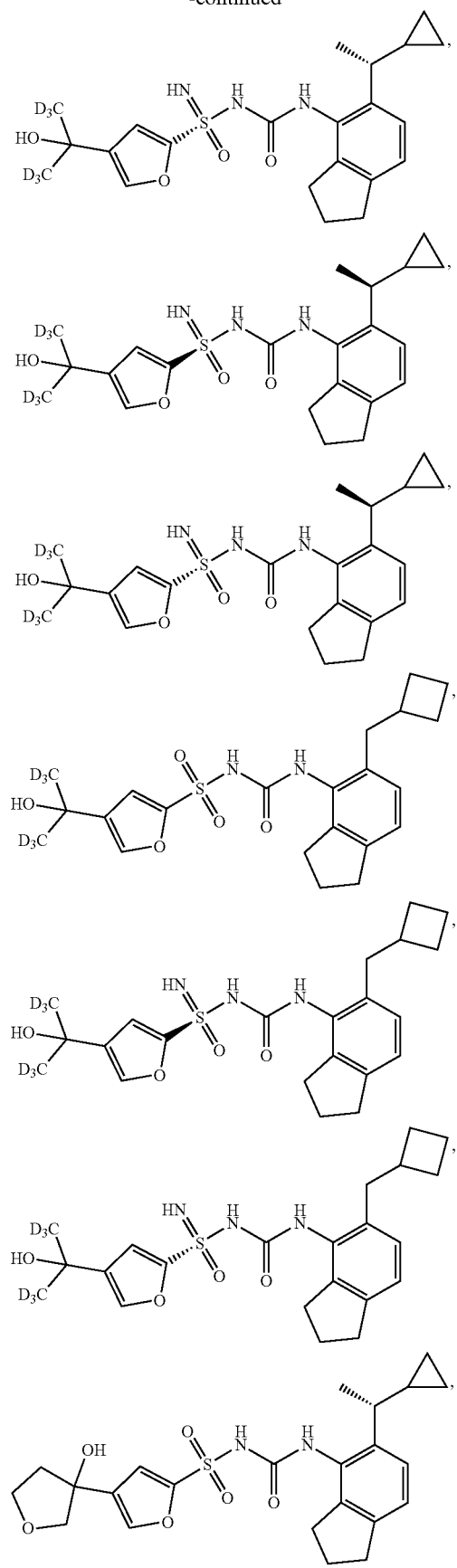
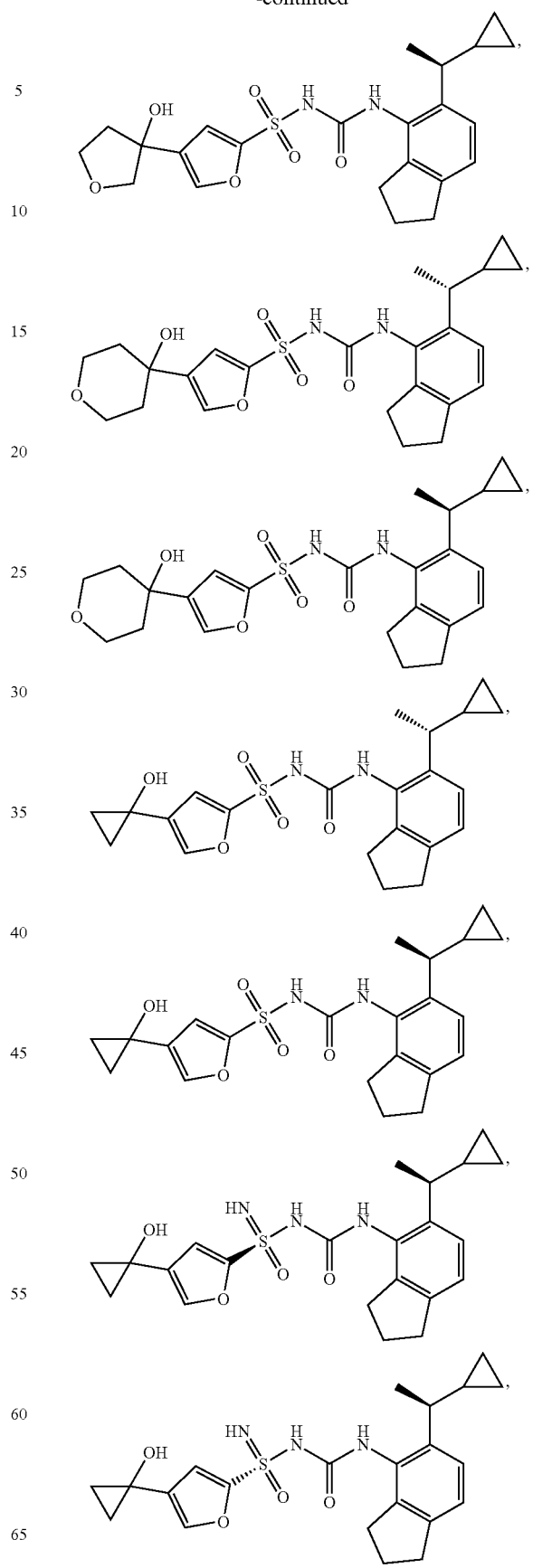

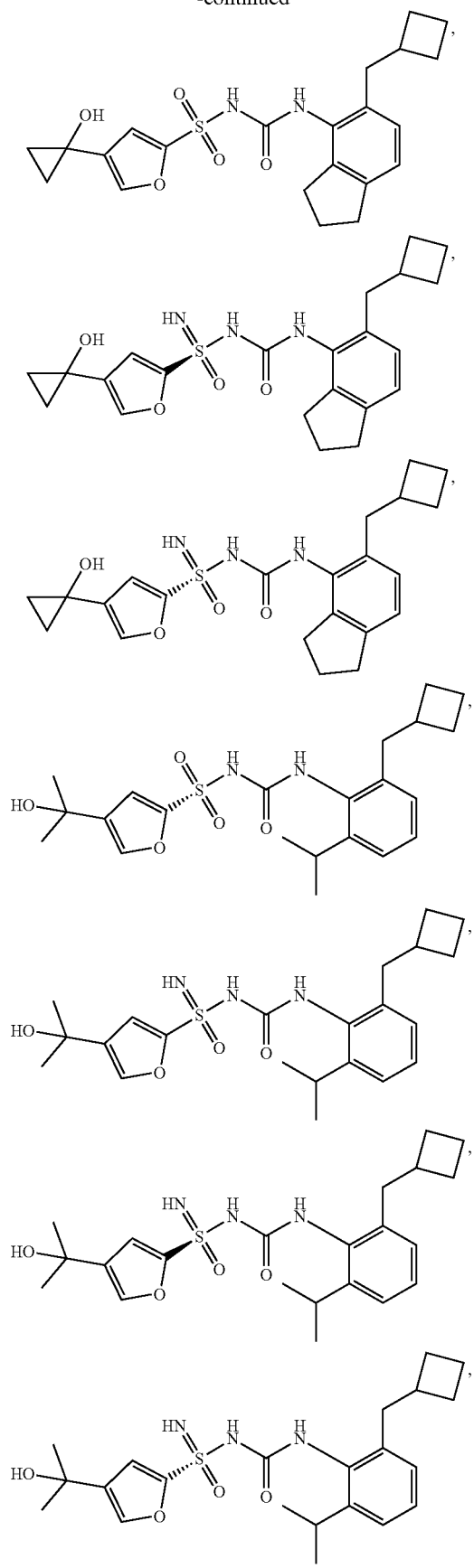
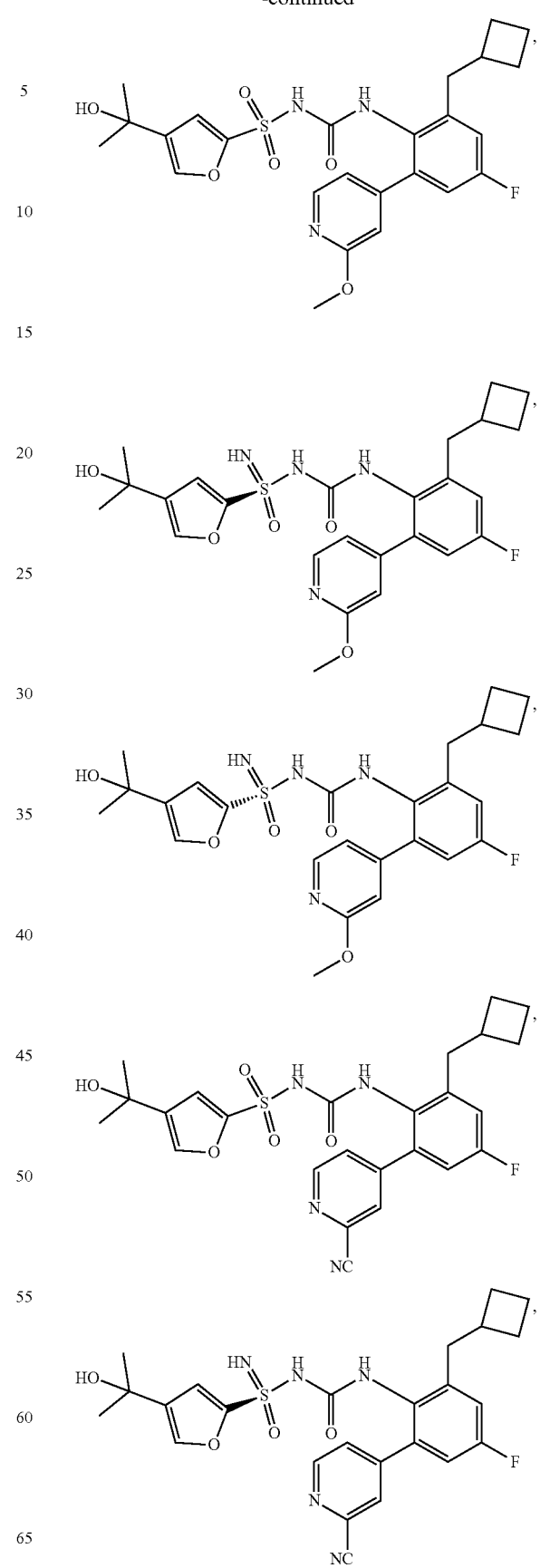

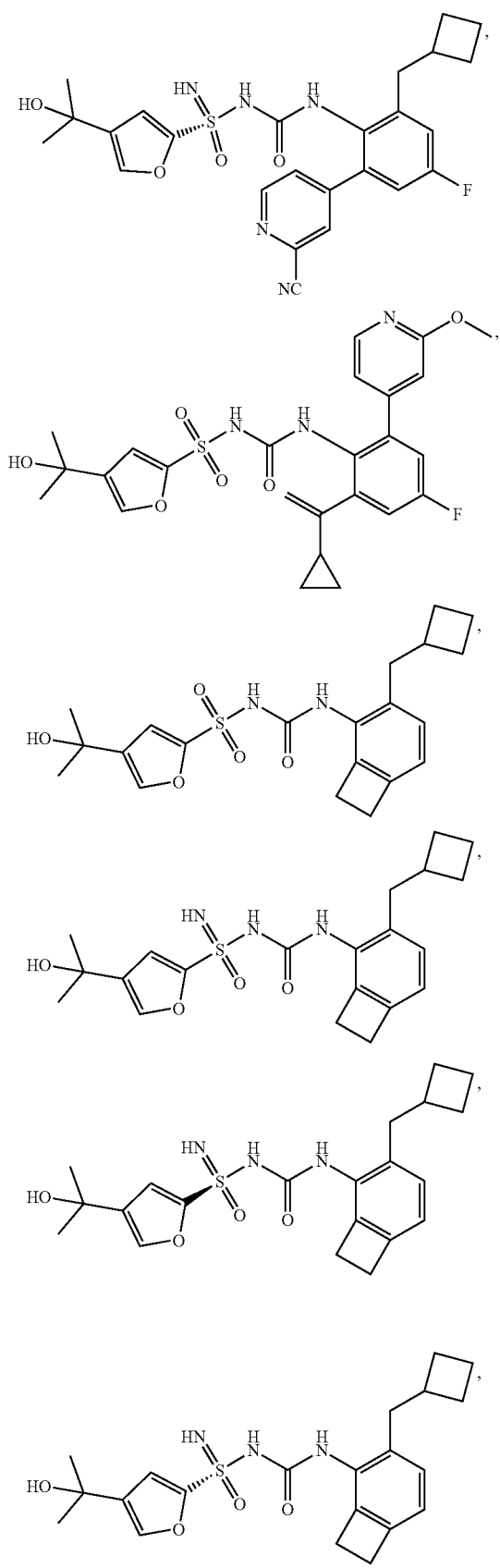
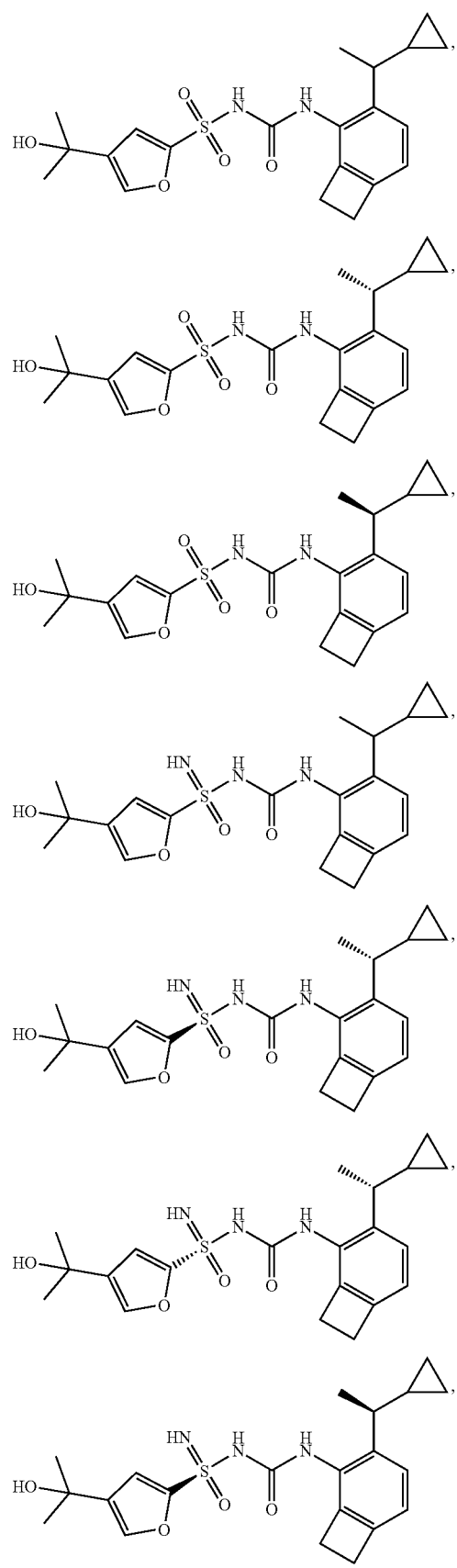

39
-continued
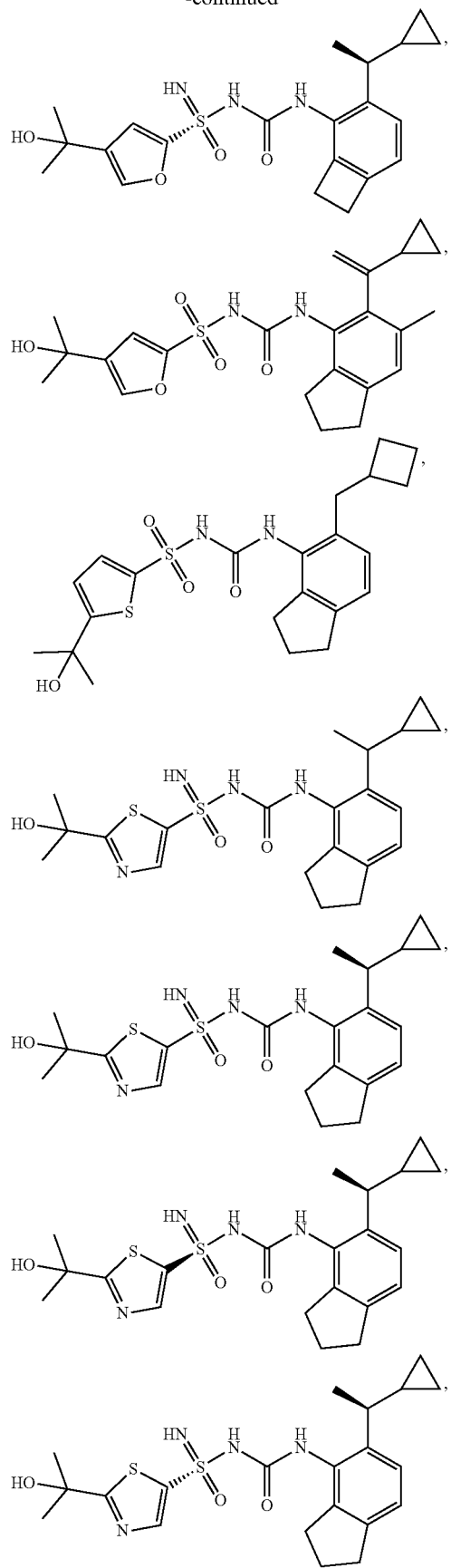
40
-continued
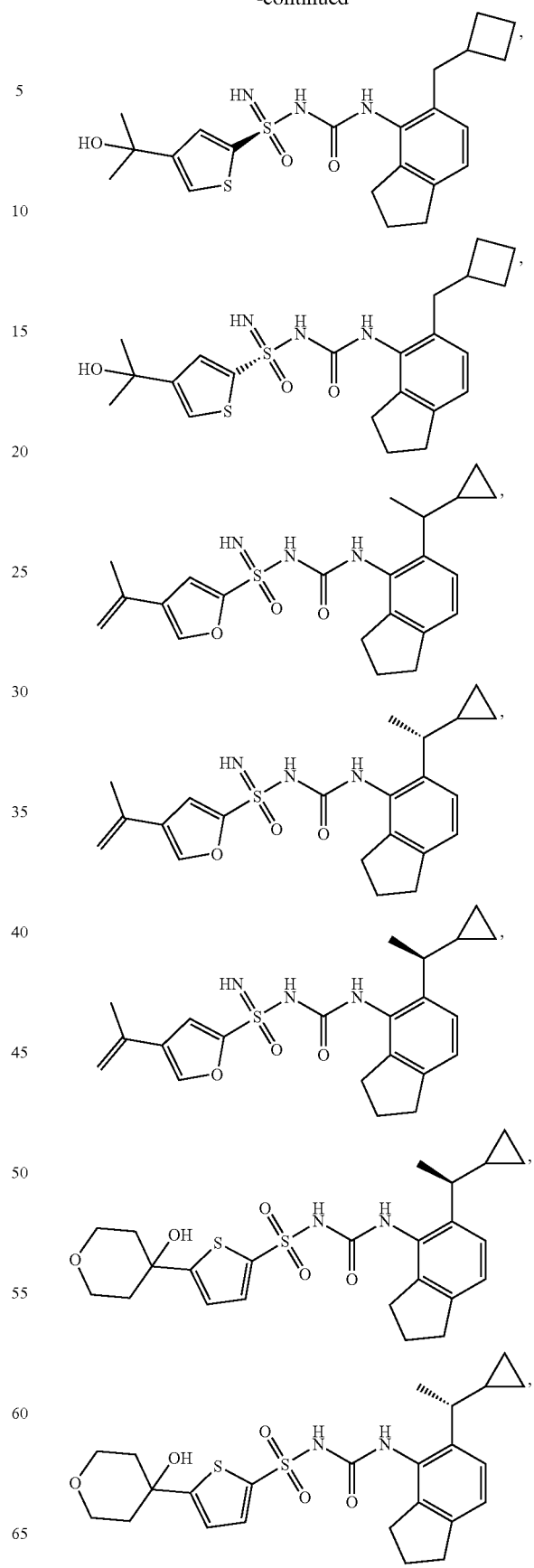

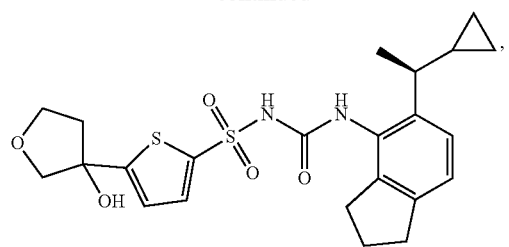
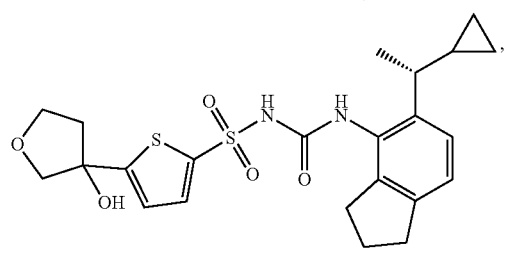
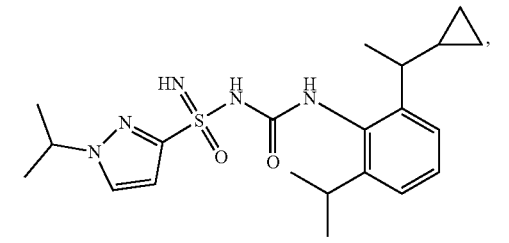
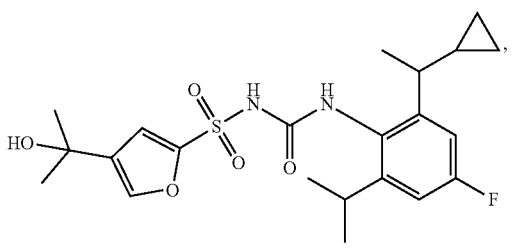
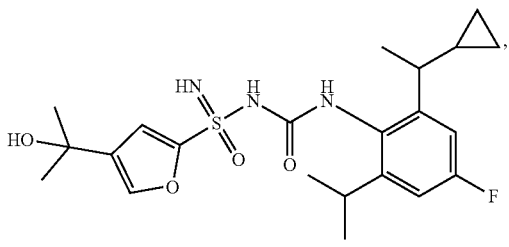
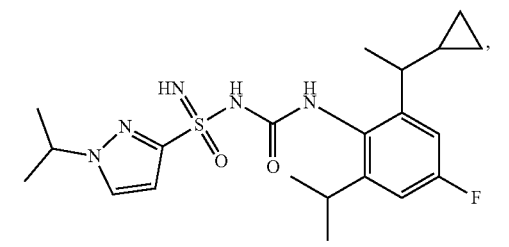
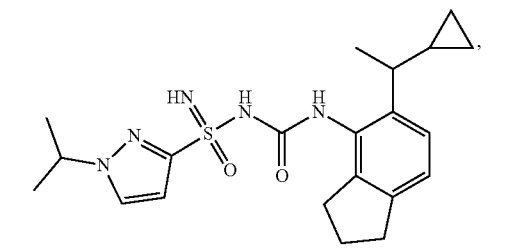
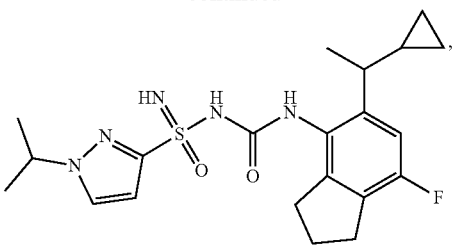
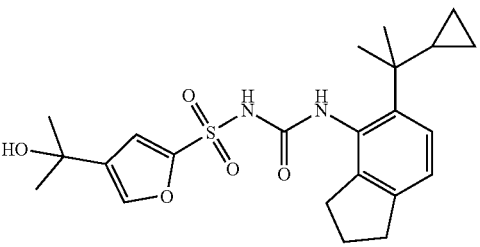
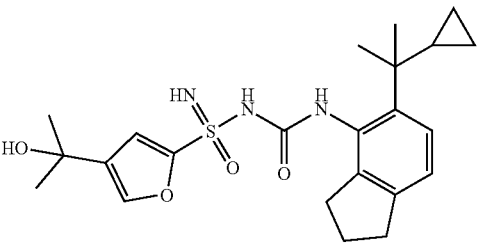
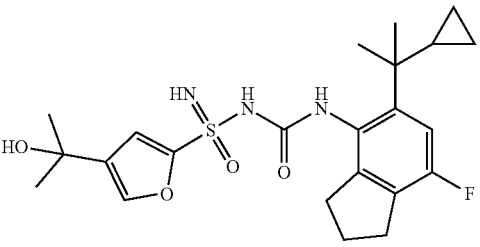
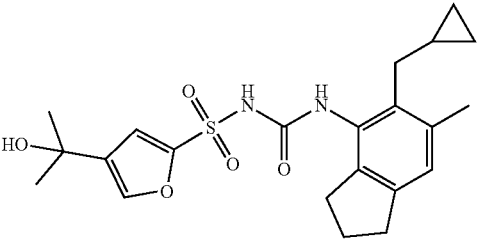
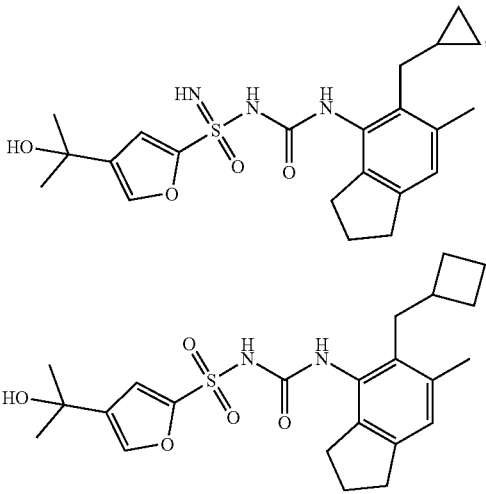

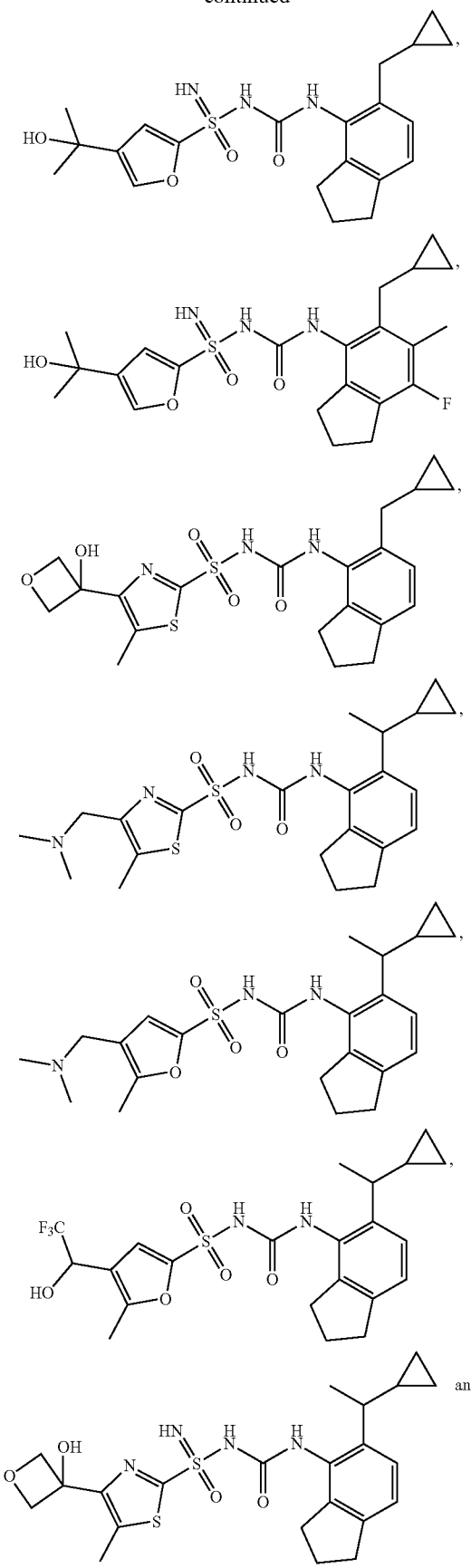
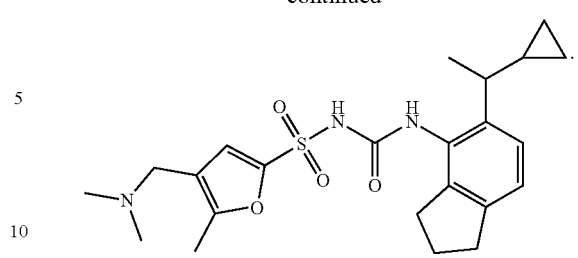
The present invention also provides an intermediate for preparing a compound of formula (I), (II), (II-1), (II-2), (III), (III-1), (IV), (V) or (VI), wherein the intermediate is selected from, but is not limited to, the following structures:
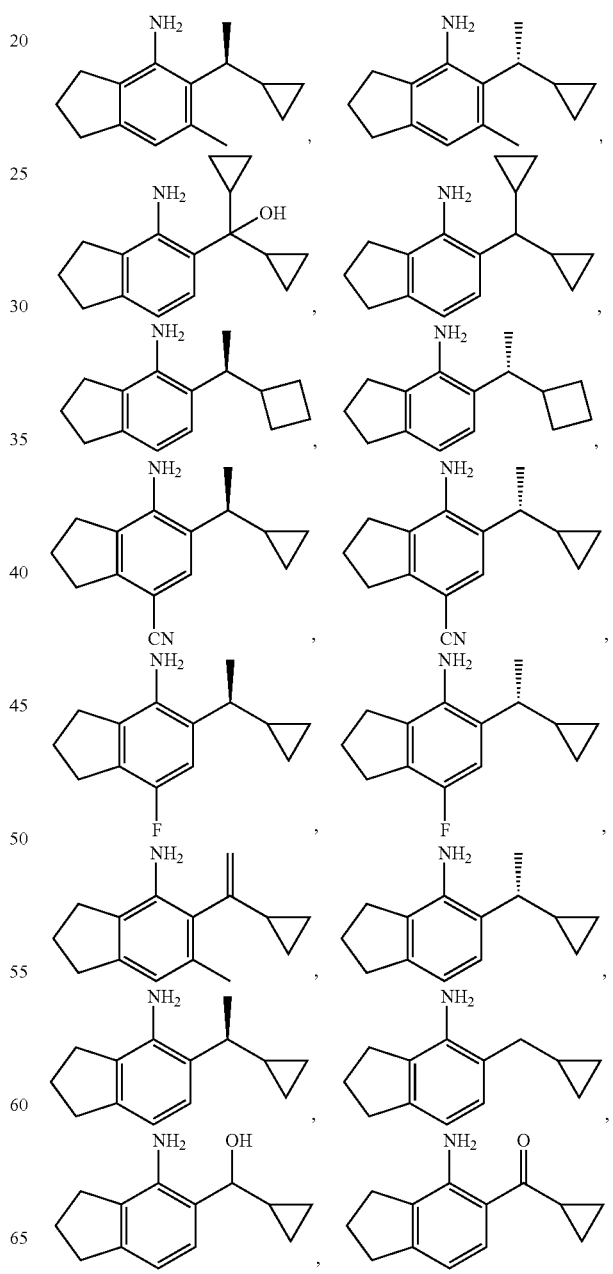

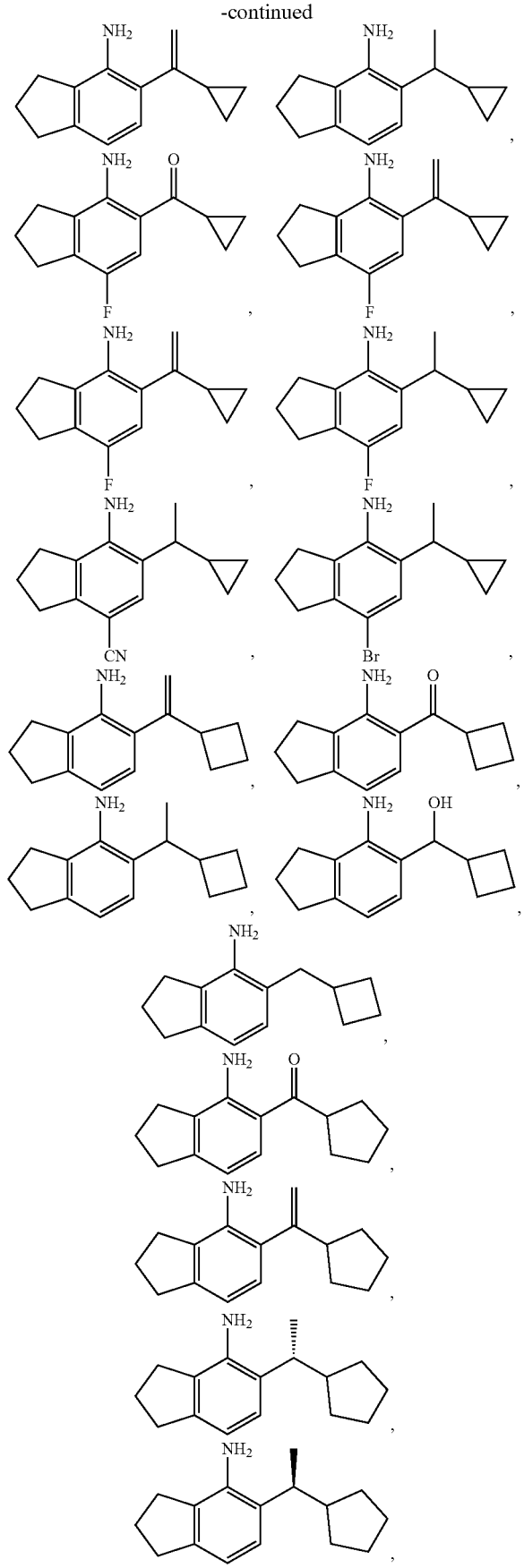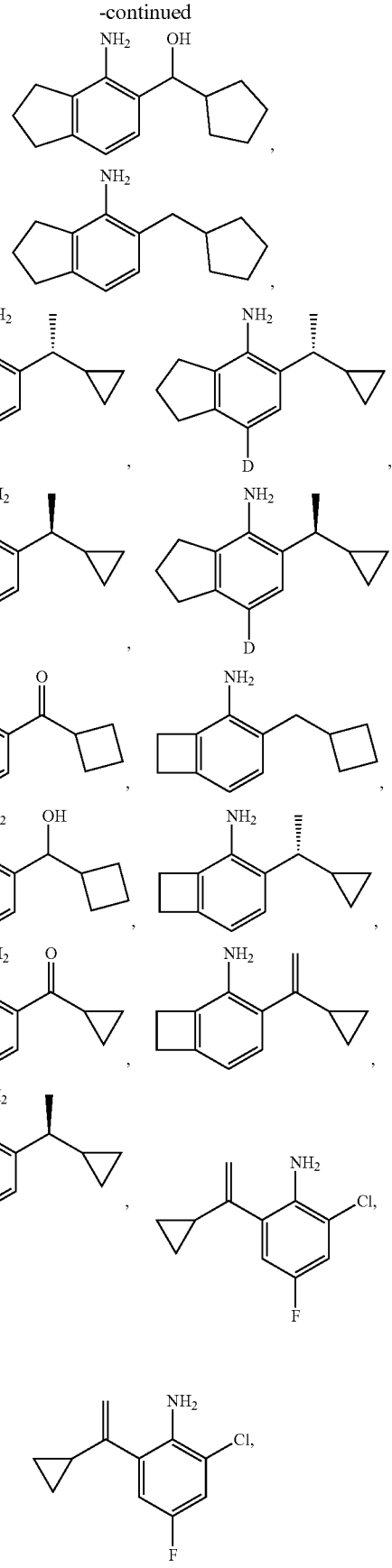

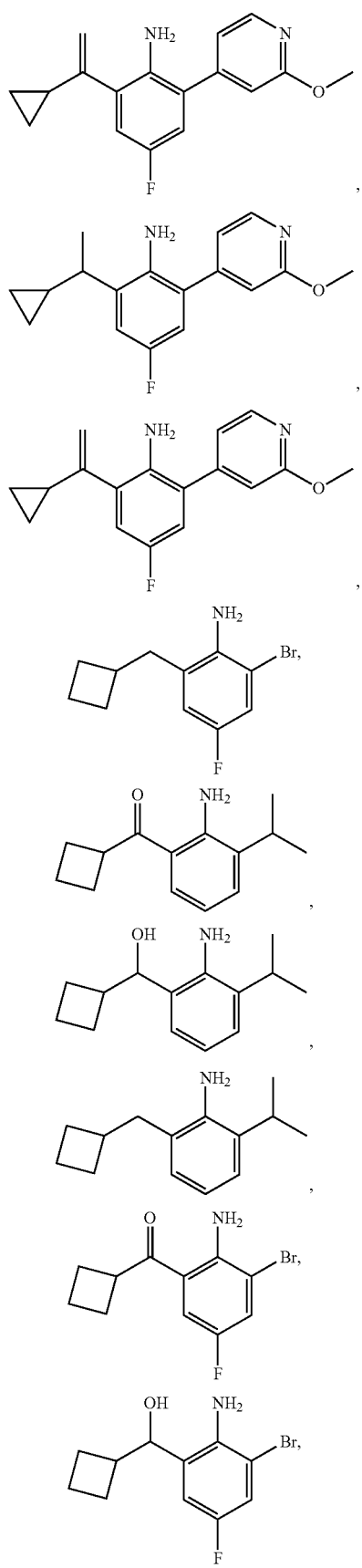
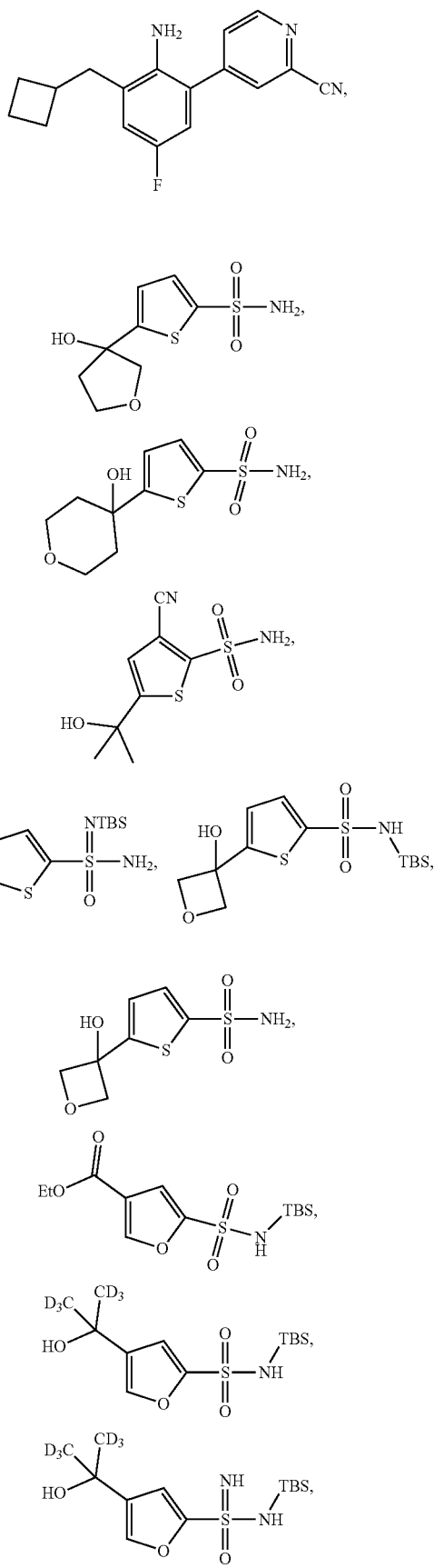

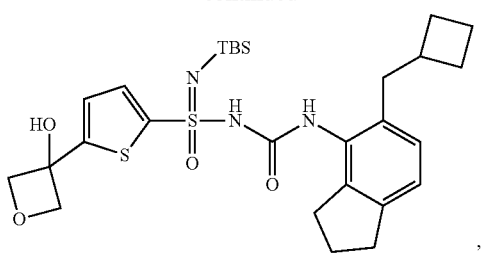
,
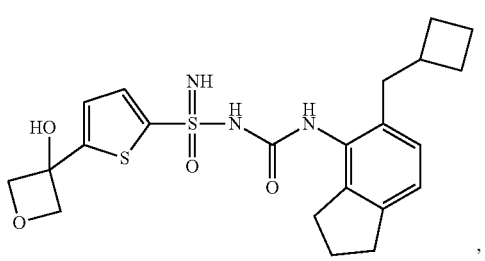
,
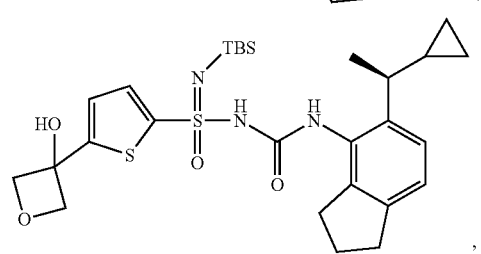
,
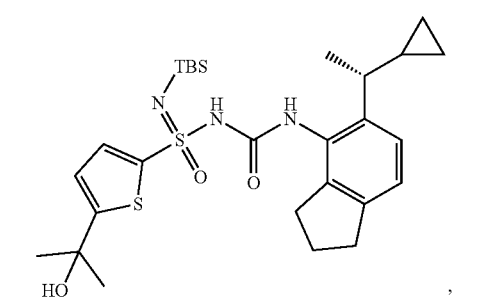
,
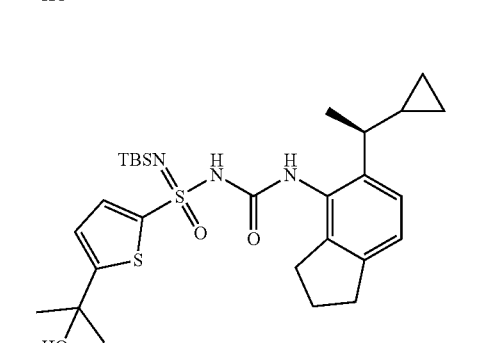
,
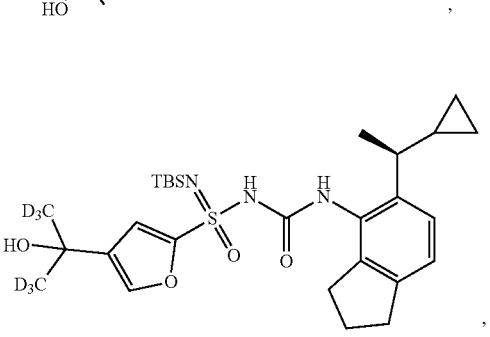
,
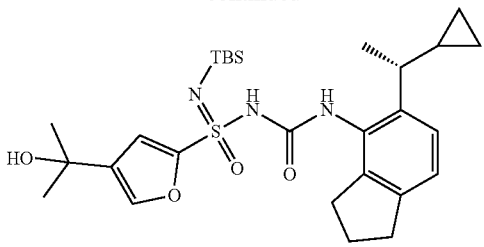
,
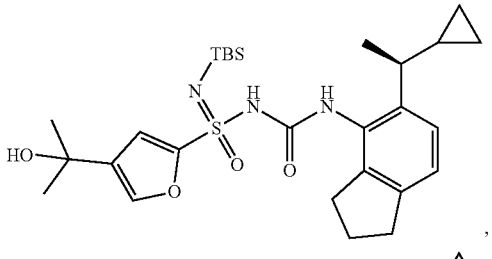
,
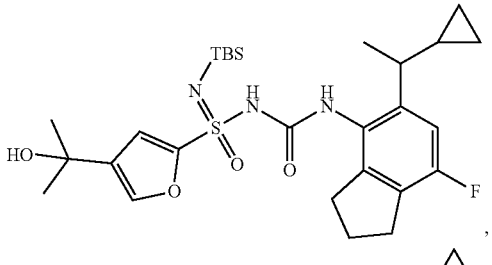
,
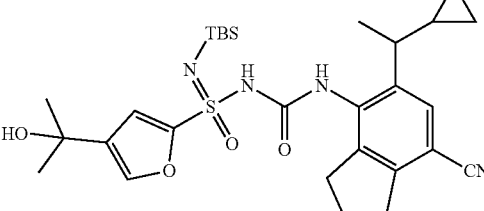
,
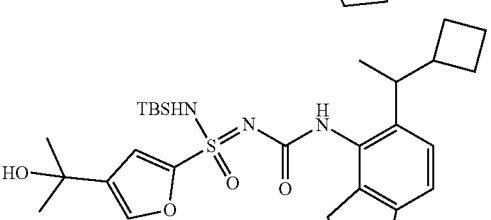
,
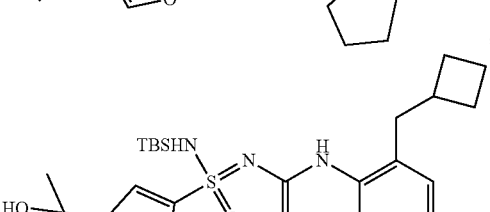
,
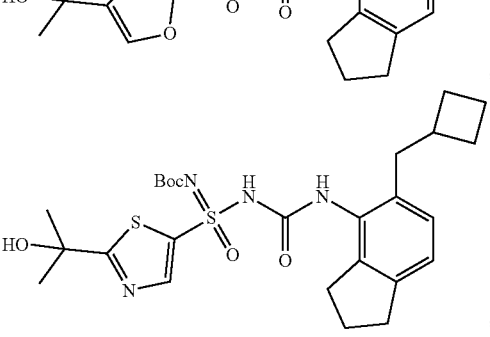
,

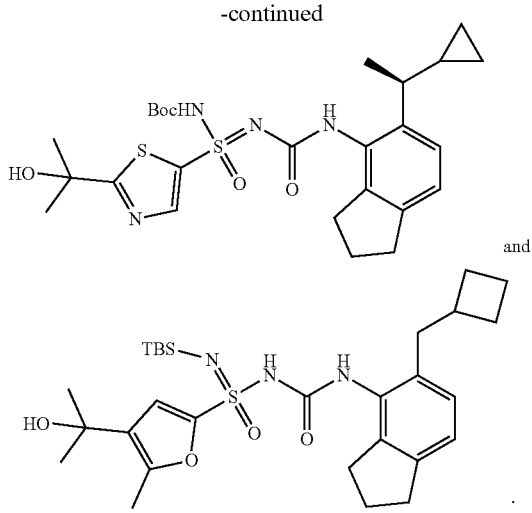

and

One or more embodiments of the present application provide a pharmaceutical composition comprising the compound of general formula (I), (II), (II-1), (II-2), (III), (III-1), (IV), (V) or (VI) or the specific structure described above or the stereoisomer, solvate, metabolite, deuteride, pharmaceutically acceptable salt, cocrystal or prodrug thereof, and one or more pharmaceutically acceptable carriers and/or excipients.

One or more embodiments of the present application provide use of the pharmaceutical composition, the compound of general formula (I), (II), (II-1), (II-2), (III), (III-1), (IV), (V) or (VI) or the specific structure described above, or the stereoisomer, solvate, metabolite, deuteride, pharmaceutically acceptable salt, cocrystal or prodrug thereof disclosed herein, in preparing an NLRP3 inhibitor.

In one or more embodiments of the present application, a disease treated by the NLRP3 inhibitor is selected from inflammatory diseases, autoimmune diseases, cardiovascular system diseases, cancers, renal system diseases, gastrointestinal diseases, respiratory system diseases, endocrine system diseases and central nervous system diseases.

In one or more embodiments of the present application, a disease treated by the NLRP3 inhibitor is selected from cryopyrin-associated periodic syndrome (CAPS), Muckle-Wells syndrome (MWS), familial cold autoinflammatory syndrome (FCAS), neonatal-onset multisystem inflammatory disease (NOMID), familial Mediterranean fever (FMF), non-alcoholic steatohepatitis, alcoholic liver disease, graft-versus-host disease, multiple sclerosis (MS), rheumatoid arthritis, type I diabetes, type II diabetes, psoriasis, Alzheimer's disease, atherosclerosis, gout and chronic kidney disease.

One or more embodiments of the present application provide a method for inhibiting NLRP3, which comprises contacting the compound of formula (I), (II), (II-1), (II-2), (III), (III-1), (IV), (V) or (VI) or the specific structure described above or the stereoisomer, solvate, metabolite, deuteride, pharmaceutically acceptable salt, cocrystal or prodrug thereof disclosed herein, or the composition disclosed herein, with a subject in need thereof.

One or more embodiments of the present application provide a method for treating a disease associated with NLRP3, which comprises administering to a subject in need thereof the compound of formula (I), (II), (II-1), (II-2), (III), (III-1), (IV), (V) or (VI) or the specific structure described above or the stereoisomer, solvate, metabolite, deuteride, pharmaceutically acceptable salt, cocrystal or prodrug thereof disclosed herein, or the composition disclosed herein.

One or more embodiments of the present application provide a compound of general formula (I), (II), (II-1), (II-2), (III), (III-1), (IV), (V) or (VI) or the specific structure described above or the stereoisomer, solvate, metabolite, deuteride, pharmaceutically acceptable salt, cocrystal or prodrug thereof, for use in treating a disease associated with NLRP3 or as an NLRP3 inhibitor. Unless stated to the contrary, the terms used in the specification and claims have the following meanings.

Carbon, hydrogen, oxygen, sulfur, nitrogen, F, $C_1$, Br and I involved in the groups and compounds described herein are each inclusive of isotopes thereof, and carbon, hydrogen, oxygen, sulfur or nitrogen involved in the groups and compounds described herein is optionally further replaced by one or more isotopes thereof corresponding thereto, wherein isotopes of carbon include $^{12}C$, $^{13}C$ and $^{14}C$, isotopes of hydrogen include protium (H), deuterium (D, also called heavy hydrogen) and tritium (T, also called superheavy hydrogen), isotopes of oxygen include $^{16}O$, $^{17}O$ and $^{18}O$, isotopes of sulfur include $^{32}S$, $^{33}S$, $^{34}S$ and $^{36}S$, isotopes of nitrogen include $^{14}N$ and $^{15}N$, isotopes of fluorine include $^{17}F$ and $^{19}F$, isotopes of chlorine include $^{35}Cl$ and $^{37}Cl$, and isotopes of bromine include $^{79}Br$ and $^{81}Br$.

"Alkyl" refers to a linear or branched saturated aliphatic hydrocarbon group consisting of 1 to 20 carbon atoms, preferably an alkyl group consisting of 1 to 8 (e.g., 1, 2, 3, 4, 5, 6, 7 or 8) carbon atoms, more preferably an alkyl group consisting of 1 to 6 carbon atoms, and further preferably an alkyl group consisting of 1 to 4 carbon atoms. Non-limiting examples include methyl, ethyl, n-propyl, isopropyl, n-butyl, sec-butyl, neobutyl, tert-butyl, n-pentyl, isopentyl, neopentyl, n-hexyl and various branched chain isomers thereof, when the alkyl is substituted, it may be optionally further substituted with 1 or more substituents.

"Alkoxy" refers to a group formed by substitution of at least 1 carbon atom of an alkyl group with an oxygen atom. Non-limiting examples include methoxy, ethoxy, n-propoxy, isopropoxy, n-butoxy, sec-butoxy, tert-butoxy, n-pentoxy, n-hexoxy, cyclopropoxy and cyclobutoxy. The alkyl is defined in the same way as for the "alkyl" described above.

"Alkenyl" refers to a linear or branched unsaturated aliphatic hydrocarbon group containing 1 to 10 (e.g., 1, 2, 3, 4, 5, 6, 7, 8, 9 or 10) carbon-carbon double bonds and consisting of 2 to 20 carbon atoms, preferably an alkenyl group consisting of 2 to 12 (e.g., 2, 3, 4, 5, 6, 7, 8, 9, 10, 11 or 12) carbon atoms, more preferably an alkenyl group consisting of 2 to 8 carbon atoms, and further preferably an alkenyl group consisting of 2 to 6 carbon atoms. Non-limiting examples include vinyl, propen-2-yl, buten-2-yl, penten-2-yl, penten-4-yl, hexen-2-yl, hexen-3-yl, hepten-2-yl, hepten-3-yl, hepten-4-yl, octen-3-yl, nonen-3-yl, decen-4-yl, and undecen-3-yl. The alkenyl may be optionally further substituted with 1 or more substituents.

"Alkynyl" refers to a linear or branched unsaturated aliphatic hydrocarbon group containing 1 to 10 (e.g., 1, 2, 3, 4, 5, 6, 7, 8, 9 or 10) carbon-carbon triple bonds and consisting of 2 to 20 carbon atoms, preferably an alkynyl group consisting of 2 to 12 (e.g., 2, 3, 4, 5, 6, 7, 8, 9, 10, 11 or 12) carbon atoms, more preferably an alkynyl group consisting of 2 to 8 carbon atoms, and further preferably an alkynyl group consisting of 2 to 6 carbon atoms. Non-limiting examples include ethynyl, propyn-1-yl, propyn-2-yl, butyn-1-yl, butyn-2-yl, butyn-3-yl, 3,3-dimethylbutyn-2-yl, pentyn-1-yl, pentyn-2-yl, hexyn-1-yl, 1-heptyn-1-yl, heptyn-3-yl, heptyn-4-yl, octyn-3-yl, nonyn-3-yl, decyn-4-yl, undec-3-yl, and dodecyn-4-yl. The alkynyl may be optionally further substituted with one or more substituents.

"Aryl" refers to a substituted or unsubstituted aromatic ring. It may be a 5-8 membered (e.g., 5, 6, 7 or 8 membered) monocyclic ring system, a 5-12 membered (e.g., 5, 6, 7, 8, 9, 10, 11 or 12 membered) bicyclic ring system or a 10-15 membered (e.g., 10, 11, 12, 13, 14 or 15 membered) tricyclic ring system, and may be a bridged ring or a spiro ring. Non-limiting examples include phenyl and naphthyl. The aryl may be optionally further substituted with 1 or more substituents. "Heteroaryl" refers to a substituted or unsubstituted aromatic ring. It may be a 3-8 membered (e.g., 3, 4, 5, 6, 7 or 8 membered) monocyclic ring system, a 5-12 membered (e.g., 5, 6, 7, 8, 9, 10, 11 or 12 membered) bicyclic ring system or a 10-15 membered (e.g., 10, 11, 12, 13, 14 or 15 membered) tricyclic ring system, and it contains 1 to 6 (e.g., 1, 2, 3, 4, 5 or 6) heteroatoms selected from N, O and S, and is preferably 5-8 membered heteroaryl. 1 to 4 (e.g., 1, 2, 3 or 4) N and S optionally substituted in the ring of the heteroaryl can be oxidized to various oxidation states. Heteroaryl may be attached to a heteroatom or carbon atom and it may be a bridged ring or a spiro ring. Non-limiting examples include cyclic pyridinyl, furanyl, thienyl, pyranyl, pyrrolyl, pyrimidinyl, pyrazinyl, pyridazinyl, imidazolyl, piperidinyl, benzimidazolyl, benzopyridinyl and pyrrolopyridinyl. Heteroaryl is optionally further substituted with 1 or more substituents.

"Carbocyclyl" or "carbocycle" refers to a saturated or unsaturated, aromatic or non-aromatic ring. When being an aromatic ring, it is defined in the same way as for the "aryl" described above; when being an non-aromatic ring, it may be a 3-10 membered (e.g., 3, 4, 5, 6, 7, 8, 9 or 10 membered) monocyclic ring system, a 4-12 membered (e.g., 4, 5, 6, 7, 8, 9, 10, 11 or 12-membered) bicyclic ring system or a 10-15 membered (e.g., 10, 11, 12, 13, 14 or 15 membered) tricyclic ring system, and it may be a bridged ring or a spiro ring. Non-limiting examples include cyclopropyl, cyclobutyl, cyclopentyl, 1-cyclopentyl-1-alkenyl, 1-cyclopentyl-2-alkenyl, 1-cyclopentyl-3-alkenyl, cyclohexyl, 1-cyclohexyl-2-alkenyl, 1-cyclohexyl-3-alkenyl, cyclohexenyl, cyclohexadienyl, cycloheptyl, cyclooctyl, cyclononyl, cyclodecyl, cycloundecyl, cyclododecyl,

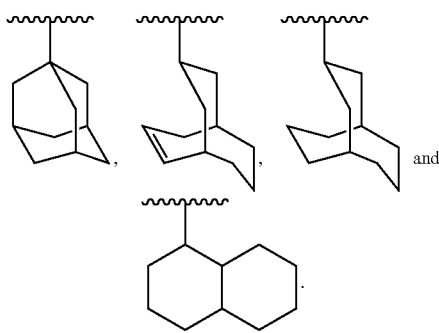

The "carbocyclyl" or "carbocycle" is optionally further substituted with 1 or more substituents.

"Heterocyclyl" or "heterocycle" refers to a saturated or unsaturated, aromatic or non-aromatic heterocycle. When being an aromatic heterocycle, it is defined in the same way as for the "heteroaryl" described above; when being a non-aromatic heterocycle, it may be a 3-10 membered (e.g., 3, 4, 5, 6, 7, 8, 9 or 10 membered) monocyclic ring system, a 4-12 membered (e.g., 4, 5, 6, 7, 8, 9, 10, 11 or 12 membered) bicyclic ring system or a 10-15 membered (e.g., 10, 11, 12, 13, 14 or 15 membered) tricyclic ring system, and it contains 1 to 4 (e.g., 1, 2, 3 or 4) heteroatoms selected from N, O and S, and is preferably 3-8 membered heterocyclyl. 1 to 4 (e.g., 1, 2, 3 or 4) N and S optionally substituted in the ring of the "heterocyclyl" or "heterocycle" can be oxidized to various oxidation states; "heterocyclyl" or "heterocycle" may be attached to a heteroatom or a carbon atom, and may be a bridged ring or a spiro ring. Non-limiting examples of "heterocyclyl" or "heterocycle" include epoxyethyl, epoxypropyl, aziridinyl, oxetanyl, azetidinyl, thietanyl, 1,3-dioxolanyl, 1,4-dioxolanyl, 1,3-dioxanyl, azepanyl, oxepanyl, thiepanyl, oxoazepinyl, diazepinyl, thiazepinyl, pyridinyl, piperidinyl, homopiperidinyl, furanyl, thienyl, pyranyl, N-alkylpyrrolyl, pyrimidinyl, pyrazinyl, pyridazinyl, piperazinyl, homopiperazinyl, imidazolyl, piperidinyl, morpholinyl, thiomorpholinyl, oxathianyl, 1,3-dithianyl, dihydrofuranyl, dithiacyclopentyl, tetrahydrofuranyl, tetrahydrothienyl, tetrahydropyranyl, tetrahydrothiopyranyl, tetrahydropyrrolyl, tetrahydroimidazolyl, tetrahydrothiazolyl, tetrahydropyranyl, benzimidazolyl, benzopyridinyl, pyrrolopyridinyl, benzodihydrofuranyl, 2-pyrrolinyl, 3-pyrrolinyl, indolinyl, 2H-pyranyl, 4H-pyranyl, dioxacyclohexyl, 1,3-dioxolanyl, pyrazolinyl, dithianyl, dithiolanyl, dihydrothienyl, pyrazolidinyl, imidazolinyl, imidazolidinyl, 1,2,3,4-tetrahydroisoquinolinyl, 3-azabicyclo[3.1.0]hexyl, 3-azabicyclo[4.1.0]heptyl, azabicyclo[2.2.2]hexyl, 3H-indolylquinolizinyl, N-pyridylurea, 1,1-dioxothiomorpholinyl, azabicyclo[3.2.1]octyl, azabicyclo[5.2.0]nonyl, oxatricyclo[5.3.1.1]dodecyl, aza-adamantyl and oxaspiro[3.3]heptyl. The "heterocyclyl" or "heterocycle" may be optionally further substituted with 1 or more substituents.

"Cycloalkyl" refers to a saturated cyclic hydrocarbon group, the ring of which may be a 3-10 membered (e.g., 3, 4, 5, 6, 7, 8, 9 or 10 membered) monocyclic ring system, a 4-12 membered (e.g., 4, 5, 6, 7, 8, 9, 10, 11 or 12 membered) bicyclic ring system or a 10-20 membered (e.g., 10, 11, 12, 13, 14, 15, 16, 17, 18, 19 or 20 membered) polycyclic ring system. The ring carbon atoms are preferably 3 to 10 carbon atoms, further preferably 3 to 8 carbon atoms. Non-limiting examples of "cycloalkyl" include cyclopropyl, cyclobutyl, cyclopentyl, cyclohexyl, cycloheptyl, cyclooctyl, cyclopropenyl, cyclobutenyl, cyclopentenyl, cyclohexenyl, cycloheptenyl, 1,5-cyclooctadienyl, 1,4-cyclohexadienyl, cycloheptatrienyl, and the like. When the cycloalkyl is substituted, it may be optionally further substituted with 1 or more substituents.

"Heterocycloalkyl" refers to a substituted or unsubstituted saturated non-aromatic cyclic group. It may be a 3-8 membered (e.g., 3, 4, 5, 6, 7 or 8 membered) monocyclic ring system, a 4-12 membered (e.g., 4, 5, 6, 7, 8, 9, 10, 11 or 12 membered) bicyclic ring system or a 10-15 membered (e.g., 10, 11, 12, 13, 14 or 15 membered) tricyclic ring system, and it contains 1, 2 or 3 heteroatoms selected from N, O and S, and is preferably 3-8 membered heterocyclyl. 1, 2 or 3 N and S optionally substituted in the ring of "heterocycloalkyl" can be oxidized to various oxidation states; "heterocycloalkyl" may be attached to a heteroatom or a carbon atom and may be a bridged ring or a spiro ring. Non-limiting examples of "heterocycloalkyl" include epoxyethyl, aziridinyl, oxetanyl, azetidinyl, 1,3-dioxolanyl, 1,4-dioxolanyl, 1,3-dioxanyl, azepanyl, piperidinyl, morpholinyl, thiomorpholinyl, 1,3-dithianyl, tetrahydrofuranyl, tetrahydropyrrolyl, tetrahydroimidazolyl, tetrahydrothiazolyl, tetrahydropyranyl, azabicyclo[3.2.1]octyl, azabicyclo[5.2.0]nonyl, oxatricyclo[5.3.1.1]dodecyl, aza-adamantyl and oxaspiro[3.3]heptyl.

When the "alkyl", "alkoxy", "alkenyl", "alkynyl", "aryl", "heteroaryl", "carbocyclyl", "carbocycle", "heterocyclyl", "heterocycle", "cycloalkyl", "heterocycloalkyl" or "heterocyclyl" described above is substituted, it may be optionally further substituted with 0, 1, 2, 3, 4, 5, 6, 7, 8, 9 or 10 substituents selected from F, Cl, Br, I, hydroxy, mercapto, nitro, cyano, amino, $C_{1-6}$ alkylamino, =O, $C_{1-6}$ alkyl, $C_{1-6}$ alkoxy, $C_{2-6}$ alkenyl, $C_{2-6}$ alkynyl, —$NR^{q4}R^{q5}$, =$NR^{q6}$, —C(=O)O$C_{1-6}$ alkyl, —OC(=O)$C_{1-6}$ alkyl, —C(=O)$NR^{q4}R^{q5}$, $C_{3-8}$ cycloalkyl, $C_{3-8}$ heterocycloalkyl, $C_{6-10}$ aryl, $C_{5-10}$ heteroaryl, —C(=O)O$C_{6-10}$ aryl, —OC(=O)$C_{6-10}$ aryl, —OC(=O)$C_{5-10}$ heteroaryl, —C(=O)O$C_{5-10}$ heteroaryl, —OC(=O)$C_{3-8}$ heterocycloalkyl, —C(=O)O$C_{3-8}$ heterocycloalkyl, —OC(=O)$C_{3-8}$ cycloalkyl, —C(=O)O$C_{3-8}$ cycloalkyl, —NHC(=O)$C_{3-8}$ heterocycloalkyl, —NHC(=O)$C_{6-10}$ aryl, —NHC(=O)$C_{5-10}$ heteroaryl, —NHC(=O)$C_{3-8}$ cycloalkyl, —NHC(=O)$C_{3-8}$ heterocycloalkyl, —NHC(=O)$C_{2-6}$ alkenyl and —NHC(=O)$C_{2-6}$ alkynyl, wherein the substituent $C_{1-6}$ alkyl, $C_{1-6}$ alkoxy, $C_{2-6}$ alkenyl, $C_{2-6}$ alkynyl, $C_{3-8}$ cycloalkyl, $C_{3-8}$ heterocycloalkyl, $C_{6-10}$ aryl, $C_{5-10}$ heteroaryl, —NHC(=O)$C_{6-10}$ aryl, —NHC(=O)$C_{5-10}$ heteroaryl, —NHC(=O)$C_{3-8}$ heterocycloalkyl or —NHC(=O)$C_{3-8}$ cycloalkyl is optionally further substituted with 1 to 3 substituents selected from OH, F, Cl, Br, I, $C_{1-6}$ alkyl, $C_{1-6}$ alkoxy, —$NR^{q4}R^{q5}$ and =O, $R^{q1}$ is selected from $C_{1-6}$ alkyl, $C_{1-6}$ alkoxy and $C_{6-10}$ aryl, and $R^{q2}$ and $R^{q3}$ are selected from H and $C_{1-6}$ alkyl, wherein $R^{q4}$ and $R^{q5}$ are selected from H, $C_{1-6}$ alkyl, —NH(C=$NR^{q1}$)$NR^{q2}R^{q3}$, —S(=O)$_2NR^{q2}R^{q3}$, —C(=O)$R^{q1}$ and —C(=O)$NR^{q2}R^{q3}$, wherein the $C_{1-6}$ alkyl is optionally further substituted with 1 or more substituents selected from OH, F, Cl, Br, I, $C_{1-6}$ alkyl, $C_{1-6}$ alkoxy, $C_{6-10}$ aryl, $C_{5-10}$ heteroaryl, $C_{3-8}$ cycloalkyl and $C_{3-8}$ heterocycloalkyl; or $R^{q4}$ and $R^{q5}$, together with an N atom, form a 3-8 membered heterocycle, which may contain 1 or more heteroatoms selected from N, O and S.

"Pharmaceutically acceptable salt" or "pharmaceutically acceptable salt thereof" refers to a salt obtained by reaction of a compound disclosed herein in a free acid form with a nontoxic inorganic or organic base or by reaction of a compound disclosed herein in a free base form with a nontoxic inorganic or organic acid, and in this salt, the bioavailability and characteristics of the compound disclosed herein in the free acid or free base form is retained.

"Pharmaceutical composition" refers to a mixture of one or more compounds described herein or pharmaceutically acceptable salts or prodrugs thereof and other chemical components, wherein the "other chemical components" refer to pharmaceutically acceptable carriers, excipients and/or one or more other therapeutic agents.

"Carrier" refers to a material that does not cause significant irritation to an organism and does not eliminate the biological activity and characteristics of the administered compound.

"Excipient" refers to an inert substance added to a pharmaceutical composition to facilitate administration of a compound. Non-limiting examples include calcium carbonate, calcium phosphate, sugars, starches, cellulose derivatives (including microcrystalline cellulose), gelatin, vegetable oils, polyethylene glycols, diluents, granulating agents, lubricants, binders and disintegrants.

"Prodrug" refers to a compound disclosed herein that can be metabolized in vivo to become biologically active. A prodrug disclosed herein is prepared by modifying amino or carboxyl in a compound disclosed herein, and the modification can be removed by conventional operation or be removed in vivo to obtain the parent compound. When a prodrug disclosed herein is administered to a mammalian subject, the prodrug is cleaved to form free amino or carboxyl.

"Cocrystal" refers to a crystal formed by binding of an active pharmaceutical ingredient (API) and a cocrystal former (CCF) via a hydrogen bond or other non-covalent bonds, wherein the API and CCF are both solid in their pure state at room temperature, and the components are present in a fixed stoichiometric ratio. A cocrystal is a multi-component crystal, including both a binary cocrystal formed by two neutral solids and a multiple cocrystal formed by a neutral solid and a salt or solvate.

"Stereoisomer" refers to isomers resulting from different spatial arrangements of atoms in a molecule, including cis-trans isomers, enantiomers and conformers.

"Optional", "optionally", "selective" or "selectively" means that the subsequently described event or circumstance may, but does not necessarily, occur, and the description includes cases where the event or circumstance occurs and cases where it does not. For example, "heterocyclyl optionally substituted with alkyl" means that the alkyl may, but does not necessarily, be present, and the description includes the case where the heterocyclyl is substituted with alkyl and the case where the heterocyclyl is not substituted with alkyl.

DETAILED DESCRIPTION

The following examples illustrate the technical schemes of the present invention in detail, but the protection scope of the present invention includes but is not limited thereto.

The structure of a compound is determined by nuclear magnetic resonance (NMR) and/or mass spectrometry (MS). NMR shifts (δ) are expressed in $10^{-6}$ (ppm). NMR determination is performed using NMR spectrometers (Bruker Avance III 400 and Bruker Avance 300), with deuterated dimethyl sulfoxide (DMSO-$d_6$), deuterated chloroform (CDCl$_3$) and deuterated methanol (CD$_3$OD) as solvents and tetramethylsilane (TMS) as an internal standard; MS determination is performed using Agilent 6120B (ESI) and Agilent 6120B (APCI); HPLC determination is performed using Agilent 1260DAD high pressure liquid chromatograph (Zorbax SB-C18 100×4.6 mm, 3.5 μM);

Yantai Yellow Sea HSGF254 or Qingdao GF254 silica gel plate is used as a thin layer chromatography (TLC) silica gel plate. The specification of the silica gel plate for TLC is 0.15-0.20 mm, and that for product separation and purification of TLC is 0.4-0.5 mm; Yantai Yellow Sea silica gel of 200-300 mesh is generally used as a carrier in column chromatography;

known starting materials of the present invention can be synthesized by methods known in the art or can be purchased from companies such as Shanghai Titan Scientific, Energy Chemical, Shanghai DEMO Medical, Chengdu Kelong Chemical, Accela ChemBio, and J&K Scientific; nitrogen atmosphere means that a reaction flask is connected with a nitrogen balloon with a volume of about 1 L;

hydrogen atmosphere means that a reaction flask is connected with a nitrogen balloon with a volume of about 1 L;

in hydrogenation reaction, the operation of vacuumizing and introducing hydrogen is usually performed, and repeated 3 times;

reactions are performed under nitrogen atmosphere if not otherwise specified in examples; a solution is an aqueous solution if not otherwise specified in examples;

reaction temperature is room temperature and the optimum reaction temperature of room temperature is 20-30° C. if not otherwise specified in examples;
DCM: dichloromethane;
EA: ethyl acetate;
HCl: hydrochloric acid;
THF: tetrahydrofuran;
DMF: N,N-dimethylformamide;
PE: petroleum ether;
TLC: thin layer chromatography;
SFC: supercritical fluid chromatography;
NCS: N-chlorosuccinimide;
Pd(dppf)Cl$_2$: [1,1'-bis(diphenylphosphino)ferrocene]palladium dichloride.

EXAMPLE

Intermediate 1

5-(1-cyclopropylethyl)-2,3-dihydro-1H-inden-4-amine (Intermediate 1)

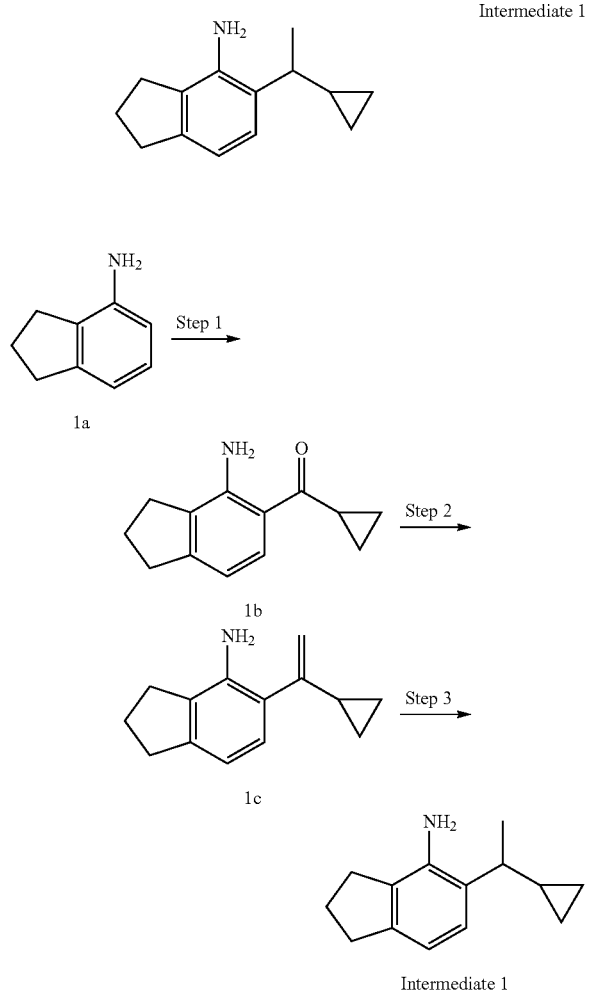

Step 1

(4-amino-2,3-dihydro-1H-inden-5-yl)(cyclopropyl)methanone (1b)

Compound 1a (20.0 g, 150.16 mmol) was dissolved in 1,2-dichloroethane (200 mL) in a 500 mL three-necked flask under nitrogen atmosphere, and the solution was cooled to 0° C. in an ice salt bath. A solution of boron trichloride (150 mL, 1 M, 150.16 mmol) in dichloromethane was then added dropwise slowly, and the temperature was maintained and the resulting solution was reacted for 10 min after the dropwise addition was completed. Aluminum trichloride (22.0 g, 165.20 mmol) and cyclopropyl cyanide (15.1 g, 225.24 mmol) were then added, and the reaction system was warmed to 80° C., reacted for 4 h and then cooled to room temperature. 2 M HCl (160 mL) was added in an ice bath, and the resulting reaction system was warmed to reflux and reacted for 1 h. After the reaction was completed, the reaction system was cooled to room temperature and extracted with DCM (200 mL×3). The organic phase was washed with 2 M sodium hydroxide solution (160 mL), dried over anhydrous sodium sulfate and filtered, and the organic solvent was removed under reduced pressure. The residue was purified by column chromatography (petroleum ether:ethyl acetate=20:1) to give compound 1b in the form of a white solid (17.1 g, 57.2% yield).
$^1$H NMR (400 MHz, DMSO-d6) δ=7.87 (d, 1H), 6.90 (br, 2H), 6.54 (d, 1H), 2.84 (t, 2H), 2.80-2.74 (m, 1H), 2.67 (t, 2H), 2.06-1.98 (m, 2H), 0.96-0.87 (m, 4H); LCMS m/z (ESI)=202.1[M+1].

Step 2

5-(1-cyclopropylvinyl)-2,3-dihydro-1H-inden-4-amine (1c)

Compound methyl triphenyl phosphonium bromide (24.8 g, 69.6 mmol) was dissolved in THF (300 mL) in a 500 mL three-necked flask under nitrogen atmosphere, and the solution was cooled to 0° C. in an ice salt bath. Potassium tert-butoxide (7.8 g, 69.6 mmol) was added slowly, and the temperature was maintained and the reaction system was reacted for 30 min. Compound 1b (7.0 g, 34.8 mmol) was added, and the resulting reaction system was reacted at room temperature for 4 h. After the reaction was completed, water was added to quench the reaction, and EA (100 mL×3) was added for extraction. The organic phase was dried over anhydrous sodium sulfate and filtered, and the organic solvent was removed under reduced pressure. The residue was purified by column chromatography (petroleum ether: ethyl acetate=30:1) to give compound 1c in the form of a pale yellow oil (6.4 g, 92.3% yield).
$^1$H NMR (400 MHz, DMSO-d6) δ=6.64 (d, 1H), 6.45 (d, 1H), 5.15 (d, 1H), 4.78 (d, 1H), 4.37 (br, 2H), 2.77 (t, 2H), 2.64 (t, 2H), 2.02-1.96 (m, 2H), 1.62-1.57 (m, 1H), 0.69-0.64 (m, 2H), 0.40-0.36 (m, 2H); LC-MS m/z (ESI)=200.1 [M+1].

Step 3

5-(1-cyclopropylethyl)-2,3-dihydro-1H-inden-4-amine (Intermediate 1)

Compound 1c (700 mg, 3.51 mmol) and triethylsilane (1.23 g, 10.54 mmol) were dissolved in DCM (10 mL) in a 50 mL round-bottomed flask under nitrogen atmosphere, and trifluoroacetic acid (2.0 g, 17.56 mmol) was added dropwise in an ice bath. After the dropwise addition was completed, the reaction system was warmed to room temperature and reacted for 5 h. After the reaction was completed, water was added to quench the reaction, saturated sodium bicarbonate was added to adjust pH to weak alkalinity, and DCM (20 mL×3) was added for extraction. The organic phase was dried over anhydrous sodium sulfate and filtered, and the organic solvent was removed under reduced pressure. The residue was purified by column chromatography (petroleum ether:ethyl acetate=10:1) to give intermediate 1 in the form of a pale yellow oil (261 mg, 37.2% yield).

$^1$H NMR (400 MHz, DMSO-d6) δ=6.93 (d, 1H), 6.47 (d, 1H), 4.60 (br, 2H), 2.75 (t, 2H), 2.63 (t, 2H), 2.28-2.18 (m, 1H), 2.00-1.94 (m, 2H), 1.14 (d, 3H), 1.02-0.97 (m, 1H), 0.49-0.44 (m, 1H), 0.33-0.30 (m, 1H), 0.15-0.12 (m, 1H), 0.05-0.01 (m, 1H); LC-MS m/z (ESI)=202.2[M+1].

Intermediate 2

N-(tert-butyldimethylsilyl)-4-(2-hydroxypropan-2-yl)furan-2-sulfonimidamide (Intermediate 2)

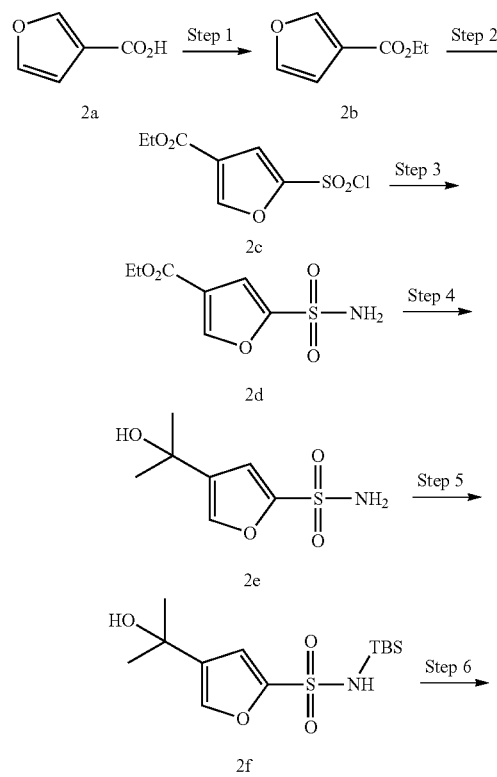

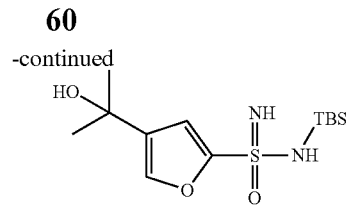

Intermediate 2

Step 1

Ethyl furan-3-carboxylate (2b)

Compound 2a (50 g, 0.446 mol) was dissolved in absolute ethanol (300 mL) in an ice bath, and thionyl chloride (65 mL, 0.892 mol) was added dropwise slowly. After the dropwise addition was completed, the reaction system was warmed to reflux and reacted for 2 h. After the reaction was completed as detected by TLC, the reaction system was concentrated under reduced pressure to remove the solvent and excess thionyl chloride. Water (200 mL) was added, and ethyl acetate (150 mL×3) was added for extraction. The organic phases were combined, washed with saturated brine (100 mL×2), dried over anhydrous sodium sulfate, and concentrated under reduced pressure to remove the solvent, and the residue was purified by silica gel column chromatography (ethyl acetate:petroleum ether=1:50-1:10) to give compound 2b in the form of a pale brown oil (38.1 g, 61% yield).

Step 2

Ethyl furan-2-sulfonyl chloride-4-formate (2c)

Compound 2b (22.00 g, 0.157 mol) was dissolved in DCM (250 mL) at room temperature, and the solution was cooled to −15° C. in an ice salt bath. Sulfonyl chloride (23.31 g, 0.173 mol) was added dropwise slowly while controlling the temperature to be not higher than −10° C. After dropwise addition was completed, the reaction system was reacted for 12 h at room temperature and cooled to −15° C. or lower in an ice salt bath. Pyridine (13.66 g, 0.173 mol) was added dropwise slowly, and then phosphorus pentachloride (36.00 g, 0.137 mol) was added in batches while controlling the temperature to be not higher than −10° C. After the addition was completed, the reaction system was reacted for 2 h at room temperature. After the reaction was completed as detected by TLC, the reaction system was added into ice water (200 mL) to quench the reaction, and then extracted with EA (200 mL×3). The organic phases were combined, washed with saturated brine (100 mL), dried over anhydrous sodium sulfate and concentrated under reduced pressure to remove the solvent, so as to give compound 2c in the form of a brown oil (33.00 g, 90% yield), which was directly used in the next step without purification.

Step 3

Furan-2-sulfonamide-4-ethyl formate (2d)

Compound 2c (33.00 g, 0.138 mol) was dissolved in acetone (350 mL) at room temperature, and then a solution of saturated aqueous ammonium bicarbonate (49.74 g, 0.553 mol) solution was added dropwise at room temperature. The reaction system was reacted for 3 h at room temperature. After the reaction was completed as detected by TLC, the reaction system was extracted with EA (200 mL×3). The organic phases were combined, washed with saturated brine (100 mL), dried over anhydrous sodium sulfate and concentrated under reduced pressure to remove the solvent, so as to give compound 2d in the form of a brown solid powder (23 g, 77% yield).

$^1$H NMR (400 MHz, DMSO-d6) δ=8.64 (s, 1H), 7.97 (s, 2H), 7.13 (s, 1H), 4.27 (q, 2H), 1.28 (t, 3H); LCMS m/z=218.2[M−1].

Step 4

4-(2-hydroxypropan-2-yl)furan-2-sulfonamide (2e)

Compound 2d (23 g, 0.105 mol) was dissolved in dry THF (500 mL) at room temperature, and then the solution was cooled to −15° C. in an ice salt bath. Methylmagnesium bromide (140 mL, 0.418 mol) was added dropwise slowly while maintaining the temperature to be not higher than 0° C. After the addition was completed, the reaction system was reacted for 4 h at room temperature. After the reaction was completed as detected by TLC, the reaction system was poured into ice water (200 mL) to quench the reaction, and then extracted with EA (200 mL×3). The organic phases were combined, washed with saturated brine (100 mL), dried over anhydrous sodium sulfate, and concentrated under reduced pressure to remove the solvent, and the residue was purified by silica gel column chromatography (ethyl acetate:petroleum ether=1:4-1:1) to give compound 2e in the form of a white solid powder (16 g, 76% yield).

LCMS m/z=204.2[M−1].

Step 5

N-(tert-butyldimethylsilyl)-4-(2-hydroxypropan-2-yl)furan-2-sulfonamide (2f)

Compound 2e (5.0 g, 24.39 mmol) was dissolved in dry THF (50 mL) at room temperature, and then the solution was cooled to −10° C. in an ice salt bath. Sodium hydride (0.9 g, 36.58 mmol) was added slowly while controlling the temperature to be lower than −10° C., and then a solution of tert-butyldimethylchlorosilane (4.8 g, 31.70 mmol) in THF (50 mL) was added. The reaction system was reacted at room temperature for 12 h. After the reaction was completed as detected by TLC, the reaction system was poured into ice water (20 mL) to quench the reaction, and then extracted with EA (50 mL×3). The organic phases were combined, washed with saturated brine (50 mL), dried over anhydrous sodium sulfate, and concentrated under reduced pressure to remove the solvent, and the residue was purified by silica gel column chromatography (ethyl acetate:petroleum ether=1:2-2:1) to give compound 2f in the form of a white solid (5.1 g, 66% yield).

$^1$H NMR (400 MHz, CDCl3) δ=7.85 (s, 1H), 7.68 (s, 1H), 6.93 (s, 1H), 5.07 (s, 1H), 1.38 (s, 6H), 0.88 (s, 9H), 0.16 (s, 6H); LCMS m/z=320.2[M+1].

Step 6

N-(tert-butyldimethylsilyl)-4-(2-hydroxypropan-2-yl)furan-2-sulfonimidamide (Intermediate 2)

DCM (100 mL) and triphenylphosphine dichloride (11.3 g, 33.86 mmol) were added into a 250 mL three-necked flask under nitrogen atmosphere, and then the reaction system was cooled to 0° C. in an ice bath, and diisopropylethylamine (5.8 g, 45.16 mmol) was added dropwise slowly. After the dropwise addition was completed, the reaction system was warmed to room temperature, reacted for 10 min, and then cooled to 0° C. A solution of 2f (3.6 g, 11.29 mmol) in dichloromethane (10 mL) was added, and after the addition was completed, the temperature was maintained at 0° C. and the reaction system was reacted for 30 min. Ammonia gas was introduced into the reaction system for 15 min, and then the reaction system was warmed to room temperature and reacted for 2 h. After the reaction was completed as detected by TLC, the reaction system was concentrated under reduced pressure to remove the solvent, and the crude product was purified by column chromatography (petroleum ether:ethyl acetate=2:1) to give intermediate 2 in the form of a white solid (816 mg, 23% yield).

$^1$H NMR (400 MHz, DMSO-d6) δ=7.56 (s, 1H), 6.86 (s, 2H), 6.73 (s, 1H), 5.01 (s, 1H), 1.37 (s, 6H), 0.85 (s, 9H), 0.03 (s, 3H), 0.01 (s, 3H); LCMS m/z=319.2[M+1].

Intermediate 3-Intermediate 4

For synthesis of intermediates 3 and 4, reference was made to preparation method of intermediate 2.

| Intermediate | Structures | NMR | LCMS m/z |
|---|---|---|---|
| 3 | (structure) | $^1$H NMR (400 MHz, DMSO-d$_6$) δ = 6.81(s, 2H), 6.61(s, 1H), 4.99(s, 1H), 2.41(s, 3H), 1.41(s, 6H), 0.89(s, 9H), 0.01(d, 6H); | 315.1[M + 1] |
| 4 | (structure) | — | 335.1[M + 1] |

Intermediate 5

5-(3-hydroxyoxetan-3-yl)thiophene-2-sulfonamide (Intermediate 5)

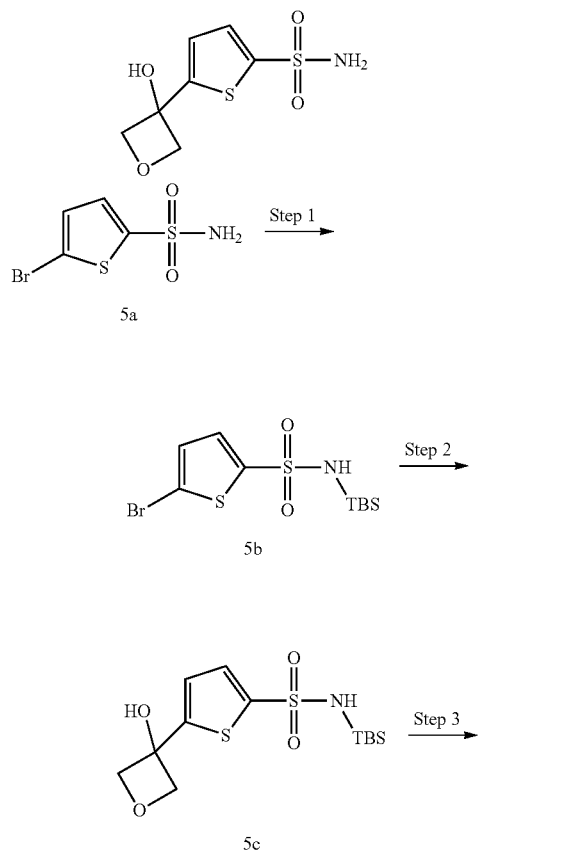

Step 1

5-bromo-N-(tert-butyldimethylsilyl)thiophene-2-sulfonamide (5b)

5a (10.0 g, 41.31 mmol) was dissolved in anhydrous THF (200 mL) in a 500 mL three-necked flask under nitrogen atmosphere, and then sodium hydride (2.5 g, 61.96 mmol) was added in an ice bath. After the addition was completed, the temperature was maintained and the reaction system was reacted for 20 min. A solution of tert-butyldimethylchlorosilane (7.2 g, 49.67 mmol) in THF (50 mL) was then added dropwise slowly, and after the addition was completed, the reaction system was warmed to room temperature and reacted for 2 h. After the reaction was completed, water was added to quench the reaction, and ethyl acetate (100 mL×3) was added for extraction. The organic phases were combined, dried over anhydrous sodium sulfate and filtered, and the organic solvent was removed under reduced pressure. The residue was purified by silica gel column chromatography (petroleum ether:ethyl acetate=4:1) to give compound 5b in the form of a yellow solid (10.3 g, 70.0% yield).

LCMS m/z (ESI)=356.0[M+1].

Step 2

N-(tert-butyldimethylsilyl)-5-(3-hydroxyoxetan-3-yl)thiophene-2-sulfonamide (5c)

Compound 5b (10.0 g, 29.4 mmol) was dissolved in tetrahydrofuran (100 mL) in a 1 L three-necked flask under nitrogen atmosphere, and then the solution was cooled to −70° C. in a dry ice-ethanol bath. n-butyllithium (3.0 M in THF, 24.5 mL, 73.5 mmol) was added dropwise slowly, and then the reaction system was reacted for 30 min while maintaining the temperature at −70° C. 3-oxetanone (3.1 g, 44.0 mmol) was then added, and after the addition was completed, the reaction system was slowly warmed to room temperature and reacted for 1 h. After the reaction was completed, the reaction system was poured into ice water (200 mL) and extracted with ethyl acetate (100 mL×3). The organic phases were combined, dried over anhydrous sodium sulfate and filtered, and the organic solvent was removed under reduced pressure. The crude product was purified by column chromatography (petroleum ether:ethyl acetate=1:1) to give compound 5c in the form of a yellow solid (6 g, 61.2% yield).

$^1$H NMR (400 MHz, DMSO) δ=7.89 (s, 1H), 7.43 (d, 1H), 7.25 (d, 1H), 7.03 (s, 1H), 4.75 (d, 2H), 4.68 (d, 2H), 0.88 (s, 9H), 0.16 (s, 6H); LCMS m/z (ESI)=350.3[M+1].

Step 3

5-(3-hydroxyoxetan-3-yl)thiophene-2-sulfonamide (Intermediate 5)

5c (6.0 g, 17.17 mmol) and THF (100 mL) were added successively into a 100 mL round-bottomed flask under nitrogen atmosphere, and then the reaction system was cooled to 0° C. in an ice bath. Tetrabutylammonium fluoride (35 mL, 1 M in THF, 34.34 mmol) was then added dropwise slowly, and the reaction system was warmed to room temperature and reacted for 2 h after the dropwise addition was completed. After the reaction was completed, water was added to quench the reaction, and EA (30 mL×3) was added for extraction. The organic phase was dried over anhydrous sodium sulfate and filtered, and the solvent was removed under reduced pressure. The residue was purified by column chromatography (petroleum ether:ethyl acetate=1:1) to give intermediate 5 in the form of a pale yellow solid (3.3 g, 82.5% yield).

LCMS m/z (ESI)=236.0[M+1].

Intermediate 6-intermediate 7

For preparation of intermediates 6 and 7, reference was made to preparation method of intermediate 5.

| Intermediate | Structures | NMR | LCMS m/z |
|---|---|---|---|
| 6 | (structure: HO-tetrahydrofuran-thiophene-SO2NH2) | $^1$H NMR (400 MHz, DMSO); δ = 7.66(d, 1H), 7.47(s, 1H), 7.21(d, 1H), 5.93(s, 1H), 3.96 – 3.90(m, 4H), 2.55 – 2.51(m, 1H), 2.26 – 2.21(m, 1H); | 250.0[M + 1] |
| 7 | (structure: OH-tetrahydropyran-thiophene-SO2NH2) | $^1$H NMR (400 MHz, DMSO) δ = 7.83(s, H), 7.34(d, 1H), 6.95(d, 1H), 5.87(s, 1H), 3.70(d, 4H), 1.98 – 1.92(m, 2H), 1.69 – 1.66(m, 2H); | 264.0[M + 1] |

Intermediate 8

(R)-5-(1-cyclopropylethyl)-2,3-dihydro-1H-inden-4-amine (Intermediate 8)

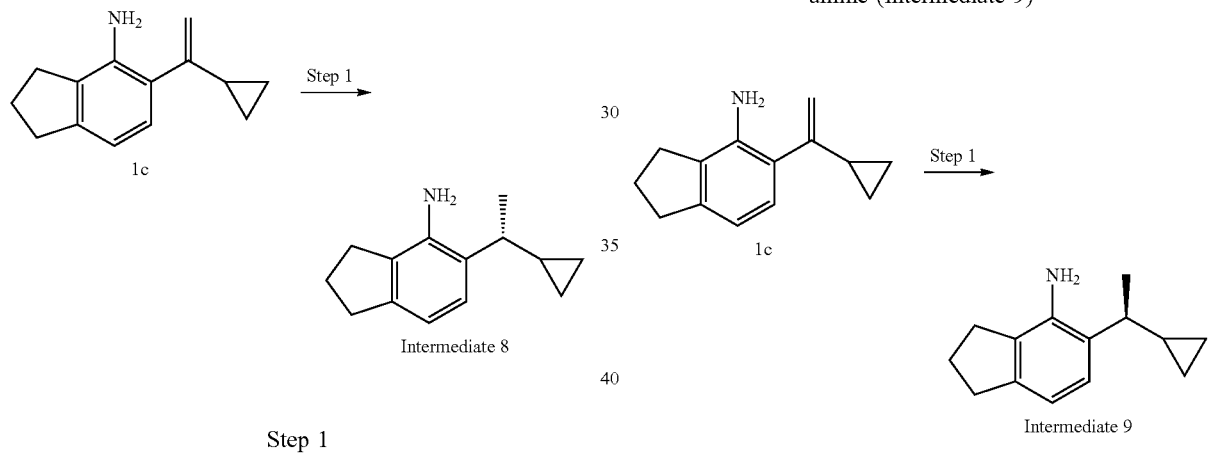

Step 1

For synthesis of intermediate 8, reference was made to patent CN108017559. 1c (8.3 g, 41.7 mmol) and dichloromethane (90 mL) were added into a 500 mL autoclave, and then a catalyst ruthenium [(R)-2,2'-bis(diphenylphosphino)-1,11-binaphthyl]diacetate (1.8 g, 2.09 mmol) was added. After the addition was completed, the autoclave was tightly closed and sealed, and purged with hydrogen 3 times. The hydrogen was introduced until the pressure gauge on the autoclave showed 12 atm, and then the reaction system was reacted for 30 h at room temperature. The reaction system was concentrated under reduced pressure to remove the solvent, and the residue was purified by silica gel column chromatography (petroleum ether/ethyl acetate=30:1) to give intermediate 8 in the form of a pale yellow oil (8.2 g, 97.8% yield, ee %: 97.74%, chiral HPLC (CHIRALPAK AY-3 (4.6×100 mm); mobile phase: methanol; column temperature: 35° C.; mobile phase (%): 15; column pressure: 2000 psi; flow rate: 2 mL/min; detector signal channel: 215 nm@4.8 nm; start/stop wavelength of diode array detector: 200-400 nm): RT=3.295 min).

$^1$H NMR (400 MHz, DMSO-d6) δ=6.92 (d, 1H), 6.45 (d, 1H), 4.43 (s, 2H), 2.75 (t, 2H), 2.62 (t, 2H), 2.26-2.20 (m, 1H), 2.00-1.92 (m, 2H), 1.14 (d, 3H), 1.02-0.96 (m, 1H), 0.50-0.44 (m, 1H), 0.34-0.28 (m, 1H), 0.17-0.11 (m, 1H), 0.06-0.00 (m, 1H); LCMS m/z (ESI)=202.1[M+1].

Intermediate 9

(S)-5-(1-cyclopropylethyl)-2,3-dihydro-1H-inden-4-amine (Intermediate 9)

Step 1

For synthesis of intermediate 9, reference was made to patent CN108017559. 1c (7.3 g, 36.7 mmol) and dichloromethane (80 mL) were added into a 500 mL autoclave, and then a catalyst ruthenium [(S)-2,2'-bis(diphenylphosphino)-1,11-binaphthyl]diacetate (1.54 g, 1.83 mmol) was added. After the addition was completed, the autoclave was tightly closed and sealed, and purged with hydrogen 3 times. The hydrogen was introduced until the pressure gauge on the autoclave showed 12 atm, and then the reaction system was reacted for 30 h at room temperature. The reaction system was concentrated under reduced pressure to remove the solvent, and the residue was purified by silica gel column chromatography (petroleum ether/ethyl acetate=30:1) to give intermediate 9 in the form of a pale yellow oil (7.1 g, 96.3% yield, ee %: 98.18%, chiral HPLC (CHIRALPAK AY-3 (4.6×100 mm); mobile phase: methanol; column temperature: 35° C.; mobile phase (%): 15; column pressure: 2000 psi; flow rate: 2 mL/min; detector signal channel: 215 nm@4.8 nm; start/stop wavelength of diode array detector: 200-400 nm): RT=2.802 min).

$^1$H NMR (400 MHz, DMSO-d6) δ=6.92 (d, 1H), 6.46 (d, 1H), 4.43 (s, 2H), 2.75 (t, 2H), 2.63 (t, 2H), 2.26-2.20 (m, 1H), 2.00-1.93 (m, 2H), 1.15 (d, 3H), 1.02-0.96 (m, 1H), 0.50-0.44 (m, 1H), 0.36-0.28 (m, 1H), 0.17-0.11 (m, 1H), 0.06-0.01 (m, 1H); LCMS m/z (ESI)=202.1[M+1].

Example 1

N-((5-(1-cyclopropylethyl)-2,3-dihydro-1H-inden-4-yl)carbamoyl)-4-(2-hydroxypropan-2-yl)furan-2-sulfonamide (Compound 1)

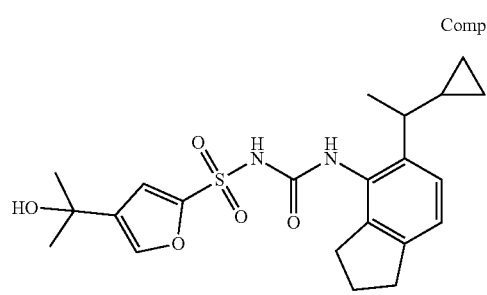

Compound 1 the solids. 2e (367 mg, 1.79 mmol) and sodium methoxide (194 mg, 3.58 mmol) were added to the filtrate, and the mixture was reacted at room temperature for 2 h. After the reaction was completed as detected by TLC, water (100 mL) was added to quench the reaction, and DCM (30 mL×3) was added for extraction. The organic phase was dried over anhydrous sodium sulfate and filtered, and the organic solvent was removed. The crude product was purified by preparative medium pressure liquid chromatography to give compound 1 in the form of a yellow solid (190 mg, 24.5% yield). $^1$H NMR (400 MHz, DMSO-d6) δ=7.69 (d, 1H), 7.54 (s, 1H), 7.10 (d, 1H), 7.02 (d, 1H), 6.84 (br, 1H), 5.00 (s, 1H), 2.81 (t, 2H), 2.62 (t, 2H), 2.28-2.17 (m, 1H), 1.94-1.87 (m, 2H), 1.38 (d, 6H), 1.11 (d, 3H), 0.95-0.90 (m, 1H), 0.47-0.44 (m, 1H), 0.22-0.18 (m, 1H), 0.10-0.07 (m, 1H), 0.01-0.01 (m, 1H); LCMS m/z=433.1[M+1].

Example 2

N-((5-(1-cyclopropylethyl)-2,3-dihydro-1H-inden-4-yl)carbamoyl)-4-(2-hydroxypropan-2-yl)furan-2-sulfonamide (Compound 2)

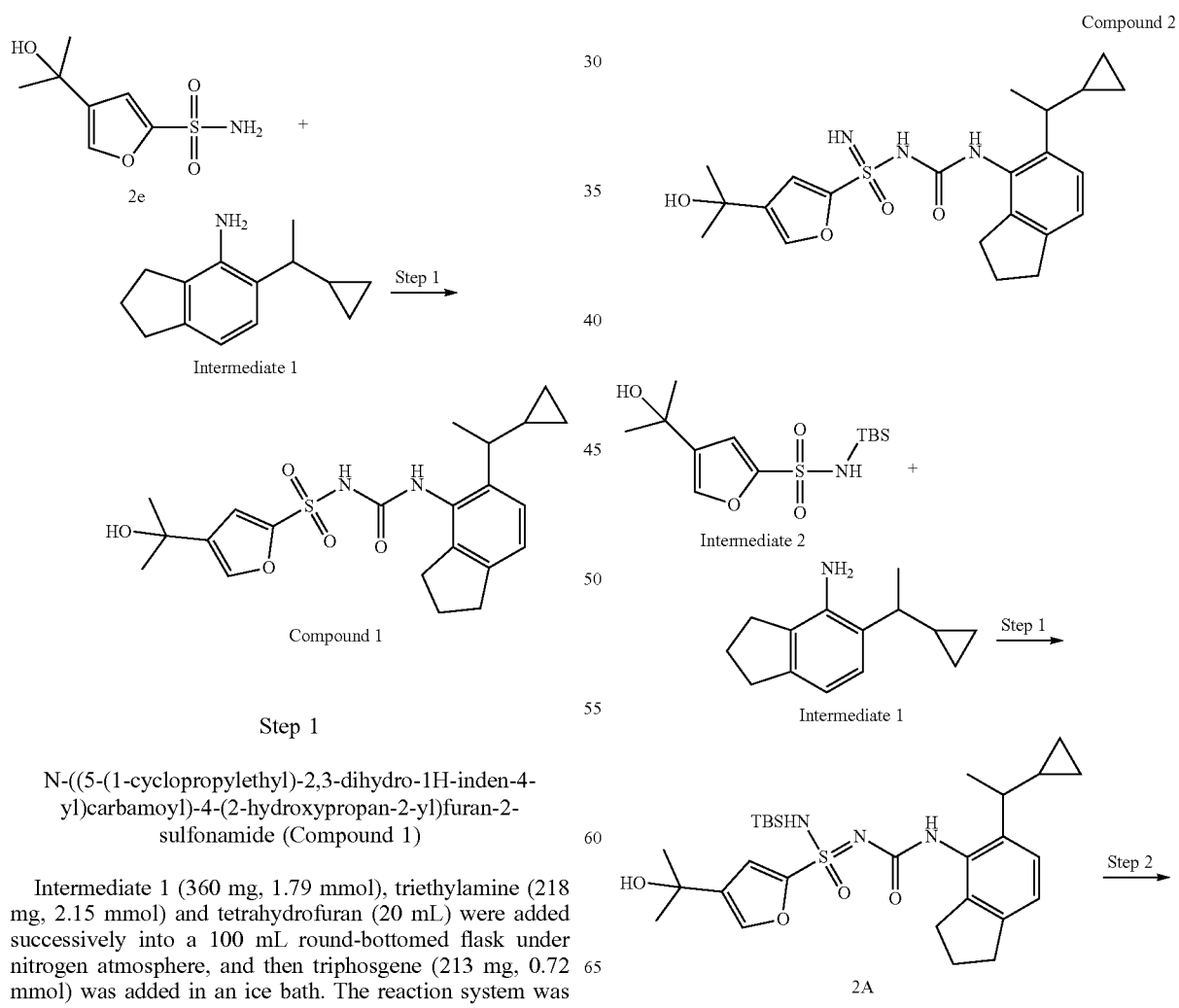

Step 1

N-((5-(1-cyclopropylethyl)-2,3-dihydro-1H-inden-4-yl)carbamoyl)-4-(2-hydroxypropan-2-yl)furan-2-sulfonamide (Compound 1)

Intermediate 1 (360 mg, 1.79 mmol), triethylamine (218 mg, 2.15 mmol) and tetrahydrofuran (20 mL) were added successively into a 100 mL round-bottomed flask under nitrogen atmosphere, and then triphosgene (213 mg, 0.72 mmol) was added in an ice bath. The reaction system was warmed to reflux, reacted for 2 h, and then filtered to remove -continued

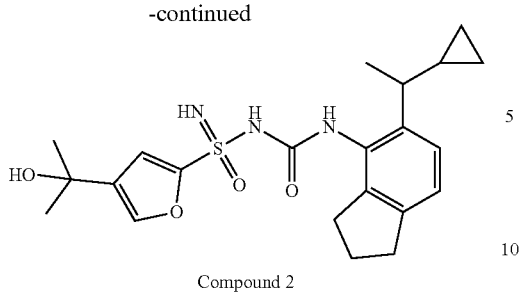

Compound 2

Step 1

N-(tert-butyldimethylsilyl)-N-((5-(1-cyclopropyl-ethyl)-2,3-dihydro-1H-inden-4-yl)carbamoyl)-4-(2-hydroxypropan-2-yl)furan-2-sulfonimidamide (2A)

Intermediate 1 (400 mg, 1.99 mmol), triethylamine (242 mg, 2.397 mmol) and tetrahydrofuran (20 mL) were added successively into a 100 mL round-bottomed flask under nitrogen atmosphere, and then triphosgene (237 mg, 0.796 mmol) was added in an ice bath. The reaction system was warmed to reflux, reacted for 2 h, and then filtered to remove the solids.

Intermediate 2 (632 mg, 1.99 mmol) and sodium methoxide (215 mg, 3.98 mmol) were added to the filtrate, and the mixture was reacted at room temperature for 12 h. After the reaction was completed as detected by TLC, water (100 mL) was added to quench the reaction, and DCM (30 mL×3) was added for extraction. The organic phase was dried over anhydrous sodium sulfate and filtered, and the organic solvent was removed. The crude product was purified by thin layer chromatography to give 2A in the form of a pale yellow oily solid (639 mg, 59% yield).

LCMS m/z=546.3[M+1].

Step 2

N-((5-(1-cyclopropylethyl)-2,3-dihydro-1H-inden-4-yl)carbamoyl)-4-(2-hydroxypropan-2-yl)furan-2-sulfonamide (Compound 2)

2A (639 mg, 1.17 mmol) and THF (10 mL) were added successively into a 100 mL round-bottomed flask under nitrogen atmosphere, and then the reaction system was cooled to 0° C. in an ice bath. Tetrabutylammonium fluoride (2.4 mL, 1 M in THF, 2.34 mmol) was then added dropwise slowly, and the reaction system was warmed to room temperature and reacted for 2 h after the dropwise addition was completed. After the reaction was completed, water was added to quench the reaction, and EA (30 mL×3) was added for extraction. The organic phase was dried over anhydrous sodium sulfate and filtered, and the solvent was removed under reduced pressure. The residue was purified by preparative medium pressure liquid chromatography to give compound 2 in the form of a white solid (221 mg, 43.8% yield).

$^1$H NMR (400 MHz, DMSO-d6) δ=8.24 (s, 1H), 7.68 (s, 1H), 7.64 (br, 1H), 7.13 (d, 1H), 7.04 (d, 1H), 6.98 (s, 1H), 4.54 (br, 1H), 2.82 (t, 2H), 2.67 (t, 2H), 2.29-2.19 (m, 1H), 1.99-1.91 (m, 2H), 1.38 (s, 6H), 1.17-1.03 (m, 3H), 0.97-0.91 (m, 1H), 0.48-0.42 (m, 1H), 0.23-0.18 (m, 1H), 0.15-0.08 (m, 1H), 0.004-0.01 (m, 1H); LCMS m/z=432.2[M+1].

Example 3

N-((5-(cyclopropylmethyl)-2,3-dihydro-1H-inden-4-yl)carbamoyl)-4-(2-hydroxypropan-2-yl)furan-2-sulfonamide (Compound 3)

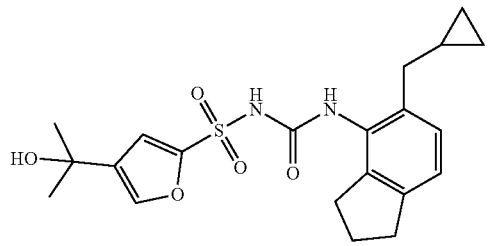

Compound 3

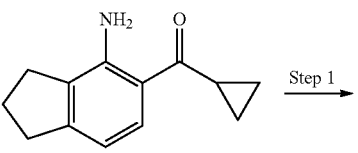

1b

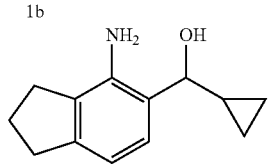

3A

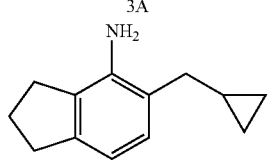

3B

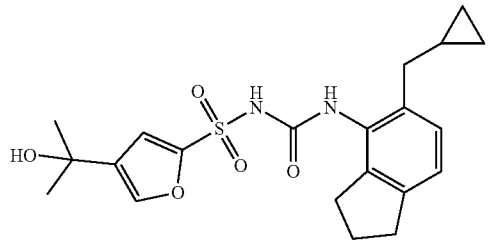

Compound 3

Step 1

(4-amino-2,3-dihydro-1H-inden-5-yl)(cyclopropyl)methanol (3A)

Methanol (20 mL) and compound 1b (1.8 g, 8.96 mmol) were added into a 50 mL round-bottomed flask under nitrogen atmosphere, and then the reaction system was cooled to 0° C. in an ice bath. Sodium borohydride (678 mg, 17.91 mmol) was then added slowly, and the reaction system was warmed to room temperature and reacted for 1 h after the addition was completed. After the reaction was completed, the reaction system was cooled to 0° C., water (20 mL) was added dropwise to quench the reaction, and DCM (30 mL×3) was added for extraction. The organic phase was dried over anhydrous sodium sulfate and filtered, and the filtrate was concentrated under reduced pressure to remove the solvent. The residue was purified by column chromatography (petroleum ether:ethyl acetate=1:1) to give compound 3A in the form of a colorless oil (1.2 g, 66% yield).

LCMS m/z=186.1[M−17].

Step 2

5-(cyclopropylmethyl)-2,3-dihydro-1H-inden-4-amine (3B)

Compound 3A (1.2 g, 5.91 mmol) and triethylsilane (2.1 g, 17.73 mmol) were dissolved in DCM (20 mL) under nitrogen atmosphere, and then the solution was cooled to 0° C. in an ice bath. Trifluoroacetic acid (3.4 g, 29.63 mmol) was then added dropwise slowly, and the reaction system was reacted overnight at room temperature after the addition was completed. After the reaction was completed, saturated aqueous sodium bicarbonate was added to quench the reaction, and DCM (50 mL×3) was added for extraction. The organic phase was dried over anhydrous sodium sulfate and filtered, and the organic solvent was removed under reduced pressure. The residue was purified by column chromatography (petroleum ether:ethyl acetate=20:1) to give 3B in the form of a colorless oil (832 mg, 75.6% yield).

$^1$H NMR (400 MHz, DMSO-d6) δ=6.83 (d, 1H), 6.41 (d, 1H), 4.50 (s, 2H), 2.75 (t, 2H), 2.63 (t, 2H), 2.34 (d, 2H), 2.00-1.92 (m, 2H), 1.01-0.93 (m, 1H), 0.45-0.39 (m, 2H), 0.13-0.10 (m, 2H); LCMS m/z (ESI)=188.1[M+1].

Step 3

N-((5-(cyclopropylmethyl)-2,3-dihydro-1H-inden-4-yl)carbamoyl)-4-(2-hydroxypropan-2-yl)furan-2-sulfonamide (Compound 3)

3B (116 mg, 0.62 mmol), triethylamine (75 mg, 0.74 mmol) and tetrahydrofuran (10 mL) were added successively into a 100 mL round-bottomed flask under nitrogen atmosphere, and then triphosgene (74 mg, 0.25 mmol) was added in an ice bath. The reaction system was warmed to reflux, reacted for 2 h, and then filtered to remove the solids. 2e (127 mg, 0.62 mmol) and sodium methoxide (67 mg, 1.24 mmol) were added to the filtrate, and the mixture was reacted at room temperature for 12 h. After the reaction was completed as detected by TLC, water (100 mL) was added to quench the reaction, and DCM (30 mL×3) was added for extraction. The organic phase was dried over anhydrous sodium sulfate and filtered, and the organic solvent was removed. The residue was purified by preparative medium pressure liquid chromatography to give compound 3 in the form of a yellow solid (73 mg, 28.2% yield).

$^1$H NMR (400 MHz, DMSO-d6) δ=7.98 (s, 1H), 7.78 (s, 1H), 7.20 (s, 1H), 7.11-7.00 (m, 2H), 5.12 (s, 1H), 2.82 (t, 2H), 2.58 (t, 2H), 2.35 (d, 2H), 1.96-1.89 (m, 2H), 1.37 (s, 6H), 0.84-0.80 (m, 1H), 0.39-0.37 (m, 2H), 0.11-0.07 (m, 2H); LCMS m/z=419.2[M+1].

Example 4

N-((2-(1-cyclopropylethyl)-4-fluoro-6-(2-methoxypyridin-4-yl)phenyl)carbamoyl)-4-(2-hydroxypropan-2-yl)furan-2-sulfonamide (Compound 4)

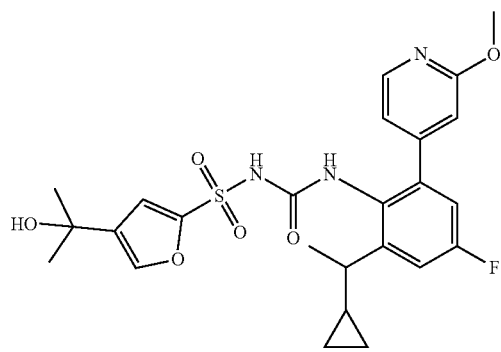

Compound 4

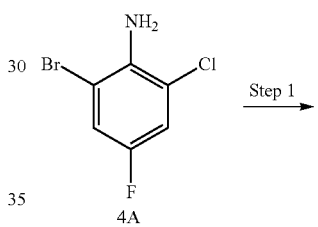

4A

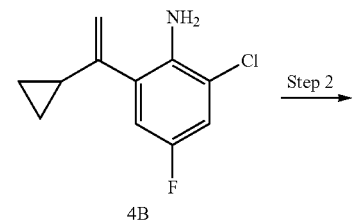

4B

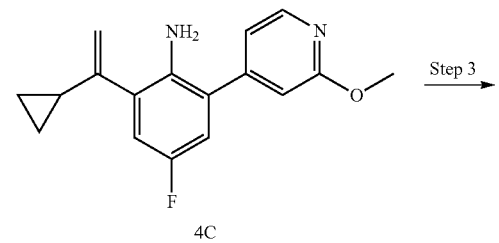

4C

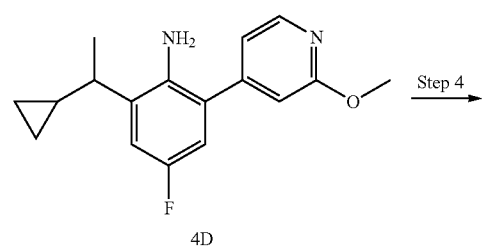

4D

-continued

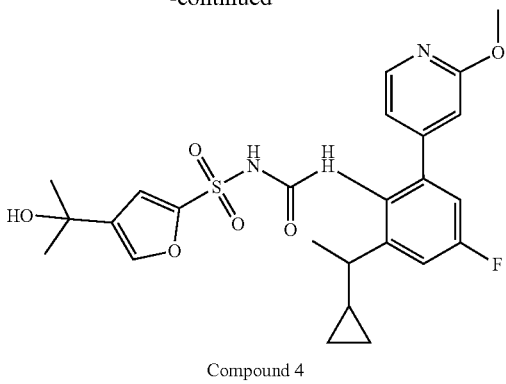

Compound 4

Step 1

2-chloro-6-(1-cyclopropylvinyl)-4-fluoroaniline (4B)

4A (8.66 g, 38.56 mmol), 2-(1-cyclopropylvinyl)-4,4,5,5-tetramethyl-1,3,2-dioxaborolane (9.73 g, 50.13 mmol), potassium phosphate (16.30 g, 77.12 mmol), bis(triphenylphosphine)palladium(II) chloride (4.23 g, 5.78 mmol) and 1,4-dioxane/water (120 mL/40 mL) were added successively into a 500 mL three-necked flask under nitrogen atmosphere, and then the reaction system was warmed to 100° C. and reacted for 8 h. After the reaction was completed, the reaction system was cooled to room temperature and filtered to remove the solids. The filtrate was poured into water, and EA (100 mL×3) was added for extraction. The organic phase was dried over anhydrous sodium sulfate and filtered, and the organic solvent was removed. The residue was purified by column chromatography (ethyl acetate:petroleum ether=1:200) to give compound 4B in the form of a pale yellow oil (5.4 g, 66% yield).

LCMS m/z=212.1[M+1].

Step 2

2-(1-cyclopropylvinyl)-4-fluoro-6-(2-methoxypyridin-4-yl)aniline (4C)

4B (4.24 g, 20.09 mmol), (2-methoxypyridin-4-yl)boronic acid (4.61 g, 30.14 mmol), potassium phosphate (12.80 g, 60.27 mmol), pd(dppf)Cl$_2$ (2.20 g, 3.01 mmol) and DMF (60 mL) were added successively into a 100 mL three-necked flask under nitrogen atmosphere, and then the reaction system was warmed to 140° C. and reacted for 4 h, and then filtered to remove the solids. The filtrate was poured into water, and EA (50 mL×3) was added for extraction. The organic phase was dried over anhydrous sodium sulfate and filtered, and the organic solvent was removed. The residue was purified by column chromatography (ethyl acetate:petroleum ether=1:5) to give compound 4C in the form of a pale yellow oil (330 mg, 5.7% yield).

LCMS m/z=285.1[M+1].

Step 3

2-(1-cyclopropylethyl)-4-fluoro-6-(2-methoxypyridin-4-yl)aniline (4D)

4C (170 mg, 0.60 mmol), Pd/C (25.5 mg, 0.15% w/w) and methanol/tetrahydrofuran (5 mL/10 mL) were added into a 100 mL round-bottomed flask, and then purge with hydrogen was performed 3 times. The reaction system was then reacted at 45° C. for 3 h under hydrogen atmosphere. After the reaction was completed as detected by TLC, the reaction system was filtered to remove the solids, and the organic solvent was removed under reduced pressure. The residue was purified by preparative medium pressure liquid chromatography to give 4D in the form of a pale yellow oil (155 mg, 90.6% yield).

$^1$H NMR (400 MHz, DMSO-d6) δ=8.23 (d, 1H), 7.04 (dd, 1H), 6.94 (dd, 1H), 6.85 (s, 1H), 6.81 (dd, 1H), 3.89 (s, 3H), 2.65-2.61 (m, 1H), 1.23-1.16 (m, 3H), 0.94-0.85 (m, 1H), 0.42-0.38 (m, 2H), 0.10-0.08 (m, 2H); LCMS m/z=287.2 [M+1].

Step 4

N-((2-(1-cyclopropylethyl)-4-fluoro-6-(2-methoxypyridin-4-yl)phenyl)carbamoyl)-4-(2-hydroxypropan-2-yl)furan-2-sulfonamide (Compound 4)

4D (155 mg, 0.54 mmol), triethylamine (66 mg, 0.65 mmol) and tetrahydrofuran (10 mL) were added successively into a 100 mL round-bottomed flask under nitrogen atmosphere, and then triphosgene (64 mg, 0.22 mmol) was added in an ice bath. The reaction system was warmed to reflux, reacted for 2 h, and then filtered to remove the solids. 2e (111 mg, 0.54 mmol) and sodium methoxide (59 mg, 1.08 mmol) were added to the filtrate, and the mixture was reacted at room temperature for 12 h. After the reaction was completed as detected by TLC, water (100 mL) was added to quench the reaction, and DCM (30 mL×3) was added for extraction. The organic phase was dried over anhydrous sodium sulfate and filtered, and the organic solvent was removed. The residue was purified by preparative medium pressure liquid chromatography to give compound 4 in the form of a yellow solid (70 mg, 25.0% yield).

$^1$H NMR (400 MHz, DMSO-d6) δ=8.07 (d, 1H), 7.49 (s, 1H), 7.38 (s, 1H), 7.08 (dd, 1H), 6.97-6.94 (m, 2H), 6.79 (s, 1H), 6.57 (br, 1H), 4.93 (s, 1H), 3.86 (s, 3H), 2.68-2.57 (m, 1H), 1.36 (s, 6H), 1.24 (s, 3H), 0.87-0.81 (m, 1H), 0.40-0.35 (m, 2H), 0.05-0.04 (m, 2H); LCMS m/z=518.2[M+1].

Example 5

(R)-N-((5-(1-cyclopropylethyl)-2,3-dihydro-1H-inden-4-yl)carbamoyl)-4-(2-hydroxypropan-2-yl)furan-2-sulfonamide (Compound 5)

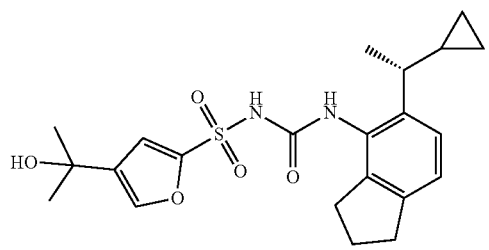

Compound 5

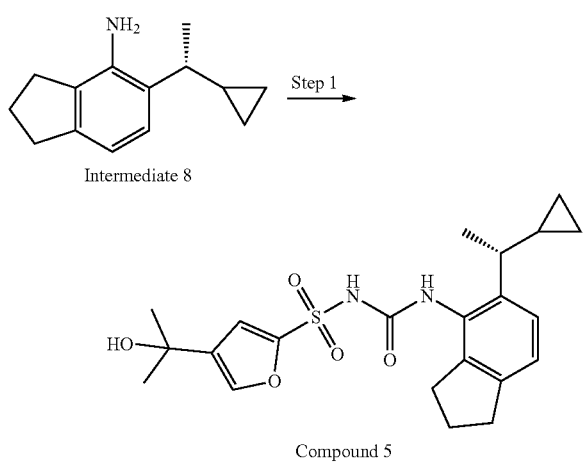

Step 1

(R)-N-((5-(1-cyclopropylethyl)-2,3-dihydro-1H-inden-4-yl)carbamoyl)-4-(2-hydroxypropan-2-yl)furan-2-sulfonamide (Compound 5)

Intermediate 8 (745 mg, 3.7 mmol), triethylamine (450 mg, 4.45 mmol) and tetrahydrofuran (30 mL) were added successively into a 100 mL round-bottomed flask under nitrogen atmosphere, and then triphosgene (440 mg, 1.48 mmol) was added in an ice bath. The reaction system was warmed to reflux, reacted for 2 h, and then filtered to remove the solids. 2e (111 mg, 0.54 mmol) and sodium methoxide (59 mg, 1.08 mmol) were added to the filtrate, and the mixture was reacted at room temperature for 12 h. After the reaction was completed as detected by TLC, water (100 mL) was added to quench the reaction, and DCM (30 mL×3) was added for extraction. The organic phase was dried over anhydrous sodium sulfate and filtered, and the organic solvent was removed. The residue was purified by preparative medium pressure liquid chromatography (acetonitrile/water=45%) to give compound 5 in the form of a white solid (320 mg, 20.0% yield, ee %: 98.46%, chiral HPLC (OZ); mobile phase: n-hexane/ethanol=90/10; column temperature: 35° C.; column pressure: 80 bar; flow rate: 0.8 mL/min; detector signal channel: 215 nm@4.8 nm; wavelength of diode array detector: 200-400 nm; RT=14.707 min).

$^1$H NMR (400 MHz, DMSO-d6) δ=7.68 (br, 1H), 7.53 (s, 1H), 7.11 (d, 1H), 7.02 (d, 1H), 6.81 (br, 1H), 5.00 (s, 1H), 2.81 (t, 2H), 2.71-2.53 (m, 2H), 2.30-2.16 (m, 1H), 1.91 (t, 2H), 1.36 (s, 6H), 1.11 (d, 3H), 1.00-0.86 (m, 1H), 0.51-0.38 (m, 1H), 0.27-0.14 (m, 1H), 0.12-0.06 (m, 1H), 0.04-0.01 (m, 1H); LCMS m/z (ESI)=433.2[M+1].

Example 6

($R_S$, $R_C$)- and ($S_S$, $R_C$)-N-((5-(-1-cyclopropylethyl)-2,3-dihydro-1H-inden-4-yl)carbamoyl)-4-(2-hydroxypropan-2-yl)furan-2-sulfonimidamide (Compounds 6-1 and 6-2)

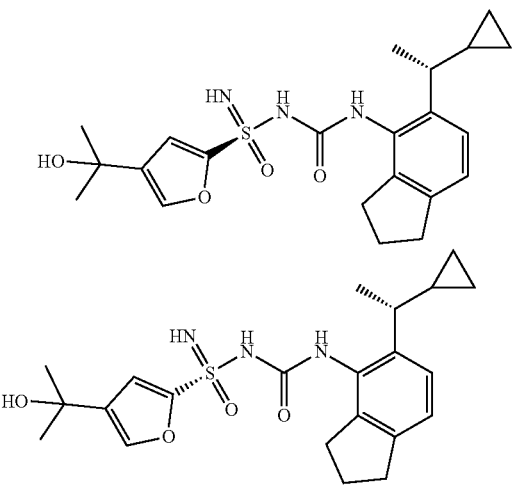

Compounds 6-1 and 6-2

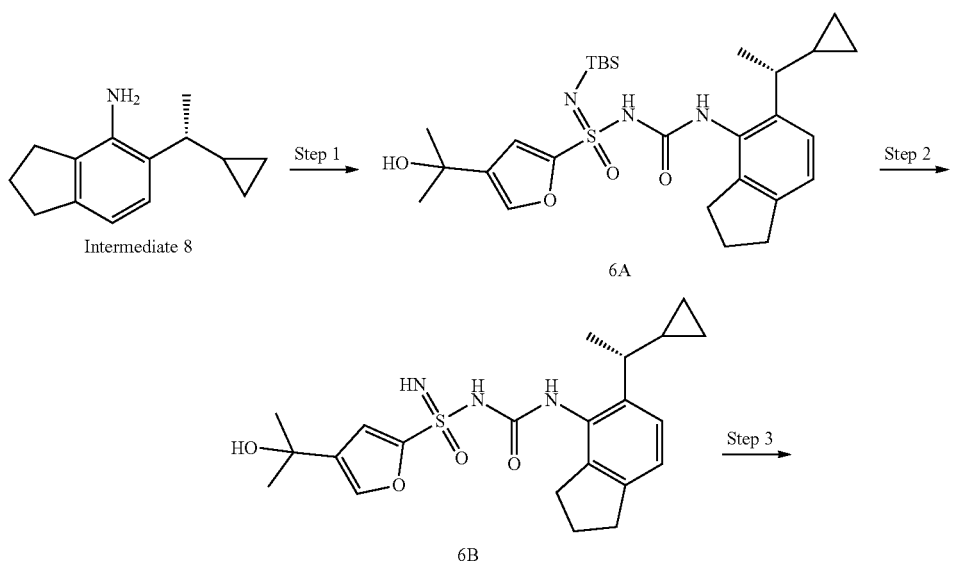

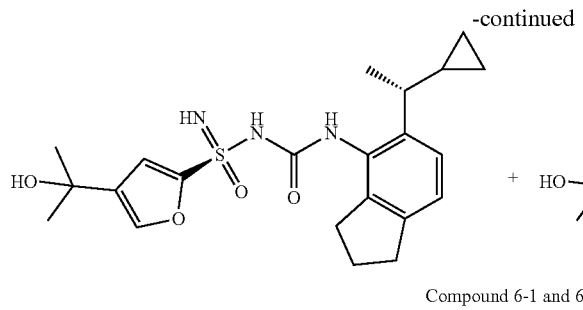
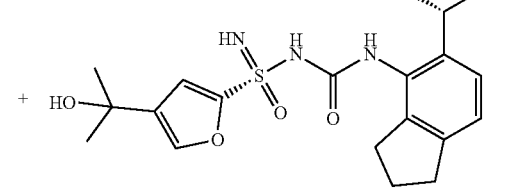

Compound 6-1 and 6-2

Step 1

(R)-N'-(tert-butyldimethylsilyl)-N-((5-(1-cyclopropylethyl)-2,3-dihydro-1H-inden-4-yl)carbamoyl)-4-(2-hydroxypropan-2-yl)furan-2-sulfonimidamide (6A)

Intermediate 8 (3.1 g, 15.4 mmol), triethylamine (1.87 g, 18.5 mmol) and tetrahydrofuran (100 mL) were added successively into a 100 mL round-bottomed flask under nitrogen atmosphere, and then triphosgene (1.83 g, 6.2 mmol) was added in an ice bath. The reaction system was warmed to reflux, reacted for 2 h, and then filtered to remove the solids. Intermediate 2 (4.9 g, 15.4 mmol) and sodium methoxide (1.66 g, 30.8 mmol) were added to the filtrate, and the mixture was reacted at room temperature for 12 h. After the reaction was completed as detected by TLC, compound 6A was obtained and was directly used in the next step without purification.

LCMS m/z=546.3[M+1].

Step 2

(R)-N-((5-(1-cyclopropylethyl)-2,3-dihydro-1H-inden-4-yl)carbamoyl)-4-(2-hydroxypropan-2-yl)furan-2-sulfonimidamide (6B)

Tetrabutylammonium fluoride (6.2 mL, 61.6 mmol, 1 M in THF) was added to the reaction system from the previous step, and the resulting reaction system was reacted overnight at room temperature. After the reaction was completed as detected by TLC, the reaction system was poured into water and extracted with ethyl acetate (100 mL×3). The organic phases were combined, washed once with 1 M diluted HCl, dried over anhydrous sodium sulfate and filtered, and the organic solvent was removed under reduced pressure. The residue was purified by preparative medium pressure liquid chromatography (acetonitrile/water=50%) to give 6B in the form of a transparent solid (1.2 g, 18.2% yield).

LCMS m/z (ESI)=432.2[M+1].

Step 3

($R_S$, $R_C$)- and ($S_S$, $R_C$)-N-((5-(-1-cyclopropylethyl)-2,3-dihydro-1H-inden-4-yl)carbamoyl)-4-(2-hydroxypropan-2-yl)furan-2-sulfonimidamide (Compounds 6-1 and 6-2)

6B was resolved by SFC to give compound 6-1 (537 mg, 44.8% yield, RT=14.041 min, ee %: 98.80%) and compound 6-2 (1.23 g, 47% yield, RT=17.846 min, ee %: 99.38%). Chiral HPLC (OZ), mobile phase: n-hexane/ethanol=90/10; column temperature: 35° C.; column pressure: 80 bar; flow rate: 1 mL/min; detector signal channel: 215 nm@4.8 nm; wavelength of diode array detector: 200-400 nm.

Compound 6-1: $^1$H NMR (400 MHz, DMSO-d6) δ=8.23 (br, 1H), 7.67 (s, 1H), 7.62 (br, 1H), 7.12 (d, 1H), 7.04 (d, 1H), 6.96 (br, 1H), 5.09 (s, 1H), 2.82 (t, 2H), 2.71-2.62 (m, 2H), 2.33-2.19 (m, 1H), 1.94-1.91 (m, 2H), 1.38 (s, 6H), 1.09 (d, 3H), 0.98-0.91 (m, 1H), 0.48-0.45 (m, 1H), 0.23-0.20 (m, 1H), 0.13-0.10 (m, 1H), 0.06-0.05 (m, 1H); LCMS m/z (ESI)=432.2[M+1].

Compound 6-2: $^1$H NMR (400 MHz, DMSO-d6) δ=8.24 (br, 1H), 7.67 (s, 1H), 7.62 (br, 1H), 7.12 (d, 1H), 7.04 (d, 1H), 6.96 (br, 1H), 5.09 (s, 1H), 2.82 (t, 2H), 2.73-2.61 (m, 2H), 2.29-2.18 (m, 1H), 1.94-1.91 (m, 2H), 1.38 (s, 6H), 1.09 (d, 3H), 0.96-0.94 (m, 1H), 0.48-0.45 (m, 1H), 0.23-0.20 (m, 1H), 0.13-0.10 (m, 1H), 0.06-0.05 (m, 1H); LCMS m/z (ESI)=432.2[M+1].

Example 7

(S)-N-((5-(1-cyclopropylethyl)-2,3-dihydro-1H-inden-4-yl)carbamoyl)-4-(2-hydroxypropan-2-yl)furan-2-sulfonamide (Compound 7)

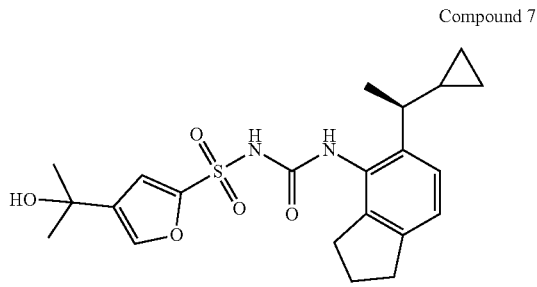 [SMILES: C[C@H](c1ccc2c(c1NC(=O)NS(=O)(=O)c1cc(C(C)(C)O)co1)CCC2)C1CC1]

Compound 7

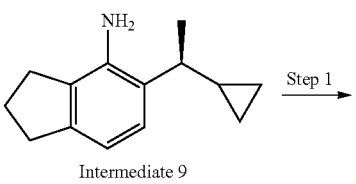

Intermediate 9

Step 1

-continued

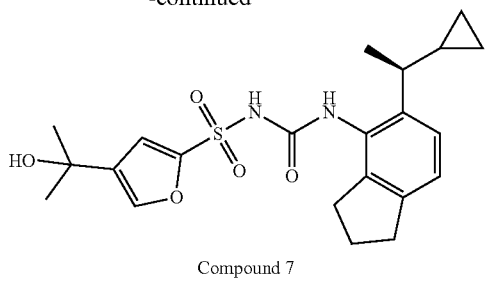

Compound 7

Step 1

(S)-N-((5-(1-cyclopropylethyl)-2,3-dihydro-1H-inden-4-yl)carbamoyl)-4-(2-hydroxypropan-2-yl)furan-2-sulfonamide (Compound 7)

Intermediate 9 (770 mg, 3.83 mmol), triethylamine (464 mg, 4.60 mmol) and tetrahydrofuran (30 mL) were added successively into a 100 mL round-bottomed flask under nitrogen atmosphere, and then triphosgene (455 mg, 1.53 mmol) was added in an ice bath. The reaction system was warmed to reflux, reacted for 2 h, and then filtered to remove the solids. 2e (785 mg, 3.83 mmol) and sodium methoxide (414 mg, 7.66 mmol) were added to the filtrate, and the mixture was reacted at room temperature for 12 h. After the reaction was completed as detected by TLC, water (100 mL) was added to quench the reaction, and DCM (30 mL×3) was added for extraction. The organic phase was dried over anhydrous sodium sulfate and filtered, and the organic solvent was removed. The residue was purified by preparative medium pressure liquid chromatography (acetonitrile/water=45%) to give compound 7 in the form of a transparent solid (300 mg, 18.1% yield, ee %: 98.9%, chiral HPLC (OZ); mobile phase: n-hexane/ethanol=90/10; column temperature: 35° C.; column pressure: 80 bar; flow rate: 0.8 mL/min; detector signal channel: 215 nm@4.8 nm; wavelength of diode array detector: 200-400 nm; RT=15.935 min).

$^1$H NMR (400 MHz, DMSO-d6) δ=7.80 (br, 1H), 7.63 (s, 1H), 7.12 (d, 1H), 7.02 (d, 1H), 6.95-6.91 (m, 1H), 5.05 (s, 1H), 2.81 (t, 2H), 2.60-2.56 (m, 2H), 2.25-2.14 (m, 1H), 1.99-1.89 (m, 2H), 1.37 (s, 6H), 1.11 (d, 3H), 0.96-0.89 (m, 1H), 0.48-0.42 (m, 1H), 0.24-0.17 (m, 1H), 0.11-0.06 (m, 1H), 0.03-0.05 (m, 1H); LCMS m/z (ESI)=433.2[M+1].

Example 8

($R_S$, $S_C$)- and ($S_S$, $S_C$)-N-((5-(1-cyclopropylethyl)-2,3-dihydro-1H-inden-4-yl)carbamoyl)-4-(2-hydroxypropan-2-yl)furan-2-sulfonimidamide (Compounds 8-1 and 8-2)

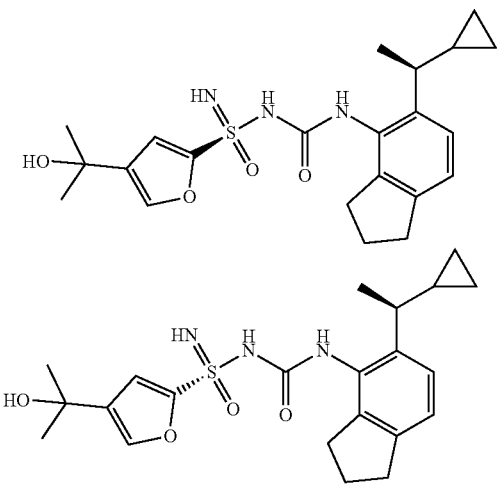

Compounds 8-1 and 8-2

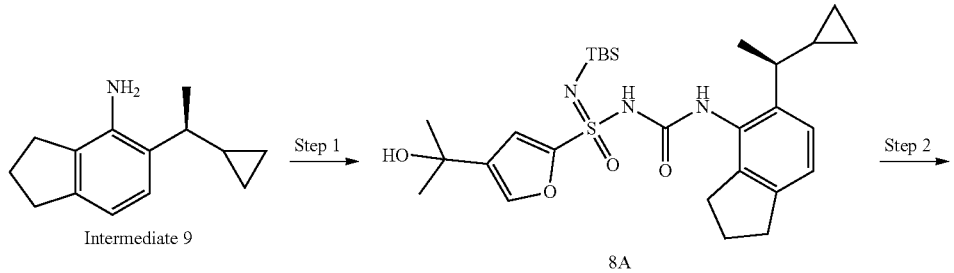

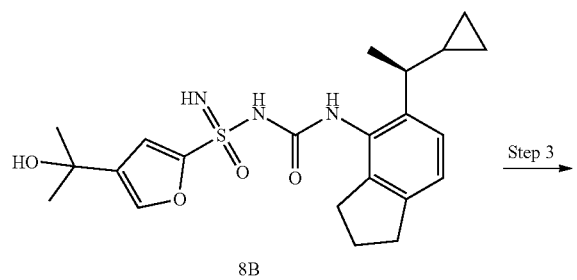

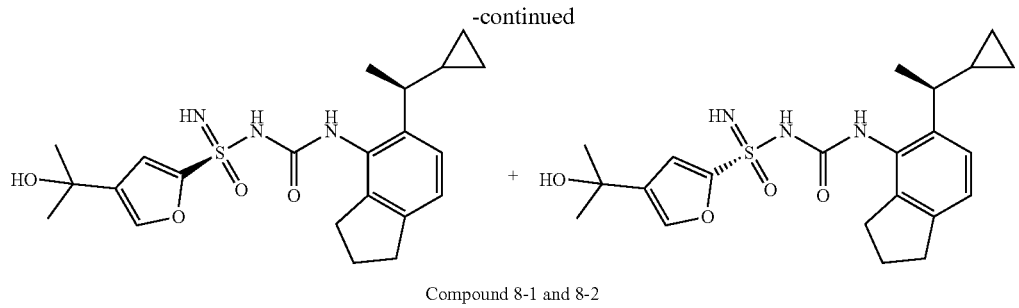

Compound 8-1 and 8-2

Step 1

(S)-N'-(tert-butyldimethylsilyl)-N-((5-(1-cyclopropylethyl)-2,3-dihydro-1H-inden-4-yl)carbamoyl)-4-(2-hydroxypropan-2-yl)furan-2-sulfonimidamide (8A)

Intermediate 9 (2.60 g, 12.9 mmol), triethylamine (1.57 g, 15.5 mmol) and tetrahydrofuran (100 mL) were added successively into a 100 mL round-bottomed flask under nitrogen atmosphere, and then triphosgene (1.54 g, 5.2 mmol) was added in an ice bath. The reaction system was warmed to reflux, reacted for 2 h, and then filtered to remove the solids.

Intermediate 2 (4.10 g, 12.9 mmol) and sodium methoxide (1.40 g, 25.8 mmol) were added to the filtrate, and the mixture was reacted at room temperature for 12 h. After the reaction was completed as detected by TLC, compound 8A was obtained and was directly used in the next step without purification.

LCMS m/z (ESI)=546.3[M+1].

Step 2

(S)-N-((5-(1-cyclopropylethyl)-2,3-dihydro-1H-inden-4-yl)carbamoyl)-4-(2-hydroxypropan-2-yl)furan-2-sulfonimidamide (Compound 8B)

Tetrabutylammonium fluoride (5.2 mL, 51.7 mmol, 1 M/THF) was added to the reaction system from the previous step, and the resulting reaction system was reacted overnight at room temperature. After the reaction was completed as detected by TLC, the reaction system was poured into water and extracted with ethyl acetate (100 mL×3). The organic phases were combined, washed once with 1 M diluted HCl, dried over anhydrous sodium sulfate and filtered, and the organic solvent was removed under reduced pressure. The residue was purified by preparative medium pressure liquid chromatography (acetonitrile/water=50%) to give 8B in the form of a transparent solid (2.6 g, 46.6% yield).

LCMS m/z=432.2[M+1].

Step 3

($R_S$, $S_C$)- and ($S_S$, $S_C$)-N-((5-(1-cyclopropylethyl)-2,3-dihydro-1H-inden-4-yl)carbamoyl)-4-(2-hydroxypropan-2-yl)furan-2-sulfonimidamide (Compounds 8-1 and 8-2)

8B was resolved by SFC to give compound 8-1 (1.17 g, 45% yield, ee %: 99.70%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=14.463 min) and compound 8-2 (1.23 g, 47% yield, ee %: 99.66%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=19.375 min).

Compound 8-1: $^1$H NMR (400 MHz, DMSO-d6) δ=8.24 (br, 1H), 7.67 (s, 1H), 7.62 (br, 1H), 7.12 (d, 1H), 7.04 (d, 1H), 6.97 (br, 1H), 5.09 (s, 1H), 2.82 (t, 2H), 2.74-2.66 (m, 2H), 2.28-2.19 (m, 1H), 1.94-1.91 (m, 2H), 1.38 (s, 6H), 1.11 (d, 3H), 0.98-0.85 (m, 1H), 0.48-0.43 (m, 1H), 0.23-0.14 (m, 1H), 0.11-0.08 (m, 1H), 0.04-0.0 (m, 1H); LCMS m/z=432.2[M+1].

Compound 8-2: $^1$H NMR (400 MHz, DMSO-d6) δ=8.24 (br, 1H), 7.67 (s, 1H), 7.64 (br, 1H), 7.12 (d, 1H), 7.04 (d, 1H), 6.97 (br, 1H), 5.09 (s, 1H), 2.82 (t, 2H), 2.71-2.62 (m, 2H), 2.28-2.19 (m, 1H), 1.99-1.91 (m, 2H), 1.38 (s, 6H), 1.09 (d, 3H), 0.96-0.94 (m, 1H), 0.47-0.45 (m, 1H), 0.22-0.20 (m, 1H), 0.12-0.10 (m, 1H), 0.04-0.0 (m, 1H); LCMS m/z=432.2[M+1].

Example 9

N-((5-(1-cyclopropylethyl)-7-fluoro-2,3-dihydro-1H-inden-4-yl)carbamoyl)-4-(2-hydroxypropan-2-yl)furan-2-sulfonamide (Compound 9)

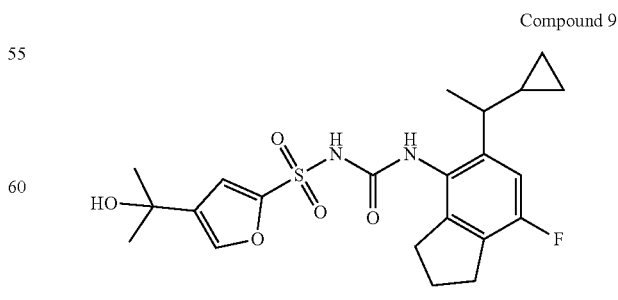

Compound 9

9

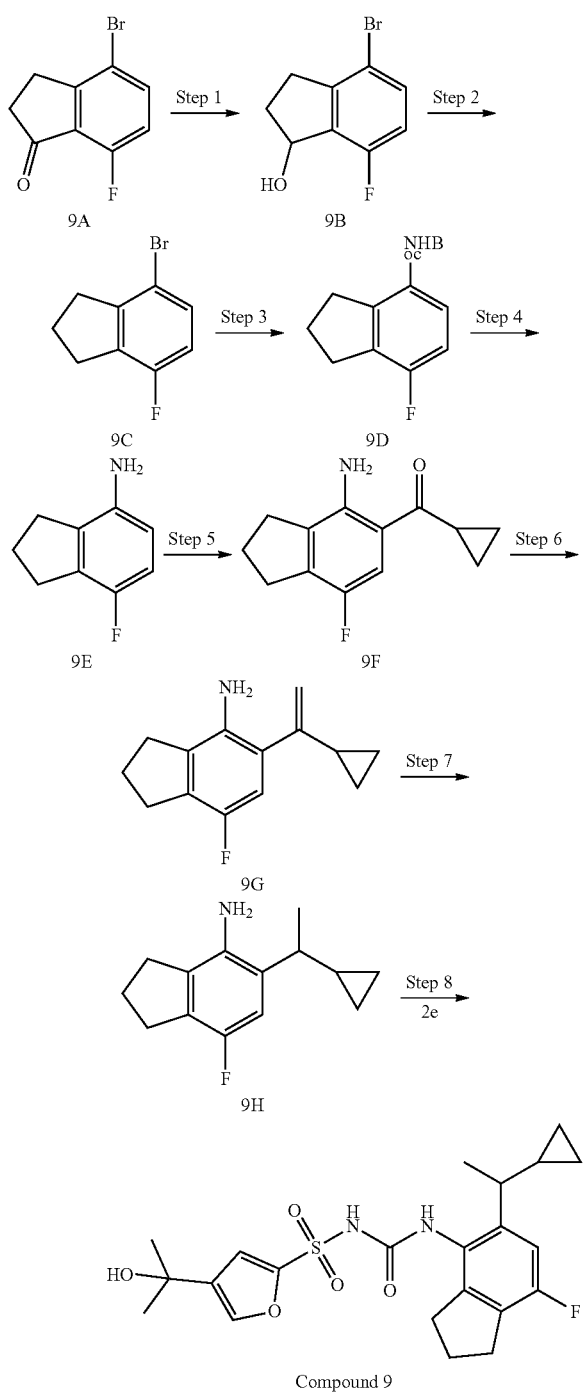

Compound 9

Step 1

4-bromo-7-fluoro-2,3-dihydro-1H-inden-1-ol (9B)

9A (25.0 g, 109.15 mmol) and methanol (300 mL) were added successively into a 1000 mL round-bottomed flask under nitrogen atmosphere, and then sodium borohydride (8.3 g, 218.3 mmol) was added slowly in an ice bath. The reaction system was warmed to room temperature and reacted for 2 h after the addition was completed. After the reaction was completed, the reaction system was poured into ice water and filtered to give compound 9B in the form of a white solid (23.8 g, 94% yield).

$^1$H NMR (400 MHz, DMSO-d6) δ=7.50 (dd, 1H), 7.00 (t, 1H), 5.42 (br, 1H), 5.32 (br, 1H), 3.04-2.98 (m, 1H), 2.77-2.70 (m, 1H), 2.34-2.27 (m, 1H), 1.94-1.87 (m, 1H); LCMS m/z (ESI)=214.0[M−17].

Step 2

4-bromo-7-fluoro-2,3-dihydro-1H-indene (9C)

9B (23.0 g, 99.6 mmol), triethylsilane (69.3 g, 597.4 mmol) and dichloromethane (300 mL) are added successively into a 500 mL round-bottomed flask under nitrogen atmosphere, and then trifluoroacetic acid (34.1 g, 298.7 mmol) was added dropwise slowly in an ice bath. The reaction system was warmed to room temperature and reacted for 12 h after the addition was completed. After the reaction was completed, the reaction system was poured into ice water, saturated sodium bicarbonate was added to adjust the pH to alkalinity, and dichloromethane (150 mL×3) was added for extraction. The organic phase was dried over anhydrous sodium sulfate and filtered, and the organic solvent was removed under reduced pressure. The residue was purified by column chromatography (petroleum ether: ethyl acetate=100:1-40:1) to give compound 9C in the form of a pale yellow oil (19.4 g, 87.7% yield).

$^1$H NMR (400 MHz, DMSO-d6) δ=7.38 (dd, 1H), 6.75 (t, 1H), 2.99 (t, 2H), 2.88 (t, 2H), 2.11-2.04 (m, 2H).

Step 3

Tert-butyl (7-fluoro-2,3-dihydro-1H-inden-4-yl) carbamate (9D)

9C (19.0 g, 88.3 mmol), tert-butyl carbamate (15.5 g, 132.5 mmol), 2-dicyclohexylphosphino-2,4,6-triisopropyl-biphenyl (4.2 g, 8.83 mmol), palladium acetate (992 mg, 4.42 mmol), cesium carbonate (57.6 g, 176.7 mmol) and 1,4-dioxane (200 mL) were added successively into a 500 mL round-bottomed flask under nitrogen atmosphere, and the reaction system was warmed to 100° C. and reacted for 8 h. After the reaction was completed, the reaction system was cooled to room temperature, poured into water and extracted with ethyl acetate (150 mL×3). The organic phase was dried over anhydrous sodium sulfate and filtered, and the organic solvent was removed under reduced pressure. The residue was purified by column chromatography (petroleum ether:ethyl acetate=20:1) to give compound 9D in the form of a pale yellow solid (7.7 g, 34.8% yield).

LCMS m/z (ESI)=195.1[M−56].

Step 4

7-fluoro-2,3-dihydro-1H-inden-4-amine (9E)

9D (7.7 g, 30.7 mmol) and dichloromethane (100 mL) were added successively into a 250 mL round-bottomed flask under nitrogen atmosphere, and trifluoroacetic acid (25 mL) was added dropwise in an ice bath. The reaction system was reacted at room temperature for 3 h after the dropwise addition was completed. After the reaction was completed, the reaction system was poured into water, saturated sodium bicarbonate was added to adjust the pH, and dichloromethane (100 mL×3) was added for extraction. The organic phase was dried over anhydrous sodium sulfate and filtered, and the organic solvent was removed under reduced pressure.

The crude product was purified by preparative medium pressure liquid chromatography to give compound 9E in the form of a pale yellow oil (3.9 g, 84.7% yield).

$^1$H NMR (400 MHz, DMSO-d6) δ=6.63 (t, 1H), 6.37-6.34 (dd, 1H), 4.68 (s, 2H), 2.80 (t, 2H), 2.65 (t, 2H), 2.04-1.97 (m, 2H); LCMS m/z (ESI)=152.1[M+1].

Step 5

(4-amino-7-fluoro-2,3-dihydro-1H-inden-5-yl)(cyclopropyl)methanone (9F)

Compound 9E (3.9 g, 25.8 mmol) was dissolved in 1,2-dichloroethane (50 mL) in a 250 mL three-necked flask under nitrogen atmosphere, and the solution was cooled to 0° C. in an ice salt bath. A solution of boron trichloride (28 mL, 1 M, 28.4 mmol) in dichloromethane was then added dropwise slowly, and the temperature was maintained and the resulting solution was reacted for 10 min after the dropwise addition was completed. Aluminum trichloride (7.5 g, 30.9 mmol) and cyclopropyl cyanide (2.6 g, 38.7 mmol) were then added, and the reaction system was warmed to 80° C., reacted for 4 h and then cooled to room temperature. 2 M HCl (28 mL) was added in an ice bath, and the resulting reaction system was warmed to reflux and reacted for 1 h. After the reaction was completed, the reaction system was cooled to room temperature and extracted with DCM (100 mL×3). The organic phase was washed with 2 M sodium hydroxide solution (28 mL), dried over anhydrous sodium sulfate and filtered, and the organic solvent was removed under reduced pressure. The residue was purified by column chromatography (petroleum ether: ethyl acetate=20:1) to give compound 9F in the form of a white solid (4.8 g, 86.3% yield).

$^1$H NMR (400 MHz, DMSO-d6) δ=7.68 (d, 1H), 6.78 (s, 2H), 2.90 (t, 2H), 2.80-2.77 (m, 1H), 2.72 (t, 2H), 2.12-2.05 (m, 2H), 0.95-0.89 (m, 4H); LCMS m/z (ESI)=220.1[M+1].

Step 6

5-(1-cyclopropylvinyl)-7-fluoro-2,3-dihydro-1H-inden-4-amine (9G)

Compound methyl triphenyl phosphonium bromide (15.7 g, 43.8 mmol) was dissolved in THF (100 mL) in a 250 mL three-necked flask under nitrogen atmosphere, and the solution was cooled to 0° C. in an ice salt bath. Potassium tert-butoxide (4.9 g, 43.8 mmol) was added slowly, and the temperature was maintained and the reaction system was reacted for 30 min. Compound 9F (7.0 g, 21.9 mmol) was added, and the resulting reaction system was reacted at room temperature for 4 h. After the reaction was completed, water was added to quench the reaction, and EA (100 mL×3) was added for extraction. The organic phase was dried over anhydrous sodium sulfate and filtered, and the organic solvent was removed under reduced pressure. The residue was purified by column chromatography (petroleum ether: ethyl acetate=20:1) to give compound 9G in the form of a pale yellow oil (4.6 g, 95% yield).

$^1$H NMR (400 MHz, DMSO-d6) δ 6.49 (d, 1H), 5.17 (s, 1H), 4.83 (s, 1H), 4.28 (s, 2H), 2.81 (t, 2H), 2.69 (t, 2H), 2.07-1.98 (m, 2H), 1.61-1.57 (m, 1H), 0.71-0.66 (m, 2H), 0.42-0.39 (m, 2H); LCMS m/z (ESI)=218.1[M+1].

Step 7

5-(1-cyclopropylethyl)-7-fluoro-2,3-dihydro-1H-inden-4-amine (9H)

Compound 9G (1.0 g, 4.59 mmol) and Pd/C (20 mg, w/w=5%, Pd content 10%) were dissolved in a mixed solvent of tetrahydrofuran/methanol (10/5 mL) in a 250 mL three-necked flask, and the solution was reacted at room temperature for 15 min under hydrogen atmosphere. After the reaction was completed, Pd/C was removed by filtration, and the organic solvent was removed under reduced pressure. The residue was purified by preparative medium pressure liquid chromatography to give compound 9H in the form of a pale yellow oil (343 mg, 34.3% yield).

$^1$H NMR (400 MHz, DMSO-d6) δ 6.74 (d, 1H), 4.34 (s, 2H), 2.79 (t, 2H), 2.68-2.65 (m, 2H), 2.25-2.20 (m, 1H), 2.05-1.97 (m, 2H), 1.13 (d, 3H), 1.02-0.94 (m, 1H), 0.51-0.45 (m, 1H), 0.37-0.30 (m, 1H), 0.19-0.13 (m, 1H), 0.06-0.01 (m, 1H); LCMS m/z (ESI)=220.1[M+1].

Step 8

N-((5-(1-cyclopropylethyl)-7-fluoro-2,3-dihydro-1H-inden-4-yl)carbamoyl)-4-(2-hydroxypropan-2-yl)furan-2-sulfonamide (Compound 9)

Compound 9H (120 mg, 0.55 mmol), triethylamine (65 mg, 0.66 mmol) and tetrahydrofuran (20 mL) were added successively into a 100 mL round-bottomed flask under nitrogen atmosphere, and then triphosgene (65 mg, 0.22 mmol) was added in an ice bath. The reaction system was warmed to reflux, reacted for 2 h, and then filtered to remove the solids. 2e (113 mg, 0.55 mmol) and sodium methoxide (59 mg, 1.1 mmol) were added to the filtrate, and the mixture was reacted at room temperature for 12 h. After the reaction was completed as detected by TLC, water (20 mL) was added to quench the reaction, and DCM (30 mL×3) was added for extraction. The organic phase was dried over anhydrous sodium sulfate and filtered, and the organic solvent was removed. The crude product was purified by preparative medium pressure liquid chromatography (acetonitrile/water=45%) to give compound 9 in the form of a white solid (28 mg, 11.3% yield).

$^1$H NMR (400 MHz, DMSO-d6) δ=7.68 (s, 1H), 7.15 (br, 2H), 6.88 (d, 1H), 6.56 (s, 1H), 4.94 (s, 1H), 2.83 (t, 2H), 2.74-2.64 (m, 2H), 2.32-2.25 (m, 1H), 1.97-1.90 (m, 2H), 1.35 (s, 6H), 1.10 (d, 3H), 0.97-0.88 (m, 1H), 0.448-0.40 (m, 1H), 0.26-0.19 (m, 1H), 0.13-0.01 (m, 2H); LCMS m/z (ESI)=451.2[M+1].

Example 10

N-((5-(1-cyclopropylethyl)-7-fluoro-2,3-dihydro-1H-inden-4-yl)carbamoyl)-4-(2-hydroxypropan-2-yl)furan-2-sulfonimidamide (Compound 10)

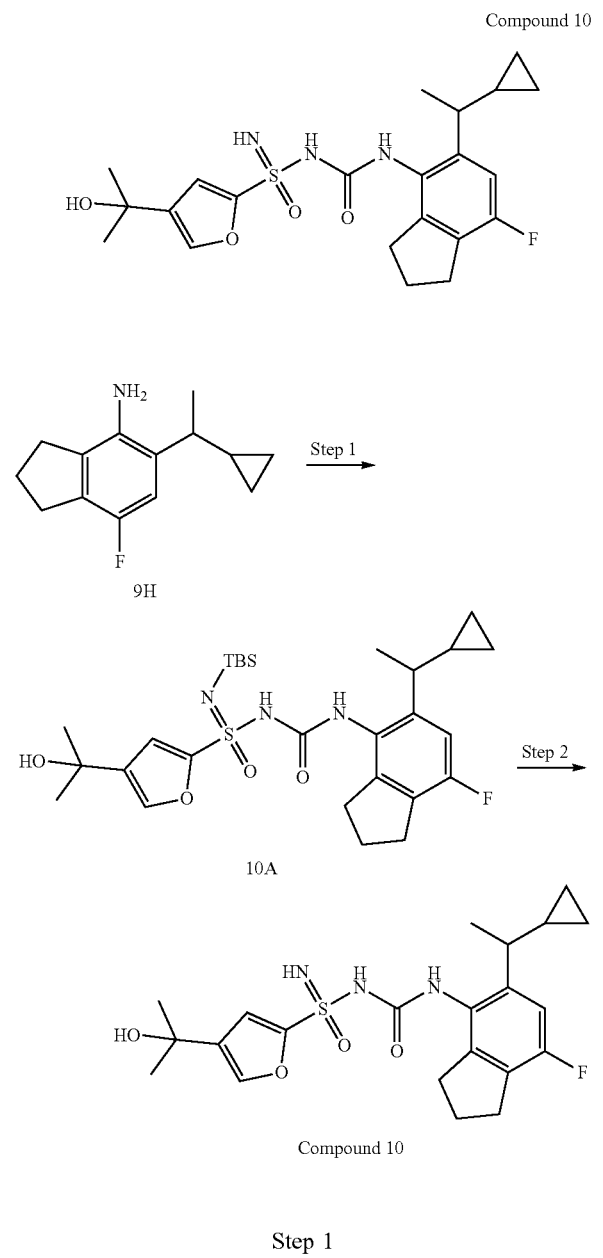

Step 1

N'-(tert-butyldimethylsilyl)-N-((5-(1-cyclopropylethyl)-7-fluoro-2,3-dihydro-1H-inden-4-yl)carbamoyl)-4-(2-hydroxypropan-2-yl)furan-2-sulfonimidamide (10A)

9H (190 mg, 0.87 mmol), triethylamine (105 mg, 1.04 mmol) and tetrahydrofuran (30 mL) were added successively into a 100 mL round-bottomed flask under nitrogen atmosphere, and then triphosgene (103 mg, 0.35 mmol) was added in an ice bath. The reaction system was warmed to reflux, reacted for 2 h, and then filtered to remove the solids. Intermediate 2 (277 mg, 0.87 mmol) and sodium methoxide (94 mg, 1.74 mmol) were added to the filtrate, and the mixture was reacted at room temperature for 12 h. After the reaction was completed as detected by TLC, compound 10A was obtained and was directly used in the next step without purification.

LCMS m/z=564.3[M+1].

Step 2

N-((5-(1-cyclopropylethyl)-7-fluoro-2,3-dihydro-1H-inden-4-yl)carbamoyl)-4-(2-hydroxypropan-2-yl)furan-2-sulfonimidamide (Compound 10)

Tetrabutylammonium fluoride (3.5 mL, 3.48 mmol, 1 M/THF) was added to the reaction system from the previous step, and the resulting reaction system was reacted overnight at room temperature. After the reaction was completed as detected by TLC, the reaction system was poured into water and extracted with ethyl acetate (50 mL×3). The organic phases were combined, washed once with 1 M diluted HCl, dried over anhydrous sodium sulfate and filtered, and the organic solvent was removed under reduced pressure. The residue was purified by preparative medium pressure liquid chromatography (acetonitrile/water=50%) to give compound 10 in the form of a transparent solid (95 mg, 23.4% yield).

$^1$H NMR (400 MHz, DMSO-d6) δ=8.18 (br, 1H), 7.64 (s, 1H), 7.45 (br, 1H), 6.94 (s, 1H), 6.91 (s, 1H), 5.08 (s, 1H), 2.84 (t, 2H), 2.71-2.66 (m, 2H), 2.28-2.17 (m, 1H), 2.01-1.92 (m, 2H), 1.37 (s, 6H), 1.09 (t, 3H), 0.96-0.91 (m, 1H), 0.48-0.40 (m, 1H), 0.25-0.20 (m, 1H), 0.16-0.08 (m, 1H), 0.04-0.02 (m, 1H); LCMS m/z (ESI)=45 0.2[M+1].

Example 11

N-((7-cyano-5-(1-cyclopropylethyl)-2,3-dihydro-1H-inden-4-yl)carbamoyl)-4-(2-hydroxypropan-2-yl)furan-2-sulfonamide (Compound 11)

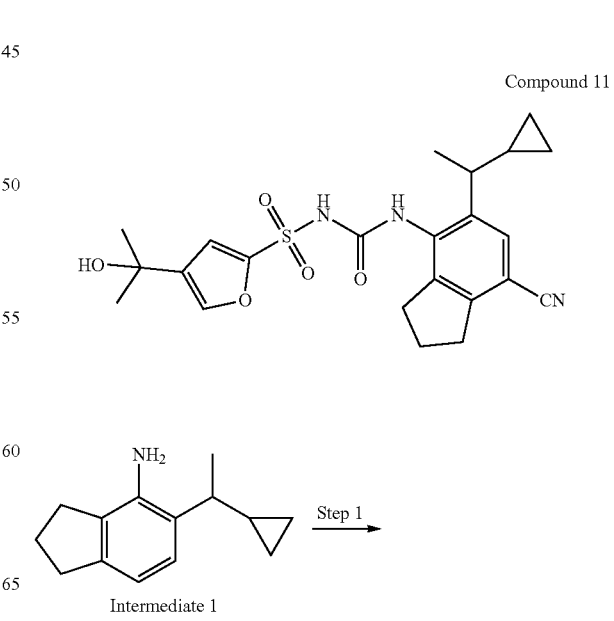

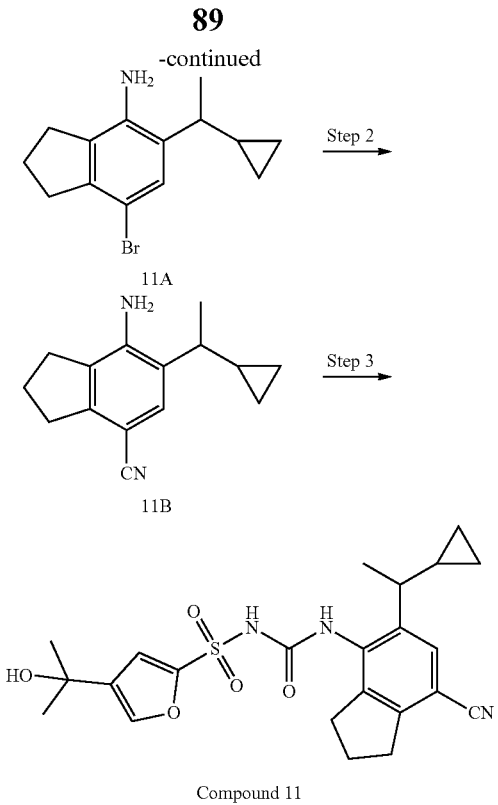

water (1:1, 20 mL) were added successively into a 100 mL three-necked flask under nitrogen atmosphere, and the reaction system was warmed to 85° C., reacted for 6 h, and then cooled to room temperature after the reaction was completed. The reaction system was then poured into water and extracted with ethyl acetate (20 mL×3). The organic phase was dried over anhydrous sodium sulfate and filtered, and the organic solvent was removed under reduced pressure. The residue was purified by column chromatography (petroleum ether:ethyl acetate=10:1) to give compound 11B in the form of a pale yellow oil (304 mg, 85.6% yield).

$^1$H NMR (400 MHz, DMSO-d6) δ=7.30 (s, 1H), 5.56 (s, 2H), 2.88 (t, 2H), 2.67 (t, 2H), 2.26-2.22 (m, 1H), 2.07-1.99 (m, 2H), 1.13 (d, 3H), 1.07-1.02 (m, 1H), 0.52-0.48 (m, 1H), 0.38-0.34 (m, 1H), 0.17-0.14 (m, 1H), 0.02-0.01 (m, 1H); LCMS m/z (ESI)=227.2[M+1].

Step 3

N-((7-cyano-5-(1-cyclopropylethyl)-2,3-dihydro-1H-inden-4-yl)carbamoyl)-4-(2-hydroxypropan-2-yl)furan-2-sulfonamide (Compound 11)

Compound 11B (116 mg, 0.51 mmol), triethylamine (62 mg, 0.62 mmol) and tetrahydrofuran (20 mL) were added successively into a 100 mL round-bottomed flask under nitrogen atmosphere, and then triphosgene (61 mg, 0.20 mmol) was added in an ice bath. The reaction system was warmed to reflux, reacted for 2 h, and then filtered to remove the solids. 2e (105 mg, 0.55 mmol) and sodium methoxide (55 mg, 1.02 mmol) were added to the filtrate, and the mixture was reacted at room temperature for 12 h. After the reaction was completed as detected by TLC, water (20 mL) was added to quench the reaction, and DCM (30 mL×3) was added for extraction. The organic phase was dried over anhydrous sodium sulfate and filtered, and the organic solvent was removed. The residue was purified by preparative medium pressure liquid chromatography (acetonitrile/water=45%) to give compound 11 in the form of a pale yellow solid (60 mg, 27.5% yield).

$^1$H NMR (400 MHz, DMSO-d6) δ=7.83 (s, 1H), 7.52 (s, 1H), 7.38 (s, 1H), 7.09 (br, 1H), 6.57 (s, 1H), 4.93 (s, 1H), 2.95 (t, 2H), 2.80-2.74 (m, 2H), 2.39-2.32 (m, 1H), 2.03-1.96 (m, 2H), 1.35 (s, 6H), 1.22 (d, 3H), 1.03-0.94 (m, 1H), 0.52-0.44 (m, 1H), 0.29-0.23 (m, 1H), 0.14-0.10 (m, 1H), 0.07-0.01 (m, 1H); LCMS m/z (ESI)=458.2[M+1].

Example 12

N-((7-cyano-5-(1-cyclopropylethyl)-2,3-dihydro-1H-inden-4-yl)carbamoyl)-4-(2-hydroxypropan-2-yl)furan-2-sulfonimidamide (Compound 12)

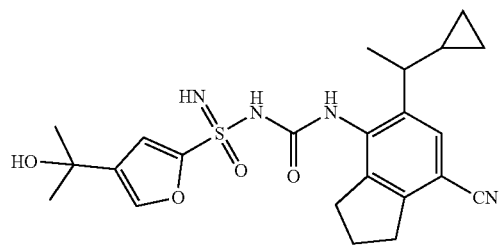

Compound 12

Step 1

7-bromo-5-(1-cyclopropylethyl)-2,3-dihydro-1H-inden-4-amine (11A)

Intermediate 1 (600 mg, 2.98 mmol) and dichloromethane (20 mL) were added successively into a 100 mL round-bottomed flask under nitrogen atmosphere, and then pyridinium tribromide (1.0 g, 3.28 mmol) was added dropwise slowly in an ice bath. The reaction system was warmed to room temperature and reacted for 1 h after the addition was completed. After the reaction was completed, the reaction system was added into aqueous sodium sulfite solution to quench the reaction, and dichloromethane (20 mL×3) was added for extraction. The organic phase was dried over anhydrous sodium sulfate and filtered, and the organic solvent was removed under reduced pressure. The residue was purified by column chromatography (petroleum ether: ethyl acetate=10:1-5:1) to give compound 11A in the form of a pale yellow oil (446 mg, 53% yield).

$^1$H NMR (400 MHz, DMSO-d6) δ=7.05 (s, 1H), 4.67 (s, 2H), 2.77-2.72 (dd, 4H), 2.24-2.20 (m, 1H), 2.03-1.95 (m, 2H), 1.13 (d, 3H), 1.01-0.96 (m, 1H), 0.50-0.47 (m, 1H), 0.36-0.32 (m, 1H), 0.17-0.13 (m, 1H), 0.05-0.01 (m, 1H); LCMS(ESI) m/z=280.0[M+1].

Step 2

7-amino-6-(1-cyclopropylethyl)-2,3-dihydro-1H-indene-4-carbonitrile (11B)

Compound 11A (440 mg, 1.57 mmol), potassium ferrocyanide (266 mg, 0.63 mmol), tetrakis(triphenylphosphine) palladium (182 mg, 0.16 mmol), 1,8-diazabicycloundec-7-ene (24 mg, 0.16 mmol) and a mixed solvent of tert-butanol/

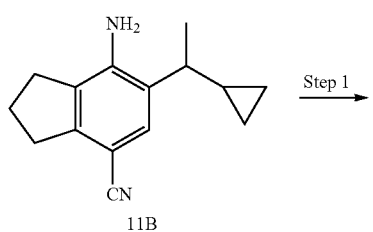

11B

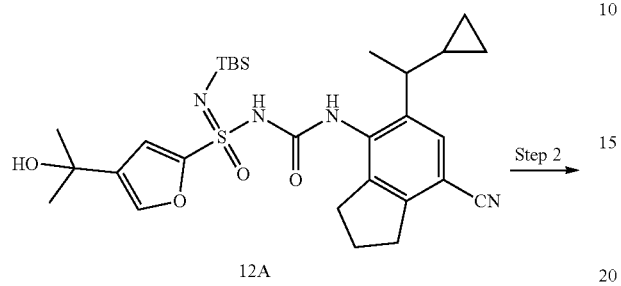

12A

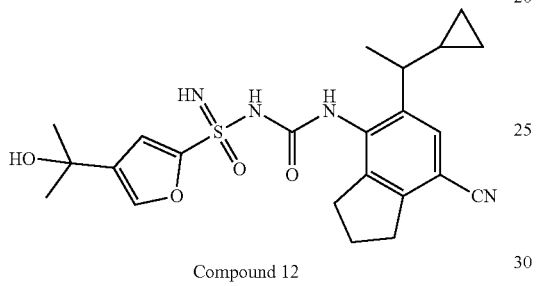

Compound 12

Step 1

N-(tert-butyldimethylsilyl)-N-((7-cyano-5-(1-cyclopropylethyl)-2,3-dihydro-1H-inden-4-yl)carbamoyl)-4-(2-hydroxypropan-2-yl)furan-2-sulfonimidamide (12A)

11B (200 mg, 0.88 mmol), triethylamine (107 mg, 1.06 mmol) and tetrahydrofuran (30 mL) were added successively into a 100 mL round-bottomed flask under nitrogen atmosphere, and then triphosgene (104 mg, 0.35 mmol) was added in an ice bath. The reaction system was warmed to reflux, reacted for 2 h, and then filtered to remove the solids. Intermediate 2 (280 mg, 0.88 mmol) and sodium methoxide (95 mg, 1.76 mmol) were added to the filtrate, and the mixture was reacted at room temperature for 12 h. After the reaction was completed as detected by TLC, compound 12A was obtained and was directly used in the next step without purification.

LCMS m/z=571.3[M+1].

Step 2

N-((5-(1-cyclopropylethyl)-7-fluoro-2,3-dihydro-1H-inden-4-yl)carbamoyl)-4-(2-hydroxypropan-2-yl)furan-2-sulfonimidamide (Compound 12)

Tetrabutylammonium fluoride (3.5 mL, 3.52 mmol, 1 M/THF) was added to the reaction system from the previous step, and the resulting reaction system was reacted overnight at room temperature. After the reaction was completed as detected by TLC, the reaction system was poured into water and extracted with ethyl acetate (50 mL×3). The organic phases were combined, washed once with 1 M diluted HCl, dried over anhydrous sodium sulfate and filtered, and the organic solvent was removed under reduced pressure. The residue was purified by preparative medium pressure liquid chromatography (acetonitrile/water=50%) to give compound 12 in the form of a transparent solid (160 mg, 39.6% yield).

$^1$H NMR (400 MHz, DMSO-d6) δ=8.62 (s, 1H), 7.70 (br, 1H), 7.69 (s, 1H), 7.59 (s, 1H), 6.99 (s, 1H), 5.09 (s, 1H), 2.98 (t, 2H), 2.78-2.67 (m, 2H), 2.32-2.23 (m, 1H), 2.05-2.00 (m, 2H), 1.38 (s, 6H), 1.14-1.09 (dd, 3H), 1.07-0.96 (m, 1H), 0.53-0.44 (m, 1H), 0.26-0.22 (m, 1H), 0.15-0.11 (m, 1H), 0.05-0.01 (m, 1H); LCMS m/z (ESI)=457.2[M+1].

Example 13

(R)-N-((5-(1-cyclopropylethyl)-2,3-dihydro-1H-inden-4-yl)carbamoyl)-4-(2-hydroxypropan-2-yl)thiazole-2-sulfonamide (Compound 13)

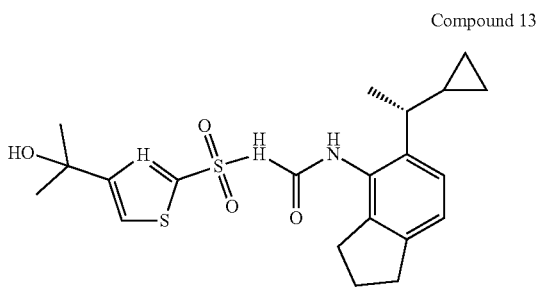

Compound 13

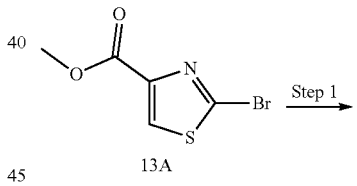

13A

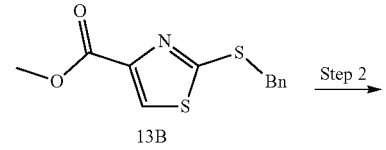

13B

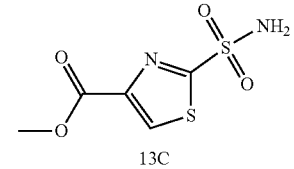

13C

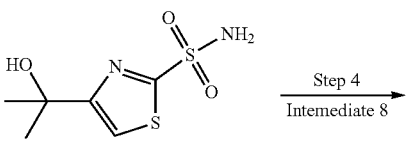

13D

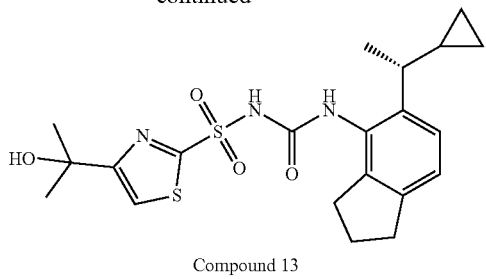

Compound 13

Step 1

Methyl 2-(benzylthio)thiazole-4-carboxylate (13B)

Compound 13A (25.0 g, 112.58 mmol), DMF (150 mL), potassium carbonate (46.7 g, 150.16 mmol) and benzyl mercaptan (14.3 g, 114.84 mmol) were added successively into a 500 mL three-necked flask under nitrogen atmosphere, and the reaction system was stirred overnight at room temperature. After the reaction was completed as determined by TLC, water was added to the reaction system in an ice bath, and EA was added for extraction 3 times. The organic phases were combined, washed with saturated brine 3 times, dried and concentrated, and the residue was separated by column chromatography to give compound 13B in the form of a pale yellow wax (6.5 g, 22% yield).

$^1$H NMR (400 MHz, DMSO-$d_6$) δ=8.44 (s, 1H), 7.45 (d, 1H), 7.43 (t, 1H), 7.37-7.24 (m, 3H), 4.52 (s, 2H), 3.83 (s, 3H); LCMS m/z (ESI)=266.0[M+1].

Step 2

Methyl 2-sulfamoylthiazole-4-carboxylate (13C)

Compound 13B (2.5 g, 9.42 mmol) was added into a 100 mL three-necked flask, and then glacial acetic acid (20 mL) was added. The reaction system was stirred until it was clarified, and then water (10 mL) was added, followed by addition of N-chlorosuccinimide (6.3 g, 47.11 mmol). The reaction system was stirred for 3 h at room temperature. After the reaction was completed as detected by TLC, the reaction system was extracted with water and ethyl acetate for 3 times. The organic phases were combined, dried and concentrated by rotary evaporation to give the crude product. The crude product was dissolved in acetone until the solution was clarified, and the solution was then stirred for 10 min in an ice bath. Ammonium bicarbonate (6.5 g, 24.54 mmol) was added, the temperature was maintained and the reaction system was stirred for 2 h. After the reaction was completed as determined by TLC, water was added into the reaction system, and DCM was added for extraction 3 times. The organic phases were combined, dried and concentrated by rotary evaporation, and the residue was separated by column chromatography to give compound 13C in the form of a pale yellow solid (210 mg, 10% yield).

$^1$H NMR (400 MHz, DMSO-$d_6$) δ=8.79 (s, 1H), 8.30 (s, 2H), 3.87 (s, 3H); LCMS m/z (ESI)=222.9[M+1].

Step 3

4-(2-hydroxypropan-2-yl)thiazole-2-sulfonamide (13D)

Compound 13C (210 mg, 0.94 mmol) and THF (10 mL) were added into a 50 mL three-necked flask under nitrogen atmosphere, and the reaction system was cooled to −10° C. in an ice salt bath. A solution of methylmagnesium bromide in tetrahydrofuran (34 mL, 34 mmol, 1 M) was added dropwise, and the reaction system was stirred at room temperature for 2 h. After the reaction was completed, saturated aqueous ammonium chloride solution was added to quench the reaction, and ethyl acetate (20 mL×3) was added for extraction. The organic phase was dried over anhydrous sodium sulfate and filtered, and the organic solvent was removed under reduced pressure. The residue was purified by column chromatography (dichloromethane:methanol=20:1) to give compound 13D in the form of a pale brown oil (194 mg, 92% yield).

$^1$H NMR (400 MHz, DMSO-$d_6$) δ 8.05 (s, 1H), 7.70 (s, 2H), 5.38 (s, 1H), 1.46 (s, 6H); LCMS m/z (ESI)=223.1 [M+1].

Step 4

(R)-N-((5-(1-cyclopropylethyl)-2,3-dihydro-1H-inden-4-yl)carbamoyl)-4-(2-hydroxypropan-2-yl)thiazole-2-sulfonamide (Compound 13)

Intermediate 8 (120 mg, 0.597 mmol) and triethylamine (114 mg, 0.716 mmol) were dissolved in tetrahydrofuran (10 mL) in a 100 mL three-necked flask under nitrogen atmosphere, and the solution was cooled to 0° C. in an ice salt bath. Triphosgene (70 mg, 0.239 mmol) was added slowly, the temperature was maintained, and the reaction system was reacted for 5 min. The reaction system was then warmed to 80° C., reacted for 1 h, and then cooled to room temperature. The reaction system was filtered and the filtrate was collected. Compound 13D (121 mg, 0.597 mmol) and sodium methoxide (64 mg, 1.194 mmol) were dissolved in methanol (10 mL) in a 100 mL single-necked flask, and the solution was stirred at room temperature for 1 h and then concentrated by rotary evaporation to remove methanol. The residue was dissolved in the previously collected filtrate, purge with nitrogen was performed three times, and the resulting mixture was warmed to 80° C. and reacted for 1 h. After the reaction was completed, water (50 mL) was added, and ethyl acetate (50 mL×2) was added for extraction. The organic phase was dried over anhydrous sodium sulfate and filtered, and the organic solvent was removed under reduced pressure. The residue was purified by preparative chromatography (acetonitrile/water=45%) to give compound 13 in the form of a pale yellow solid (35.0 mg, 13.3% yield).

$^1$H NMR (400 MHz, DMSO-d6) δ 7.46 (s, 1H), 7.35 (br, 1H), 7.06 (d, 1H), 6.95 (d, 1H), 5.37 (s, 1H), 2.78 (t, 2H), 2.68-2.62 (m, 2H), 2.337-2.25 (m, 1H), 1.87 (t, 2H), 1.42 (s, 6H), 1.09 (d, 3H), 0.99-0.88 (m, 1H), 0.51-0.39 (m, 1H)), 0.23-0.16 (m, 1H)), 0.11-0.07 (m, 2H); LCMS m/z (ESI)= 450.1[M+1].

Example 14

(S)-N-((5-(1-cyclopropylethyl)-2,3-dihydro-1H-inden-4-yl)carbamoyl)-4-(2-hydroxypropan-2-yl)thiazole-2-sulfonamide (Compound 14)

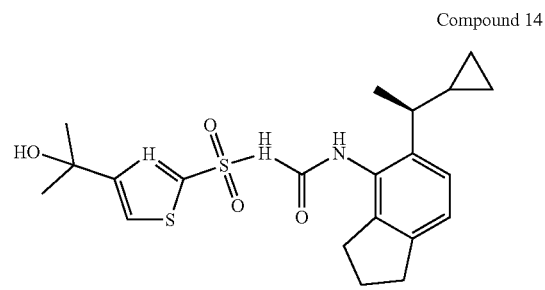

Compound 14

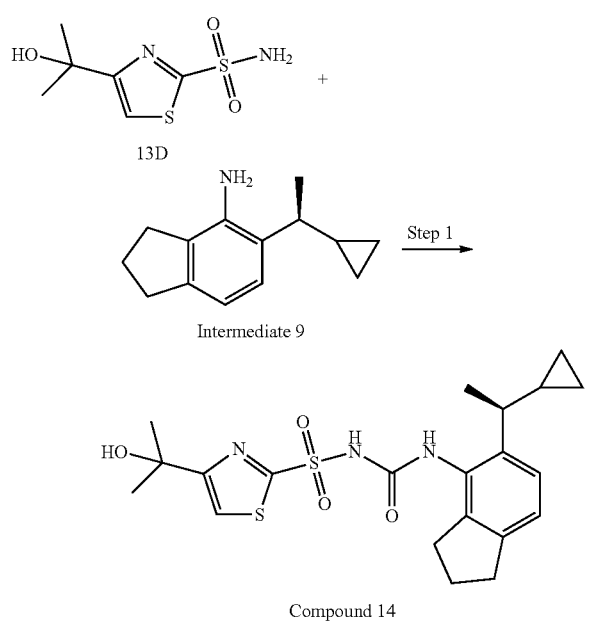

Step 1

(S)-N-((5-(1-cyclopropylethyl)-2,3-dihydro-1H-inden-4-yl)carbamoyl)-4-(2-hydroxypropan-2-yl)thiazole-2-sulfonamide (Compound 14)

Intermediate 9 (120 mg, 0.597 mmol) and triethylamine (114 mg, 0.716 mmol) were dissolved in tetrahydrofuran (10 mL) in a 100 mL three-necked flask under nitrogen atmosphere, and the solution was cooled to 0° C. in an ice salt bath. Triphosgene (70 mg, 0.239 mmol) was added slowly, the temperature was maintained, and the reaction system was reacted for 5 min. The reaction system was then warmed to 80° C., reacted for 1 h, and then cooled to room temperature. The reaction system was filtered and the filtrate was collected. 13D (121 mg, 0.597 mmol) and sodium methoxide (64 mg, 1.194 mmol) were dissolved in methanol (10 mL) in a 100 mL single-necked flask, and the solution was stirred at room temperature for 1 h and then concentrated by rotary evaporation to remove methanol. The residue was dissolved in the previously collected filtrate, purge with nitrogen was performed three times, and the resulting mixture was warmed to 80° C. and reacted for 1 h. After the reaction was completed, water (50 mL) was added, and ethyl acetate (50 mL×2) was added for extraction. The organic phase was dried over anhydrous sodium sulfate and filtered, and the organic solvent was removed under reduced pressure. The residue was purified by preparative chromatography (acetonitrile/water=45%) to give compound 14 in the form of a pale yellow solid (30.0 mg, 11.2% yield).

$^1$H NMR (400 MHz, DMSO-d6) δ 7.36 (s, 1H), 7.19 (br, 1H), 7.06 (d, 1H), 6.96 (d, 1H), 5.16 (s, 1H), 2.79 (t, 2H), 2.68-2.60 (m, 2H), 2.37-2.28 (m, 1H), 1.95-1.82 (m, 2H), 1.42 (s, 6H), 1.09 (d, 3H), 1.01-0.87 (m, 1H), 0.51-0.38 (m, 1H)), 0.29-0.12 (m, 1H)), 0.07-0.02 (m, 2H); LCMS m/z (ESI)=450.1[M+1].

Example 15

N-((5-(1-cyclobutylethyl)-2,3-dihydro-1H-inden-4-yl)carbamoyl)-4-(2-hydroxypropan-2-yl)furan-2-sulfonamide (Compound 15)

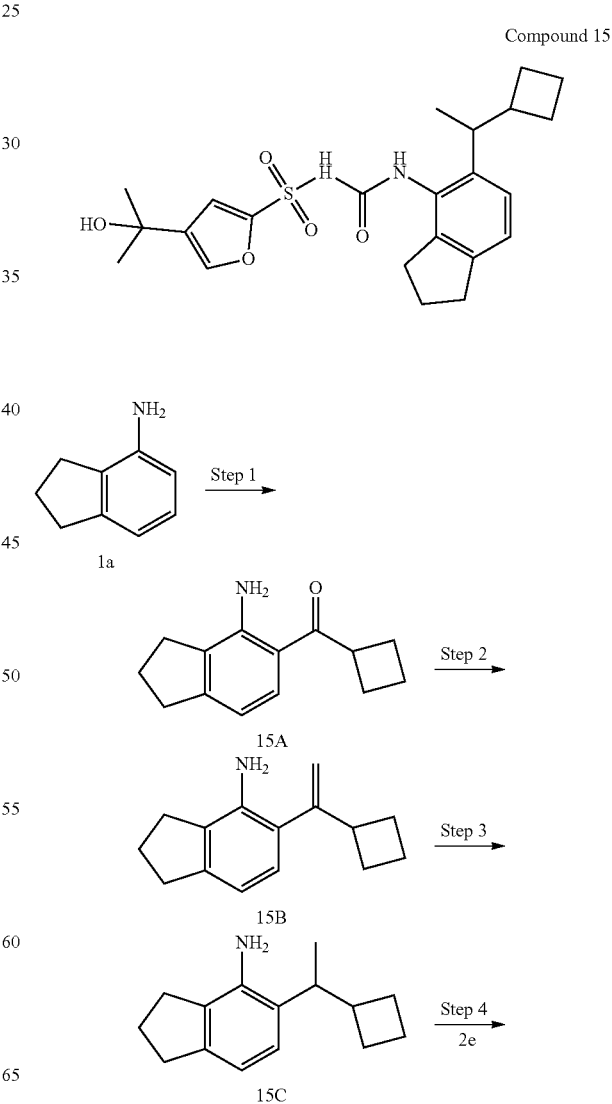

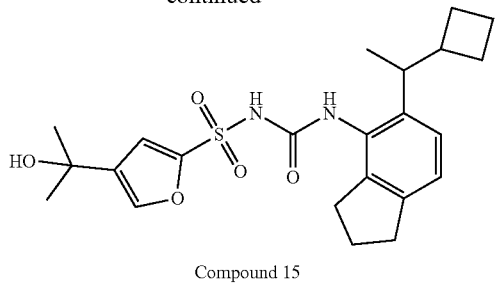

Compound 15

Step 1

(4-amino-2,3-dihydro-1H-inden-5-yl)(cyclobutyl)methanone (15A)

Compound 1a (5.0 g, 37.54 mmol) was dissolved in 1,2-dichloroethane (50 mL) in a 500 mL three-necked flask under nitrogen atmosphere, and the solution was cooled to 0° C. in an ice salt bath. A solution of boron trichloride (37.5 mL, 1 M, 37.54 mmol) in dichloromethane was then added dropwise slowly, and the temperature was maintained and the resulting solution was reacted for 10 min after the dropwise addition was completed. Aluminum trichloride (5.5 g, 41.3 mmol) and cyclobutyl cyanide (4.5 g, 56.3 mmol) were then added, and the reaction system was warmed to 80° C., reacted for 4 h and then cooled to room temperature. 2 M HCl (40 mL) was added in an ice bath, and the resulting reaction system was warmed to reflux and reacted for 1 h. After the reaction was completed, the reaction system was cooled to room temperature and extracted with DCM (75 mL×3). The organic phase was washed with 2 M NaOH solution (40 mL), dried over anhydrous sodium sulfate and filtered, and the organic solvent was removed under reduced pressure. The residue was purified by column chromatography (petroleum ether:ethyl acetate=20:1) to give compound 15A in the form of a white solid (2.6 g, 32.2% yield).

$^1$H NMR (400 MHz, CDCl$_3$) δ=7.45 (d, 1H), 6.56 (d, 1H), 4.00-3.96 (m, 1H), 2.91 (t, 2H), 2.70 (t, 2H), 2.44-2.3 (m, 2H), 2.25 (m, 2H), 2.14-2.08 (m, 2H), 2.07-2.00 (m, 1H), 1.90-1.81 (m, 1H); LCMS m/z (ESI)=216.1[M+1].

Step 2

5-(1-cyclobutylvinyl)-2,3-dihydro-1H-inden-4-amine (15B)

Compound methyl triphenyl phosphonium bromide (4.0 g, 11.2 mmol) was dissolved in THF (30 mL) in a 100 mL three-necked flask under nitrogen atmosphere, and the solution was cooled to 0° C. in an ice salt bath. Potassium tert-butoxide (1.3 g, 11.2 mmol) was added slowly, and the temperature was maintained and the reaction system was reacted for 30 min. Compound 15A (1.6 g, 7.43 mmol) was added, and the resulting reaction system was reacted at room temperature for 4 h. After the reaction was completed, water was added to quench the reaction, and EA (50 mL×3) was added for extraction. The organic phase was dried over anhydrous sodium sulfate and filtered, and the organic solvent was removed under reduced pressure. The residue was purified by column chromatography (petroleum ether:ethyl acetate=30:1) to give compound 15B in the form of a pale yellow oil (1.3 g, 82.0% yield).

$^1$H NMR (400 MHz, CDCl$_3$) δ=6.80 (d, 1H), 6.66 (d, 1H), 5.27 (t, 1H), 5.07 (t, 1H), 3.29-1.24 (m, 1H), 2.92 (t, 2H), 2.74 (t, 2H), 2.16-2.06 (m, 3H), 2.04-1.96 (m, 2H), 1.94-1.88 (m, 1H), 1.87-1.80 (m, 1H), 1.75-1.68 (m, 1H); LCMS m/z (ESI)=214.1[M+1].

Step 3

5-(1-cyclobutylethyl)-2,3-dihydro-1H-inden-4-amine (15C)

Compound 15B (1.3 g, 6.10 mmol) was dissolved in methanol (20 mL) in a 50 mL round-bottomed flask, and then the catalyst Pd/C (70 mg) was added. The reaction system was stirred at room temperature for three hours under hydrogen atmosphere. After the reaction was completed, the reaction system was filtered with celite, and the filtrate was concentrated under reduced pressure to remove the organic solvent. The residue was purified by column chromatography (petroleum ether:ethyl acetate=10:1) to give compound 15C in the form of a pale yellow oil (1.0 g, 76.2% yield).

$^1$H NMR (400 MHz, CDCl$_3$) δ=6.86 (d, 1H), 6.68 (d, 1H), 2.90 (t, 2H), 2.74 (t, 2H), 2.69-2.59 (m, 2H), 2.18-2.08 (m, 3H), 1.98-1.90 (m, 1H), 1.85-1.72 (m, 3H), 1.61-1.55 (m, 1H), 1.11 (d, 3H); LCMS m/z (ESI)=216.2[M+1].

Step 4

N-((5-(1-cyclobutylethyl)-2,3-dihydro-1H-inden-4-yl)carbamoyl)-4-(2-hydroxypropan-2-yl)furan-2-sulfonamide (Compound 15)

Compound 15C (200 mg, 0.93 mmol), triethylamine (112 mg, 1.12 mmol) and tetrahydrofuran (10 mL) were added successively into a 100 mL round-bottomed flask under nitrogen atmosphere, and then triphosgene (110 mg, 0.37 mmol) was added in an ice bath. The reaction system was warmed to reflux, reacted for 2 h, and then filtered to remove the solids. 2e (190 mg, 0.93 mmol) and sodium methoxide (100 mg, 1.86 mmol) were added to the filtrate, and the mixture was reacted at room temperature for 2 h. After the reaction was completed as detected by TLC, water (20 mL) was added to quench the reaction, and DCM (30 mL×3) was added for extraction. The organic phase was dried over anhydrous sodium sulfate and filtered, and the organic solvent was removed. The crude product was purified by preparative medium pressure liquid chromatography to give compound 15 in the form of a yellow solid (100 mg, 24.1% yield).

$^1$H NMR (400 MHz, DMSO-d6) δ=7.54 (s, 1H), 7.36 (d, 1H), 6.91 (d, 1H), 6.83 (d, 1H), 6.60 (s, 1H), 4.91 (s, 1H), 2.98-2.94 (m, 1H), 2.79-2.75 (t, 2H), 2.68-2.63 (m, 2H), 2.45-2.41 (m, 1H), 2.05-2.02 (m, 1H), 1.90-1.86 (m, 2H), 1.78-1.59 (m, 4H), 1.49-1.46 (m, 1H), 1.34 (s, 6H), 0.96 (d, 3H); LCMS m/z (ESI)=447.2[M+1].

Example 16

N-((5-(1-cyclobutylethyl)-2,3-dihydro-1H-inden-4-yl)carbamoyl)-4-(2-hydroxypropan-2-yl)furan-2-sulfonimidamide (Compound 16)

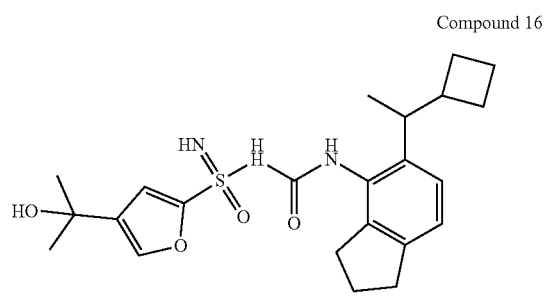

Compound 16

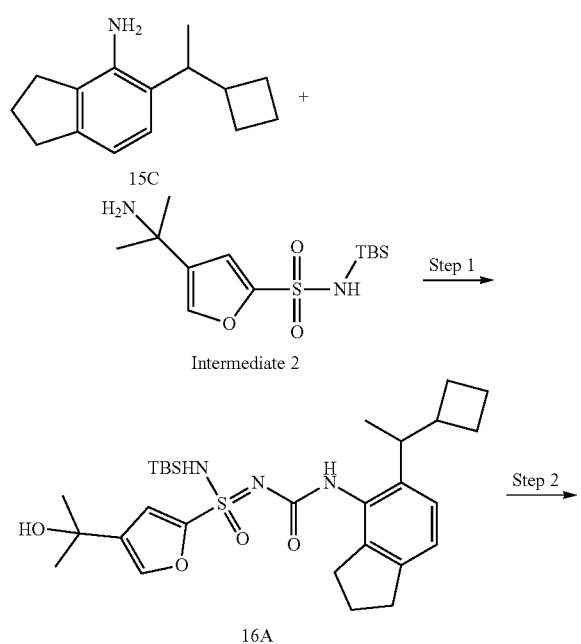

Step 1

N-(tert-butyldimethylsilyl)-N-((5-(1-cyclobutylethyl)-2,3-dihydro-1H-inden-4-yl)carbamoyl)-4-(2-hydroxypropan-2-yl)furan-2-sulfonimidamide (16A)

Compound 15C (200 mg, 0.93 mmol), triethylamine (112 mg, 1.12 mmol) and tetrahydrofuran (10 mL) were added successively into a 100 mL round-bottomed flask under nitrogen atmosphere, and then triphosgene (110 mg, 0.37 mmol) was added in an ice bath. The reaction system was warmed to reflux, reacted for 2 h, and then filtered to remove the solids. Intermediate 2 (296 mg, 0.93 mmol) and sodium methoxide (100 mg, 1.86 mmol) were added to the filtrate, and the mixture was reacted at room temperature for 12 h. After the reaction was completed as detected by TLC, water (50 mL) was added to quench the reaction, and DCM (30 mL×3) was added for extraction. The organic phase was dried over anhydrous sodium sulfate and filtered, and the organic solvent was removed. The crude product was purified by thin layer chromatography to give Compound 16A in the form of a pale yellow oily solid (320 mg, 61.5% yield).

LCMS m/z (ESI)=560.3[M+1].

Step 2

N-((5-(1-cyclobutylethyl)-2,3-dihydro-1H-inden-4-yl)carbamoyl)-4-(2-hydroxypropan-2-yl)furan-2-sulfonimidamide (Compound 16)

Compound 16A (320 mg, 0.57 mmol) and THF (10 mL) were added successively into a 100 mL round-bottomed flask under nitrogen atmosphere, and then the reaction system was cooled to 0° C. in an ice bath. Tetrabutylammonium fluoride (1.14 mL, 1 M in THF, 1.14 mmol) was then added dropwise slowly, and the reaction system was warmed to room temperature and reacted for 2 h after the dropwise addition was completed. After the reaction was completed, water was added to quench the reaction, and EA (30 mL×3) was added for extraction. The organic phase was dried over anhydrous sodium sulfate and filtered, and the solvent was removed under reduced pressure. The residue was purified by preparative medium pressure liquid chromatography to give compound 16 in the form of a white solid (100 mg, 43.8% yield).

$^1$H NMR (400 MHz, DMSO-d6) δ=8.33 (s, 1H), 7.66 (s, 1H), 7.65 (br, 2H), 6.98 (d, 2H), 6.88 (d, 1H), 5.09 (br, 1H), 2.92-2.88 (m, 1H), 2.82-2.78 (t, 2H), 2.66-2.63 (m, 2H), 2.45-2.40 (m, 1H), 2.07-2.05 (m, 1H), 1.93-1.90 (m, 2H), 1.69-1.59 (m, 4H), 1.47-1.42 (m, 1H), 1.34 (s, 6H), 0.96 (d, 3H); LCMS m/z (ESI)=446.2[M+1].

Example 17

N-((5-(cyclobutylmethyl)-2,3-dihydro-1H-inden-4-yl)carbamoyl)-4-(2-hydroxypropan-2-yl)furan-2-sulfonamide (Compound 17)

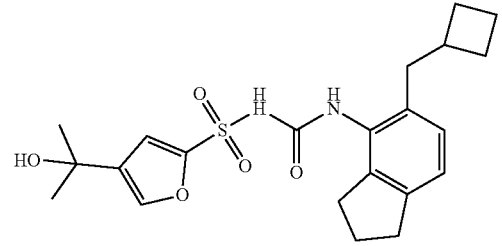

Compound 17

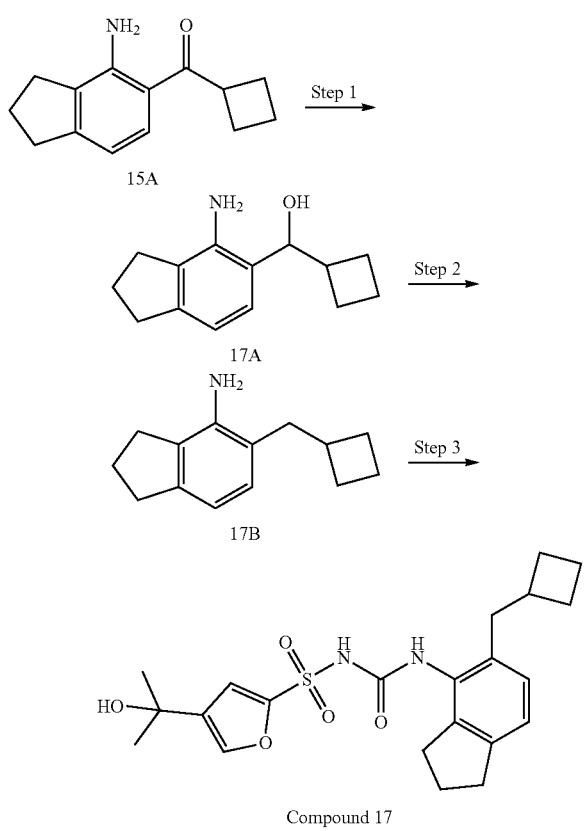

Step 1

(4-amino-2,3-dihydro-1H-inden-5-yl)(cyclobutyl)methanol (17A)

Ethanol (20 mL) and compound 15A (2.0 g, 9.30 mmol) were added into a 50 mL round-bottomed flask under nitrogen atmosphere, and then the reaction system was cooled to 0° C. in an ice bath. Sodium borohydride (703 mg, 18.60 mmol) was then added slowly, and the reaction system was warmed to room temperature and reacted for 1 h after the addition was completed. After the reaction was completed, the reaction system was cooled to 0° C., water (20 mL) was added dropwise to quench the reaction, and DCM (30 mL×3) was added for extraction. The organic phase was dried over anhydrous sodium sulfate and filtered, and the filtrate was concentrated under reduced pressure to remove the solvent. The crude product was purified by column chromatography (petroleum ether:ethyl acetate=1:1) to give compound 17A in the form of a colorless oil (1.8 g, 89% yield).

LCMS m/z (ESI)=200.1[M−17].

Step 2

5-(cyclobutylmethyl)-2,3-dihydro-1H-inden-4-amine (17B)

Compound 17A (1.3 g, 5.98 mmol) and triethylsilane (2.1 g, 17.94 mmol) were dissolved in DCM (20 mL) under nitrogen atmosphere, and then the solution was cooled to 0° C. in an ice bath. Trifluoroacetic acid (3.5 g, 29.90 mmol) was then added dropwise slowly, and the reaction system was reacted overnight at room temperature after the addition was completed. After the reaction was completed, saturated aqueous sodium bicarbonate was added to quench the reaction, and DCM (50 mL×3) was added for extraction. The organic phase was dried over anhydrous sodium sulfate and filtered, and the organic solvent was removed under reduced pressure. The residue was purified by column chromatography (petroleum ether:ethyl acetate=20:1) to give compound 17B in the form of a colorless oil (1.0 g, 83.1% yield).

$^1$H NMR (400 MHz, CDCl$_3$) δ=6.83 (d, 1H), 6.66 (d, 1H), 2.89 (t, 2H), 2.74 (t, 2H), 2.66-2.62 (m, 1H), 2.59 (d, 2H), 2.13-2.07 (m, 4H), 1.88-1.83 (m, 2H), 1.77-1.70 (m, 2H); LCMS m/z (ESI)=201.1[M+1].

Step 3

N-((5-(cyclobutylmethyl)-2,3-dihydro-1H-inden-4-yl)carbamoyl)-4-(2-hydroxypropan-2-yl)furan-2-sulfonamide (Compound 17)

Compound 17B (201 mg, 1.00 mmol), triethylamine (121 mg, 1.20 mmol) and tetrahydrofuran (10 mL) were added successively into a 100 mL round-bottomed flask under nitrogen atmosphere, and then triphosgene (103 mg, 0.40 mmol) was added in an ice bath. The reaction system was warmed to reflux, reacted for 2 h, and then filtered to remove the solids. 2e (205 mg, 1.00 mmol) and sodium methoxide (108 mg, 2.00 mmol) were added to the filtrate, and the mixture was reacted at room temperature for 12 h. After the reaction was completed as detected by TLC, water (100 mL) was added to quench the reaction, and dichloromethane (30 mL×3) was added for extraction. The organic phase was dried over anhydrous sodium sulfate and filtered, and the organic solvent was removed. The residue was purified by preparative medium pressure liquid chromatography to give compound 17 in the form of a yellow solid (70 mg, 16.2% yield).

$^1$H NMR (400 MHz, DMSO-d6) δ=7.47 (s, 1H), 7.36 (s, 1H), 6.86 (d, 1H), 6.80 (d, 1H), 6.56 (d, 1H), 4.91 (s, 1H), 2.77 (t, 2H), 2.66 (t, 2H), 2.58 (d, 2H), 2.48-2.44 (m, 1H), 1.92-1.89 (m, 2H), 1.88-1.85 (m, 2H), 1.78-1.74 (m, 2H), 1.65-1.58 (m, 2H), 1.34 (s, 6H); LCMS m/z (ESI)=433.2 [M+1].

Example 18

$R_S$- and $S_S$-N-((5-(cyclobutylmethyl)-2,3-dihydro-1H-inden-4-yl)carbamoyl)-4-(2-hydroxypropan-2-yl)furan-2-sulfonimidamide (Compounds 18-1 and 18-2)

Compounds 18-1 and 18-2

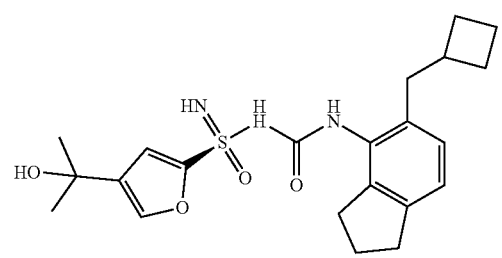

103

-continued

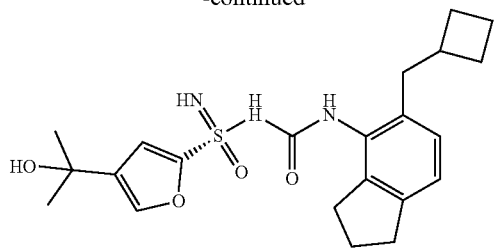

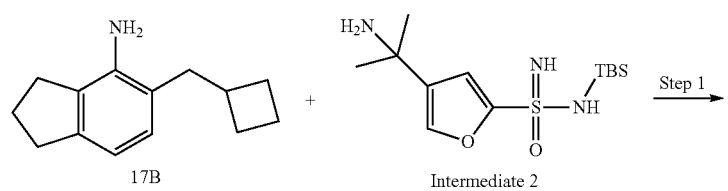

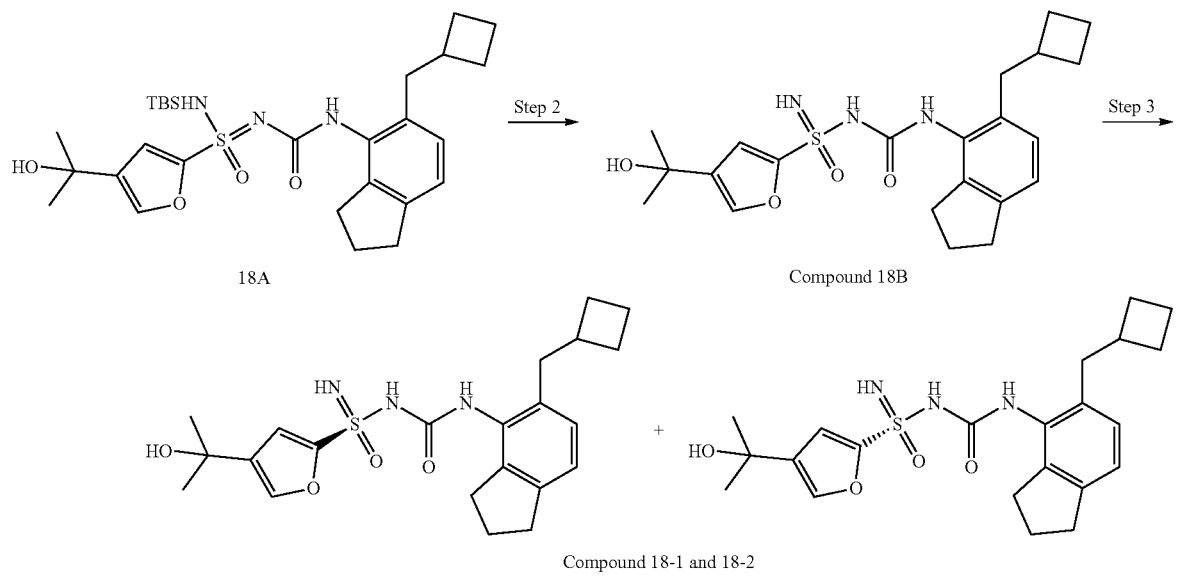

Step 1

N-(tert-butyldimethylsilyl)-N-((5-(cyclobutylmethyl)-2,3-dihydro-1H-inden-4-yl)carbamoyl)-4-(2-hydroxypropan-2-yl)furan-2-sulfonimidamide (18A)

17B (1.5 g, 7.46 mmol), triethylamine (11.02 g, 8.95 mmol) and tetrahydrofuran (10 mL) were added successively into a 100 mL round-bottomed flask under nitrogen atmosphere, and then triphosgene (882 mg, 2.98 mmol) was added in an ice bath. The reaction system was warmed to reflux, reacted for 2 h, and then filtered to remove the solids. Intermediate 2 (2.4 g, 7.46 mmol) and sodium methoxide (806 mg, 14.9 mmol) were added to the filtrate, and the mixture was reacted at room temperature for 12 h. After the reaction was completed as detected by TLC, water (50 mL) was added to quench the reaction, and DCM (100 mL×3) was added for extraction. The organic phase was dried over anhydrous sodium sulfate and filtered, and the organic solvent was removed to give 18A, which was directly used in the next step without purification.

LCMS m/z (ESI)=546.3[M+1].

104

Step 2

N-((5-(cyclobutylmethyl)-2,3-dihydro-1H-inden-4-yl)carbamoyl)-4-(2-hydroxypropan-2-yl)furan-2-sulfonimidamide (Compound 18B)

Tetrabutylammonium fluoride (15 mL, 1 M in THF, 15 mmol) was added dropwise into the reaction system from the previous step under nitrogen atmosphere, and the resulting reaction system was warmed to room temperature and reacted for 2 h after the dropwise addition was completed. After the reaction was completed, water was added to quench the reaction, and ethyl acetate (30 mL×3) was added for extraction. The organic phase was dried over anhydrous sodium sulfate and filtered, and the solvent was removed under reduced pressure. The residue was purified by preparative medium pressure liquid chromatography to give compound 18B in the form of a white solid (1.43 g, 44.0% yield).

LCMS m/z (ESI)=432.2[M+1].

Step 3

$R_S$- and $S_S$-N-((5-(cyclobutylmethyl)-2,3-dihydro-1H-inden-4-yl)carbamoyl)-4-(2-hydroxypropan-2-yl)furan-2-sulfonimidamide (Compounds 18-1 and 18-2)

18B was resolved by SFC to give compound 18-1 (670 mg, ee %: 99.68%, chiral HPLC (OX-3); mobile phase:

methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=15.062 min) and compound 18-2 (680 mg, ee %: 99.45%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=10.896 min).

Compound 18-1: $^1$H NMR (400 MHz, DMSO-d6) δ=8.30 (s, 1H), 7.69 (d, 1H), 7.68 (s, 2H), 6.98 (s, 1H), 6.95 (d, 1H), 6.86 (d, 1H), 5.09 (s, 1H), 2.80 (t, 2H), 2.66 (d, 2H), 2.58 (d, 2H), 2.00-1.84 (m, 4H), 1.83-1.70 (m, 2H), 1.63 (dd, 2H), 1.38 (s, 6H); LCMS m/z (ESI)=432.2[M+1].

Compound 18-2: $^1$H NMR (400 MHz, DMSO-d6) δ=8.30 (s, 1H), 7.69 (d, 1H), 7.67 (s, 2H), 6.99 (s, 1H), 6.95 (d, 1H), 6.86 (d, 1H), 5.10 (s, 1H), 2.80 (t, 2H), 2.66 (d, 2H), 2.58 (d, 2H), 2.00-1.84 (m, 4H), 1.83-1.70 (m, 2H), 1.63 (dd, 2H), 1.38 (s, 6H); LCMS m/z (ESI)=432.2[M+1].

Example 19

$R_S$- and $S_S$-N-((5-(cyclobutylmethyl)-2,3-dihydro-1H-inden-4-yl)carbamoyl)-2-(2-hydroxypropan-2-yl)thiazole-5-sulfonimidamide (Compounds 19-1 and 19-2)

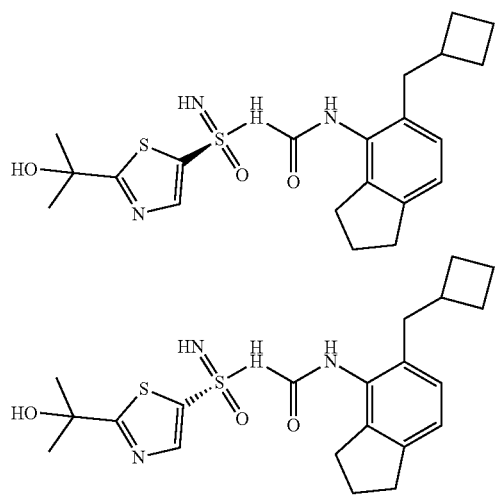

Compounds 19-1 and 19-2

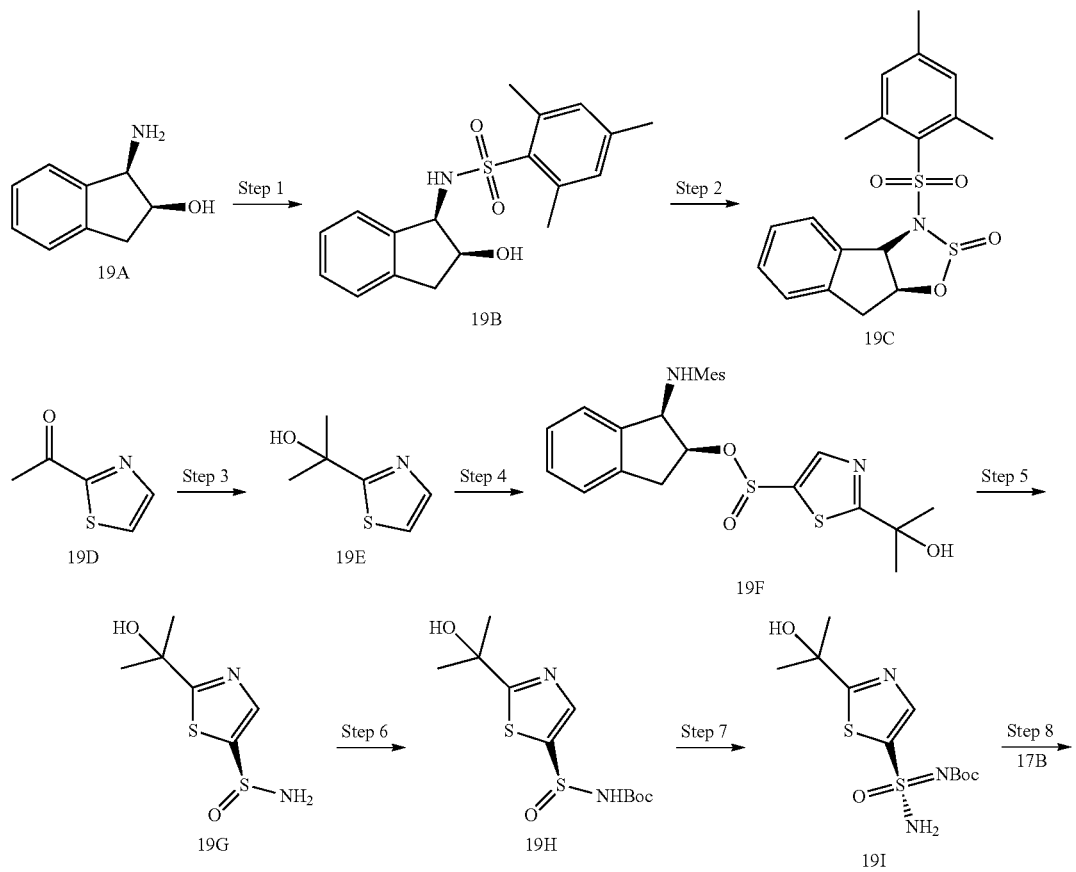

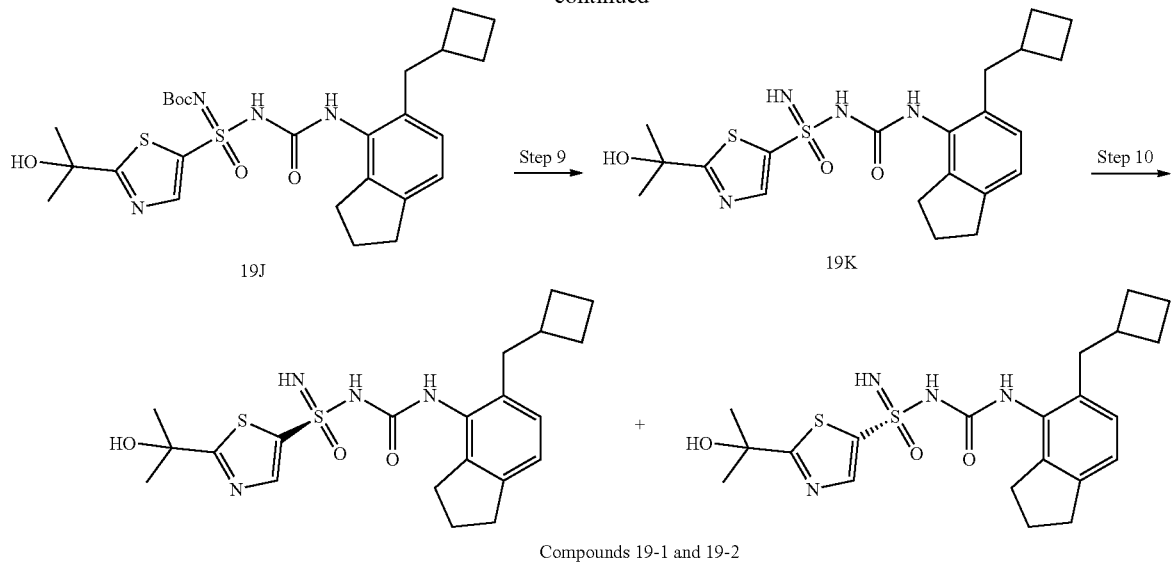

Compounds 19-1 and 19-2

Step 1

N-((1R,2S)-2-hydroxy-2,3-dihydro-1H-inden-1-yl)-2,4,6-trimethylbenzenesulfonamide (19B)

Sodium bicarbonate (28.2 g, 33.5 mmol) was dissolved in a mixed solvent of $H_2O$/THF/EA (1:2:5, 100:200:250 mL) in a 500 mL three-necked flask under nitrogen atmosphere, and the solution was cooled to 0° C. in an ice bath. Compound 19A (25.0 g, 16.76 mmol) was added with stirring, and the temperature was maintained and the reaction system was reacted for 10 min. 2,4,6-trimethylbenzenesulfonyl chloride (36.7 g, 16.76 mmol) was added, and the reaction system was slowly warmed to room temperature and reacted for 6 h. After the reaction was completed as detected by TLC, the reaction system was poured into water, 1 M HCl was added to adjust the pH to weak acidity, and ethyl acetate (200 mL×3) was added for extraction. The organic phase was dried over anhydrous sodium sulfate and filtered, and the organic solvent was removed under reduced pressure. The crude product was purified by slurring with petroleum ether to give compound 19B in the form of a white solid (26.4 g, 59% yield).
LCMS m/z (ESI)=314.1[M+1].

Step 2

(3aS,8aS)-3-(mesitylsulfonyl)-3,3a,8,8a-tetrahydroindeno[1,2-d][1,2,3]oxathiazole 2-oxide (19C)

19B (16.3 g, 4.92 mmol) and THF (300 mL) were added into a 500 mL three-necked flask, and the reaction system was cooled to −45° C. Thionyl chloride (7.3 g, 8.80 mmol) was added dropwise slowly, and the temperature was maintained and the reaction system was reacted for 30 min after the addition was completed. 2,4,6-trimethylpyridine (6.0 g, 9.84 mmol) was then added dropwise slowly. After the dropwise addition was completed, the reaction system was warmed to room temperature slowly and reacted overnight. After the reaction was completed as detected by TLC, the reaction system was poured into ice saturated sodium bicarbonate solution to quench the reaction, and extracted with ethyl acetate (300 mL×3). The solvent was removed by concentration under reduced pressure, and the residue was slurried with petroleum ether to give the crude product, which was slurried with ice acetonitrile to give compound 19C in the form of a white solid (16.7 g, 90.2% yield).
LCMS m/z (ESI)=378.1[M+1].

Step 3

2-(thiazol-2-yl)propan-2-ol (19E)

19D (30.0 g, 23.60 mmol) was dissolved in tetrahydrofuran (300 mL) in a 500 mL three-necked flask, and the solution was cooled to −78° C. A solution of methylmagnesium bromide (9.5 mL, 28.32 mmol, 3 M) in tetrahydrofuran was added dropwise slowly, and the temperature was maintained and the reaction system was reacted for 2 h after the dropwise addition was completed. After the reaction was completed as detected by TLC, saturated aqueous ammonium chloride solution was added to quench the reaction, and ethyl acetate (300 mL×3) was added for extraction. The solvent was removed by concentration under reduced pressure, and the residue was purified by column chromatography (petroleum ether:ethyl acetate=20:1-5:1) to give 19E in the form of a pale yellow oil (20 g, 58.8% yield).
LCMS m/z (ESI)=144.0 [M+1].

Step 4

(1R, 2S)-1-((2,4,6-trimethylphenyl)sulfonamido)-2,3-dihydro-1H-inden-2-yl (S)-2-(2-hydroxypropan-2-yl)thiazole-5-sulfinate (19F)

19E (15.0 g, 10.42 mmol) was dissolved in tetrahydrofuran (300 mL) in a 500 mL three-necked flask, and the solution was cooled to −78° C. Lithium diisopropylamide (11 mL, 20.83 mmol, 2 M) was added dropwise slowly, and the temperature was maintained and the reaction system was reacted for 1 h after the dropwise addition was completed. 1 h later, a solution of 19C (39.3 g, 10.42 mmol) in THF was added dropwise slowly, and the temperature was maintained and the reaction system was reacted for 3 h after the dropwise addition was completed. After the reaction was completed as detected by TLC, saturated aqueous ammonium chloride solution was added to quench the reaction, and ethyl acetate (200 mL×3) was added for extraction. The solvent was removed by concentration under reduced pressure, and the residue was purified by column chromatography (petroleum ether:ethyl acetate=20:1-3:1) to give 19F in the form of a pale yellow solid (25.0 g, 46.1% yield).

$^1$H NMR (400 MHz, CDCl$_3$) δ=7.23-7.15 (m, 3H), 7.11 (d, 1H), 7.00 (s, 2H), 5.40 (d, 1H), 4.63-4.59 (dd, 1H), 4.41-4.38 (m, 1H), 3.09-3.04 (dd, 1H), 2.90 (d, 1H), 2.71 (s, 6H), 2.23 (s, 3H); LCMS m/z (ESI)=521.1[M+1].

Step 5

(S)-2-(2-hydroxypropan-2-yl)thiazole-5-sulfinamide (19G)

19F (25 g, 4.81 mmol) was dissolved in THF (300 mL) in a 500 mL three-necked flask, and the solution was cooled to −78° C. A solution of lithium bis(trimethylsilyl)amide (5 mL, 14.42 mmol, 3 M) in THF was added dropwise slowly, and the temperature was maintained and the reaction system was reacted for 1 h after the dropwise addition was completed. After the reaction was completed as detected by TLC, saturated aqueous ammonium chloride solution was added to quench the reaction, and ethyl acetate (200 mL×3) was added for extraction. The solvent was removed by concentration under reduced pressure, and the residue was purified by column chromatography (dichloromethane:methanol=20:1-15:1) to give 19G in the form of a pale yellow solid (8.5 g, 86.7% yield).

$^1$H NMR (400 MHz, DMSO-d6) δ=7.76 (s, 1H), 6.72 (br, 2H), 6.16 (s, 1H), 1.50 (s, 6H); LCMS m/z (ESI)=207.1[M+1].

Step 6

Tert-butyl (S)-((2-(2-hydroxypropan-2-yl)thiazol-5-yl)sulfinyl)carbamate (19H)

19G (8.0 g, 3.88 mmol) was dissolved in THF (100 mL) in a 250 mL three-necked flask, and the solution was cooled to 0° C. Potassium tert-butoxide (5.2 g, 4.67 mmol) was added slowly, and the temperature was maintained and the reaction system was reacted for 30 min after the addition was completed. A solution of di-tert-butyl dicarbonate (8.9 g, 4.07 mmol) in THF was then added dropwise slowly, and the reaction system was warmed to room temperature and reacted for 1 h after the dropwise addition was completed. After the reaction was completed as detected by TLC, water was added to quench the reaction, 1 M HCl was added to adjust the pH to neutrality, and ethyl acetate (100 mL×3) was added for extraction. The solvent was removed by concentration under reduced pressure, and the residue was purified by column chromatography (petroleum ether:ethyl acetate=2:1) to give 19H in the form of a pale yellow solid (8.8 g, 74%).

$^1$H NMR (400 MHz, DMSO-d6) δ=10.98 (s, 1H), 8.00 (s, 1H), 6.27 (s, 1H), 1.51 (d, 6H), 1.45 (s, 9H); LCMS m/z (ESI)=307.1[M+1].

Step 7

Tert-butyl (amino(2-(2-hydroxypropan-2-yl)thiazol-5-yl)(oxo)-λ$^6$-sulfanylidene)carbamate (19I)

19H (8.8 g, 2.64 mmol) was dissolved in tetrahydrofuran (100 mL) in a 250 mL three-necked flask, and the solution was cooled to 0° C. Trichloroisocyanuric acid (215 mg, 0.924 mmol) was added dropwise slowly, and the temperature was maintained and the reaction system was reacted for 10 min after the addition was completed. A solution of ammonia solution (10 mL, 7 M) was then added dropwise slowly, and the temperature was maintained and the reaction system was reacted for 3 h after the dropwise addition was completed. After the reaction was completed as detected by TLC, water was added to quench the reaction, 1 M HCl was added to adjust the pH to neutrality, and ethyl acetate (100 mL×3) was added for extraction. The solvent was removed by concentration under reduced pressure, and the residue was purified by column chromatography (petroleum ether: ethyl acetate=2:1 to dichloromethane:methanol=15:1) to give 19I in the form of a pale yellow solid (1.8 g, 19.6%).

$^1$H NMR (400 MHz, DMSO-d6) δ=8.04 (s, 1H), 8.03 (s, 1H), 6.33 (s, 1H), 5.76 (s, 1H), 1.51 (d, 6H), 1.28 (s, 9H); LCMS m/z (ESI)=322.1[M+1].

Step 8

Tert-butyl ((3-(5-(cyclobutylmethyl)-2,3-dihydro-1H-inden-4-yl)ureido)(2-(2-hydroxypropan-2-yl)thiazol-5-yl)(oxo)-λ$^6$-sulfanylidene)carbamate (Compound 19J)

Compound 17B (607 mg, 3.02 mmol), triethylamine (366 mg, 3.62 mmol) and tetrahydrofuran (20 mL) were added successively into a 100 mL round-bottomed flask under nitrogen atmosphere, and then triphosgene (61.7 mg, 0.21 mmol) was added in an ice bath. The reaction system was warmed to reflux, reacted for 2 h, and then filtered to remove the solids. Compound 19I (970 mg, 3.02 mmol) and sodium methoxide (327 mg, 6.04 mmol) were added to the filtrate, and the mixture was reacted at room temperature for 2 h. After the reaction was completed as detected by TLC, water (20 mL) was added to quench the reaction, and DCM (50 mL×3) was added for extraction. The organic phase was dried over anhydrous sodium sulfate and filtered, and the organic solvent was removed to give the crude product compound 19J, which was directly used in the next step without purification.

Step 9

N-((5-(cyclobutylmethyl)-2,3-dihydro-1H-inden-4-yl)carbamoyl)-2-(2-hydroxypropan-2-yl)thiazole-5-sulfonimidamide (Compound 19K)

The crude product from the previous step was dissolved in DCM (30 mL) in a 250 mL round-bottomed flask, and then trifluoroacetic acid (3 mL) was added dropwise in an ice bath. After the dropwise addition was completed, the reaction system was reacted at room temperature for 1.5 h. After the reaction was completed as detected by TLC, the reaction system was poured into ice aqueous sodium bicarbonate solution, and DCM (30 mL×3) was added for extraction. The organic phase was dried over anhydrous sodium sulfate and filtered, and the organic solvent was removed under reduced pressure. The crude product was purified by thin layer chromatography (dichloromethane:methanol=15:1) to give 19K in the form of a white solid (201 mg, 14.1% yield).

LCMS m/z=449.2[M+1].

111
Step 10

R$_S$- and S$_S$-N-((5-(cyclobutylmethyl)-2,3-dihydro-1H-inden-4-yl)carbamoyl)-2-(2-hydroxypropan-2-yl)thiazole-5-sulfonimidamide (Compounds 19-1 and 19-2)

19K was resolved by SFC to give compound 19-1 (98 mg, ee %: 99.90%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=9.566 min) and compound 19-2 (85 mg, ee %: 99.38%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=11.442 min).

Compound 19-1: $^1$H NMR (400 MHz, DMSO-d6) δ=8.30 (s, 1H), 8.04 (s, 1H), 7.80 (s, 2H), 6.92 (d, 2H), 6.26 (s, 1H), 2.89-2.82 (m, 2H), 2.77-2.63 (m, 2H), 2.38-2.24 (m, 1H), 2.05-1.91 (m, 4H), 1.81-1.70 (m, 2H), 1.70-1.67 (m, 2H), 1.60-1.58 (m, 2H), 1.51 (s, 6H); LCMS m/z=449.2[M+1].

Compound 19-2: $^1$H NMR (400 MHz, DMSO-d6) δ=8.25 (s, 1H), 8.02 (s, 1H), 7.72 (br, 2H), 6.95 (d, 1H), 6.86 (d, 1H), 6.24 (s, H), 2.81 (t, 2H), 2.72-2.64 (m, 2H), 2.61-2.55 (m, 2H), 2.38-2.28 (m, 1H), 1.91-1.89 (m, 4H), 1.80-1.69 (m, 2H), 1.61-1.58 (m, 2H), 1.50 (s, 6H); LCMS m/z=449.2 [M+1].

112
Example 20

(R$_S$, S$_C$)- and (S$_S$, S$_C$)-N-((5-(1-cyclopropylethyl)-2,3-dihydro-1H-inden-4-yl)carbamoyl)-2-(2-hydroxypropan-2-yl)thiazole-5-sulfonimidamide (Compounds 20-1 and 20-2)

Compounds 20-1 and 20-2

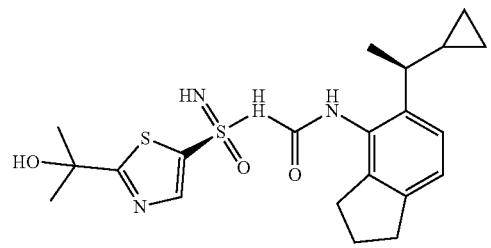

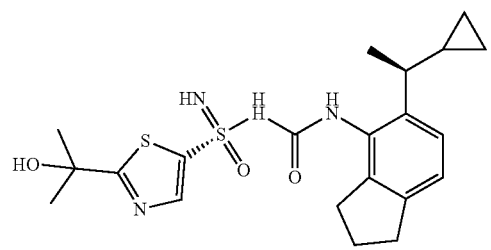

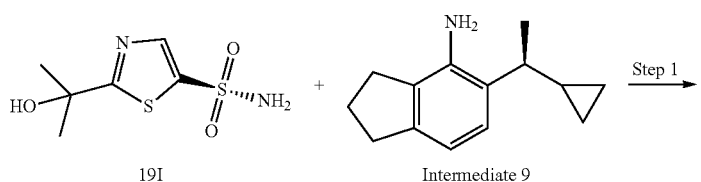

19I + Intermediate 9 → Step 1

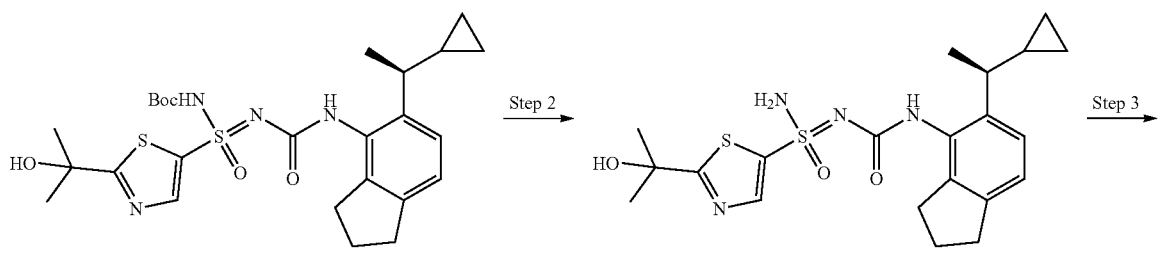

20A → Step 2 → 20B → Step 3

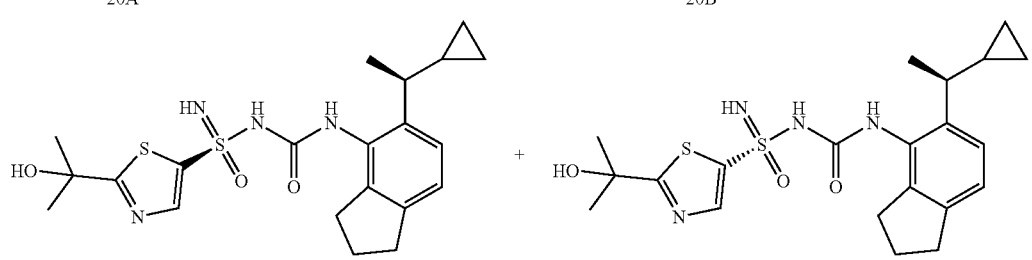

Compounds 20-1 and 20-2

Step 1

Tert-butyl (N-((5-((S)-1-cyclopropylethyl)-2,3-dihydro-1H-inden-4-yl)carbamoyl)-2-(2-hydroxypropan-2-yl)thiazole-5-sulfonimidoyl)carbamate (Compound 20A)

Intermediate 9 (289 mg, 1.44 mmol), triethylamine (175 mg, 1.73 mmol) and tetrahydrofuran (20 mL) were added successively into a 100 mL round-bottomed flask under nitrogen atmosphere, and then triphosgene (171 mg, 0.58 mmol) was added in an ice bath. The reaction system was warmed to reflux, reacted for 2 h, and then filtered to remove the solids. Compound 19I (462 mg, 1.44 mmol) and sodium methoxide (156 mg, 2.88 mmol) were added to the filtrate, and the mixture was reacted at room temperature for 2 h. After the reaction was completed as detected by TLC, water (20 mL) was added to quench the reaction, and DCM (50 mL×3) was added for extraction. The organic phase was dried over anhydrous sodium sulfate and filtered, and the organic solvent was removed to give the crude product compound 20A, which was directly used in the next step without purification.

Step 2

N-((5-((S)-1-cyclopropylethyl)-2,3-dihydro-1H-inden-4-yl)carbamoyl)-2-(2-hydroxypropan-2-yl)thiazole-5-sulfonimidamide (Compound 20B)

The crude product from the previous step was dissolved in DCM (30 mL) in a 250 mL round-bottomed flask, and then TFA (3 mL) was added dropwise in an ice bath. After the dropwise addition was completed, the reaction system was reacted at room temperature for 1.5 h. After the reaction was completed as detected by TLC, the reaction system was poured into ice aqueous sodium bicarbonate solution, and DCM (30 mL×3) was added for extraction. The organic phase was dried over anhydrous sodium sulfate and filtered, and the organic solvent was removed under reduced pressure. The crude product was purified by thin layer chromatography (dichloromethane:methanol=15:1) to give 20B in the form of a white solid (272 mg, 42.1% yield).

Step 3

($R_S$, $S_C$)- and ($S_S$, $S_C$)-N-((5-(1-cyclopropylethyl)-2,3-dihydro-1H-inden-4-yl)carbamoyl)-2-(2-hydroxypropan-2-yl)thiazole-5-sulfonimidamide (Compounds 20-1 and 20-2)

20B was resolved by SFC to give compound 20-1 (161 mg, ee %: 99.90%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=5.420 min) and compound 20-2 (89 mg, ee %: 97.76%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=8.16 min).

Compound 20-1: $^1$H NMR (400 MHz, DMSO-d6) δ=8.30 (s, 1H), 8.04 (s, 1H), 7.80 (s, 2H), 6.92 (d, 2H), 6.26 (s, 1H), 2.89-2.82 (m, 2H), 2.77-2.63 (m, 2H), 2.38-2.24 (m, 1H), 2.05-1.91 (m, 4H), 1.81-1.70 (m, 2H), 1.70-1.67 (m, 2H), 1.60-1.58 (m, 2H), 1.51 (s, 6H); LCMS m/z=449.2[M+1].

Compound 20-2: $^1$H NMR (400 MHz, DMSO-d6) δ=8.25 (s, 1H), 8.02 (s, 1H), 7.72 (br, 2H), 6.95 (d, 1H), 6.86 (d, 1H), 6.24 (s, H), 2.81 (t, 2H), 2.72-2.64 (m, 2H), 2.61-2.55 (m, 2H), 2.38-2.28 (m, 1H), 1.91-1.89 (m, 4H), 1.80-1.69 (m, 2H), 1.61-1.58 (m, 2H), 1.50 (s, 6H); LCMS m/z=449.2 [M+1].

Example 21

$R_S$- and $S_S$-N-((5-(cyclobutylmethyl)-2,3-dihydro-1H-inden-4-yl)carbamoyl)-4-(2-hydroxypropan-2-yl)-5-methylfuran-2-sulfonimidamide (Compounds 21-1 and 21-2)

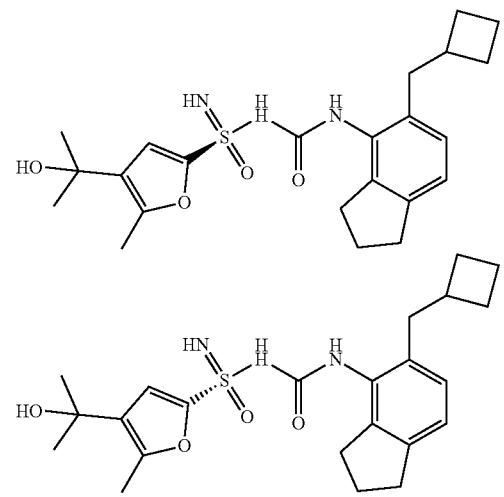

Compounds 21-1 and 21-2

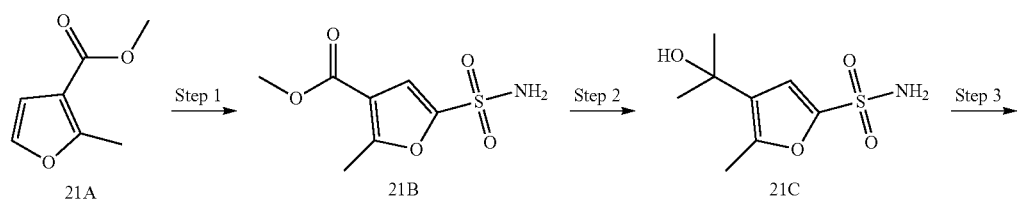

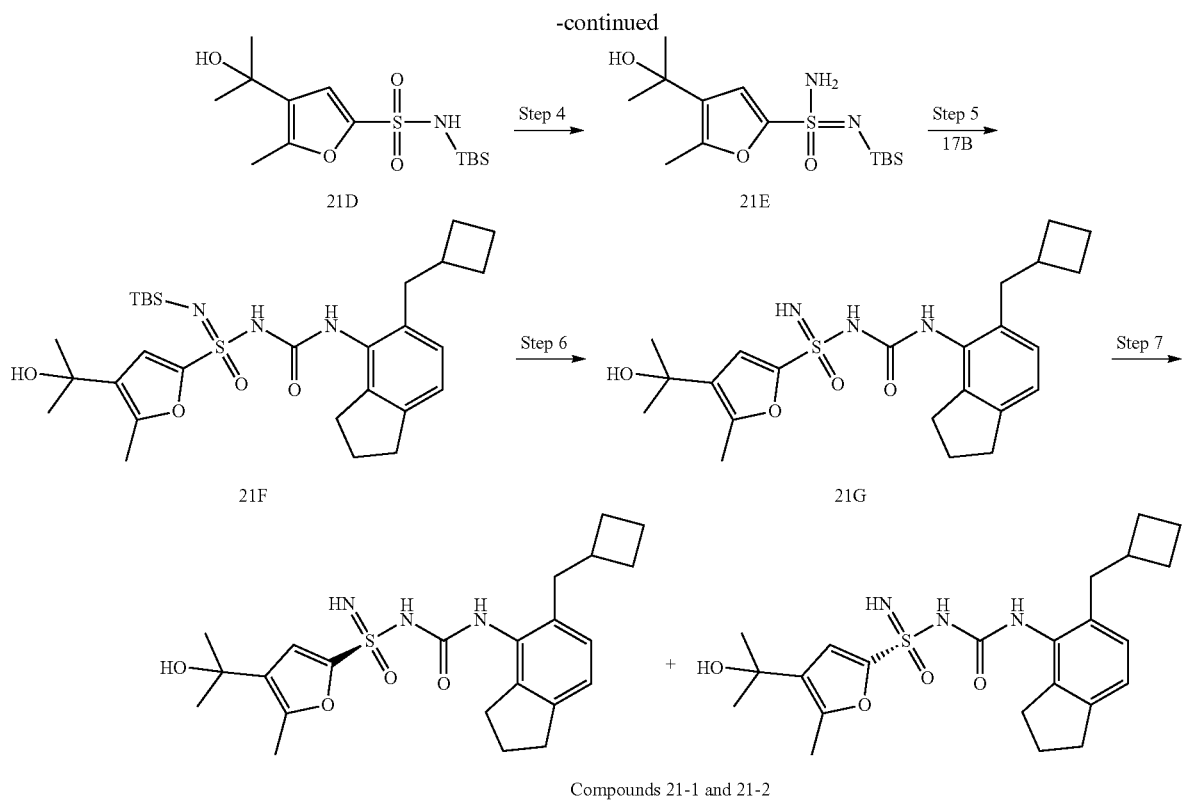

Compounds 21-1 and 21-2

Step 1

Methyl 2-methyl-5-sulfamoylfuran-3-carboxylate (21B)

Compound 21A (40 g, 285.43 mmol) was dissolved in DCM (300 mL) in a 500 mL three-necked flask, and the solution was cooled to −10° C. under nitrogen atmosphere. Chlorosulfonic acid (21 mL, 313.98 mmol) was added dropwise slowly, and the reaction system was stirred at room temperature until the starting material 21A was completely consumed. The reaction system was then cooled to −15° C., and pyridine (26 mL, 313.98 mmol) was added dropwise slowly. The temperature was maintained at −15° C., and phosphorus pentachloride (47.6 g, 228.35 mmol) was added in batches. After no starting material was left as detected by TLC, the reaction system was poured into ice water (500 mL) to quench the reaction, and extracted with ethyl acetate (500 mL×3). The organic phases were combined, washed once with saturated brine, dried over anhydrous sodium sulfate, and concentrated under reduced pressure to remove the solvent to give the crude product, which was directly used in the next step without purification. The crude product was dissolved in acetone (400 mL), and saturated aqueous ammonium bicarbonate solution (80 g, 1.01 mol) was added slowly. After the addition was completed, the reaction system was reacted at room temperature. After the reaction was completed as detected by TLC, ice water (300 mL) was added to quench the reaction, and EA (300 mL×3) was added for extraction. The organic phases were combined, washed once with saturated brine, dried over anhydrous sodium sulfate, and concentrated under reduced pressure to remove the solvent. The residue was purified by column chromatography (petroleum ether:ethyl acetate=1:2) to give compound 21B in the form of a white solid (31.2 g, 49.86% yield).

$^1$H NMR (400 MHz, DMSO-$d_6$) δ=7.88 (s, 2H), 7.02 (s, 1H), 3.79 (s, 3H), 2.61 (s, 3H).

LCMS m/z (ESI)=220.0[M+1].

Step 2

4-(2-hydroxypropan-2-yl)-5-methylfuran-2-sulfonamide (21C)

21B (31.2 g, 142.33 mmol) was dissolved in THF (300 mL) in a 500 mL three-necked flask under nitrogen atmosphere, and the solution was cooled to −15° C. Methylmagnesium bromide (150 mL, 455.45 mmol, 3.0 mol/L) was added dropwise slowly, and the reaction system was stirred overnight at room temperature after the dropwise addition was completed. After 21B disappeared as detected by TLC, ammonium chloride (200 mL) was added to quench the reaction, and EA (300 mL×3) was added for extraction. The organic phases were combined, washed once with saturated brine, dried over anhydrous sodium sulfate, and concentrated under reduced pressure to remove the solvent. The residue was purified by column chromatography (ethyl acetate:petroleum ether=1:10-1:3) to give compound 21C in the form of a pale yellow oil (27 g, 86.52% yield).

$^1$H NMR (400 MHz, DMSO-$d_6$) δ=7.56 (s, 2H), 6.80 (s, 1H), 5.00 (s, 1H), 2.40 (s, 3H), 1.38 (s, 6H); LCMS m/z (ESI)=202.1[M−17].

Step 3

N-(tert-butyldimethylsilyl)-4-(2-hydroxypropan-2-yl)-5-methylfuran-2-sulfonamide (21D)

21C (20.0 g, 91.32 mmol) was dissolved in tetrahydrofuran (300 mL) in a 500 mL three-necked flask under nitrogen atmosphere, and the solution was cooled to −10° C. in an ice salt bath. Sodium hydride (7.3 g, 182.44 mmol) was added in batches, and the reaction system was stirred at room temperature for 30 min after the addition was completed. A solution of tert-butyldimethylchlorosilane (20.6 g, 136.83 mmol) in tetrahydrofuran (30 mL) was then added dropwise slowly at this temperature, and the reaction system was reacted at −10° C. for 3 h. After the reaction was completed, water was added to quench the reaction, 2 M HCl was added to adjust the pH to weak acidity, and ethyl acetate (200 mL×3) was added for extraction. The organic phases were combined, dried over anhydrous sodium sulfate, and concentrated under reduced pressure, and the residue was purified by column chromatography (ethyl acetate:petroleum ether=1:3) to give 21D in the form of a white solid (15.0 g, 49.31% yield).

$^1$H NMR (400 MHz, DMSO-$d_6$) δ=7.74 (s, 1H), 6.76 (s, 1H), 5.00 (s, 1H), 2.39 (s, 3H), 1.38 (s, 6H), 0.88 (s, 9H), 0.15 (s, 6H); LCMS m/z (ESI)=334.1[M+1].

Step 4

N-(tert-butyldimethylsilyl)-4-(2-hydroxypropan-2-yl)-5-methylfuran-2-sulfonimidamide (21E)

Triphenylphosphine (8.65 g, 32.98 mmol) and hexachloroethane (8.52 g, 35.98 mmol) were dissolved in chloroform (120 mL) in a 500 mL three-necked flask under nitrogen atmosphere, and the solution was warmed to reflux, reacted for 1 h, and cooled to −10° C. Diisopropylethylamine (6 g, 46.47 mmol) was added dropwise slowly, and the reaction system was reacted at this temperature for 10 min after the dropwise addition was completed. A solution of 21D (10 g, 29.98 mmol) in chloroform was then added dropwise slowly, and the reaction system was reacted for 30 min after the dropwise addition was completed. Ammonia gas was introduced for 1 h at this temperature. After the reaction was completed as detected by TLC, water was added to quench the reaction, and DCM (120 mL×3) was added for extraction. The organic phases were combined, dried over anhydrous sodium sulfate, and concentrated under reduced pressure, and the residue was purified by column chromatography (ethyl acetate:petroleum ether (v/v)=1:5) to give the product compound 21E in the form of a white solid (3 g, 30% yield).

$^1$H NMR (400 MHz, DMSO-$d_6$) δ 6.81 (s, 2H), 6.61 (s, 1H), 4.99 (s, 1H), 2.41 (s, 3H), 1.41 (s, 6H), 0.89 (s, 9H), 0.01 (d, 6H); LCMS m/z (ESI)=333.1[M+1].

Step 5

N'-(tert-butyldimethylsilyl)-N-((5-(cyclobutylmethyl)-2,3-dihydro-1H-inden-4-yl)carbamoyl)-4-(2-hydroxypropan-2-yl)-5-methylfuran-2-sulfonimidamide (21F)

Compound 17B (800 mg, 3.97 mmol), triethylamine (482.56 mg, 4.77 mmol) and tetrahydrofuran (100 mL) were added successively into a 100 mL round-bottomed flask under nitrogen atmosphere, and then triphosgene (471.67 mg, 1.59 mmol) was added in an ice bath. The reaction system was warmed to reflux, reacted for 2 h, and then filtered to remove the solids. Compound 21E (1.32 g, 3.97 mmol) and sodium methoxide (257.64 mg, 4.77 mmol) were added to the filtrate, and the mixture was reacted at room temperature for 12 h. After the reaction was completed as detected by TLC, compound 21F was obtained and was directly used in the next step without purification.

LCMS m/z (ESI)=560.3 [M+1].

Step 6

R- and S-N-((5-(cyclobutylmethyl)-2,3-dihydro-1H-inden-4-yl)carbamoyl)-4-(2-hydroxypropan-2-yl)-5-methylfuran-2-sulfonimidamide (21G)

Tetrabutylammonium fluoride (5.2 mL, 51.7 mmol, 1 M/THF) was added to the reaction system from the previous step, and the resulting reaction system was reacted overnight at room temperature. After the reaction was completed as detected by TLC, the reaction system was poured into water and extracted with ethyl acetate (100 mL×3). The organic phases were combined, washed once with 1 M diluted HCl, dried over anhydrous sodium sulfate and filtered, and the organic solvent was removed under reduced pressure. The residue was purified by preparative medium pressure liquid chromatography (acetonitrile/water=50%) to give 21G in the form of a transparent solid (180 mg, 10% yield).

LCMS m/z (ESI)=446.2[M+1].

Step 7

$R_S$- and $S_S$-N-((5-(cyclobutylmethyl)-2,3-dihydro-1H-inden-4-yl)carbamoyl)-4-(2-hydroxypropan-2-yl)-5-methylfuran-2-sulfonimidamide (Compounds 21-1 and 21-2)

21G was resolved by SFC to give compound 21-1 (75 mg, ee %: 99.99%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=13.716 min) and compound 21-2 (70 mg, ee %: 99.99%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=16.660 min).

Compound 21-1: $^1$H NMR (400 MHz, DMSO-d6) δ=8.28 (s, 1H), 7.58 (s, 2H), 6.95 (d, 1H), 6.90-6.81 (m, 2H), 5.03 (s, 1H), 2.81 (dd, 2H), 2.71-2.62 (m, 3H), 2.59 (d, 2H), 2.41 (s, 3H), 1.96-1.87 (m, 4H), 1.82-1.73 (m, 2H), 1.67-1.57 (m, 2H), 1.38 (s, 6H); LCMS m/z (ESI)=446.2[M+1].

Compound 21-2: $^1$H NMR (400 MHz, DMSO-d6) δ=8.28 (s, 1H), 7.58 (s, 2H), 6.95 (d, 1H), 6.90-6.80 (m, 2H), 5.03 (s, 1H), 2.81 (dd, 2H), 2.71-2.62 (m, 3H), 2.59 (d, 2H), 2.41 (s, 3H), 1.96-1.86 (m, 4H), 1.82-1.73 (m, 2H), 1.67-1.57 (m, 2H), 1.38 (s, 6H); LCMS m/z (ESI)=446.2[M+1].

Example 22

(R)-N-((5-(1-cyclopropylethyl)-2,3-dihydro-1H-inden-4-yl)carbamoyl)-4-(2-hydroxypropan-2-yl)-5-methylfuran-2-sulfonamide (Compound 22)

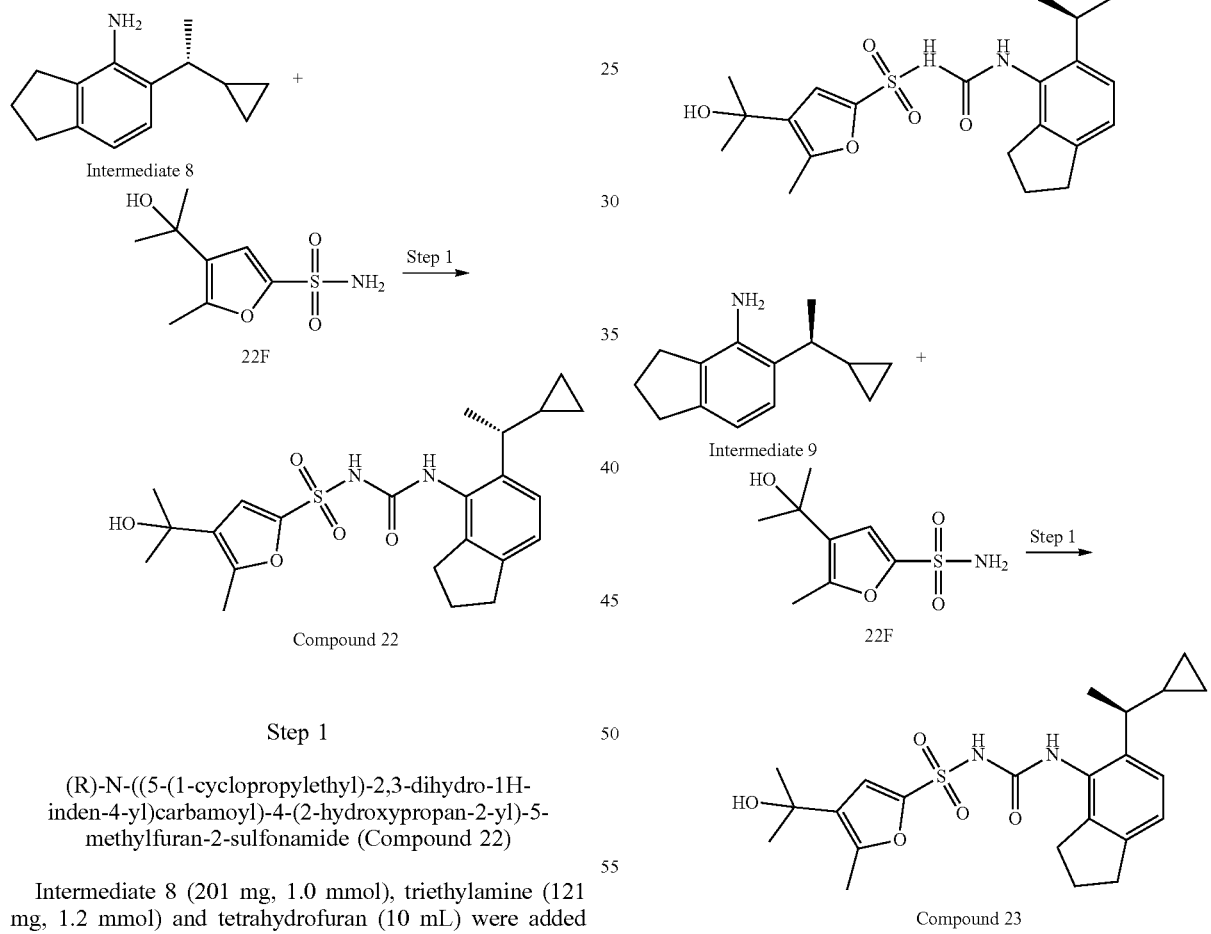

Step 1

(R)-N-((5-(1-cyclopropylethyl)-2,3-dihydro-1H-inden-4-yl)carbamoyl)-4-(2-hydroxypropan-2-yl)-5-methylfuran-2-sulfonamide (Compound 22)

Intermediate 8 (201 mg, 1.0 mmol), triethylamine (121 mg, 1.2 mmol) and tetrahydrofuran (10 mL) were added successively into a 100 mL round-bottomed flask under nitrogen atmosphere, and then triphosgene (118.4 mg, 0.4 mmol) was added in an ice bath. The reaction system was warmed to reflux, reacted for 2 h, and then filtered to remove the solids. Compound 22F (218 mg, 1.0 mmol) and sodium methoxide (108 mg, 2.0 mmol) were added to the filtrate, and the mixture was reacted at room temperature for 12 h. After the reaction was completed as detected by TLC, water (100 mL) was added to quench the reaction, and DCM (30 mL×3) was added for extraction. The organic phase was dried over anhydrous sodium sulfate and filtered, and the organic solvent was removed. The residue was purified by preparative high pressure liquid chromatography to give compound 22 in the form of a white solid (120 mg, 26.9% yield).

$^1$H NMR (400 MHz, DMSO-d6) δ=7.80 (s, 1H), 7.55 (s, 1H), 7.14 (d, 1H), 7.07 (d, 1H) 4.99 (d, 1H), 2.82 (t, 2H), 2.59 (t, 2H), 2.40 (s, 3H), 2.18-2.13 (m, 1H), 1.96-1.90 (m, 2H), 1.37 (s, 6H), 1.11 (d, 3H), 0.96-0.90 (m, 1H), 0.50-0.41 (m, 1H), 0.23-0.18 (m, 1H), 0.10-0.06 (m, 1H), 0.06-0.01 (m, 1H); LCMS m/z=447.2[M+1].

Example 23

(S)-N-((5-(1-cyclopropylethyl)-2,3-dihydro-1H-inden-4-yl)carbamoyl)-4-(2-hydroxypropan-2-yl)-5-methylfuran-2-sulfonamide (Compound 23)

Step 1

(S)-N-((5-(1-cyclopropylethyl)-2,3-dihydro-1H-inden-4-yl)carbamoyl)-4-(2-hydroxypropan-2-yl)-5-methylfuran-2-sulfonamide (Compound 23)

Intermediate 9 (201 mg, 1.0 mmol), triethylamine (121 mg, 1.2 mmol) and tetrahydrofuran (10 mL) were added successively into a 100 mL round-bottomed flask under nitrogen atmosphere, and then triphosgene (118.4 mg, 0.4 mmol) was added in an ice bath. The reaction system was warmed to reflux, reacted for 2 h, and then filtered to remove the solids. Compound 22F (218 mg, 1.0 mmol) and sodium methoxide (108 mg, 2.0 mmol) were added to the filtrate, and the mixture was reacted at room temperature for 12 h. After the reaction was completed as detected by TLC, water (100 mL) was added to quench the reaction, and DCM (30 mL×3) was added for extraction. The organic phase was dried over anhydrous sodium sulfate and filtered, and the organic solvent was removed. The residue was purified by preparative high pressure liquid chromatography to give compound 23 in the form of a white solid (100 mg, 22.4% yield).

$^1$H NMR (400 MHz, DMSO-d6) δ=7.84 (s, 1H), 7.56 (s, 1H), 7.15 (d, 1H), 7.08 (d, 1H) 5.00 (d, 1H), 2.82 (t, 2H), 2.59 (t, 2H), 2.40 (s, 3H), 2.18-2.13 (m, 1H), 1.96-1.90 (m, 2H), 1.37 (s, 6H), 1.11 (d, 3H), 0.96-0.90 (m, 1H), 0.50-0.41 (m, 1H), 0.23-0.18 (m, 1H), 0.10-0.06 (m, 1H), 0.06-0.01 (m, 1H); LCMS m/z=447.2[M+1].

Example 24

R$_S$- and S$_S$-N-((5-(1-cyclopropylethyl)-2,3-dihydro-1H-inden-4-yl)carbamoyl)-4-(2-hydroxypropan-2-yl)-5-methylfuran-2-sulfonimidamide (Compounds 24-1 and 24-2)

Compounds 24-1 and 24-2

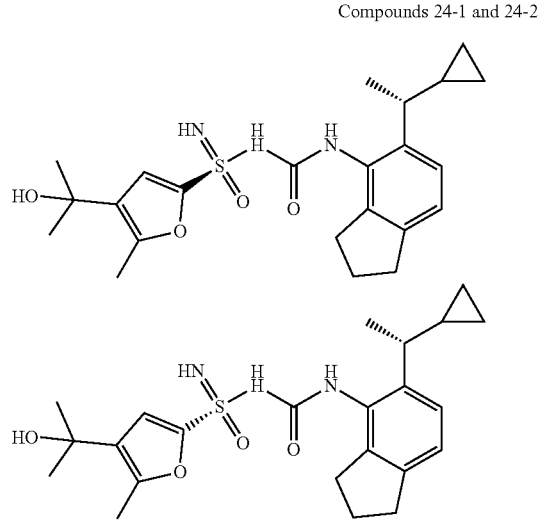

For preparation of compound 24-1 and compound 24-2, reference was made to preparation method of compounds 21-1 and 21-2. Compound 24-1 (310 mg, ee %: 99.5%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=6.453 min) and compound 24-2 (311 mg, ee %: 97.1%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=8.147 min).

Compound 24-1: $^1$H NMR (400 MHz, DMSO-d6) δ 8.21 (s, 1H), 7.55 (s, 2H), 7.12 (d, 1H), 7.04 (d, 1H), 6.83 (s, 1H), 5.00 (s, 1H), 2.82 (dd, 2H), 2.75-2.56 (m, 2H), 2.41 (s, 3H), 2.31-2.19 (m, 1H), 2.01-1.85 (m, 2H), 1.38 (s, 6H), 1.13-1.11 (m, 3H), 0.98-0.88 (m, 1H), 0.50-0.40 (m, 1H), 0.24-0.15 (m, 1H), 0.13-0.06 (m, 1H), 0.04-0.00 (m, 1H); LCMS m/z (ESI)=446.20[M+1].

Compound 24-2: $^1$H NMR (400 MHz, DMSO-d6) δ 8.21 (s, 1H), 7.56 (s, 2H), 7.13 (d, 1H), 7.04 (d, 1H), 6.82 (s, 1H), 5.00 (s, 1H), 2.82 (t, 2H), 2.75-2.56 (m, 2H), 2.40 (s, 3H), 2.31-2.19 (m, 1H), 1.97-1.89 (m, 2H), 1.38 (s, 6H), 1.11-1.06 (m, 3H), 0.98-0.92 (m, 1H), 0.50-0.40 (m, 1H), 0.24-0.15 (m, 1H), 0.13-0.06 (m, 1H), 0.04-0.00 (m, 1H); LCMS m/z (ESI)=446.20[M+1].

Example 25

(R$_S$, S$_C$)- and (S$_S$, S$_C$)-N-((5-(1-cyclopropylethyl)-2,3-dihydro-1H-inden-4-yl)carbamoyl)-4-(2-hydroxypropan-2-yl)-5-methylfuran-2-sulfonimidamide (Compounds 25-1 and 25-2)

Compounds 25-1 and 25-2

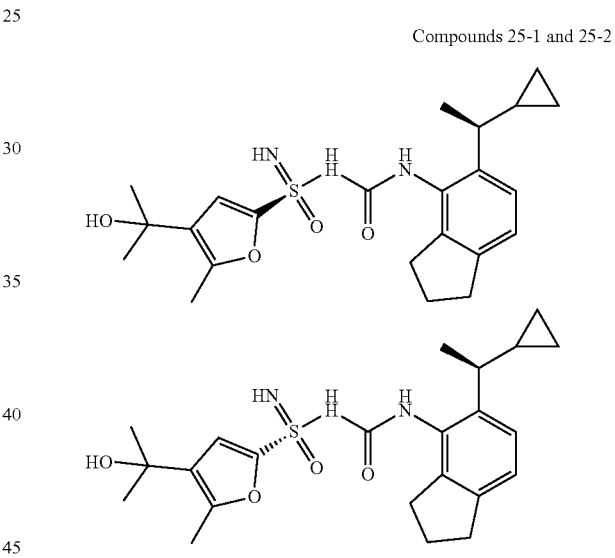

For preparation of compound 25-1 and compound 25-2, reference was made to preparation method of compounds 21-1 and 21-2. Compound 25-1 (290 mg, ee %: 100%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=10.626 min) and compound 25-2 (302 mg, ee %: 97.56%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=14.722 min).

Compound 25-1: $^1$H NMR (400 MHz, DMSO-d6) δ=8.23 (s, 1H), 7.56 (s, 2H), 7.12 (d, 1H), 7.03 (d, 1H), 6.82 (s, 1H), 5.01 (s, 1H), 2.82 (t, 2H), 2.75-2.59 (m, 2H), 2.39 (s, 3H), 2.30-2.18 (m, 1H), 1.93 (dd, 2H), 1.38 (s, 6H), 1.13-1.04 (m, 3H), 1.0-0.90 (m, 1H), 0.49-0.42 (m, 1H), 0.25-0.17 (m, 1H), 0.13-0.07 (m, 1H), 0.06-0.01 (m, 1H); LCMS m/z (ESI)=446.20[M+1].

Compound 25-2: $^1$H NMR (400 MHz, DMSO-d6) δ=8.23 (s, 1H), 7.57 (s, 2H), 7.13 (d, 1H), 7.04 (d, 1H), 6.83 (s, 1H), 5.02 (s, 1H), 2.82 (dd, 2H), 2.75-2.58 (m, 2H), 2.41 (s, 3H), 2.30-2.18 (m, 1H), 1.93 (dd, 2H), 1.38 (s, 6H), 1.13-1.07 (m, 3H), 1.0-0.90 (m, 1H), 0.47-0.43 (m, 1H), 0.25-0.17 (m, 1H), 0.14-0.08 (m, 1H), 0.07-0.01 (m, 1H); LCMS m/z (ESI)=446.20[M+1].

Example 26

(R)-N-((5-(1-cyclopentylethyl)-2,3-dihydro-1H-inden-4-yl)carbamoyl)-4-(2-hydroxypropan-2-yl)furan-2-sulfonamide (Compound 26)

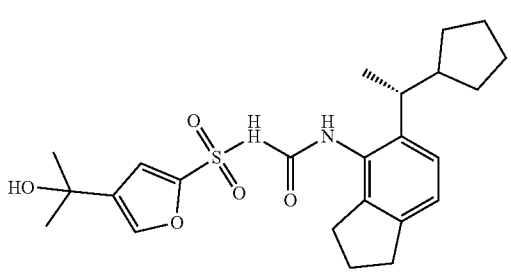

Compound 26

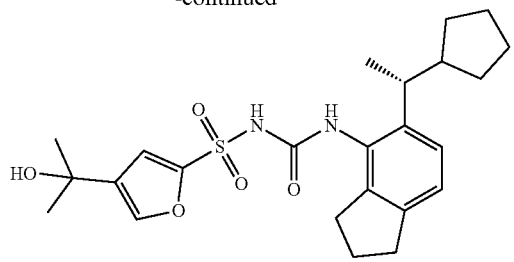

Compound 26

Step 1

(4-amino-2,3-dihydro-1H-inden-5-yl)(cyclopentyl)methanone (26A)

1a (23.0 g, 172.68 mmol) was dissolved in dichloroethane (300 mL) in a 500 mL three-necked flask, and the solution was cooled to −10° C. under nitrogen atmosphere. A solution of boron trichloride (210 mL, 210 mmol, 1 mol/L) in dichloromethane was added dropwise slowly, and the reaction system was reacted at −10° C. for 10 min after the dropwise addition was completed. Anhydrous aluminum chloride (27.6 g, 207.22 mmol) and cyclopentyl cyanide (24.7 g, 259.02 mmol) were added under nitrogen atmosphere, and the reaction system warmed to reflux, and reacted for 4-6 h after the addition was completed. The reaction system was cooled to room temperature, and then cooled to −10° C. in an ice salt bath. 1 M diluted HCl (210 mL) was added dropwise, and then the reaction system was warmed to reflux and reacted for 30 min after the dropwise addition was completed. After the reaction was completed as detected by TLC, the reaction system was cooled to room temperature, water (400 mL) was added to quench the reaction, and DCM (300 mL×3) was added for extraction. The organic phases were combined, dried over anhydrous sodium sulfate, and concentrated under reduced pressure to remove the organic solvent. The residue was purified by column chromatography (petroleum ether:ethyl acetate=10:1) to give 26A in the form of a pale yellow oil (31 g, 78.3% yield).

$^1$H NMR (400 MHz, DMSO-d$_6$) δ 7.66 (d, 1H), 6.96 (s, 2H), 6.50 (d, 1H), 3.78-3.70 (m, 1H), 2.82 (dd, 2H), 2.66 (dd, 2H), 2.05-1.94 (m, 2H), 1.88-1.77 (m, 2H), 1.76-1.65 (m, 2H), 1.63-1.53 (m, 4H); LCMS m/z (ESI)=230.2[M+1].

Step 2

5-(1-cyclopentylvinyl)-2,3-dihydro-1H-inden-4-amine (26B)

Methyl triphenyl phosphonium bromide (11.7 g, 32.70 mmol) was dissolved in THF (80 mL) in a 1 L three-necked flask under nitrogen atmosphere, and the solution was cooled to 0° C. in an ice bath. Potassium tert-butoxide (3.7 g, 32.70 mmol) was added, the temperature was maintained, and the reaction system was reacted for 1 h. 1 h 1 ater, a solution of 26A (5.0 g, 21.80 mmol) in THF was added dropwise at 0° C., an d the reaction system was reacted for 3 h at room temperature. After the reaction was completed as detected by TLC, water was added to quench the reaction, and EA (100 mL×3) was added for extraction. The organic phase was dried over anhydrous sodium sulfate and con-

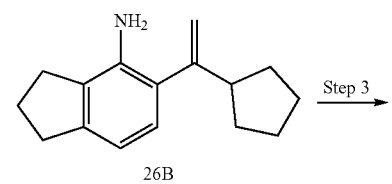

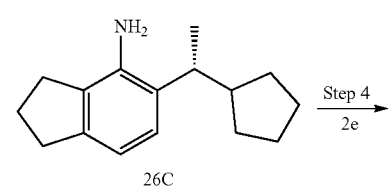

centrated under reduced pressure, and the residue was purified by column chromatography (petroleum ether:ethyl acetate=1:20) to give 26B in the for m of a pale yellow oil (4.2 g, 84.73% yield).

$^1$H NMR (400 MHz, DMSO-d$_6$) δ=6.64 (d, 1H), 6.45 (d, 1H), 5.21 (s, 1H), 4.85 (d, 1H), 4.31 (s, 2H), 2.77 (dd, 2H), 2.65 (dd, 2H), 2.02-1.94 (m, 3H), 1.74-1.66 (m, 2H), 1.65-1.54 (m, 2H), 1.55-1.47 (m, 2H), 1.42-1.34 (m, 2H); LCMS m/z (ESI)=228.1 [M+1].

Step 3

(R)-5-(1-cyclopentylethyl)-2,3-dihydro-1H-inden-4-amine (26C)

26B (2.1 g, 9.24 mmol) and dichloromethane (30 mL) were added into a 500 mL autoclave, and then a catalyst ruthenium [(R)-(−)-2,2'-bis(diphenylphosphino)-1,11-binaphthyl]diacetate (1.5 g, 1.83 mmol) was added. After the addition was completed, the autoclave was tightly closed and sealed, purged with nitrogen 3 times, and then purged with hydrogen 3 times. The hydrogen was introduced until the pressure gauge on the autoclave showed 12 atm, and then the reaction system was reacted for 30 h at room temperature. The reaction system was concentrated under reduced pressure to remove the solvent, and the residue was purified by silica gel column chromatography (petroleum ether/ethyl acetate=50:1) to give 26C in the form of a pale yellow oil (1.0 g, 47.17% yield).

$^1$H NMR (400 MHz, DMSO-d$_6$) δ=6.78 (d, 1H), 6.43 (d, 1H), 4.45 (s, 2H), 2.74 (t, 2H), 2.67-2.58 (m, 3H), 2.06-1.92 (m, 3H), 1.85-1.78 (m, 1H), 1.68-1.58 (m, 1H), 1.53-1.38 (m, 4H), 1.29-1.17 (m, 1H), 1.07 (d, 3H), 1.02-0.91 (m, 1H); LCMS m/z (ESI)=230.2[M+1].

Step 4

(R)-N-((5-(1-cyclopentylethyl)-2,3-dihydro-1H-inden-4-yl)carbamoyl)-4-(2-hydroxypropan-2-yl)furan-2-sulfonamide (Compound 26)

Compound 26C (200 mg, 0.872 mmol), triethylamine (106.0 mg, 1.05 mmol) and tetrahydrofuran (30 mL) were added successively into a 100 mL round-bottomed flask un der nitrogen atmosphere, and then triphosgene (104.0 mg, 0.349 mmol) was added in an ice bath. The reaction system was warmed to reflux, reacted for 2 h, and then filtered to remove the solids. 2e (179.0 mg, 0.872 mmol) and sodium methoxide (57.0 m g, 1.05 mmol) were added to the filtrate, and the mixture was reacted at room temperature for 12 h. After the reaction was completed as detected by TLC, water (100 mL) was added to quench the reaction, and DCM (30 mL×3) was added for extraction.

The organic phase was dried over anhydrous sodium sulfate and filtered, and the organic solvent was removed. The crude product was purified by preparative medium pressure liquid chromatography (acetonitrile/water=45%) to give compound 26 in the form of a white powdered solid (150 mg, 37.35% yield, ee %: 79%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=3.8 54 min).

$^1$H NMR (400 MHz, DMSO-d6) δ 7.95 (s, 1H), 7.78 (s, 1H), 7.22 (s, 1H), 7.08 (d, 1H), 7.02 (d, 1H), 5.11 (s, 1H), 2.82 (dd, 2H), 2.64-2.52 (m, 3H), 1.98-1.88 (m, 3H), 1.84-1.77 (m, 1H), 1.62-1.55 (m, 1H), 1.52-1.41 (m, 2H), 1.38 (s, 6H), 1.30-1.10 (m, 3H), 1.04 (d, 3H), 0.85-0.76 (m, 1H); LCMS m/z (ESI)=443.20[M+1].

Example 27

(S)-N-((5-(1-cyclopentylethyl)-2,3-dihydro-1H-inden-4-yl)carbamoyl)-4-(2-hydroxypropan-2-yl)furan-2-sulfonamide (Compound 27)

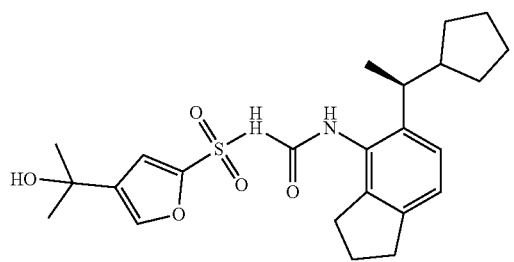

Compound 27

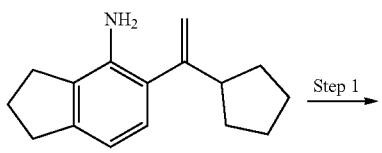

26B

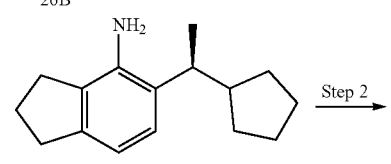

27A

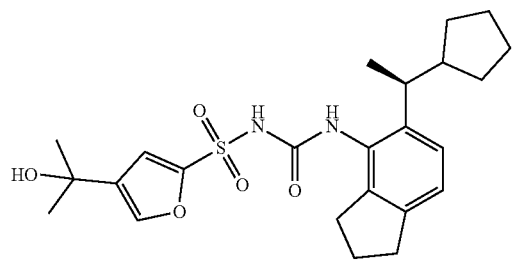

Compound 27

Step 1

(S)-5-(1-cyclopentylethyl)-2,3-dihydro-1H-inden-4-amine (27A)

26B (2.1 g, 9.24 mmol) and dichloromethane (30 mL) were added into a 500 mL autoclave, and then a catalyst ruthenium [(S)-(−)-2,2'-bis(diphenylphosphino)-1,11-binaphthyl]diacetate (1.5 g, 1.83 mmol) was added. After the addition was completed, the autoclave was tightly closed and sealed, purged with nitrogen 3 times, and then purged with hydrogen 3 times. The hydrogen was introduced until the pressure gauge on the autoclave showed 12 atm, and then the reaction system was reacted for 30 h at room temperature. The reaction system was concentrated under reduced pressure to remove the solvent, and the residue was purified by silica gel column chromatography (petroleum ether/ethyl acetate=50:1) to give compound 27A in the form of a pale yellow oil (1 g, 47.17% yield).

$^1$H NMR (400 MHz, DMSO-d$_6$) δ 6.78 (d, 1H), 6.43 (d, 1H), 4.45 (s, 2H), 2.74 (t, 2H), 2.67-2.58 (m, 3H), 2.06-1.92 (m, 3H), 1.85-1.78 (m, 1H), 1.68-1.58 (m, 1H), 1.5 3-1.38 (m, 4H), 1.29-1.17 (m, 1H), 1.07 (d, 3H), 1.02-0.91 (m, 1H); LCMS m/z (ES I)=230.2[M+1].

Step 2

(R)-N-((5-(1-cyclopentylethyl)-2,3-dihydro-1H-inden-4-yl)carbamoyl)-4-(2-hydroxypropan-2-yl)furan-2-sulfonamide (Compound 27)

Compound 27A (200 mg, 0.872 mmol), triethylamine (106.0 mg, 1.05 mmol) and tetrahydrofuran (30 mL) were added successively into a 100 mL round-bottomed flask un der nitrogen atmosphere, and then triphosgene (104.0 mg, 0.349 mmol) was added in an ice bath. The reaction system was warmed to reflux, reacted for 2 h, and then filtered to remove the solids. 2e (179.0 mg, 0.872 mmol) and sodium methoxide (57.0 m g, 1.05 mmol) were added to the filtrate, and the mixture was reacted at room temperature for 12 h. After the reaction was completed as detected by TLC, water (100 mL) was added to quench the reaction, and DCM (30 mL×3) was added for extraction.

The organic phase was dried over anhydrous sodium sulfate and filtered, and the organic solvent was removed. The crude product was purified by preparative medium pressure liquid chromatography (acetonitrile/water=45%) to give compound 27 in the form of a white powdered solid (145 mg, 36.1% yield, ee %: 77.8%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=5.005 min).

$^1$H NMR (400 MHz, DMSO-d6) δ=7.96 (s, 1H), 7.79 (d, 1H), 7.23 (d, 1H), 7.08 (d, 1H), 7.02 (d, 1H), 5.12 (s, 1H), 2.82 (t, 2H), 2.64-2.52 (m, 3H), 1.97-1.87 (m, 3H), 1.65-1.54 (m, 1H), 1.60 (dtd, 1H), 1.53-1.43 (m, 2H), 1.38 (s, 6H), 1.29-1.10 (m, 3H), 1.05 (d, 3H), 0.86-0.74 (m, 1H). LCMS m/z (ESI)=443.20[M+1].

Example 28

N-((5-(cyclopentylmethyl)-2,3-dihydro-1H-inden-4-yl)carbamoyl)-4-(2-hydroxypropan-2-yl)furan-2-sulfonamide (Compound 28)

Compound 28

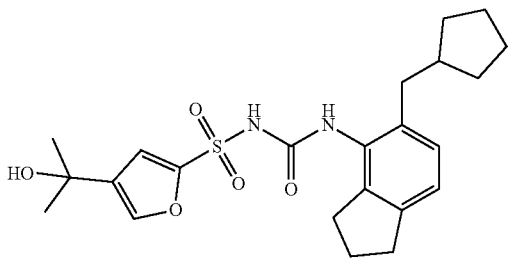

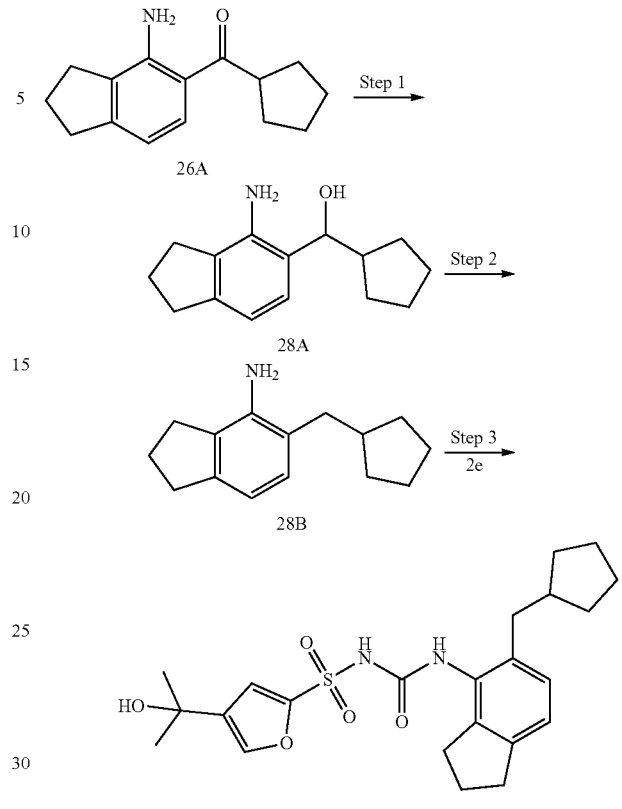

Compound 28

Step 1

(4-amino-2,3-dihydro-1H-inden-5-yl)(cyclopentyl)methanol (28A)

Compound 26A (5.0 g, 21.80 mmol) was dissolved in ethanol (80 mL) in a 250 mL three-necked flask, and sodium borohydride (3.5 g, 92.51 mmol) was added in an ice bath. The reaction system was reacted at room temperature for 4 h. After the reaction was completed as detected by TLC, water was added to quench the reaction, and the reaction system was filtered to give the crude product, which was slurried with ethyl acetate/petroleum ether (1:100) to give 28A (5 g, 99.13% yield).

LCMS m/z (ESI)=214.1 [M−17].

Step 2

5-(cyclopentylmethyl)-2,3-dihydro-1H-inden-4-amine (28B)

Compound 28A (5.0 g, 21.61 mmol) was dissolved in DCM (60 mL) in a 250 mL three-necked flask, and triethylsilane (12.6 g, 108.36 mmol) and trifluoroacetic acid (4.9 g, 49.99 mmol) were added in an ice bath. After the addition was completed, the reaction system was stirred overnight at room temperature. After the reaction was completed, the reaction system was poured into water, saturated sodium bicarbonate was added to adjust pH to neutrality, and DCM (30 mL×3) was added for extraction. The organic phases were combined, dried over anhydrous sodium sulfate and filtered, and the organic solvent was removed under reduced pressure. The residue was purified by column chromatography (ethyl acetate:petroleum ether=1:5) to give compound 28B (3.0 g, 64.46%).

LCMS m/z (ESI)=216.1[M+1].

Step 3

N-((5-(cyclopentylmethyl)-2,3-dihydro-1H-inden-4-yl)carbamoyl)-4-(2-hydroxypropan-2-yl)furan-2-sulfonamide (Compound 28)

28B (500 mg, 2.32 mmol), triethylamine (282.0 mg, 2.79 mmol) and tetrahydrofuran (30 mL) were added successively into a 100 mL round-bottomed flask under nitrogen atmosphere, and then triphosgene (276.0 mg, 0.929 mmol) was added in an ice bath. The reaction system was warmed to reflux, reacted for 2 h, and then filtered to remove the solids. 2e (1.48 g, 2.32 mmol) and sodium methoxide (151.0 mg, 2.79 mmol) were added to the filtrate, and the mixture was reacted at room temperature for 12 h. After the reaction was completed as detected by TLC, water (20 mL) was added to quench the reaction, and DCM (30 mL×3) was added for extraction. The organic phase was dried over anhydrous sodium sulfate and filtered, and the organic solvent was removed. The crude product was purified by preparative medium pressure liquid chromatography (acetonitrile/water=45%) to give compound 28 in the form of a white powdered solid (350 mg, 33.76% yield).

$^1$H NMR (400 MHz, DMSO-d$_6$) δ=7.81 (s, 1H), 7.63 (s, 1H), 6.98 (d, 2H), 6.92 (d, 1H), 5.04 (s, 1H), 2.81 (dd, 2H), 2.60 (dd, 2H), 2.45 (d, 2H), 1.98-1.84 (m, 3H), 1.62-1.50 (m, 4H), 1.47-1.39 (m, 2H), 1.37 (s, 6H), 1.15-1.04 (m, 2H); LCMS m/z (ESI)=429.1[M+1].

Example 29

(R)-N-((5-(1-cyclopropylethyl)-2,3-dihydro-1H-inden-4-yl-7-d)carbamoyl)-4-(2-hydroxypropan-2-yl)furan-2-sulfonamide (Compound 29)

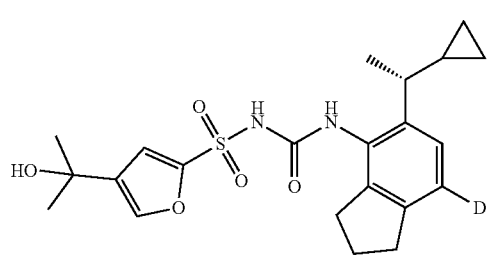

29

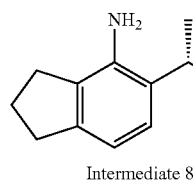

Intermediate 8

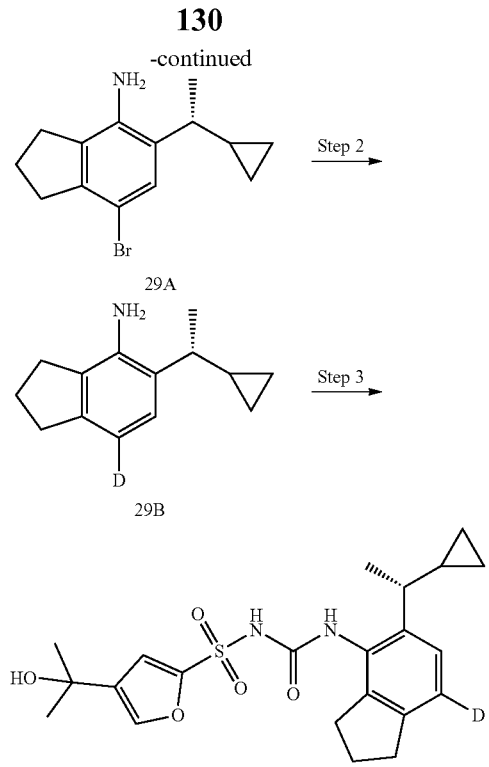

Step 1

(R)-7-bromo-5-(1-cyclopropylethyl)-2,3-dihydro-1H-inden-4-amine (29A)

Intermediate 8 (2.0 g, 9.95 mmol) and dichloromethane (50 mL) were added successively into a 100 mL round-bottomed flask under nitrogen atmosphere, and pyridinium tribromide (3.5 g, 10.9 mmol) was added slowly in an ice bath. After the addition was completed, the reaction system was warmed to room temperature and reacted for 1 h. After the reaction was completed, aqueous sodium sulfite solution was added into the reaction system to quench the reaction, and dichloromethane (50 mL×3) was added for extraction. The organic phase was dried over anhydrous sodium sulfate and filtered, and the organic solvent was removed under reduced pressure. The residue was purified by column chromatography (petroleum ether:ethyl acetate=50:1-20:1) to give compound 29A in the form of a pale yellow oil (2.7 g, 97% yield).

$^1$H NMR (400 MHz, DMSO-d6) δ=7.05 (s, 1H), 4.64 (s, 2H), 2.77-2.72 (m, 4H), 2.24-2.20 (m, 1H), 2.00-1.96 (m, 2H), 1.12 (d, 3H), 0.99-0.97 (m, 1H), 0.50-0.48 (m, 1H), 0.34-0.33 (m, 1H), 0.17-0.16 (m, 1H), 0.09-0.05 (m, 1H); LCMS m/z=281.2[M+1].

Step 2

(R)-5-(1-cyclopropylethyl)-2,3-dihydro-1H-inden-7-d-4-amine (29B)

29A (1.5 g, 5.4 mmol), deuterated sodium formate (0.75 g, 10.8 mmol), tris(dibenzylideneacetone)dipalladium (247 mg, 0.27 mmol), tri-tert-butylphosphine (109 mg, 0.54 mmol) and dimethyl sulfoxide (30 mL) were added successively into a 100 mL round-bottomed flask under nitrogen atmosphere, and the reaction system was warmed to 80° C. and reacted for 8 h. After the reaction was completed, the reaction system was cooled to room temperature, poured into water, and extracted with ethyl acetate (50 mL×3). The organic phase was dried over anhydrous sodium sulfate and filtered, and the organic solvent was removed under reduced pressure. The crude product was purified by column chromatography (petroleum ether:ethyl acetate=20:1) to give compound 29B in the form of a pale yellow solid (1 g, 85% yield).

$^1$H NMR (400 MHz, DMSO-d6) δ=6.92 (s, 1H), 4.43 (s, 1H), 2.74 (t, 2H), 2.60 (t, 2H), 2.25-2.21 (m, 1H), 1.99-1.92 (m, 2H), 1.13 (d, 3H), 1.10-0.96 (m, 1H), 0.49-0.44 (m, 1H), 0.33-0.28 (m, 1H), 0.15-0.10 (m, 1H), 0.04-0.01 (m, 1H); LCMS m/z=203.2[M+1].

Step 3

(R)-N-((5-(1-cyclopropylethyl)-2,3-dihydro-1H-inden-4-yl-7-d)carbamoyl)-4-(2-hydroxypropan-2-yl)furan-2-sulfonamide (Compound 29)

Compound 29B (201 mg, 1.0 mmol), triethylamine (121 mg, 1.2 mmol) and tetrahydrofuran (10 mL) were added successively into a 100 mL round-bottomed flask under nitrogen atmosphere, and then triphosgene (118.4 mg, 0.4 mmol) was added in an ice bath. The reaction system was warmed to reflux, reacted for 2 h, and then filtered to remove the solids. 2e (205 mg, 1.0 mmol) and sodium methoxide (108 mg, 2.0 mmol) were added to the filtrate, and the mixture was reacted at 60° C. for 2 h. After the reaction was completed as detected by TLC, water (100 mL) was added to quench the reaction, and ethyl acetate (30 mL×3) was added for extraction. The organic phase was dried over anhydrous sodium sulfate and filtered, and the organic solvent was removed. The crude product was purified by preparative high pressure liquid chromatography to give compound 29 in the form of a white solid (100 mg, 23.1% yield, ee %: 98.64%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=12.342 min).

$^1$H NMR (400 MHz, DMSO-d$_6$) δ=7.63 (s, 1H), 7.15 (s, 2H), 5.10 (s, 1H), 2.81 (t, 2H), 2.77 (t, 2H), 2.17-2.14 (m, 1H), 1.97-1.85 (m, 2H), 1.35 (s, 6H), 1.10 (d, 3H), 0.93 (m, 1H), 0.52-0.43 (m, 1H), 0.27-0.19 (m, 1H), 0.14-0.07 (m, 1H), 0.04-0.01 (m, 1H); LCMS m/z (ESI)=434.2 [M+1].

Example 30

(S)-N-((5-(1-cyclopropylethyl)-2,3-dihydro-1H-inden-4-yl-7-d)carbamoyl)-4-(2-hydroxypropan-2-yl)furan-2-sulfonamide (Compound 30)

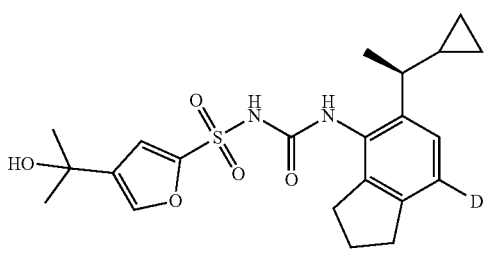

30

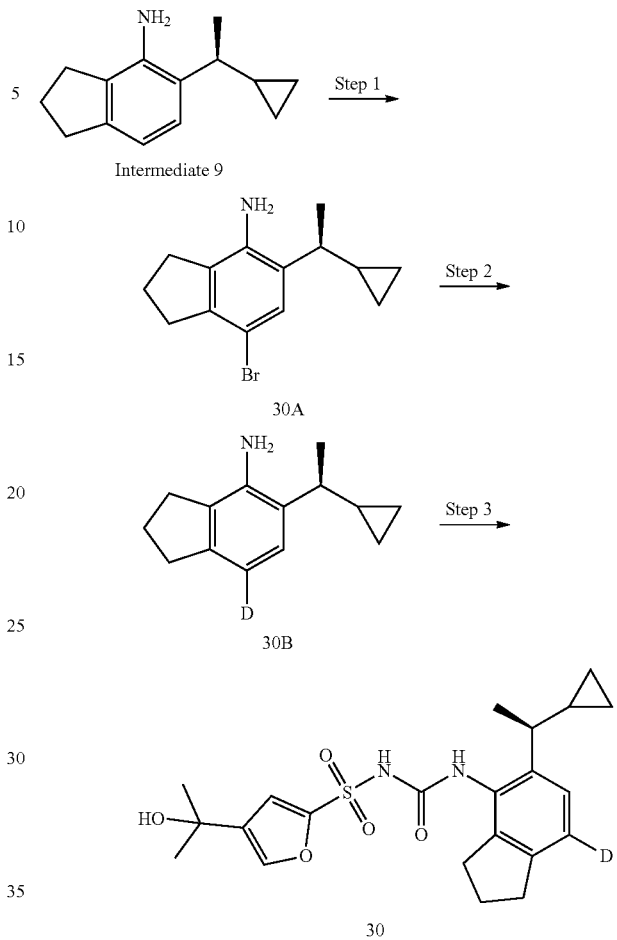

Step 1

(S)-7-bromo-5-(1-cyclopropylethyl)-2,3-dihydro-1H-inden-4-amine (30A)

Intermediate 9 (2.0 g, 9.95 mmol) and dichloromethane (50 mL) were added successively into a 100 mL round-bottomed flask under nitrogen atmosphere, and then pyridinium tribromide (3.5 g, 10.9 mmol) was added dropwise slowly in an ice bath. The reaction system was warmed to room temperature and reacted for 1 h after the addition was completed. After the reaction was completed, the reaction system was added into aqueous sodium sulfite solution to quench the reaction, and dichloromethane (50 mL×3) was added for extraction. The organic phase was dried over anhydrous sodium sulfate and filtered, and the organic solvent was removed under reduced pressure. The residue was purified by column chromatography (petroleum ether: ethyl acetate=50:1-20:1) to give compound 30A in the form of a pale yellow oil (2.7 g, 97% yield).

$^1$H NMR (400 MHz, DMSO-d6) δ=7.05 (s, 1H), 4.64 (s, 2H), 2.77-2.72 (m, 4H), 2.24-2.20 (m, 1H), 2.00-1.96 (m, 2H), 1.12 (d, 3H), 0.99-0.97 (m, 1H), 0.50-0.48 (m, 1H), 0.34-0.33 (m, 1H), 0.17-0.16 (m, 1H), 0.09-0.05 (m, 1H); LCMS m/z=281.2[M+1].

Step 2

(S)-5-(1-cyclopropylethyl)-2,3-dihydro-1H-inden-7-d-4-amine (30B)

30A (1.5 g, 5.4 mmol), deuterated sodium formate (0.75 g, 10.8 mmol), tris(dibenzylideneacetone)dipalladium (247 mg, 0.27 mmol), tri-tert-butylphosphine (109 mg, 0.54 mmol) and dimethyl sulfoxide (30 mL) were added successively into a 100 mL round-bottomed flask under nitrogen atmosphere, and the reaction system was warmed to 80° C. and reacted for 8 h. After the reaction was completed, the reaction system was cooled to room temperature, poured into water, and extracted with ethyl acetate (50 mL×3). The organic phase was dried over anhydrous sodium sulfate and filtered, and the organic solvent was removed under reduced pressure. The crude product was purified by column chromatography (petroleum ether:ethyl acetate=20:1) to give compound 30B in the form of a pale yellow solid (778 mg, 71.9% yield).

$^1$H NMR (400 MHz, DMSO-d6) δ=6.92 (s, 1H), 4.43 (s, 1H), 2.74 (t, 2H), 2.60 (t, 2H), 2.25-2.21 (m, 1H), 2.01-1.90 (m, 2H), 1.13 (d, 3H), 1.08-0.93 (m, 1H), 0.49-0.41 (m, 1H), 0.33-0.26 (m, 1H), 0.15-0.10 (m, 1H), 0.05-0.01 (m, 1H); LCMS m/z=203.2 [M+1].

Step 3

(S)-N-((5-(1-cyclopropylethyl)-2,3-dihydro-1H-inden-4-yl-7-d)carbamoyl)-4-(2-hydroxypropan-2-yl)furan-2-sulfonamide (Compound 30)

Compound 30B (201 mg, 1.0 mmol), triethylamine (121 mg, 1.2 mmol) and tetrahydrofuran (10 mL) were added successively into a 100 mL round-bottomed flask under nitrogen atmosphere, and then triphosgene (118.4 mg, 0.4 mmol) was added in an ice bath. The reaction system was warmed to reflux, reacted for 2 h, and then filtered to remove the solids. 2e (205 mg, 1.0 mmol) and sodium methoxide (108 mg, 2.0 mmol) were added to the filtrate, and the mixture was reacted at 60° C. for 2 h. After the reaction was completed as detected by TLC, water (100 mL) was added to quench the reaction, and ethyl acetate (30 mL×3) was added for extraction. The organic phase was dried over anhydrous sodium sulfate and filtered, and the organic solvent was removed. The crude product was purified by preparative high pressure liquid chromatography to give compound 30 in the form of a white solid (100 mg, 23.1% yield, ee %: 98.92%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=10.332 min).

$^1$H NMR (400 MHz, DMSO-d$_6$) δ 7.68 (s, 1H), 7.12 (s, 2H), 5.05 (s, 1H), 2.81 (t, 2H), 2.67 (t, 2H), 2.17 (m, 1H), 1.99-1.86 (m, 2H), 1.37 (s, 6H), 1.10 (d, 3H), 0.93 (m, 1H), 0.50-0.41 (m, 1H), 0.25-0.16 (m, 1H), 0.12-0.07 (m, 1H), 0.04-0.01 (m, 1H); LCMS m/z (ESI)=434.2[M+1].

Example 31

($R_S$, $R_C$)- and ($S_S$, $R_C$)-N-((5-(1-cyclopropylethyl)-2,3-dihydro-1H-inden-4-yl-7-d)carbamoyl)-4-(2-hydroxypropan-2-yl)furan-2-sulfonimidamide (Compounds 31-1 and 31-2)

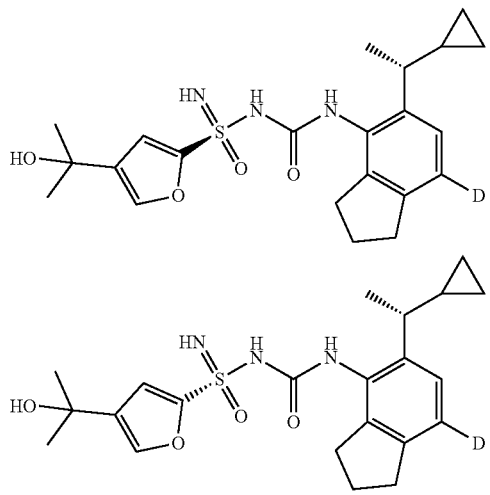

Compounds 31-1 and 31-2

For preparation of compounds 31-1 and 31-2, reference was made to preparation method of compounds 21-1 and 21-2. Compound 31-1 (57 mg, 75% yield, ee %: 97.02%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=14.234 min) and compound 31-2 (53 mg, 75% yield, ee %: 99.54%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=18.033 min).

Compound 31-1: $^1$H NMR (400 MHz, DMSO-d$_6$) δ 8.23 (s, 1H), 7.67 (d, 1H), 7.62 (s, 2H), 7.12 (s, 1H), 6.97 (s, 1H), 5.07 (s, 1H), 2.82 (t, 2H), 2.67 (t, 2H), 2.25-2.21 (m, 1H), 1.95-1.91 (m, 2H), 1.37 (s, 6H), 1.11 (d, 3H), 0.96-0.91 (m, 1H), 0.46-0.41 (m, 1H), 0.21-0.16 (m, 1H), 0.11-0.07 (m, 1H), 0.04-0.01 (m, 1H); LCMS m/z (ESI)=433.1[M+1].

Compound 31-2: $^1$H NMR (400 MHz, DMSO-d$_6$) δ 8.25 (s, 1H), 7.67 (d, 1H), 7.64 (s, 2H), 7.12 (s, 1H), 6.97 (s, 1H), 5.08 (s, 1H), 2.82 (t, 2H), 2.67 (t, 2H), 2.25-2.21 (m, 1H), 1.95-1.91 (m, 2H), 1.37 (s, 6H), 1.11 (d, 3H), 0.96-0.91 (m, 1H), 0.49-0.43 (m, 1H), 0.25-0.21 (m, 1H), 0.14-0.10 (m, 1H), 0.06-0.02 (m, 1H); LCMS m/z (ESI)=433.1[M+1].

Example 32

($R_S$, $S_C$)- and ($S_S$, $S_C$)-N-((5-(1-cyclopropylethyl)-2,3-dihydro-1H-inden-4-yl-7-d)carbamoyl)-4-(2-hydroxypropan-2-yl)furan-2-sulfonimidamide (Compounds 32-1 and 32-2)

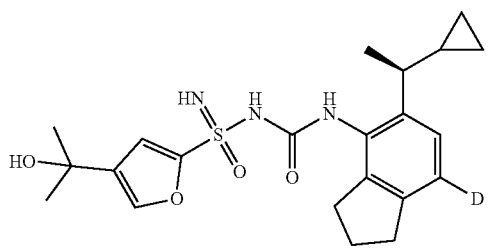

Compounds 32-1 and 32-2

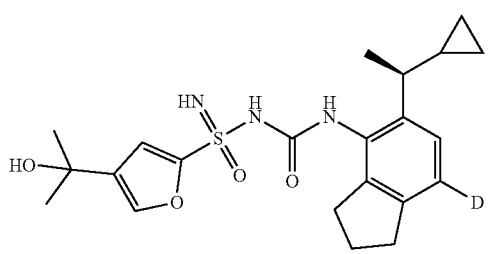

For preparation of compounds 32-1 and 32-2, reference was made to preparation method of compounds 21-1 and 21-2. Compound 32-1 (194 mg, 71.6% yield, ee %: 99.29%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=14.980 min) and compound 32-2 (164 mg, 71.6% yield, ee %: 99.20%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=19.398 min).

Compound 32-1: $^1$H NMR (400 MHz, DMSO-$d_6$) δ=8.23 (s, 1H), 7.67 (d, 1H), 7.62 (s, 2H), 7.12 (s, 1H), 6.97 (s, 1H), 5.07 (s, 1H), 2.82 (t, 2H), 2.67 (t, 2H), 2.25-2.21 (m, 1H), 1.95-1.91 (m, 2H), 1.37 (s, 6H), 1.11 (d, 3H), 0.96-0.91 (m, 1H), 0.46-0.41 (m, 1H), 0.21-0.16 (m, 1H), 0.11-0.07 (m, 1H), 0.04-0.01 (m, 1H); LCMS m/z (ESI)=433.1[M+1].

Compound 32-2: $^1$H NMR (400 MHz, DMSO-$d_6$) δ=8.25 (s, 1H), 7.67 (d, 1H), 7.64 (s, 2H), 7.12 (s, 1H), 6.97 (s, 1H), 5.08 (s, 1H), 2.82 (t, 2H), 2.67 (t, 2H), 2.25-2.21 (m, 1H), 1.95-1.91 (m, 2H), 1.37 (s, 6H), 1.11 (d, 3H), 0.96-0.91 (m, 1H), 0.49-0.43 (m, 1H), 0.25-0.21 (m, 1H), 0.14-0.10 (m, 1H), 0.06-0.02 (m, 1H); LCMS m/z (ESI)=433.1[M+1].

Example 33

N-((3-(cyclobutylmethyl)bicyclo[4.2.0]octa-1(6),2,4-trien-2-yl)carbamoyl)-4-(2-hydroxypropan-2-yl)furan-2-sulfonamide (Compound 33)

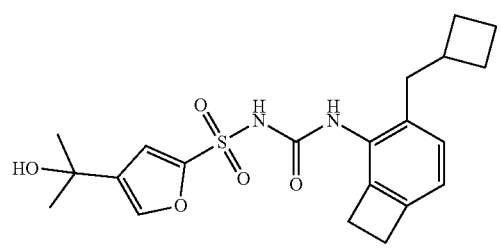

Compound 33

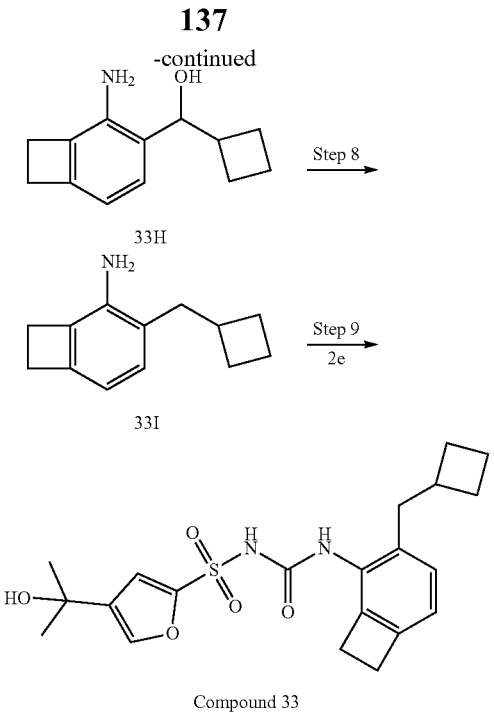

Step 1

2-(2,6-dibromophenyl)ethan-1-ol (33B)

33A (60.0 g, 0.2 mol) and anhydrous tetrahydrofuran (300 mL) were added into a 1 L three-necked flask, and a solution of borane in tetrahydrofuran (300 mL, 1 M) was added dropwise slowly at 0° C. under nitrogen atmosphere. After the dropwise addition was completed, the reaction system was warmed to 80° C. and reacted for 1 h. After the reaction was completed as detected by TLC, the reaction system was cooled to room temperature. Water (150 mL) and diluted hydrochloric acid (20 mL, 2 N) were added to quench the reaction in an ice bath. Part of the reaction solution was concentrated under reduced pressure, and then ethyl acetate (100 mL×3) was added for extraction. The organic phase was dried over anhydrous sodium sulfate and filtered, and the organic solvent was removed under reduced pressure. The residue was purified by column chromatography (petroleum ether:ethyl acetate=5:1) to give 33B in the form of a white solid (50.0 g, 88% yield).

$^1$H NMR (400 MHz, CDCl$_3$) δ=7.52 (d, 2H), 6.94 (t, 1H), 3.88 (t, 2H), 3.33 (t, 2H).

Step 2

1,3-dibromo-2-(2-bromoethyl)benzene (33C)

33B (50.0 g, 0.18 mol), N-bromosuccinimide (38.0 g, 0.2 mmol) and dichloromethane (400 mL) were added successively into a 1 L round-bottomed flask, and the reaction system was stirred until it was clarified. The flask was then placed in an ice bath, and triphenylphosphine (65 g, 0.2 mol) was added slowly. After the addition was completed, the reaction system was reacted at room temperature for 24 h. After the reaction was completed as detected by TLC, tert-butyl hydroperoxide (8 mL) was added, and the reaction system was reacted for 2 h to remove excess triphenylphosphine. Saturated sodium bisulfite solution (200 mL) was added to quench the reaction, and dichloromethane (200 mL×3) was added for extraction. The organic phase was dried over anhydrous sodium sulfate and concentrated until a large number of solids were precipitated out. The solids were slurried with n-hexane and filtered under vacuum. The filtrate was concentrated and purified by column chromatography (petroleum ether:ethyl acetate=50:1) to give 33C in the form of a white solid (60.0 g, 98% yield).

$^1$H NMR (400 MHz, CDCl$_3$) δ=7.52 (d, 2H), 6.97 (t, 1H), 3.63-3.43 (m, 4H).

Step 3

2-bromobicyclo[4.2.0]octa-1(6),2,4-triene (33D)

33C (5.0 g, 15 mmol) and anhydrous tetrahydrofuran (150 mL) were added successively into a 250 mL three-necked flask, and n-butyllithium (5.5 mL, 2.5 M) was added dropwise slowly at −68° C. under nitrogen atmosphere. After the dropwise addition was completed, the reaction system was reacted at −68° C. for 2 h. After the reaction was completed as detected by UPLC, water (20 mL) was added dropwise slowly to quench the reaction, and ethyl acetate (100 mL×3) was added for extraction. The organic phase was dried over anhydrous sodium sulfate and filtered, and the organic solvent was removed under reduced pressure to give compound 33D in the form of a pale yellow oil (2.5 g, 90% yield).

Step 4

Tert-butyl bicyclo[4.2.0]octa-1(6),2,4-trien-2-ylcarbamate (33E)

33D (2.3 g, 0.013 mol), dioxane (50 mL), tert-butyl carbamate (2.2 g, 0.019 mol), 2-dicyclohexylphosphino-2,4,6-triisopropylbiphenyl (476 mg, 1 mmol) and cesium carbonate (8.0 g, 0.025 mol) were added successively into a 250 mL round-bottomed flask, and palladium acetate (132 mg, 6 mmol) was added under nitrogen atmosphere. The reaction system was reacted at 100° C. for 2 h, and after the reaction was completed as detected by TLC, the reaction system was cooled to room temperature. Saturated sodium bicarbonate (50 mL) was added to quench the reaction, and ethyl acetate (50 mL×3) was added for extraction. The organic phase was dried over anhydrous sodium sulfate and filtered, and the organic solvent was removed under reduced pressure. The crude product was purified by column chromatography (petroleum ether:ethyl acetate=20:1) to give 33E in the form of a brown oil (2.3 g, 83% yield).

$^1$H NMR (400 MHz, CDCl$_3$) δ=7.27 (d, 1H), 7.13 (t, 1H), 6.76 (d, 1H), 6.31 (s, 1H), 3.27-3.16 (m, 2H), 3.16-3.06 (m, 2H), 1.52 (s, 9H).

Step 5

Bicyclo[4.2.0]octa-1(6),2,4-trien-2-amine (33F)

33E (2.3 g, 10.5 mmol), dichloromethane (40 mL) and trifluoroacetic acid (6 mL) were added successively into a 100 mL round-bottomed flask, and the reaction system was reacted at room temperature for 7 h. After the reaction was completed as detected by TLC, saturated sodium bicarbonate solution (40 mL) was added to quench the reaction, and dichloromethane (50 mL×3) was added for extraction. The organic phase was dried over anhydrous sodium sulfate and filtered, and the organic solvent was removed under reduced pressure. The crude product was purified by column chromatography (petroleum ether:ethyl acetate=10:1) to give 33F in the form of a brown oil (1.0 g, 80% yield).

$^1$H NMR (400 MHz, CDCl$_3$) δ=7.02 (dd, 1H), 6.51 (dd, 2H), 3.11 (dd, 2H), 3.04 (dd, 2H).

Step 6

(2-aminobicyclo[4.2.0]octa-1(6),2,4-trien-3-yl)(cyclobutyl)methanone (33G)

33F (1.0 g, 8.4 mmol) and dichloroethane (10 mL) were added successively into a 100 mL three-necked flask, and the reaction system was placed in an ice water bath after it was clarified. A solution of boron trichloride in toluene (10 mL, 1 M) was added dropwise slowly under nitrogen atmosphere, and anhydrous aluminum trichloride (1.3 g, 10 mmol) was added 10 min later. Cyclobutyl cyanide (1.2 mL, 12.6 mmol) was then added dropwise slowly. After the dropwise addition was completed, the reaction system was reacted at 90° C. for 7 h and then cooled to room temperature. Diluted hydrochloric acid solution (10 mL, 2 N) was added, and the reaction system was warmed to reflux, and reacted for 30 min. The organic phase was separated out, washed with saturated sodium bicarbonate (20 mL) to weak acidity, and extracted with dichloromethane (20 mL×3). The organic phase was dried over anhydrous sodium sulfate and filtered, and the organic solvent was removed under reduced pressure. The crude product was purified by column chromatography (petroleum ether:ethyl acetate=10:1) to give compound 33G in the form of a brown oil (800 mg, 47% yield).

$^1$H NMR (400 MHz, CDCl$_3$) δ 7.51 (d, 1H), 6.45 (d, 1H), 4.05-3.91 (m, 1H), 3.06 (d, 2H), 3.02 (d, 2H), 2.47-2.35 (m, 2H), 2.29-2.20 (m, 2H), 2.05 (ddd, 1H), 1.87 (ddd, 1H).

Step 7

(2-aminobicyclo[4.2.0]octa-1(6),2,4-trien-3-yl)(cyclobutyl)methanol (33H)

33G (800 mg, 4 mmol), absolute methanol (20 mL) and sodium borohydride (227 mg, 6 mmol) were added successively into a 50 mL round-bottomed flask, and the reaction system was reacted at room temperature for 8 h. After the reaction was completed as detected by TLC, water (20 mL) was added dropwise slowly to quench the reaction, and dichloromethane (20 mL×3) was added for extraction. The organic phase was dried over anhydrous sodium sulfate and filtered, and the organic solvent was removed under reduced pressure. The crude product was purified by column chromatography (petroleum ether:ethyl acetate=5:1) to give 33H in the form of a brown oil (600 mg, 75% yield).

LCMS m/z (ESI)=186.1[M−17].

Step 8

3-(cyclobutylmethyl)bicyclo[4.2.0]octa-1(6),2,4-trien-2-amine (33I)

33H (600 mg, 3 mmol), dichloromethane (20 mL), triethylsilane (1.4 mL, 9 mmol) and trifluoroacetic acid (1.1 mL, 15 mmol) were added successively into a 50 mL round-bottomed flask, and the reaction system was reacted at room temperature for 2 h. After the reaction was completed as detected by TLC, saturated sodium bicarbonate solution (20 mL) was added dropwise slowly to quench the reaction, and dichloromethane (20 mL×3) was added for extraction. The organic phase was dried over anhydrous sodium sulfate and filtered, and the organic solvent was removed under reduced pressure. The crude product was purified by column chromatography (petroleum ether:ethyl acetate=10:1) to give 33I in the form of a brown oil (150 mg, 32% yield).

$^1$H NMR (400 MHz, CDCl$_3$) δ=6.88 (d, 1H), 6.50 (d, 1H), 3.08 (d, 2H), 3.06-3.01 (m, 2H), 2.69-2.55 (m, 3H), 2.09 (ddd, 2H), 1.88 (ddd, 2H), 1.74 (dt, 2H).

Step 9

N-((3-(cyclobutylmethyl)bicyclo[4.2.0]octa-1(6),2,4-trien-2-yl)carbamoyl)-4-(2-hydroxypropan-2-yl)furan-2-sulfonamide (Compound 33)

Compound 33I (170 mg, 0.9 mmol), triethylamine (152 μL, 1.0 mmol) and tetrahydrofuran (10 mL) were added successively into a 100 mL round-bottomed flask under nitrogen atmosphere, and then triphosgene (118 mg, 0.4 mmol) was added in an ice bath. The reaction system was warmed to reflux, reacted for 2 h, and then filtered to remove the solids.

Intermediate 2e (143 mg, 0.7 mmol) and sodium methoxide (97 mg, 1.8 mmol) were added to the filtrate, and the mixture was reacted at room temperature for 2 h. After the reaction was completed as detected by TLC, water (20 mL) was added to quench the reaction, and dichloromethane (30 mL×3) was added for extraction. The organic phase was dried over anhydrous sodium sulfate and filtered, and the organic solvent was removed. The crude product was purified by preparative medium pressure liquid chromatography to give compound 33 in the form of a white solid (25 mg, 8% yield).

$^1$H NMR (400 MHz, DMSO-d$_6$) δ=7.90 (s, 1H), 7.67 (s, 1H), 7.05 (s, 1H), 6.91 (d, 1H), 6.73 (d, 1H), 5.07 (s, 1H), 3.00 (dd, 2H), 2.93 (d, 2H), 2.57 (d, 2H), 2.47-2.35 (m, 1H), 1.96-1.85 (m, 2H), 1.77 (tt, 2H), 1.70-1.55 (m, 2H), 1.37 (s, 6H); LCMS m/z (ESI)=401.1[M−17].

Example 34

R$_S$- and S$_S$-N-((3-(cyclobutylmethyl)bicyclo[4.2.0]octa-1(6),2,4-trien-2-yl)carbamoyl)-4-(2-hydroxypropan-2-yl)furan-2-sulfonimidamide (Compounds 34-1 and 34-2)

Compounds 34-1 and 34-2

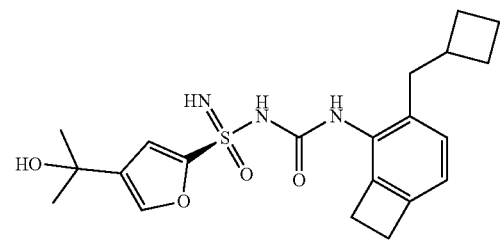

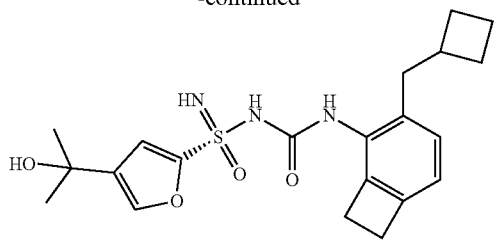

For preparation of compounds 34-1 and 34-2, reference was made to preparation method of compounds 21-1 and 21-2. Compound 34-1 (40 mg, ee %: 99.88%, chiral HPLC (OX-3); mobile phase: methanol; column temperature: 35° C.; column pressure: 80 bar; flow rate: 2 mL/min; detector signal channel: 215 nm@4.8 nm; start wavelength of diode array detector: 200 nm; stop wavelength of diode array detector: 400 nm; RT=10.722 min) and compound 34-2 (33 mg, ee %: 99.16%, chiral HPLC (OX-3); mobile phase: methanol; column temperature: 35° C.; column pressure: 80 bar; flow rate: 2 mL/min; detector signal channel: 215 nm@4.8 nm; start wavelength of diode array detector: 200 nm; stop wavelength of diode array detector: 400 nm; RT=12.380 min).

Compound 34-1: $^1$H NMR (400 MHz, DMSO-$d_6$) δ 8.28 (s, 1H), 7.70 (d, 2H), 7.01 (d, 1H), 6.88 (d, 1H), 6.73 (d, 1H), 5.10 (s, 1H), 2.95 (t, 4H), 2.63 (dd, 2H), 2.49-2.41 (m, 1H), 1.94-1.87 (m, 2H), 1.83-1.72 (m, 2H), 1.63 (dt, 2H), 1.39 (s, 6H); LCMS m/z=418.2[M+1].

Compound 34-2: $^1$H NMR (400 MHz, DMSO-$d_6$) δ 8.27 (s, 1H), 7.78-7.62 (m, 2H), 7.01 (d, 1H), 6.88 (d, 1H), 6.73 (d, 1H), 5.10 (s, 1H), 2.95 (s, 4H), 2.63 (dd, 2H), 2.45 (dd, 1H), 1.99-1.86 (m, 2H), 1.77 (tt, 2H), 1.69-1.56 (m, 2H), 1.39 (s, 6H); LCMS m/z=418.2[M+1].

Example 35

(S)-N-((3-(1-cyclopropylethyl)bicyclo[4.2.0]octa-1 (6),2,4-trien-2-yl)carbamoyl)-4-(2-hydroxypropan-2-yl)furan-2-sulfonamide (Compound 35)

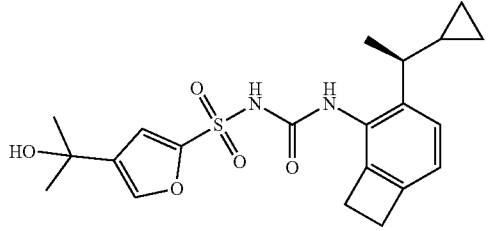

Compound 35

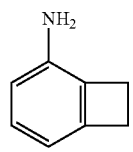

33F

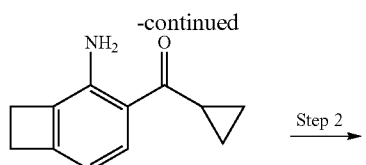

35A

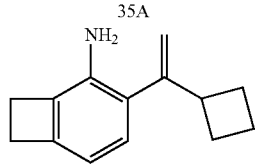

35B

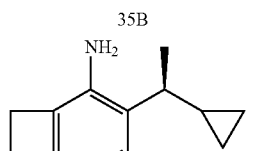

35C

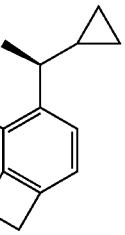

Compound 35

Step 1

(2-aminobicyclo[4.2.0]octa-1(6),2,4-trien-3-yl)(cyclopropyl)methanone (35A)

33F (100 mg, 0.84 mmol) and dichloroethane (5 mL) were added successively into a 25 mL three-necked flask, and the reaction system was placed in an ice water bath after it was clarified. A solution of boron trichloride in toluene (900 μL, 1 M) was added dropwise slowly under nitrogen atmosphere, and anhydrous aluminum trichloride (123 mg, 0.9 mmol) was added 10 min later. Cyclobutyl cyanide (74 μL, 1 mmol) was then added dropwise slowly. After the dropwise addition was completed, the reaction system was reacted at 90° C. for 3 h and then cooled to room temperature. Diluted hydrochloric acid solution (1 mL, 2 N) and water (5 mL) were added, and the reaction system was warmed to reflux, and reacted for 30 min. The organic phase was separated out, washed with saturated sodium bicarbonate (10 mL) to weak acidity, and extracted with dichloromethane (10 mL×3). The organic phase was dried over anhydrous sodium sulfate and filtered, and the organic solvent was removed under reduced pressure. The crude product was purified by column chromatography (petroleum ether:ethyl acetate=10:1) to give compound 35A in the form of a brown oil (60 mg, 38% yield).

$^1$H NMR (400 MHz, CDCl$_3$) δ=7.91 (d, 1H), 6.51 (d, 1H), 3.12-3.05 (m, 2H), 3.04-2.95 (m, 2H), 2.67-2.54 (m, 1H), 1.19-1.10 (m, 2H), 1.00-0.87 (m, 2H).

Step 2

3-(1-cyclopropylvinyl)bicyclo[4.2.0]octa-1(6),2,4-trien-2-amine (35B)

Methyl triphenyl phosphonium bromide (8 g, 22 mmol) and anhydrous tetrahydrofuran (40 mL) were added successively into a 25 mL three-necked flask, and the reaction system was placed in an ice water bath after it was clarified. Potassium tert-butoxide (2.5 g, 22 mmol) was added under nitrogen atmosphere, and a solution of 35A (1.4 g, 7.5 mmol) in tetrahydrofuran (20 mL) was added 40 min later. 10 min later, the reaction system was reacted at room temperature for 2 h, and then water (20 mL) was added to quench the reaction and ethyl acetate (20 mL×3) was added for extraction. The organic phase was dried over anhydrous sodium sulfate and filtered, and the organic solvent was removed under reduced pressure. The residue was purified by column chromatography (petroleum ether:ethyl acetate=10:1) to give 35B in the form of a brown oil (1.2 g, 85% yield).

$^1$H NMR (400 MHz, CDCl$_3$) δ=6.87 (d, 1H), 6.49 (d, 1H), 5.17 (d, 1H), 4.91 (d, 1H), 3.09 (dd, 2H), 3.03 (dd, 2H), 1.63 (tt, 1H), 0.77-0.67 (m, 2H), 0.54-0.44 (m, 2H).

Step 3

(S)-3-(1-cyclopropylethyl)bicyclo[4.2.0]octa-1(6),2,4-trien-2-amine (35C)

35B (500 mg, 2.7 mmol) and dichloromethane (50 mL) were added into a 500 mL autoclave, and then a catalyst ruthenium [(S)-2,2'-bis(diphenylphosphino)-1,11-binaphthyl]diacetate (113 mg, 0.14 mmol) was added. After the addition was completed, the autoclave was tightly closed and sealed, and purged with hydrogen 3 times. The hydrogen was introduced until the pressure gauge on the autoclave showed 12 atm, and then the reaction system was reacted for 5 h at room temperature. The reaction system was concentrated under reduced pressure to remove the solvent, and the crude product was purified by column chromatography (petroleum ether:ethyl acetate=10:1) to give 35C in the form of a pale yellow oil (360 mg, 72% yield).

$^1$H NMR (400 MHz, MeOD) δ=7.04 (d, 1H), 6.43 (d, 1H), 3.00 (s, 4H), 2.31-2.14 (m, 1H), 1.24 (d, 3H), 1.09-0.94 (m, 1H), 0.62-0.46 (m, 1H), 0.36 (dt, 1H), 0.15 (dt, 1H), 0.06 (dt, 1H).

Step 4

(S)-N-((3-(1-cyclopropylethyl)bicyclo[4.2.0]octa-1(6),2,4-trien-2-yl)carbamoyl)-4-(2-hydroxypropan-2-yl)furan-2-sulfonamide (Compound 35)

35C (100 mg, 0.5 mmol), tetrahydrofuran (10 mL), N,N-diisopropylethylamine (165 μL, 1.0 mmol) and 2,2,2-trichloroethyl chloroformate (103 μL, 0.75 mmol) were added successively into a 100 mL round-bottomed flask under nitrogen atmosphere, and the reaction system was reacted at room temperature for 1 h. Water (10 mL) was added to quench the reaction, and ethyl acetate (20 mL×3) was added for extraction. The organic phase was dried over anhydrous sodium sulfate and filtered, and the organic solvent was removed under reduced pressure. The residue was dissolved in tetrahydrofuran (10 mL), and intermediate 2e (82 mg, 0.4 mmol) and sodium hydride (24 mg, 0.6 mmol) were added. The mixture was reacted at room temperature for 2 h. After the reaction was completed as detected by TLC, water (20 mL) was added to quench the reaction, and ethyl acetate (30 mL×3) was added for extraction. The organic phase was dried over anhydrous sodium sulfate and filtered, and the organic solvent was removed. The crude product was purified by preparative medium pressure liquid chromatography to give compound 35 in the form of a yellow solid (56 mg, 26.7% yield, UPLC: 95.6%, ee %: 98.12%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=10.052 min).

$^1$H NMR (400 MHz, DMSO-d$_6$) δ=7.79 (s, 1H), 7.58 (s, 1H), 7.15 (d, 1H), 6.90 (s, 1H), 6.80 (d, 1H), 5.03 (s, 1H), 3.05-2.85 (m, 4H), 2.25 (dd, 1H), 1.36 (s, 6H), 1.14 (d, 3H), 0.96 (tt, 1H), 0.47 (dq, 1H), 0.26 (tq, 1H), 0.10 (dt, 1H), 0.04-0.05 (m, 1H); LCMS m/z (ESI)=419.1[M+1].

Example 36

($R_S$, $S_C$)- and ($S_S$, $S_C$)-N-((3-(1-cyclopropylethyl)bicyclo[4.2.0]octa-1(6),2,4-trien-2-yl)carbamoyl)-4-(2-hydroxypropan-2-yl)furan-2-sulfonimidamide (Compounds 36-1 and 36-2)

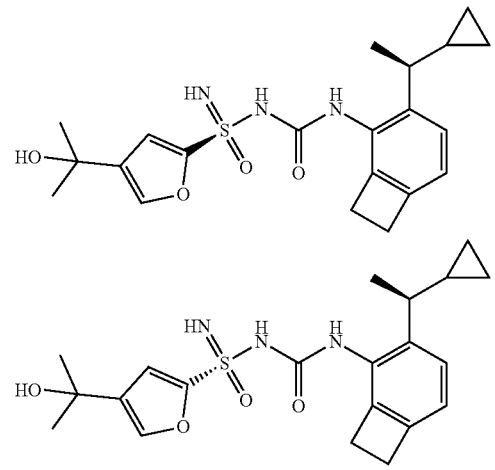

Compounds 36-1 and 36-2

For synthesis of compounds 36-1 and 36-2, reference was made to preparation method of compounds 21-1 and 21-2. Compound 36-1 (80 mg, ee %: 98.94%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=5.836 min) and compound 36-2 (100 mg, ee %: 98.74%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=8.054 min).

Compound 36-1: $^1$H NMR (400 MHz, DMSO-d$_6$) δ=8.24 (s, 1H), 7.69 (d, 2H), 7.67 (s, 1H), 7.17 (d, 1H), 6.99 (s, 1H), 6.83 (d, 1H), 5.09 (s, 1H), 2.96 (s, 4H), 2.33 (dd, 1H), 1.38

(s, 6H), 1.10 (d, 3H), 0.95 (tt, 1H), 0.47 (dt, 1H), 0.24 (dt, 1H), 0.13 (dd, 1H), 0.05 (dt, 1H); LCMS m/z (ESI)=418.1 [M+1].

Compound 36-2: $^1$H NMR (400 MHz, DMSO-d$_6$) δ=8.24 (s, 1H), 7.69 (d, 2H), 7.67 (s, 1H), 7.16 (d, 1H), 6.99 (d, 1H), 6.84 (d, 1H), 5.09 (s, 1H), 2.96 (d, 4H), 2.35 (dd, 1H), 1.38 (s, 6H), 1.13 (d, 3H), 0.92 (tt, 1H), 0.45 (tq, 1H), 0.21 (tq, 1H), 0.10 (dq, 1H), 0.02 (dd, 1H); LCMS m/z (ESI)=418.1 [M+1].

Example 37

(R)-N-((3-(1-cyclopropylethyl)bicyclo[4.2.0]octa-1 (6),2,4-trien-2-yl)carbamoyl)-4-(2-hydroxypropan-2-yl)furan-2-sulfonamide (Compound 37)

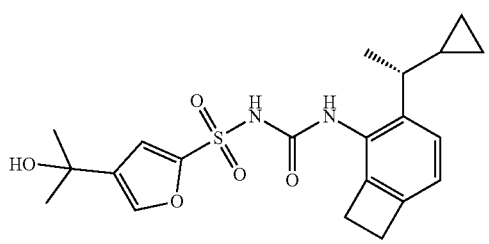
Compound 37

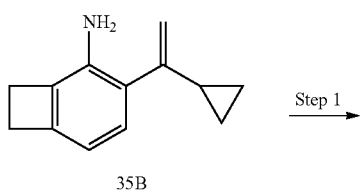
35B

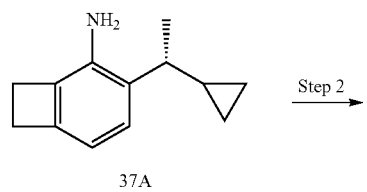
37A

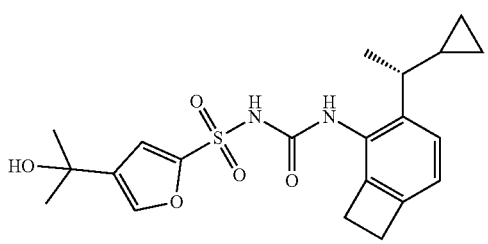
Compound 37

Step 1

(R)-3-(1-cyclopropylethyl)bicyclo[4.2.0]octa-1(6),2,4-trien-2-amine (37A)

35B (500 mg, 2.7 mmol) and dichloromethane (50 mL) were added into a 500 mL autoclave, and then a catalyst ruthenium [(S)-2,2'-bis(diphenylphosphino)-1,11-binaphthyl]diacetate (113 mg, 0.14 mmol) was added. After the addition was completed, the autoclave was tightly closed and sealed, and purged with hydrogen 3 times. The hydrogen was introduced until the pressure gauge on the autoclave showed 14 atm, and then the reaction system was reacted for 5 h at room temperature. The reaction system was concentrated under reduced pressure to remove the solvent, and the crude product was purified by column chromatography (petroleum ether:ethyl acetate=10:1) to give 37A in the form of a pale yellow oil (470 mg, 94% yield).

$^1$H NMR (400 MHz, DMSO) δ=6.95 (d, 1H), 6.30 (d, 1H), 2.88 (s, 4H), 2.2 (m, 1H), 1.23 (d, 3H), 0.97 (m, 1H), 0.46 (m, 1H), 0.29 (dt, 1H), 0.12 (dt, 1H), 0.01 (dt, 1H).

Step 2

(R)-N-((3-(1-cyclopropylethyl)bicyclo[4.2.0]octa-1 (6),2,4-trien-2-yl)carbamoyl)-4-(2-hydroxypropan-2-yl)furan-2-sulfonamide (Compound 37)

Compound 37A (100 mg, 0.5 mmol), tetrahydrofuran (10 mL), N,N-diisopropylethylamine (165 μL, 1.0 mmol) and 2,2,2-trichloroethyl chloroformate (103 μL, 0.75 mmol) were added successively into a 100 mL round-bottomed flask under nitrogen atmosphere, and the reaction system was reacted at room temperature for 1 h. Water (10 mL) was added to quench the reaction, and ethyl acetate (20 mL×3) was added for extraction. The organic phase was dried over anhydrous sodium sulfate and filtered, and the organic solvent was removed under reduced pressure. The residue was dissolved in tetrahydrofuran (10 mL), and compound 2e (82 mg, 0.4 mmol) and sodium hydride (24 mg, 0.6 mmol) were added. The mixture was reacted at 40° C. for 3 h. After the reaction was completed as detected by TLC, water (20 mL) was added to quench the reaction, and ethyl acetate (30 mL×3) was added for extraction. The organic phase was dried over anhydrous sodium sulfate and filtered, and the organic solvent was removed. The crude product was purified by preparative medium pressure liquid chromatography to give compound 37 in the form of an off-white solid (50 mg, 22.4% yield, UPLC: 94.71%, ee %: 94.1%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=10.861 min). $^1$H NMR (400 MHz, DMSO-d$_6$) δ=7.79 (s, 1H), 7.58 (s, 1H), 7.15 (d, 1H), 6.90 (s, 1H), 6.80 (d, 1H), 5.03 (s, 1H), 3.05-2.85 (m, 4H), 2.25 (dd, 1H), 1.36 (s, 6H), 1.14 (d, 3H), 0.96 (tt, 1H), 0.47 (dq, 1H), 0.26 (tq, 1H), 0.10 (dt, 1H), 0.04-0.05 (m, 1H); LCMS m/z=419.1[M+1].

Example 38

$R_S$- and $S_S$-N-((3-((R)-1-cyclopropylethyl)bicyclo[4.2.0]octa-1(6),2,4-trien-2-yl)carbamoyl)-4-(2-hydroxypropan-2-yl)furan-2-sulfonimidamide (Compounds 38-1 and 38-2)

Example 39

$R_S$- and $S_S$-N-((5-(cyclobutylmethyl)-2,3-dihydro-1H-inden-4-yl-7-d)carbamoyl)-4-(2-hydroxypropan-2-yl)furan-2-sulfonimidamide (Compounds 39-1 and 39-2)

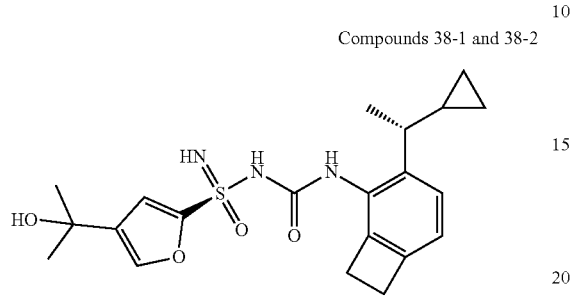

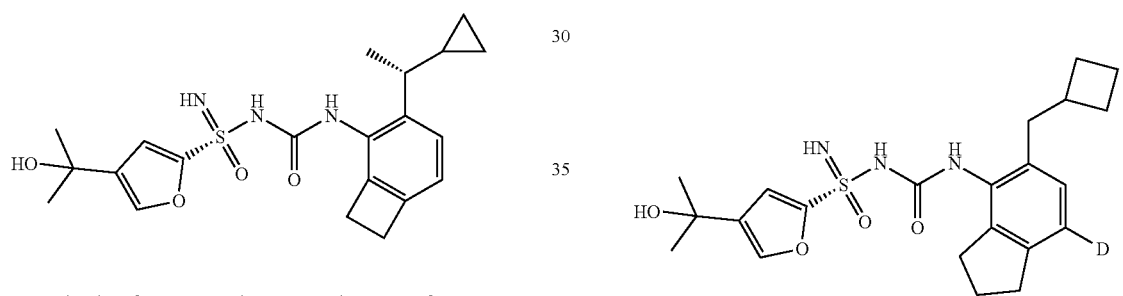

For synthesis of compounds 38-1 and 38-2, reference was made to preparation method of compounds 21-1 and 21-2. Compound 38-1 (105 mg, ee %: 99.67%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=3.900 min) and compound 38-2 (120 mg, ee %: 99.81%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=4.272 min).

Compound 38-1: $^1$H NMR (400 MHz, DMSO-$d_6$) δ=8.24 (s, 1H), 7.79-7.63 (m, 2H), 7.17 (d, 1H), 6.99 (d, 1H), 6.83 (d, 1H), 5.09 (s, 1H), 2.96 (s, 4H), 2.42-2.25 (m, 1H), 1.38 (s, 6H), 1.10 (d, 3H), 0.95 (tt, 1H), 0.56-0.43 (m, 1H), 0.24 (tt, 1H), 0.13 (dq, 1H), 0.05 (dt, 1H); LCMS m/z (ESI)=418.1[M+1].

Compound 38-2: $^1$H NMR (400 MHz, DMSO-$d_6$) δ=8.24 (s, 1H), 7.74-7.62 (m, 2H), 7.16 (d, 1H), 6.99 (d, 1H), 6.84 (d, 1H), 5.09 (s, 1H), 2.96 (d, 4H), 2.42-2.30 (m, 1H), 1.38 (s, 6H), 1.13 (d, 3H), 0.98-0.85 (m, 1H), 0.51-0.39 (m, 1H), 0.28-0.16 (m, 1H), 0.11 (dd, 1H), 0.05-0.01 (m, 1H); LCMS m/z (ESI)=418.1[M+1].

For preparation of compounds 39-1 and 39-2, reference was made to preparation method of compounds 31-1 and 31-2. Compound 39-1 (70 mg, ee %: 99%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=35.556 min) and compound 39-2 (70 mg, ee %: 99%, chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=39.131 min).

Compound 39-1: $^1$H NMR (400 MHz, Chloroform-d) δ=7.48 (s, 1H), 7.09 (s, 1H), 6.94 (s, 1H), 6.60 (s, 2H), 2.89 (t, 2H), 2.81 (t, 2H), 2.69-2.61 (m, 2H), 2.49 (dq, 1H), 2.02 (dp, 4H), 1.87-1.75 (m, 2H), 1.75-1.62 (m, 2H), 1.52 (s, 6H); LCMS m/z (ESI)=433.2[M+1].

Compound 39-2: $^1$H NMR (400 MHz, Chloroform-d) δ=7.45 (s, 1H), 7.08 (s, 1H), 6.93 (s, 1H), 6.67 (d, 2H), 2.87 (t, 2H), 2.78 (t, 2H), 2.63 (d, 2H), 2.57-2.42 (m, 1H), 2.01 (tt, 4H), 1.92-1.73 (m, 2H), 1.68 (dt, 2H), 1.49 (s, 6H); LCMS m/z (ESI)=433.2[M+1].

Example 40

N-((5-(1-cyclopropylvinyl)-6-methyl-2,3-dihydro-1H-inden-4-yl)carbamoyl)-4-(2-hydroxypropan-2-yl)furan-2-sulfonamide (Compound 40)

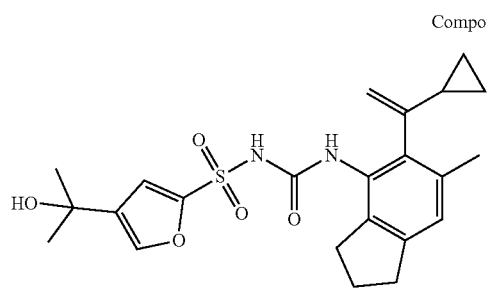

Compound 40

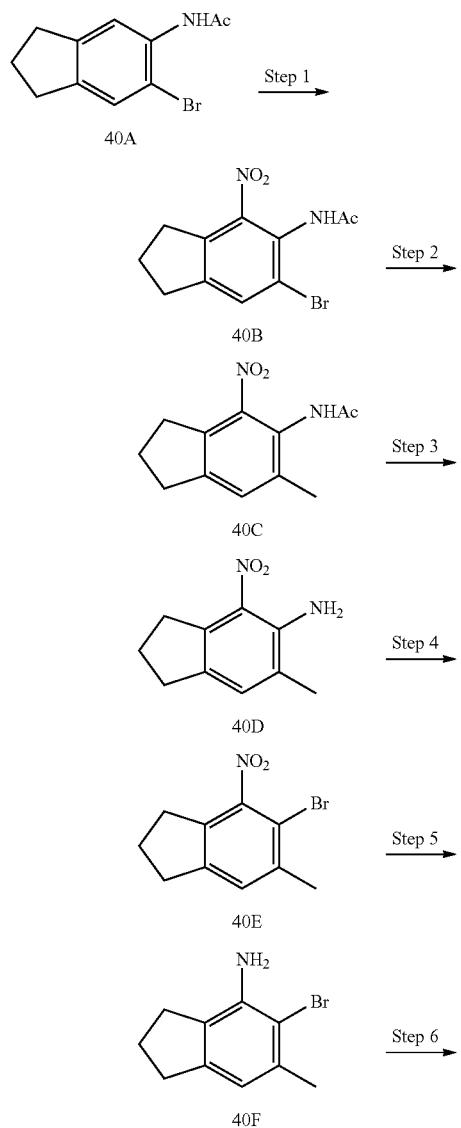

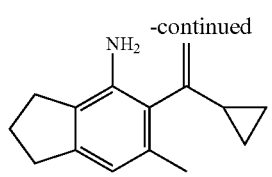

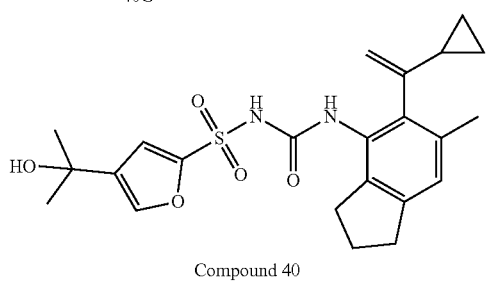

Compound 40

Step 1

N-(6-bromo-4-nitro-2,3-dihydro-1H-inden-5-yl)acetamide (40B)

Compound 40A (50 g, 198 mmol) and acetic acid (130 mL) were added successively into a 3 L round-bottomed flask, and a mixture of acetic acid:concentrated sulfuric acid (1:1, 260 mL) and a mixture of concentrated sulfuric acid:concentrated nitric acid (1:1, 260 mL) were slowly added with mechanical stirring in an ice bath. After the reaction was completed, aqueous sodium hydroxide solution was added to the reaction system to adjust the pH to neutrality. The reaction system was then filtered, and the solid was washed with water (200 mL×3) to give the crude product 40B in the form of a white solid (50 g, 85.3% yield).
$^1$H NMR (400 MHz, DMSO-d6) δ=9.98 (s, 1H), 7.86 (s, 1H), 2.99-2.93 (m, 4H), 2.09-2.05 (m, 2H), 2.00 (s, 3H); LCMS m/z=301.2[M+1].

Step 2

N-(6-methyl-4-nitro-2,3-dihydro-1H-inden-5-yl)acetamide (Compound 40C)

Compound 40B (30 g, 106 mmol) and a methyl borate (9 g, 150 mmol) were added successively into a 1 L round-bottomed flask under nitrogen atmosphere, and potassium carbonate (34.7 g, 252 mmol) was then added. After the addition was completed, the reaction system was stirred for 15 min, and bis(triphenylphosphine)palladium(II) chloride (5 g, 8.5 mmol) was added. The reaction system was warmed to reflux (100° C.). After the reaction was completed, diluted hydrochloric acid was added to adjust the reaction system to neutrality, and the reaction system was then filtered and purified by slurring (petroleum ether:ethyl acetate=10:1) to give the crude product compound 40C in the form of a black powder (19.7 g, 82.2% yield).
$^1$H NMR (400 MHz, DMSO-d6), δ=9.66 (s, 1H), 7.40 (s, 1H), 2.93-2.91 (m, 4H), 2.20 (s, 3H), 2.09-2.05 (m, 2H), 2.00 (s, 3H); LCMS m/z (ESI)=235.1[M+1].

Step 3

6-methyl-4-nitro-2,3-dihydro-1H-inden-5-amine (Compound 40D)

Compound 40C (20 g, 85.6 mmol), ethanol (90 mL) and hydrochloric acid (270 mL) were added successively into a 500 mL round-bottomed flask under nitrogen atmosphere, and the reaction system was then warmed to reflux (100° C.) after the addition was completed. After the reaction was completed, aqueous sodium hydroxide solution was added to quench the reaction, and the reaction system was filtered. The crude product was purified by column chromatography (petroleum ether:ethyl acetate=5:1) to give compound 40D in the form of a red powder (14 g, 83% yield).

$^1$H NMR (400 MHz, DMSO-d6) δ=7.20 (s, 1H), 6.62 (s, 2H), 3.17-3.13 (t, 2H), 2.77-2.73 (t, 2H), 2.15 (s, 3H), 1.98-1.93 (m, 2H); LCMS m/z=193.1[M+1].

Step 4

5-bromo-6-methyl-4-nitro-2,3-dihydro-1H-indene (Compound 40E)

Compound 40D (14 g, 73 mmol), acetonitrile (525 mL), tert-butyl nitrite (15 g, 146 mmol) and cuprous bromide (20.9 g, 146 mmol) were successively added into a 500 mL round-bottomed flask under nitrogen atmosphere in an ice salt bath, and 30 min after the addition was completed, the reaction system was reacted at room temperature for 4 h. After the reaction was completed, diluted hydrochloric acid was added into the reaction system to adjust the pH to neutrality, and ethyl acetate (200 mL×3) was added for extraction. The organic phase was dried over anhydrous sodium sulfate and filtered, and the organic solvent was removed under reduced pressure. The crude product was purified by column chromatography (petroleum ether:ethyl acetate=100:1) to give compound 40E in the form of a pale yellow solid (6.3 g, 34% yield).

$^1$H NMR (400 MHz, DMSO-d6) δ=7.48 (s, 1H), 3.06-2.87 (m, 4H), 2.40 (s, 3H), 2.12-2.05 (m, 2H).

Step 5

5-bromo-6-methyl-2,3-dihydro-1H-inden-4-amine (Compound 40F)

Compound 40E (6.3 g, 24.7 mmol), aqueous ethanol solution (4:1, 100 mL) and saturated ammonium chloride solution (25 mL) were added successively into a 250 mL round-bottomed flask, and reduced iron powder (4.2 g, 74.1 mmol) was added slowly. The reaction system was reacted at room temperature for 4 h and after the reaction was completed, the reaction system was filtered and extracted with ethyl acetate (200 mL×3). The organic phase was dried over anhydrous sodium sulfate and filtered, and the organic solvent was removed under reduced pressure to give compound 40F in the form of a pale red oil (4.0 g, 72.7% yield)

$^1$H NMR (400 MHz, DMSO-d6) δ=6.46 (s, 1H), 4.94 (s, 2H), 2.74-2.65 (m, 4H), 2.23 (s, 3H), 1.99-1.96 (m, 2H); LCMS m/z=226.0, 228.0[M+1].

Step 6

5-(1-cyclopropylvinyl)-6-methyl-2,3-dihydro-1H-inden-4-amine (Compound 40G)

Compound 40F (4.0 g, 17.8 mmol), 2-(1-cyclopropylvinyl)-4,4,5,5-tetramethyl-1,3,2-dioxaborolane (6.9 g, 35.6 mmol), cesium carbonate (11.6 g, 35.6 mmol), bis(triphenylphosphine)palladium(II) chloride (1.4 g, 1.78 mmol) and a mixed solvent of 1,4-dioxane/water (30 mL:20 mL) were added successively into a 250 mL round-bottomed flask under nitrogen atmosphere, and the reaction system was reacted at 100° C. for 12 h. After the reaction was completed, the reaction system was cooled to room temperature. Water was added to quench the reaction, and ethyl acetate (200 mL×3) was added for extraction. The organic phase was dried over anhydrous sodium sulfate and filtered, and the organic solvent was removed under reduced pressure. The residue was subjected to column chromatography (petroleum ether:ethyl acetate=60:1) and purified by preparative medium pressure liquid chromatography to give compound 40G in the form of a pale yellow oil (2.2 g, 58.3% yield).

$^1$H NMR (400 MHz, CDCl$_3$) δ=6.58 (s, 1H), 5.36 (d, 1H), 4.86 (d, 1H), 2.88-2.84 (t, 2H), 2.74-2.70 (t, 2H), 2.17 (s, 3H), 2.12-2.05 (m, 2H), 1.67-1.63 (m, 1H), 0.70-0.64 (m, 2H), 0.41-0.32 (m, 2H); LCMS m/z=214.1[M+1].

Step 7

N-((5-(1-cyclopropylvinyl)-6-methyl-2,3-dihydro-1H-inden-4-yl)carbamoyl)-4-(2-hydroxypropan-2-yl) furan-2-sulfonamide (Compound 40)

Compound 40G (200 mg, 0.94 mmol), tetrahydrofuran (10 mL), N,N-diisopropylethylamine (310 μL, 1.9 mmol) and 2,2,2-trichloroethyl chloroformate (260 μL, 1.9 mmol) were added successively into a 100 mL round-bottomed flask under nitrogen atmosphere, and the reaction system was reacted at room temperature for 1 h. Water (10 mL) was added to quench the reaction, and ethyl acetate (20 mL×3) was added for extraction. The organic phase was dried over anhydrous sodium sulfate and filtered, and the organic solvent was removed under reduced pressure. The residue was dissolved in tetrahydrofuran (10 mL), and compound 2e (164 mg, 0.8 mmol) and sodium hydride (60 mg, 1.5 mmol) were added. The mixture was reacted at room temperature for 2 h. After the reaction was completed as detected by TLC, water (20 mL) was added to quench the reaction, and ethyl acetate (30 mL×3) was added for extraction. The organic phase was dried over anhydrous sodium sulfate and filtered, and the organic solvent was removed. The crude product was purified by preparative medium pressure liquid chromatography to give compound 40 in the form of a yellow solid (150 mg, 36% yield, UPLC: 96%).

$^1$H NMR (400 MHz, Chloroform-d) δ=8.14 (s, 1H), 7.54 (s, 1H), 7.15 (s, 1H), 7.00 (s, 1H), 5.34 (d, 1H), 4.79 (d, 1H), 2.88 (q, 2H), 2.70 (dt, 1H), 2.49 (s, 1H), 2.22 (s, 3H), 2.09-2.01 (m, 1H), 1.99-1.90 (m, 1H), 1.64-1.58 (m, 1H), 1.54 (s, 6H), 0.72-0.56 (m, 2H), 0.26 (dd, 2H); LCMS m/z (ESI)=445.1[M+1].

Example 41

(R)-N-((5-(1-cyclopropylethyl)-7-fluoro-2,3-dihydro-1H-inden-4-yl)carbamoyl)-4-(2-hydroxypropan-2-yl)furan-2-sulfonamide (Compound 41)

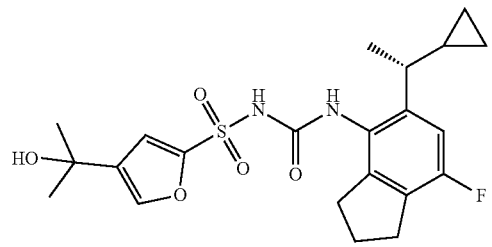

Compound 41

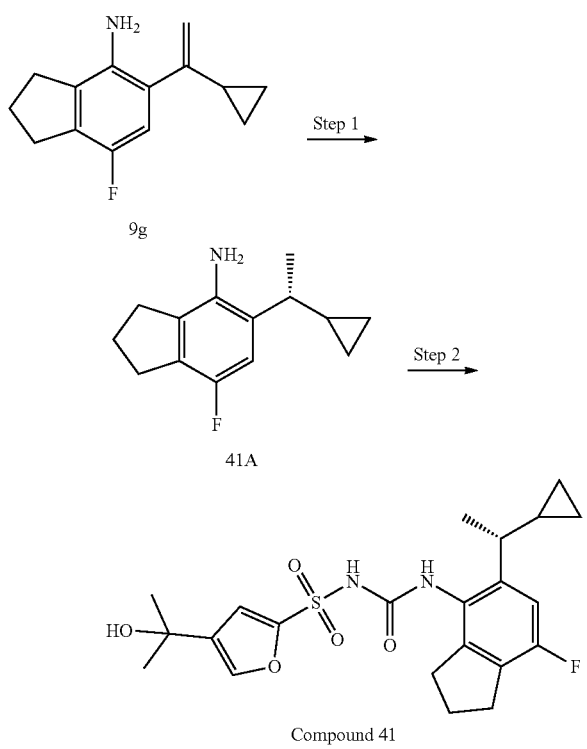 [SMILES: C=C(c1cc(F)c2c(c1N)CCC2)C1CC1 ; C[C@@H](c1cc(F)c2c(c1N)CCC2)C1CC1 ; C[C@@H](c1cc(F)c2c(c1NC(=O)NS(=O)(=O)c1cc(C(C)(C)O)co1)CCC2)C1CC1]

Compound 41

Step 1

(R)-5-(1-cyclopropylethyl)-7-fluoro-2,3-dihydro-1H-inden-4-amine (Compound 41A)

For synthesis of compound 41A, reference was made to patent CN108017559. 9G (1.0 g, 4.60 mmol) and dichloromethane (20 mL) were added into a 500 mL autoclave, and then a catalyst ruthenium [(R)-2,2'-bis(diphenylphosphino)-1,11-binaphthyl]diacetate (194 mg, 0.23 mmol) was added. After the addition was completed, the autoclave was tightly closed and sealed, and purged with hydrogen 3 times. The hydrogen was introduced until the pressure gauge on the autoclave showed 12 atm, and then the reaction system was reacted for 30 h at room temperature. The reaction system was concentrated under reduced pressure to remove the solvent and the residue was purified by silica gel column chromatography (petroleum ether/ethyl acetate=30:1) to give compound 41A in the form of a pale yellow oil (798 mg, 79.8% yield, ee %: 97.50%, chiral HPLC (2 mL_10 B4_C2); mobile phase: methanol; column temperature: 35° C.; mobile phase (%): 15; column pressure: 2000 psi; flow rate: 2 mL/min; detector signal channel: 215 nm@4.8 nm; start wavelength of diode array detector: 200; stop wavelength of diode array detector: 400 nm; RT=2.050 min).

LCMS m/z (ESI)=220.1[M+1].

Step 2

(R)-N-((5-(1-cyclopropylethyl)-7-fluoro-2,3-dihydro-1H-inden-4-yl)carbamoyl)-4-(2-hydroxypropan-2-yl)furan-2-sulfonamide (Compound 41)

Compound 41A (150 mg, 0.685 mmol), triethylamine (84 mg, 0.822 mmol) and tetrahydrofuran (20 mL) were added successively into a 100 mL round-bottomed flask under nitrogen atmosphere, and then triphosgene (82 mg, 0.274 mmol) was added in an ice bath. The reaction system was warmed to reflux, reacted for 2 h, and then filtered to remove the solids. 2e (140 mg, 0.685 mmol) and sodium methoxide (74 mg, 1.37 mmol) were added to the filtrate, and the mixture was reacted at room temperature for 2 h. After the reaction was completed as detected by TLC, water (100 mL) was added to quench the reaction, and DCM (30 mL×3) was added for extraction. The organic phase was dried over anhydrous sodium sulfate and filtered, and the organic solvent was removed. The crude product was purified by preparative medium pressure liquid chromatography to give compound 41 in the form of a yellow solid (140 mg, 45.4% yield, ee %: 96.06%, chiral HPLC (OZ2); mobile phase: methanol; column temperature: 35° C.; mobile phase (%): 15; column pressure: 2000 psi; flow rate: 2 mL/min; detector signal channel: 215 nm@4.8 nm; start wavelength of diode array detector: 200 nm; stop wavelength of diode array detector: 400 nm; RT=16.260 min).

$^1$H NMR (400 MHz, DMSO-d6) δ=7.71 (br, 1H), 7.55 (s, 1H), 6.89 (br, 1H), 6.86 (d, 1H), 6.84 (s, 1H), 4.96 (s, 1H), 2.75 (t, 2H), 2.55 (t, 2H), 2.06-2.05 (m, 1H), 1.96-1.84 (m, 2H), 1.28 (d, 6H), 1.00 (d, 3H), 0.95-0.80 (m, 1H), 0.40-0.33 (m, 1H), 0.16-0.11 (m, 1H), 0.06-0.02 (m, 1H), 0.01-0.11 (m, 1H); $^{19}$F NMR 6=120.22; LCMS m/z=451.2[M+1].

Example 42

(R)- and (S)-N-((5-((R)-1-cyclopropylethyl)-7-fluoro-2,3-dihydro-1H-inden-4-yl)carbamoyl)-4-(2-hydroxypropan-2-yl)furan-2-sulfonimidamide (Compounds 42-1 and 42-2)

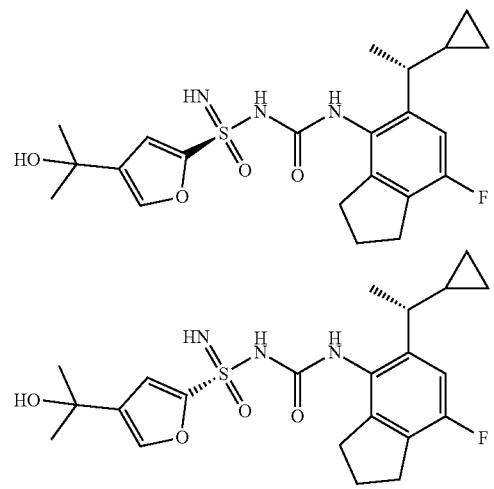

Compounds 42-1 and 42-2

For synthesis of compounds 42-1 and 42-2, reference was made to preparation method of compounds 21-1 and 21-2. Compound 42-1 (118 mg, 47.9% yield, ee %: 97.0%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=12.006 min) and compound 42-2 (113 mg, 45.9% yield, ee %: 95.56%, chiral HPLC (OZ); mobile phase: n-hexane/ethanol=90/10; column temperature: 35° C.; column pressure: 80 bar; flow rate:

1 mL/min; detector signal channel: 215 nm@4.8 nm; start wavelength of diode array detector: 200 nm; stop wavelength of diode array detector: 400 nm; RT=12.910 min).

Compound 42-1: ¹H NMR (400 MHz, DMSO-d6) δ=8.23 (br, 1H), 7.67 (s, 1H), 7.62 (br, 1H), 7.12 (d, 1H), 7.04 (d, 1H), 6.96 (br, 1H), 5.09 (s, 1H), 2.82 (t, 2H), 2.71-2.62 (m, 2H), 2.33-2.19 (m, 1H), 1.94-1.91 (m, 2H), 1.38 (s, 6H), 1.09 (d, 3H), 0.98-0.91 (m, 1H), 0.48-0.45 (m, 1H), 0.23-0.20 (m, 1H), 0.13-0.10 (m, 1H), 0.06-0.0 (m, 1H); LCMS m/z (ESI)=450.1[M+1].

Compound 42-2: ¹H NMR (400 MHz, DMSO-d6) δ=8.24 (br, 1H), 7.67 (s, 1H), 7.62 (br, 1H), 7.12 (d, 1H), 7.04 (d, 1H), 6.96 (br, 1H), 5.09 (s, 1H), 2.82 (t, 2H), 2.73-2.61 (m, 2H), 2.29-2.18 (m, 1H), 1.94-1.91 (m, 2H), 1.38 (s, 6H), 1.09 (d, 3H), 0.96-0.94 (m, 1H), 0.48-0.45 (m, 1H), 0.23-0.20 (m, 1H), 0.13-0.10 (m, 1H), 0.06--0.05 (m, 1H); LCMS m/z (ESI)=450.1[M+1].

Example 43

(S)-N-((5-(1-cyclopropylethyl)-7-fluoro-2,3-dihydro-1H-inden-4-yl)carbamoyl)-4-(2-hydroxypropan-2-yl)furan-2-sulfonamide (Compound 43)

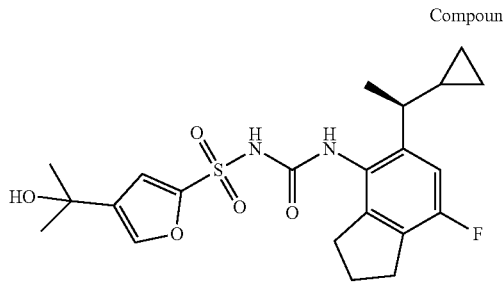

Compound 43

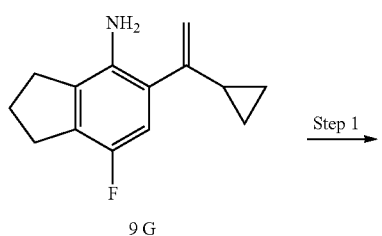

9G

Step 1

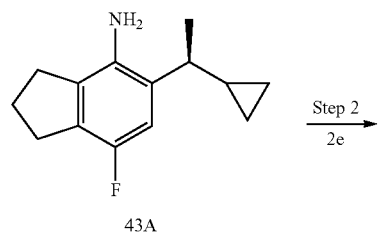

43A

Step 2
2e

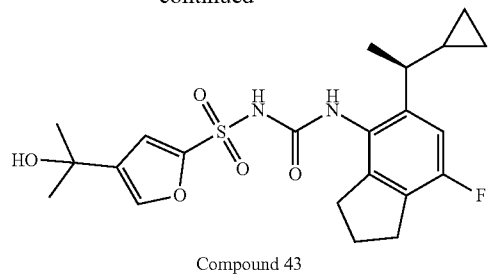

Compound 43

Step 1

(R)-5-(1-cyclopropylethyl)-7-fluoro-2,3-dihydro-1H-inden-4-amine (Compound 43A)

For synthesis of compound 43A, reference was made to patent CN108017559. 9G (1.3 g, 5.99 mmol) and dichloromethane (40 mL) were added into a 500 mL autoclave, and then a catalyst ruthenium [(S)-2,2'-bis(diphenylphosphino)-1,11-binaphthyl]diacetate (253 mg, 0.299 mmol) was added. After the addition was completed, the autoclave was tightly closed and sealed, and purged with hydrogen 3 times. The hydrogen was introduced until the pressure gauge on the autoclave showed 12 atm, and then the reaction system was reacted for 30 h at room temperature. The reaction system was concentrated under reduced pressure to remove the solvent, and the residue was purified by silica gel column chromatography (petroleum ether/ethyl acetate=30:1) to give compound 43A in the form of a pale yellow oil (1.2 g, 91.4% yield, ee %: 98.76%, chiral HPLC (2 mL_10 B4_C2); mobile phase: methanol; column temperature: 35° C.; mobile phase (%): 15; column pressure: 2000 psi; flow rate: 2 mL/min; detector signal channel: 215 nm@4.8 nm; start wavelength of diode array detector: 200; stop wavelength of diode array detector: 400 nm; RT=2.325 min).

LCMS m/z (ESI)=220.1[M+1].

Step 2

(S)-N-((5-(1-cyclopropylethyl)-7-fluoro-2,3-dihydro-1H-inden-4-yl)carbamoyl)-4-(2-hydroxypropan-2-yl)furan-2-sulfonamide (Compound 43)

Compound 43A (100 mg, 0.46 mmol) and triethylamine (62.5 mg, 0.55 mmol) were dissolved in THF (10 mL) in a 100 mL round-bottomed flask under nitrogen atmosphere, and then triphosgene (50.1 mg, 0.18 mmol) was added in an ice bath. The reaction system was warmed to reflux at 80° C., reacted for 1 h, and then filtered to remove the solids. Intermediate 2e (94.0 mg, 0.46 mmol) and sodium methoxide (49.8 mg, 0.91 mmol) were added to the filtrate, and the mixture was reacted at 80° C. for 1 h. After the reaction was completed as detected by TLC, water was added to quench the reaction, and EA (40 mL×3) was added for extraction. The organic phase was washed with saturated brine, dried over anhydrous sodium sulfate and concentrated under reduced pressure to remove the organic solvent. The crude product was purified by preparative medium pressure liquid chromatography to give compound 43 in the form of a white solid (34 mg, 97.59% purity, 16.7% yield, ee %: 99.40%, chiral HPLC (2 mL_10 B4_C2); mobile phase: methanol/n-hexane=10:90; column temperature: 35° C.; mobile phase (%): 15; column pressure: 2000 psi; flow rate: 2 mL/min;

detector signal channel: 215 nm@4.8 nm; start wavelength of diode array detector: 200 nm; stop wavelength of diode array detector: 400 nm; RT=14.133 min).

$^1$H NMR (400 MHz, DMSO): δ=8.51 (s, 1H), 7.47 (s, 1H), 7.35 (s, 1H), 6.86 (d, 1H), 6.58 (s, 1H), 4.91 (s, 1H), 2.82 (t, 2H), 2.70 (t, 2H), 2.34-2.23 (m, 1H), 1.96 (dd, 2H), 1.35 (s, 6H), 1.09 (d, 3H), 0.99-0.85 (m, 1H), 0.44-0.38 (m, 1H), 0.31-0.16 (m, 1H), 0.09-0.00 (m, 2H); $^{19}$F NMR (377 MHz, DMSO): δ=121.99; LCMS m/z (ESI)=451.2[M+1].

Example 44

(R)- and (S)-N-((5-((S)-1-cyclopropylethyl)-7-fluoro-2,3-dihydro-1H-inden-4-yl)carbamoyl)-4-(2-hydroxypropan-2-yl)furan-2-sulfonimidamide (Compounds 44-1 and 44-2)

Compounds 44-1 and 44-2

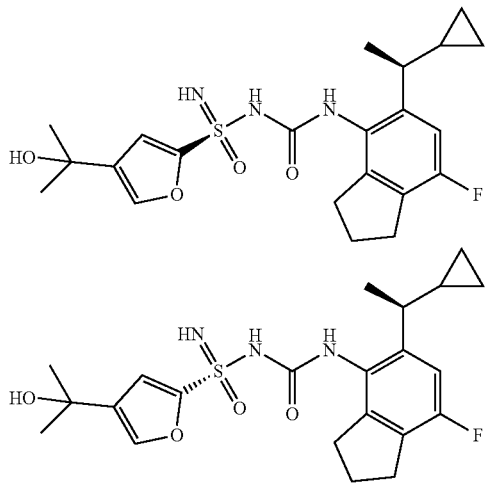

For synthesis of compounds 44-1 and 44-2, reference was made to preparation method of compounds 21-1 and 21-2. Compound 44-1 (71 mg, 44.9% yield, ee %: 99.80%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=18.855 min) and compound 44-2 (63 g, 39.6% yield, ee %: 99.07%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=14.178 min).

Compound 44-1: $^1$H NMR (400 MHz, DMSO-d6) δ=8.24 (s, 1H), 7.68 (d, 1H), 7.62 (s, 2H), 6.97 (s, 1H), 6.93 (d, 1H), 5.08 (s, 1H), 2.85 (t, 2H), 2.7-2.62 (m, 2H), 2.28-2.15 (m, 1H), 2.05-1.89 (m, 2H), 1.38 (s, 6H), 1.10 (d, 3H), 0.99-0.89 (m, 1H), 0.46 (dd, 1H), 0.26-0.15 (m, 1H), 0.15-0.06 (m, 1H), 0.05-0.00 (m, 1H); $^{19}$F NMR δ-121.99 (s); LCMS m/z=450.2[M+1].

Compound 44-2: $^1$H NMR (400 MHz, DMSO-d6) δ=8.24 (s, 1H), 7.68 (d, 1H), 7.62 (s, 2H), 6.97 (s, 1H), 6.93 (d, 1H), 5.08 (s, 1H), 2.85 (t, 2H), 2.78-2.62 (m, 2H), 2.28-2.15 (m, 1H), 2.05-1.89 (m, 2H), 1.38 (s, 6H), 1.10 (d, 3H), 0.95 (dd, 1H), 0.50-0.40 (m, 1H), 0.26-0.15 (m, 1H), 0.09-0.06 (m, 1H), 0.05-0.00 (m, 1H); $^{19}$F NMR (377 MHz, DMSO) δ 121.99 (s); LCMS m/z=450.2.

Example 45

(R)-N-((7-cyano-5-(1-cyclopropylethyl)-2,3-dihydro-1H-inden-4-yl)carbamoyl)-4-(2-hydroxypropan-2-yl)furan-2-sulfonamide (Compound 45)

Compound 45

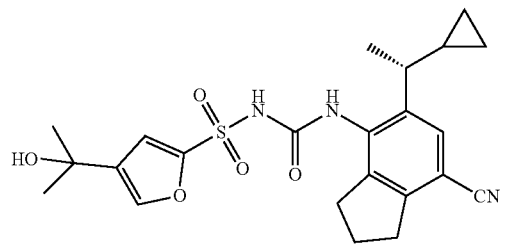

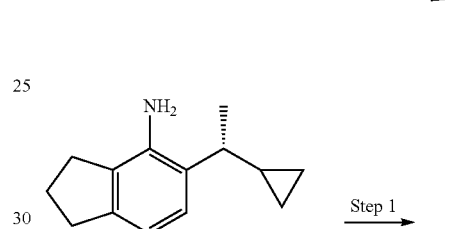

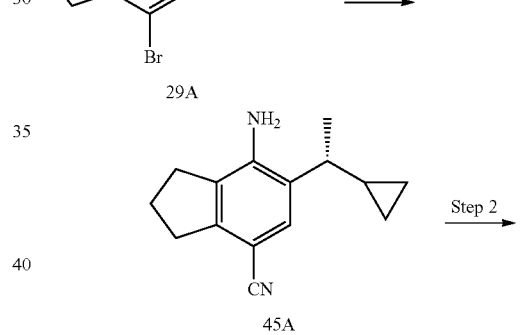

Compound 45

Step 1

(R)-7-amino-6-(1-cyclopropylethyl)-2,3-dihydro-1H-indene-4-carbonitrile (Compound 45A)

Compound 29A (803 mg, 2.88 mmol), potassium ferrocyanide (486.3 mg, 1.15 mmol), tetrakis(triphenylphosphine)palladium (166 mg, 0.144 mmol), 1,8-diazabicycloundec-7-ene (110 mg, 0.72 mmol) and a mixed solvent of tert-butanol/water (10/10 mL) were added successively into a 100 mL three-necked flask under nitrogen atmosphere, and the reaction system was warmed to 85° C., reacted for 5 h, and then cooled to room temperature after the reaction was completed. Water was added to quench the reaction, and ethyl acetate (50 mL×3) was added for extraction. The organic phase was dried over anhydrous sodium sulfate and concentrated under reduced pressure to remove the organic solvent. The crude product was purified by column chromatography to give 45A in the form of a pale yellow oil (429 mg, 66.0% yield, ee %: 97.62%, chiral HPLC (CHIRALPAK AY-3 (4.6×100 mm); mobile phase: methanol; column temperature: 35° C.; mobile phase (%): 15; column pressure: 2000 psi; flow rate: 2 mL/min; detector signal channel: 215 nm @4.8 nm; start wavelength of diode array detector: 200 nm; stop wavelength of diode array detector: 400 nm): RT=10.082 min).

LCMS m/z (ESI)=227.1 [M+1].

Step 2

(R)-N-((7-cyano-5-(1-cyclopropylethyl)-2,3-dihydro-1H-inden-4-yl)carbamoyl)-4-(2-hydroxypropan-2-yl)furan-2-sulfonamide (Compound 45)

Compound 45A (100 mg, 0.44 mmol), triethylamine (60.5 mg, 0.53 mmol) and tetrahydrofuran (20 mL) were added successively into a 100 mL round-bottomed flask under nitrogen atmosphere, and then triphosgene (52.4 mg, 0.18 mmol) was added in an ice bath. The reaction system was warmed to reflux, reacted for 2 h, and then filtered to remove the solids. 2e (90.7 mg, 0.44 mmol) and sodium methoxide (47.8 mg, 0.88 mmol) were added to the filtrate, and the mixture was reacted at room temperature for 2 h. After the reaction was completed as detected by TLC, water (100 mL) was added to quench the reaction, and DCM (30 mL×3) was added for extraction. The organic phase was dried over anhydrous sodium sulfate and filtered, and the organic solvent was removed. The crude product was purified by preparative medium pressure liquid chromatography to give compound 45 in the form of a yellow solid (32.1 mg, 15.8% yield, ee %: 98.73%, chiral HPLC (CHIRALPAK AY-3 (4.6×100 mm); mobile phase: methanol; column temperature: 35° C.; mobile phase (%): 15; column pressure: 2000 psi; flow rate: 2 mL/min; detector signal channel: 215 nm@4.8 nm; start wavelength of diode array detector: 200 nm; stop wavelength of diode array detector: 400 nm): RT=9.662 min).

$^1$H NMR (400 MHz, DMSO-d6) δ=7.83 (s, 1H), 7.51 (s, 1H), 7.36 (s, 1H), 7.09 (s, 1H), 6.57 (s, 1H), 4.91 (s, 1H), 2.95 (t, 2H), 2.75 (t, 2H), 2.35 (dd, 1H), 2.06-1.90 (m, 2H), 1.35 (s, 6H), 1.12 (d, 3H), 1.04-0.89 (m, 1H), 0.57-0.38 (m, 1H), 0.31-0.20 (m, 1H), 0.12 (m, 1H), 0.08-0.01 (m, 1H); LCMS m/z (ESI)=458.2[M+1].

Example 46

($R_S$, $R_C$)- and ($S_S$, $R_C$)-N-((7-cyano-5-(1-cyclopropylethyl)-2,3-dihydro-1H-inden-4-yl)carbamoyl)-4-(2-hydroxypropan-2-yl)furan-2-sulfonimidamide (Compounds 46-1 and 46-2)

Compounds 46-1 and 46-2

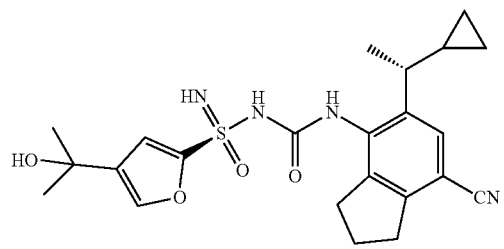

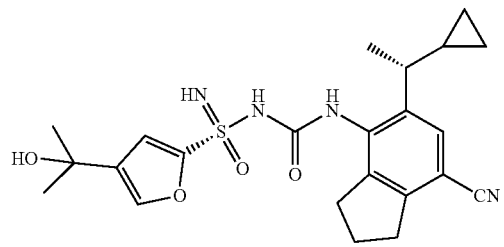

For synthesis of compounds 46-1 and 46-2, reference was made to preparation method of compounds 21-1 and 21-2; compound 46-1 (30 mg, 38.5% yield, ee %: 99.99%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=36.665 min) and compound 46-2 (32 mg, 41.0% yield, ee %: 99.99%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=29.353 min).

Compound 46-1: $^1$H NMR (400 MHz, DMSO-d6) δ=8.61 (s, 1H), 7.68 (d, 3H), 7.59 (s, 1H), 6.98 (s, 1H), 5.06 (s, 1H), 2.98 (t, 2H), 2.75 (t, 2H), 2.29 (dq, 1H), 2.09-1.93 (m, 2H), 1.36 (s, 6H), 1.14-1.05 (d, 3H), 1.04-0.92 (m, 1H), 0.53-0.46 (m, 1H), 0.30-0.25 ((m, 1H), 0.17-0.12 (m, 1H), 0.06-0.02 (m, 1H); LCMS m/z=457.2[M+1].

Compound 46-2: $^1$H NMR (400 MHz, DMSO-d6) δ=8.61 (s, 1H), 7.68 (d, 3H), 7.59 (s, 1H), 6.98 (s, 1H), 5.09 (s, 1H), 2.98 (t, 2H), 2.74 (t, 2H), 2.29 (dq, 1H), 2.07-1.91 (m, 2H), 1.38 (s, 6H), 1.16-1.08 (d, 3H), 1.05-0.94 (m, 1H), 0.55-0.47 (m, 1H), 0.29-0.21 ((m, 1H), 0.15-0.10 (m, 1H), 0.06-0.01 (m, 1H); LCMS m/z=457.2[M+1].

Example 47

(S)-N-((7-cyano-5-(1-cyclopropylethyl)-2,3-dihydro-1H-inden-4-yl)carbamoyl)-4-(2-hydroxypropan-2-yl)furan-2-sulfonamide (Compound 47)

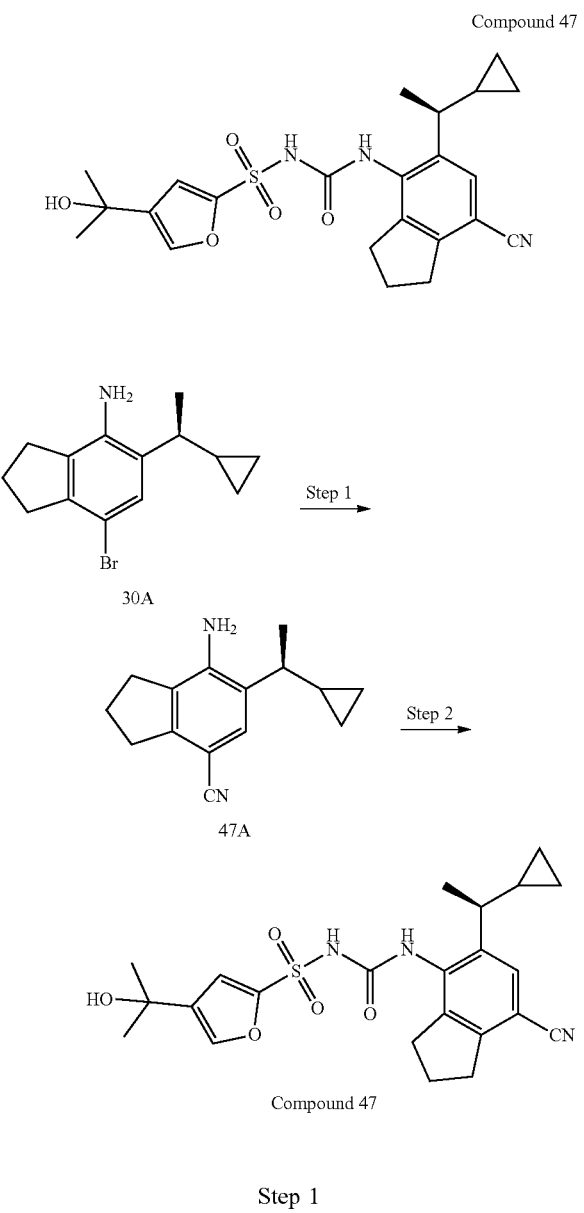

Step 1

(S)-7-amino-6-(1-cyclopropylethyl)-2,3-dihydro-1H-indene-4-carbonitrile (Compound 47A)

Compound 30A (1.43 g, 5.12 mmol), potassium ferrocyanide (866 mg, 2.05 mmol), tetrakis(triphenylphosphine) palladium (297 mg, 0.256 mmol), 1,8-diazabicycloundec-7-ene (196 mg, 1.28 mmol) and a mixed solvent of tert-butanol/water (10/10 mL) were added successively into a 100 mL three-necked flask under nitrogen atmosphere, and the reaction system was warmed to 85° C., reacted for 5 h, and then cooled to room temperature after the reaction was completed. Water was added to quench the reaction, and ethyl acetate (50 mL×3) was added for extraction. The organic phase was dried over anhydrous sodium sulfate and concentrated under reduced pressure to remove the organic solvent. The crude product was purified by column chromatography to give 47A in the form of a pale yellow oil (910 mg, 78.4% yield, ee %: 98.06%, chiral HPLC (CHIRALPAK AY-3 (4.6×100 mm); mobile phase: methanol; column temperature: 35° C.; mobile phase (%): 15; column pressure: 2000 psi; flow rate: 2 mL/min; detector signal channel: 215 nm @4.8 nm; start wavelength of diode array detector: 200 nm; stop wavelength of diode array detector: 400 nm): RT=9.513 min).

LCMS m/z (ESI)=227.1 [M+1].

Step 2

(S)-N-((7-cyano-5-(1-cyclopropylethyl)-2,3-dihydro-1H-inden-4-yl)carbamoyl)-4-(2-hydroxypropan-2-yl)furan-2-sulfonamide (Compound 47)

Compound 47A (100 mg, 0.44 mmol), triethylamine (60.5 mg, 0.53 mmol) and tetrahydrofuran (20 mL) were added successively into a 100 mL round-bottomed flask under nitrogen atmosphere, and then triphosgene (52.4 mg, 0.18 mmol) was added in an ice bath. The reaction system was warmed to reflux, reacted for 2 h, and then filtered to remove the solids. 2e (90.7 mg, 0.44 mmol) and sodium methoxide 47.8 mg, 0.88 mmol) were added to the filtrate, and the mixture was reacted at room temperature for 2 h. After the reaction was completed as detected by TLC, water (100 mL) was added to quench the reaction, and DCM (30 mL×3) was added for extraction. The organic phase was dried over anhydrous sodium sulfate and filtered, and the organic solvent was removed. The crude product was purified by preparative medium pressure liquid chromatography to give compound 47 in the form of a yellow solid (90 mg, 40.9% yield, ee %: 99.30%, chiral HPLC (CHIRALPAK AY-3 (4.6×100 mm); mobile phase: methanol; column temperature: 35° C.; mobile phase (%): 15; column pressure: 2000 psi; flow rate: 2 mL/min; detector signal channel: 215 nm@4.8 nm; start wavelength of diode array detector: 200 nm; stop wavelength of diode array detector: 400 nm): RT=9.150 min).

$^1$H NMR (400 MHz, DMSO-d6) δ=7.72 (1H, s), 7.39 (1H, s), 7.25 (1H, d, J 0.8), 6.47 (1H, d, J 0.8), 4.79 (1H, s), 2.83 (t, 2H), 2.63 (t, 2H), 2.25 (dd, 1H), 1.87 (dd, 2H), 1.23 (s, 6H), 1.00 (d, 3H), 0.92-0.80 (m, 1H), 0.40-0.30 (m, 1H), 0.16-0.08 (m, 1H), 0.07-0.04 (m, 1H), 0.03-0.01 (m, 1H); LCMS m/z (ESI)=458.2[M+1].

Example 48

($R_S$, $S_C$)- and ($S_S$, $S_C$)-N-((7-cyano-5-(1-cyclopropylethyl)-2,3-dihydro-1H-inden-4-yl)carbamoyl)-4-(2-hydroxypropan-2-yl)furan-2-sulfonimidamide (Compounds 48-1 and 48-2)

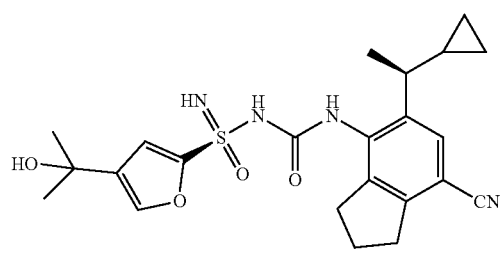

Compounds 48-1 and 48-2

163

-continued

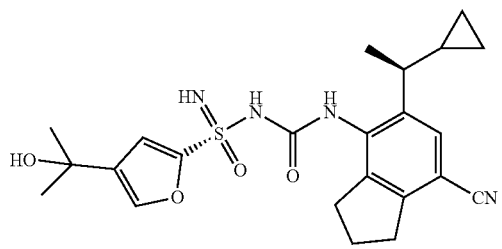

164

-continued

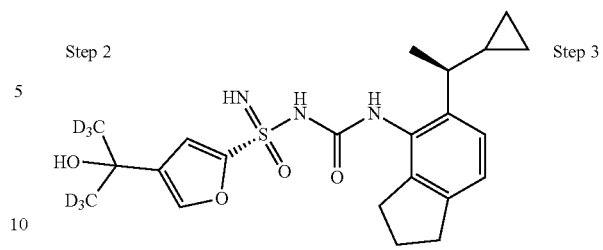

For synthesis of compounds 48-1 and 48-2, reference was made to preparation method of compounds 21-1 and 21-2; compound 48-1 (75 mg, 25% yield, ee %: 99.99%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=33.584 min) and compound 48-2 (75 mg, 25% yield, ee %: 99.22%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=43.523 min).

Compound 48-1: $^1$H NMR (400 MHz, DMSO-d6) δ=8.58 (s, 1H), 7.68 (s, 1H), 7.66-7.60 (m, 1H), 7.59 (s, 1H), 7.57-7.51 (m, 1H), 6.96 (s, 1H), 5.08 (d, 1H), 2.98 (t, 2H), 2.75 (t, 2H), 2.35-2.23 (m, 1H), 2.02 (dd, 2H), 1.38 (s, 6H), 1.16-1.06 (d, 3H), 1.05-0.95 (m, 1H), 0.55-0.44 (m, 1H), 0.31-0.18 (m, 1H), 0.18-0.07 (m, 1H), 0.05-0.01 (m, 1H); LCMS m/z=457.2[M+1].

Compound 48-2: $^1$H NMR (400 MHz, DMSO-d6) δ=8.58 (s, 1H), 7.68 (s, 1H), 7.66-7.61 (m, 1H), 7.59 (s, 1H), 7.58-7.53 (m, 1H), 6.98 (s, 1H), 5.07 (d, 1H), 2.98 (t, 2H), 2.76 (t, 2H), 2.32-2.27 (m, 1H), 2.03 (dd, 2H), 1.38 (s, 6H), 1.12-1.09 (d, 3H), 1.02-0.95 (m, 1H), 0.56-0.42 (m, 1H), 0.32-0.16 (m, 1H), 0.15-0.06 (m, 1H), 0.05-0.01 (m, 1H); LCMS m/z=457.2[M+1].

Example 49

($R_S$, $S_C$)- and ($S_S$, $S_C$)-N-((5-(1-cyclopropylethyl)-2,3-dihydro-1H-inden-4-yl)carbamoyl)-4-(2-hydroxypropan-2-yl-1,1,1,3,3,3-d6)furan-2-sulfonimidamide (Compounds 49-1 and 49-2)

Compounds 49-1 and 49-2

Step 1

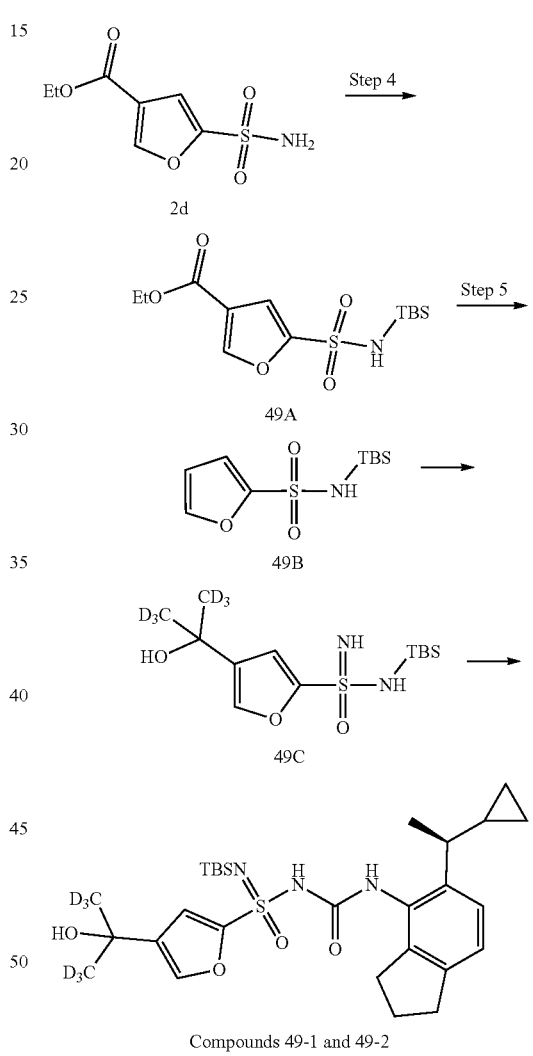

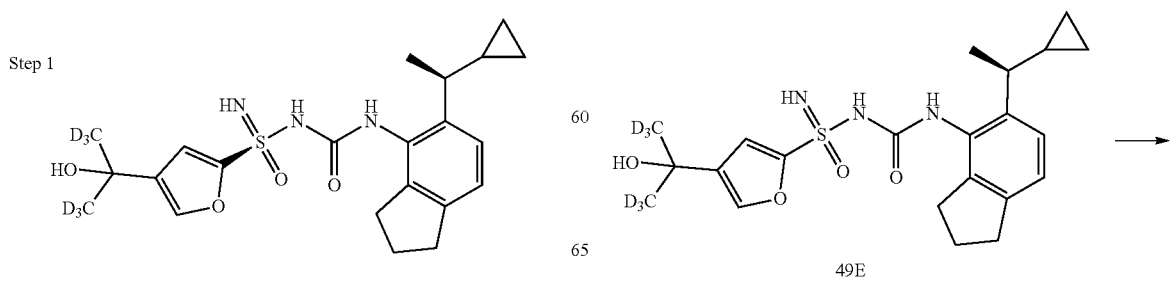

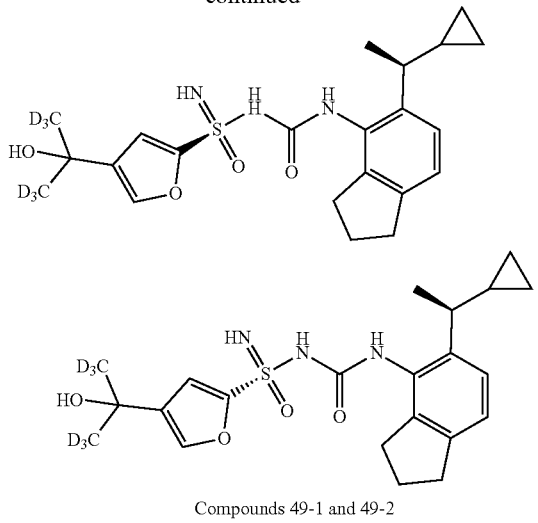

Compounds 49-1 and 49-2

Step 1 ethyl 5-(N-(tert-butyldimethylsilyl)sulfamoyl)furan-3-carboxylate (49A)

Compound 2d (15.0 g, 68.42 mmol) was dissolved in dry THF in a 500 mL round-bottomed flask under nitrogen atmosphere, and sodium hydride (4.1 g, 102.64 mmol) was added in an ice bath. After the reaction was completed, the reaction system was reacted for 30 min at 0° C., and 30 min later, a solution of tert-butyldimethylchlorosilane (12.0 g, 82.10 mmol) in THF (100 mL) was added dropwise. The reaction system was reacted at room temperature for 2 h after the dropwise addition was completed. After the reaction was completed, water was added to quench the reaction, and EA (100 mL×3) was added for extraction. The organic phase was dried over anhydrous sodium sulfate and filtered, and the organic solvent removed under reduced pressure. The crude product was purified by column chromatography to give compound 49A in the form of a pale yellow oil (10.6 g, 46.5% yield).

LCMS m/z (ESI)=334.1 [M+1].

Step 2

N-(tert-butyldimethylsilyl)-4-(2-hydroxypropan-2-yl-1,1,1,3,3,3-d6)furan-2-sulfonamide (49B)

49A (10 g, 29.99 mmol) was dissolved in THF (100 mL) in a 250 mL three-necked flask under nitrogen atmosphere, and the solution was cooled to −15° C. Deuterated methylmagnesium iodide (100 mL, 100 mmol, 1.0 mol/L in THF) was added dropwise, and the reaction system was stirred overnight at room temperature after the dropwise addition was completed. After the reaction was completed, ice ammonium chloride (100 mL) was added to quench the reaction, and EA (300 mL×3) was added for extraction. The organic phases were combined, washed once with saturated brine, dried over anhydrous sodium sulfate, and concentrated under reduced pressure to evaporate off the solvent. The residue was purified by column chromatography (EA/PE (v/v)=10%-30%) to give 49B (8 g, 81.95% yield).

$^1$H NMR (400 MHz, DMSO-d$_6$) δ 7.86 (s, 1H), 7.67 (d, 1H), 6.93 (d, 1H), 5.05 (s, 1H), 0.88 (s, 9H), 0.15 (s, 6H); LCMS m/z (ESI)=326.2[M+1].

Step 3

N-(tert-butyldimethylsilyl)-4-(2-hydroxypropan-2-yl-1,1,1,3,3,3-d6)furan-2-sulfonimidamide (49C)

Triphenylphosphine (7.1 g, 27.03 mmol) and hexachloroethane (6.4 g, 27.03 mmol) were dissolved in chloroform (100 mL) in a 250 mL three-necked flask under nitrogen atmosphere, and the solution was warmed to reflux, reacted for 2 h, and then cooled to −10° C. Diisopropylethylamine (4.8 g, 36.86 mmol) was added dropwise, and the reaction system was reacted at this temperature for 10 min after the dropwise addition was completed. A solution of 49B (8.0 g, 24.58 mmol) in chloroform was added dropwise slowly, and the reaction system was reacted for 30 min at −10° C. The temperature was maintained, and ammonia gas was introduced for 30 min. The reaction system was then warmed to room temperature and reacted overnight. After the reaction was completed as detected by TLC, water was added to quench the reaction, and DCM (100 mL×3) was added for extraction. The organic phases were combined, dried over anhydrous sodium sulfate, and concentrated under reduced pressure, and the residue was separated by column chromatography (ethyl acetate:petroleum ether (v/v)=15%-20%) to give the product compound 49C (2.4 g, 30.09% yield).

$^1$H NMR (400 MHz, DMSO-d$_6$) δ 7.65-7.61 (m, 1H), 7.60-7.54 (m, 2H), 6.88 (s, 1H), 5.01 (d, 1H), 0.85 (d, 9H), 0--0.6 (m, 6H); LCMS m/z (ESI)=325.2 [M+1].

Step 4

N'-(tert-butyldimethylsilyl)-N-((5-((S)-1-cyclopropylethyl)-2,3-dihydro-1H-inden-4-yl)carbamoyl)-4-(2-hydroxypropan-2-yl-1,1,1,3,3,3-d6)furan-2-sulfonimidamide (49D)

Compound 49C (300 mg, 1.49 mmol), triethylamine (180.96 mg, 1.79 mmol) and tetrahydrofuran (30 mL) were added successively into a 100 mL round-bottomed flask under nitrogen atmosphere, and then triphosgene (176.88 mg, 0.60 mmol) was added in an ice bath. The reaction system was warmed to reflux, reacted for 2 h, and then filtered to remove the solids. Intermediate 9 (532.0 mg, 1.64 mmol) and sodium methoxide (80.51 mg, 1.49 mmol) were added to the filtrate, and the mixture was reacted at 60° C. for 2 h. After the reaction was completed as detected by TLC, compound 49D was obtained and was directly used in the next step without purification.

LCMS m/z (ESI)=552.10 [M+1].

Step 5

N-((5-((S)-1-cyclopropylethyl)-2,3-dihydro-1H-inden-4-yl)carbamoyl)-4-(2-hydroxypropan-2-yl-1,1,1,3,3,3-d6)furan-2-sulfonimidamide (49E)

Tetrabutylammonium fluoride (5.1 mL, 5.1 mmol, 1 M/THF) was added to the reaction system from the previous step, and the resulting reaction system was reacted overnight at room temperature. After the reaction was completed as detected by TLC, the reaction system was poured into water and extracted with ethyl acetate (80 mL×3). The organic phases were combined, washed once with 1 M diluted HCl, dried over anhydrous sodium sulfate and filtered, and the organic solvent was removed under reduced pressure. The residue was purified by preparative medium pressure liquid chromatography (acetonitrile/water=50%) to give 49E in the form of a white solid (120 mg, 46.3% yield).

Step 6

($R_S$, $S_C$)- and ($S_S$, $S_C$)-N-((5-(1-cyclopropylethyl)-2,3-dihydro-1H-inden-4-yl)carbamoyl)-4-(2-hydroxypropan-2-yl-1,1,1,3,3,3-d6)furan-2-sulfonimidamide (49-1 and 49-2)

49E was resolved by SFC to give compound 49-1 (194 mg, 71.6% yield, ee %: 99.99%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=15.264 min) and compound 49-2 (164 mg, 71.6% yield, ee %: 99.99%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=19.522 min).

Compound 49-1: $^1$H NMR (400 MHz, DMSO-$d_6$) δ 8.15 (s, 1H), 7.64 (s, 1H), 7.12 (d, 1H), 7.03 (d, 1H), 6.91 (s, 1H), 5.03 (s, 1H), 2.82 (t, 2H), 2.76-2.64 (m, 2H), 2.30-2.21 (m, 1H), 1.98-1.89 (m, 2H), 1.02 (t, 4H), 0.47-0.39 (m, 1H), 0.23-0.15 (m, 1H), 0.12-0.06 (m, 1H), 0.05-0.00 (m, 1H); LCMS m/z (ESI)=438.20[M+1].

Compound 49-2: 1H NMR (400 MHz, DMSO-d6) δ 8.23 (s, 1H), 7.67 (d, 1H), 7.12 (d, 1H), 7.04 (d, 1H), 6.96 (s, 1H), 5.05 (s, 1H), 2.82 (t, 2H), 2.70-2.64 (m, 2H), 2.27-2.20 (m, 1H), 1.95-1.89 (m, 2H), 1.09 (d, 3H), 0.97-0.92 (m, 1H), 0.49-0.43 (m, 1H), 0.24-0.17 (m, 1H), 0.14-0.08 (m, 1H), 0.07-0.01 (m, 1H); LCMS m/z (ESI)=438.20 [M+1].

Example 50

$R_S$- and $S_S$-N-((5-(cyclobutylmethyl)-2,3-dihydro-1H-inden-4-yl)carbamoyl)-4-(2-hydroxypropan-2-yl-1,1,1,3,3,3-d6)furan-2-sulfonimidamide (Compounds 50-1 and 50-2)

Compounds 50-1 and 50-2

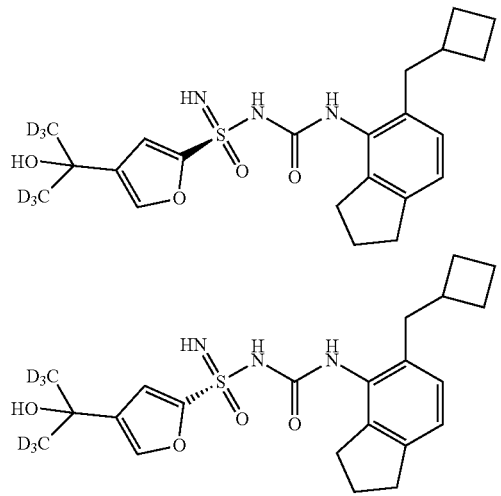

For synthesis of compounds 50-1 and 50-2, reference was made to preparation method of compounds 21-1 and 21-2; compound 50-1 (194 mg, 41.6% yield, ee %: 99.01%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=11.797 min) and compound 50-2 (164 mg, 44.6% yield, ee %: 99.99%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=18.146 min).

Compound 50-1: $^1$H NMR (400 MHz, DMSO-$d_6$) δ 8.28 (s, 1H), 7.69-7.64 (m, 3H), 7.03-6.93 (m, 2H), 6.86 (d, 1H), 5.06 (s, 1H), 2.80 (t, 2H), 2.71-2.62 (m, 2H), 2.59 (d, 2H), 2.54-2.51 (m, 1H), 1.98-1.87 (m, 4H), 1.82-1.73 (m, 2H), 1.68-1.58 (m, 2H); LCMS m/z (ESI)=438.20[M+1].

Compound 50-2: $^1$H NMR (400 MHz, DMSO-$d_6$) δ 8.28 (s, 1H), 7.71-7.62 (m, 3H), 7.02-6.92 (m, 2H), 6.86 (d, 1H), 5.05 (s, 1H), 2.80 (t, 2H), 2.72-2.63 (m, 2H), 2.58 (d, 2H), 2.54-2.51 (m, 1H), 1.97-1.87 (m, 4H), 1.82-1.73 (m, 2H), 1.67-1.58 (m, 2H); LCMS m/z (ESI)=438.20[M+1].

Example 51

($R_S$, $S_C$)- and ($S_S$, $S_C$)-N-((5-(1-cyclopropylethyl)-2,3-dihydro-1H-inden-4-yl)carbamoyl)-5-(2-hydroxypropan-2-yl)thiophene-2-sulfonimidamide (Compounds 51-1 and 51-2)

Compound 51-1 and Compound 51-2

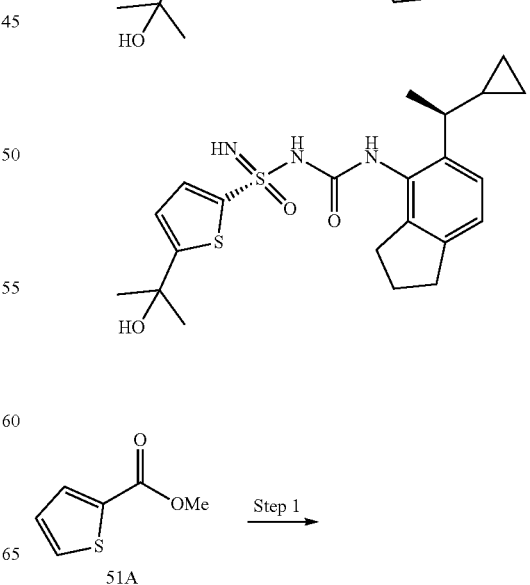

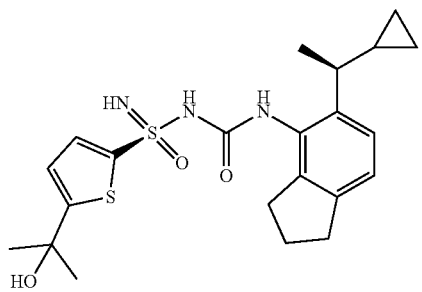

51A

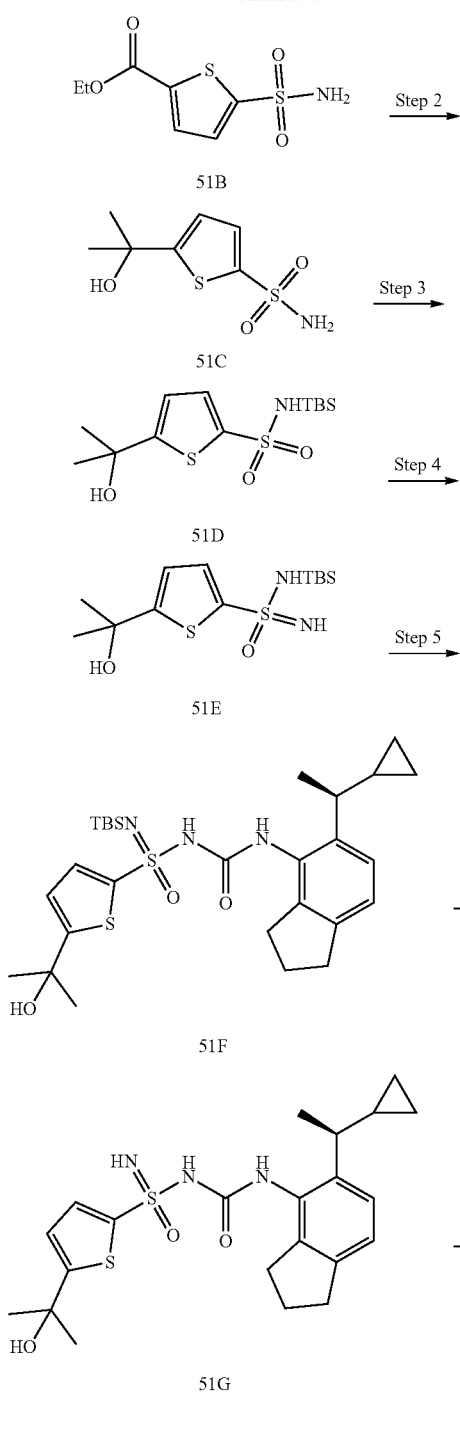

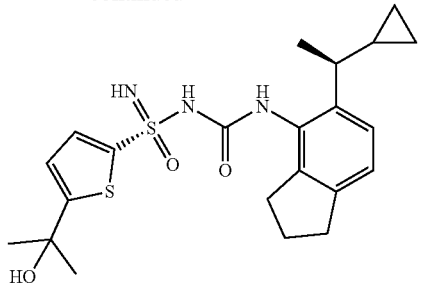

Compound 51-1 and Compound 51-2

Step 1

Methyl 5-sulfamoylthiophene-2-carboxylate (51B)

Compound 51A (10.0 g, 70.34 mmol) was dissolved in DCM (150 mL) at room temperature, and the solution was cooled to −15° C. in an ice salt bath. Sulfonyl chloride (12.3 g, 105.51 mmol) was added dropwise slowly while controlling the temperature to be not higher than −10° C. After dropwise addition was completed, the reaction system was reacted for 4 h at 40° C. and cooled to −15° C. in an ice salt bath. Phosphorus pentachloride (29.3 g, 140.68 mmol) was added in batches while controlling the temperature to be not higher than −10° C. After the addition was completed, the reaction system was reacted for 4 h at 40° C. After the reaction was completed as detected by TLC, the reaction system was added into ice water (200 mL) to quench the reaction, and then extracted with EA (200 mL×3). The organic phases were combined, washed with saturated brine (100 mL), dried over anhydrous sodium sulfate and concentrated under reduced pressure to remove the solvent to give the crude product. The crude product was dissolved in acetone (200 mL) at room temperature, and saturated aqueous ammonium bicarbonate solution (49.7 g, 0.553 mol) was added dropwise at room temperature. The reaction system was reacted overnight at room temperature. After the reaction was completed as detected by TLC, the reaction system was extracted with EA (200 mL×3), and the organic phases were combined, washed with saturated brine (100 mL), dried over anhydrous sodium sulfate, and concentrated under reduced pressure to remove the solvent to give compound 51B in the form of a brown solid powder (23.0 g, 77% yield).

$^1$H NMR (400 MHz, DMSO-d6) δ=7.95 (br, 2H), 7.77 (d, 1H), 7.58 (d, 1H), 4.32 (dd, 2H), 1.30 (t, 3H); LCMS m/z=236.0[M+1].

Step 2

5-(2-hydroxypropan-2-yl)thiophene-2-sulfonamide (51C)

Compound 51B (10.5 g, 52.55 mmol) was dissolved in dry THF (100 mL) at room temperature, and then the solution was cooled to −15° C. in an ice salt bath. Methylmagnesium bromide (71 mL, 212.77 mmol, 3 M) was added dropwise slowly while maintaining the temperature to be not higher than 0° C. After the dropwise addition was completed, the reaction system was reacted overnight at room temperature. After the reaction was completed as detected by TLC, the reaction system was poured into ice saturated ammonium chloride (200 mL) to quench the reaction, and then extracted with EA (200 mL×3). The organic phases were combined, washed with saturated brine (100 mL), dried over anhydrous sodium sulfate, and concentrated under reduced pressure to remove the solvent, and the residue was purified by silica gel column chromatography (ethyl acetate:petroleum ether=1:4-5:1) to give compound 51C in the form of a pale yellow solid (8.8 g, 88.2% yield).

$^1$H NMR (400 MHz, DMSO-d6) δ=7.54 (br, 2H), 7.35 (d, 1H), 6.90 (d, 1H), 5.75 (s, 1H), 1.50 (s, 6H); LCMS m/z=220.0[M+1].

Step 3

N-(tert-butyldimethylsilyl)-5-(2-hydroxypropan-2-yl)thiophene-2-sulfonamide (51D)

Compound 51C (6.7 g, 30.28 mmol) was dissolved in dry THF (50 mL) at room temperature, and then the solution was cooled to −10° C. in an ice salt bath. Sodium hydride (1.8 g, 45.42 mmol) was added slowly while controlling the temperature to be lower than −10° C., and then a solution of tert-butyldimethylchlorosilane (5.5 g, 36.33 mmol) in THF (50 mL) was added. The reaction system was reacted at room temperature for 3 h. After the reaction was completed as detected by TLC, the reaction system was poured into ice water (100 mL) to quench the reaction, and then extracted with EA (100 mL×3). The organic phases were combined, washed with saturated brine (50 mL), dried over anhydrous sodium sulfate, and concentrated under reduced pressure to remove the solvent, and the residue was purified by silica gel column chromatography (ethyl acetate:petroleum ether=1: 10-1:4) to give compound 51D in the form of a pale yellow oil (9.3 g, 92% yield).

LCMS m/z=336.1[M+1].

Step 4

N-(tert-butyldimethylsilyl)-5-(2-hydroxypropan-2-yl)thiophene-2-sulfonimidamide (51E)

Triphenylphosphine (8.0 g, 30.59 mmol) and hexachloroethane (8.6 g, 36.15 mmol) were dissolved in chloroform in a 250 mL three-necked flask under nitrogen atmosphere, and then the reaction system was warmed to reflux and reacted for 2 h. The reaction system was then cooled to −10° C. in an ice bath, and diisopropylethylamine (5.8 g, 44.50 mmol) was added dropwise slowly. After the dropwise addition was completed, the reaction system was reacted for 30 min at this temperature. The reaction system was then cooled to −10° C. A solution of 51D (9.3 g, 27.81 mmol) in chloroform (100 mL) was added, and after the addition was completed, the temperature was maintained at −10° C. and the reaction system was reacted for 30 min. Ammonia gas was introduced into the reaction system for 30 min, and then the reaction system was warmed to room temperature and reacted for 2 h. After the reaction was completed as detected by TLC, the reaction system was concentrated under reduced pressure to remove the solvent, and the crude product was purified by column chromatography (petroleum ether:ethyl acetate=3:1) to give 51E in the form of a pale yellow solid (7.4 g, 79.5% yield).

LCMS m/z=335.1[M+1].

Step 5

(S)-N'-(tert-butyldimethylsilyl)-N-((5-(1-cyclopropylethyl)-2,3-dihydro-1H-inden-4-yl)carbamoyl)-5-(2-hydroxypropan-2-yl)thiophene-2-sulfonimidamide (51F)

Intermediate 9 (300 mg, 1.49 mmol), triethylamine (182 mg, 1.79 mmol) and tetrahydrofuran (20 mL) were added successively into a 100 mL round-bottomed flask under nitrogen atmosphere, and then triphosgene (178 mg, 0.60 mmol) was added in an ice bath. The reaction system was warmed to reflux, reacted for 2 h, and then filtered to remove the solids. 51E (500 mg, 1.49 mmol) and sodium hydride (120 mg, 2.99 mmol) were added to the filtrate, and the mixture was reacted at room temperature for 12 h. After the reaction was completed as detected by TLC, 51F was obtained and was directly used in the next step without purification.

LCMS m/z (ESI)=562.3[M+1].

Step 6

(N)-((5-((S)-1-cyclopropylethyl)-2,3-dihydro-1H-inden-4-yl)carbamoyl)-5-(2-hydroxypropan-2-yl)thiophene-2-sulfonimidamide (51G)

Tetrabutylammonium fluoride (6 mL, 6 mmol, 1 M) was added to the reaction system from the previous step, and the resulting reaction system was reacted overnight at room temperature. After the reaction was completed as detected by TLC, the reaction system was poured into water and extracted with ethyl acetate (100 mL×3). The organic phases were combined, washed once with 1 M diluted HCl, dried over anhydrous sodium sulfate and filtered, and the organic solvent was removed under reduced pressure. The residue was purified by preparative medium pressure liquid chromatography (acetonitrile/water=50%) to give 51G in the form of a transparent solid (220 mg, two-step yield: 32.8%).

LCMS m/z=448.2[M+1].

Step 7

($R_S$, S)- and ($S_S$, $S_C$)-N-((5-(1-cyclopropylethyl)-2,3-dihydro-1H-inden-4-yl) carbamoyl)-5-(2-hydroxypropan-2-yl)thiophene-2-sulfonimidamide (Compounds 51-1 and 51-2)

51G was resolved by SFC to give compound 51-1 (106 mg, 48.2% yield, ee %: 99.99%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=19.784 min) and compound 51-2 (95 mg, 43.2% yield, ee %: 99.99%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=21.782 min).

Compound 51-1: $^1$H NMR (400 MHz, DMSO-d6) δ=8.17 (br, 1H), 7.58 (br, 2H), 7.38 (s, 1H), 7.12 (d, 1H), 7.03 (d, 1H), 6.90 (d, 1H), 5.71 (s, 1H), 2.82 (t, 2H), 2.69-2.67 (m, 2H), 2.27-2.24 (m, 1H), 1.94-1.91 (m, 2H), 1.49 (s, 6H), 1.11 (d, 3H), 0.93-0.89 (m, 1H), 0.45-0.42 (m, 1H), 0.20-0.17 (m, 1H), 0.10-0.07 (m, 1H), 0.06-0.01 (m, 1H); LCMS m/z=448.1[M+1].

Compound 51-2: $^1$H NMR (400 MHz, DMSO-d6) δ=8.18 (br, 1H), 7.57 (br, 2H), 7.39 (s, 1H), 7.12 (d, 1H), 7.03 (d, 1H), 6.91 (d, 1H), 5.72 (s, 1H), 2.82 (t, 2H), 2.74-2.62 (m, 2H), 2.26-2.24 (m, 1H), 1.94-1.91 (m, 2H), 1.49 (d, 6H), 1.08 (d, 3H), 0.95-0.93 (m, 1H), 0.45-0.43 (m, 1H), 0.21-0.20 (m, 1H), 0.11-0.09 (m, 1H), 0.05-0.01 (m, 1H); LCMS m/z=448.1[M+1].

Example 52

($R_S$, $S_C$)- and ($S_S$, $S_C$)-N-((5-(1-cyclopropylethyl)-2,3-dihydro-1H-inden-4-yl)carbamoyl)-4-(2-hydroxypropan-2-yl)furan-2-sulfonimidamide (Compounds 52-1 and 52-2)

Compounds 52-1 and 52-2

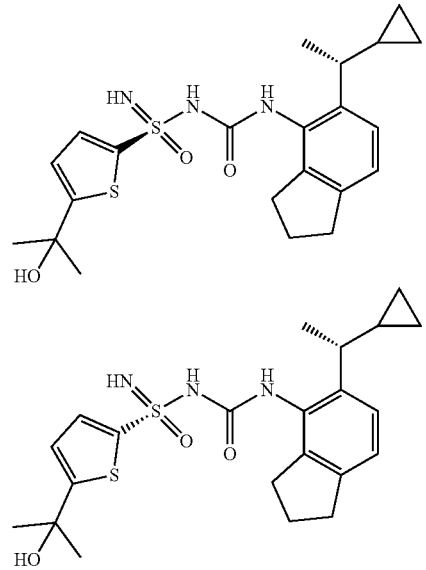

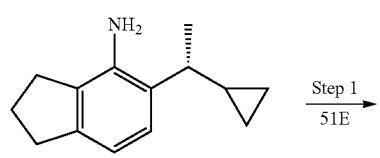

Intermediate 8

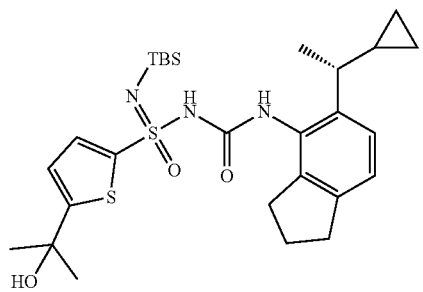

52A

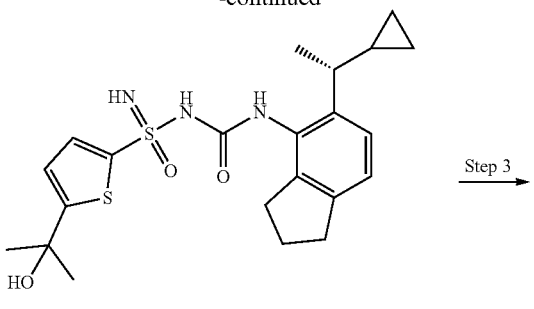

52B

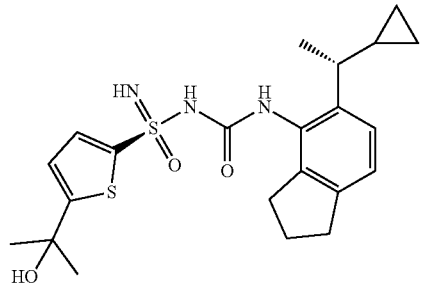

+

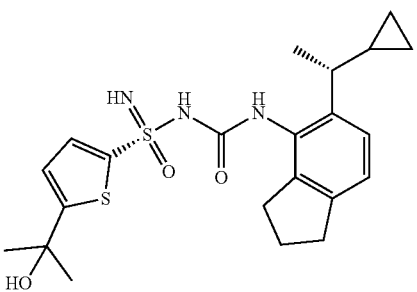

Compounds 52-1 and 52-2

Step 1

(R)-N'-(tert-butyldimethylsilyl)-N-((5-(1-cyclopropylethyl)-2,3-dihydro-1H-inden-4-yl)carbamoyl)-4-(2-hydroxypropan-2-yl)furan-2-sulfonimidamide (52A)

Intermediate 8 (300 mg, 1.49 mmol), triethylamine (182 mg, 1.79 mmol) and tetrahydrofuran (20 mL) were added successively into a 100 mL round-bottomed flask under nitrogen atmosphere, and then triphosgene (178 mg, 0.60 mmol) was added in an ice bath. The reaction system was warmed to reflux, reacted for 2 h, and then filtered to remove the solids. 51E (500 mg, 1.49 mmol) and sodium hydride (120 mg, 2.99 mmol) were added to the filtrate, and the mixture was reacted at room temperature for 12 h. After the reaction was completed as detected by TLC, 52A was obtained and was directly used in the next step without purification.

LCMS m/z (ESI)=562.3[M+1].

Step 2

(R)-N-((5-(1-cyclopropylethyl)-2,3-dihydro-1H-inden-4-yl)carbamoyl)-4-(2-hydroxypropan-2-yl)furan-2-sulfonimidamide (Compound 52B)

Tetrabutylammonium fluoride (6 mL, 6.0 mmol, 1 M) was added to the reaction system from the previous step, and the resulting reaction system was reacted overnight at room temperature. After the reaction was completed as detected by TLC, the reaction system was poured into water and extracted with ethyl acetate (50 mL×3). The organic phases were combined, washed once with 1 M diluted HCl, dried over anhydrous sodium sulfate and filtered, and the organic solvent was removed under reduced pressure. The residue was purified by preparative medium pressure liquid chromatography (acetonitrile/water=50%) to give 52B in the form of a pale yellow solid (210 mg, 31.3% yield).

LCMS m/z=448.2[M+1].

Step 3

($R_S$, $S_C$)- and ($S_S$, $S_C$)-N-((5-(1-cyclopropylethyl)-2,3-dihydro-1H-inden-4-yl)carbamoyl)-4-(2-hydroxypropan-2-yl)furan-2-sulfonimidamide (Compounds 52-1 and 52-2)

52B was resolved by SFC to give compound 52-1 (81 mg, 38.5% yield, ee %: 99.81%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=19.031 min) and compound 52-2 (74 mg, 35.2% yield, ee %: 99.99%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=20.638 min).

Compound 52-1: $^1$H NMR (400 MHz, DMSO-d6) δ=8.17 (br, 1H), 7.57 (br, 2H), 7.39 (s, 1H), 7.12 (d, 1H), 7.04 (d, 1H), 6.90 (d, 1H), 5.72 (s, 1H), 2.82 (t, 2H), 2.67-2.50 (m, 2H), 2.30-2.20 (m, 1H), 1.98-1.86 (m, 2H), 1.50 (s, 6H), 1.11 (d, 3H), 0.97-0.87 (m, 1H), 0.48-0.42 (m, 1H), 0.23-0.13 (m, 1H), 0.12-0.04 (m, 1H), 0.03-0.00 (m, 1H); LCMS m/z=448.2[M+1].

Compound 52-2: $^1$H NMR (400 MHz, DMSO-d6) δ=8.08 (br, 1H), 7.47 (br, 2H), 7.28 (s, 1H), 7.02 (d, 1H), 6.93 (d, 1H), 6.80 (d, 1H), 5.62 (s, 1H), 2.72 (t, 2H), 2.65-2.50 (m, 2H), 2.17-2.14 (m, 1H), 1.84-1.81 (m, 2H), 1.39 (d, 6H), 0.99 (d, 3H), 0.84-0.82 (m, 1H), 0.36-0.33 (m, 1H), 0.12-0.09 (m, 1H), 0.02-0.00 (m, 1H), 0.01--0.00 (m, 1H); LCMS m/z=448.2[M+1].

Example 53

($R_S$)- and ($S_S$)-N-((5-(cyclobutylmethyl)-2,3-dihydro-1H-inden-4-yl)carbamoyl)-5-(2-hydroxypropan-2-yl)thiophene-2-sulfonimidamide (Compounds 53-1 and 53-2)

Compounds 53-1 and 53-2

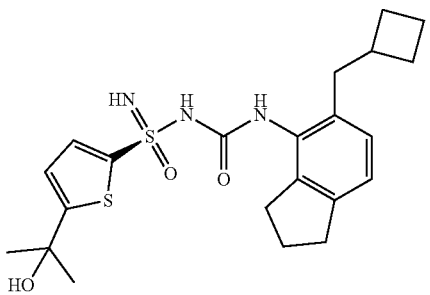

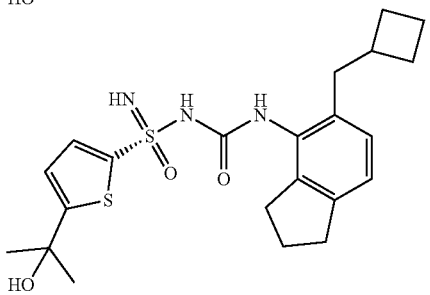

For synthesis of compounds 53-1 and 53-2, reference was made to preparation method of compounds 21-1 and 21-2; compound 53-1 (61 mg, 30.2% yield, ee %: 99.99%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=23.761 min) and compound 53-2 (54 mg, 26.7% yield, ee %: 98.48%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=28.959 min).

Compound 53-1: $^1$H NMR (400 MHz, DMSO-d6) δ=8.22 (br, 1H), 7.61 (br, 2H), 7.41 (d, 1H), 6.94 (d, 1H), 6.91 (d, 1H), 6.85 (d, 1H), 5.72 (s, 1H), 2.81 (t, 2H), 2.73-2.67 (m, 2H), 2.59 (d, 2H), 2.46-2.44 (m, 1H), 1.95-1.88 (m, 4H), 1.80-1.72 (m, 2H), 1.66-1.57 (m, 2H), 1.49 (d, 6H); LCMS m/z=448.1[M+1].

Compound 53-2: $^1$H NMR (400 MHz, DMSO-d6) δ=8.22 (br, 1H), 7.61 (br, 2H), 7.41 (d, 1H), 6.94 (d, 1H), 6.91 (d, 1H), 6.85 (d, 1H), 5.72 (s, 1H), 2.80 (t, 2H), 2.75-2.63 (m, 2H), 2.59 (d, 2H), 2.48-2.41 (m, 1H), 1.95-1.88 (m, 4H), 1.80-1.74 (m, 2H), 1.66-1.59 (m, 2H), 1.49 (d, 6H); LCMS m/z=448.1[M+1].

| Compound | Structures | Chiral HPLC (OZ) | 1H NMR |
| --- | --- | --- | --- |
| 54-1 | 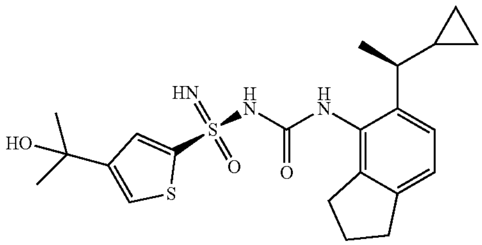 [SMILES: C[C@H](c1ccc2c(c1NC(=O)N[S@@](=N)(=O)c1cc(C(C)(C)O)cs1)CCC2)C1CC1] | Mobile phase: n-hexane/ethanol = 90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT = 14.088 min. ee%: 99.99% | 1H NMR (400 MHz, DMSO) δ = 8.21 (s, 1H), 7.65 (s, 2H), 7.58(d, 2H), 7.13 (d, 1H), 7.04(d, 1H), 5.19 (s, 1H), 2.82(t, 2H), 2.67 (s, 2H), 2.34 – 2.20(m, 1H), 2.00 – 1.83(m, 2H), 1.41(d, 7H), 1.09(d, 3H), 1.00 – 0.88 (m, 1H), 0.52 – 0.39(m, 1H), 0.28 – 0.16(m, 1H), 0.14 – 0.08(m, 1H), 0.07 – 0.00(m, 1H)。 |
| 54-2 | 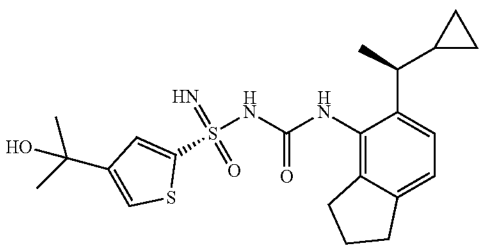 [SMILES: C[C@H](c1ccc2c(c1NC(=O)N[S@](=N)(=O)c1cc(C(C)(C)O)cs1)CCC2)C1CC1] | Mobile phase: n-hexane/ethanol = 90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT = 11.485 min. ee%: 98.48% | $^1$H NMR (400 MHz, DMSO) δ = 8.20(s, 1H), 7.64(s, 2H), 7.59(s, 1H), 7.57(s, 1H), 7.12(d, 1H), 7.04(d, 1H), 5.19(s, 1H), 2.82(t, 2H), 2.76 – 2.58(m, 2H), 2.32 – 2.21(m, 1H), 1.98 – 1.81(m, 2H), 1.41(d, 6H), 1.11(d, 3H), 0.98 – 0.88(m, 1H), 0.49 – 0.36(m, 1H), 0.25 – 0.15(m, 1H), 0.14 – 0.05(m, 1H), 0.04 – 0.00(m, 1H)。 |
| 55-1 | 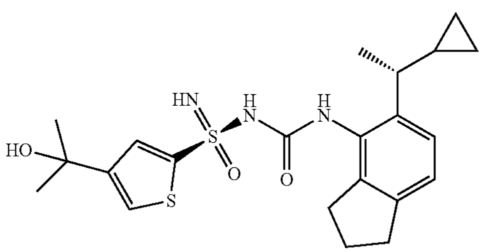 [SMILES: C[C@@H](c1ccc2c(c1NC(=O)N[S@@](=N)(=O)c1cc(C(C)(C)O)cs1)CCC2)C1CC1] | Mobile phase: n-hexane/ethanol = 90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT = 20.748 min. ee%: 99.99% | $^1$H NMR (400 MHz, DMSO) δ = 8.20(s, 1H), 7.64(s, 2H), 7.60(s, 1H), 7.57(s, 1H), 7.12(d, 1H), 7.04(d, 1H), 5.19(s, 1H), 2.82(t, 2H), 2.76 – 2.58 (m, 2H), 2.30 – 2.20 (m, 1H), 2.01 – 1.85 (m, 2H), 1.41(d, 6H), 1.11 (d, 3H), 0.99 – 0.88 (m, 1H), 0.48 – 0.38(m, 1H), 0.25 – 0.14(m, 1H), 0.12 – 0.05(m, 1H), 0.04 – 0.00(m, 1H)。 |
| 55-2 | 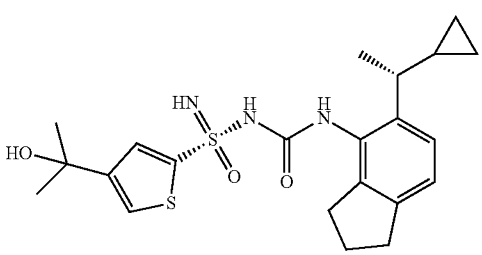 [SMILES: C[C@@H](c1ccc2c(c1NC(=O)N[S@](=N)(=O)c1cc(C(C)(C)O)cs1)CCC2)C1CC1] | Mobile phase: n-hexane/ethanol = 90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT = 16.320 min. ee%: 98.48% | $^1$H NMR (400 MHz, DMSO) δ = 8.21 (s, 1H), 7.65 (s, 2H), 7.59 (s, 1H), 7.57 (s, 1H), 7.13(d, 1H), 7.04 (d, 1H), 5.19(s, 1H), 2.82 (t, 2H), 2.73 – 2.61(m, 2H), 2.31 – 2.21(m, 1H), 1.97 – 1.86 (m, 2H), 1.41 (d, 6H), 1.09 (d, 3H), 0.95 (dd, 1H), 0.50 – 0.41(m, 1H), 0.24 – 0.16 (m, 1H), 0.13 – 0.08(m, 1H), 0.06 – 0.01(m, 1H)。 |

Example 56

N-((5-(cyclobutylmethyl)-2,3-dihydro-1H-inden-4-yl)carbamoyl)-5-(2-hydroxypropan-2-yl)thiophene-2-sulfonamide (Compound 56)

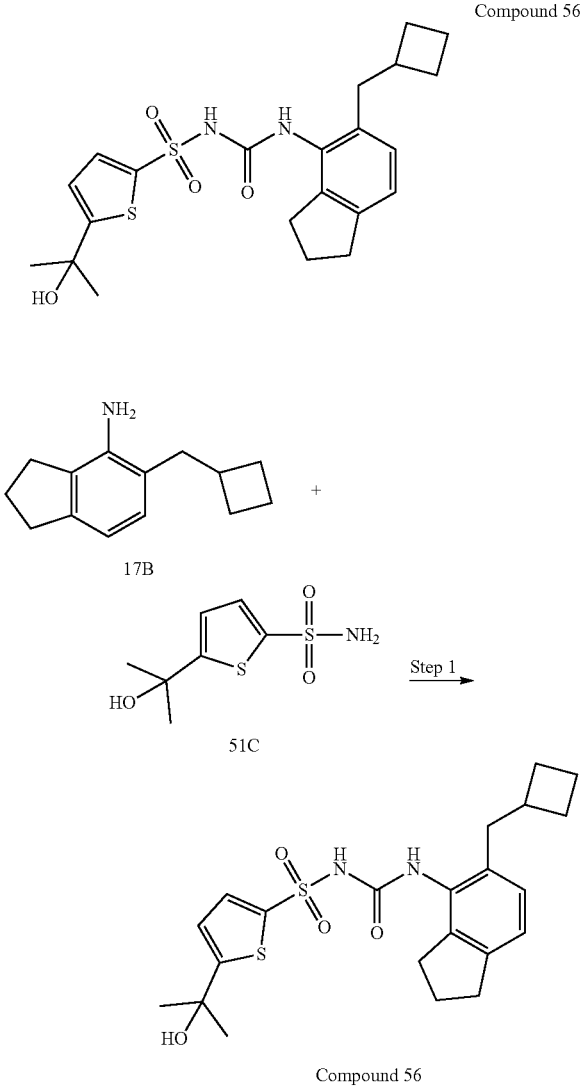

Step 1

N-((5-(cyclobutylmethyl)-2,3-dihydro-1H-inden-4-yl)carbamoyl)-5-(2-hydroxypropan-2-yl)thiophene-2-sulfonamide (Compound 56)

Compound 17B (200 mg, 0.993 mmol), triethylamine (120.64 mg, 1.19 mmol) and tetrahydrofuran (20 mL) were added successively into a 100 mL round-bottomed flask under nitrogen atmosphere, and then triphosgene (117.92 mg, 0.4 mmol) was added in an ice bath. The reaction system was warmed to reflux, reacted for 2 h, and then filtered to remove the solids. Compound 51C (220 mg, 0.993 mmol) and sodium hydride (35.76 mg, 1.49 mmol) were added to the filtrate, and the mixture was reacted at 60° C. for 2 h. After the reaction was completed as detected by TLC, EA (50 mL×3) was added for extraction, and preparative medium pressure liquid chromatography was performed to give compound 56 (135 mg, 30.29% yield).

$^1$H NMR (400 MHz, DMSO-$d_6$) δ=10.89 (s, 1H), 7.81 (s, 1H), 7.49 (d, 1H), 6.99 (d, 1H), 6.90 (dd, 2H), 5.74 (s, 1H), 2.80 (t, 2H), 2.57 (t, 2H), 2.42-2.30 (m, 1H), 1.96-1.79 (m, 4H), 1.77-1.65 (m, 2H), 1.62-1.63 (m, 2H), 1.49 (s, 6H), 1.29-1.20 (s, 1H), 0.89-0.81 (m, 1H); LCMS m/z (ESI)=449.20[M+1].

Example 57

(S)-N-((5-(1-cyclopropylethyl)-2,3-dihydro-1H-inden-4-yl)carbamoyl)-5-(2-hydroxypropan-2-yl)thiophene-2-sulfonamide (Compound 57)

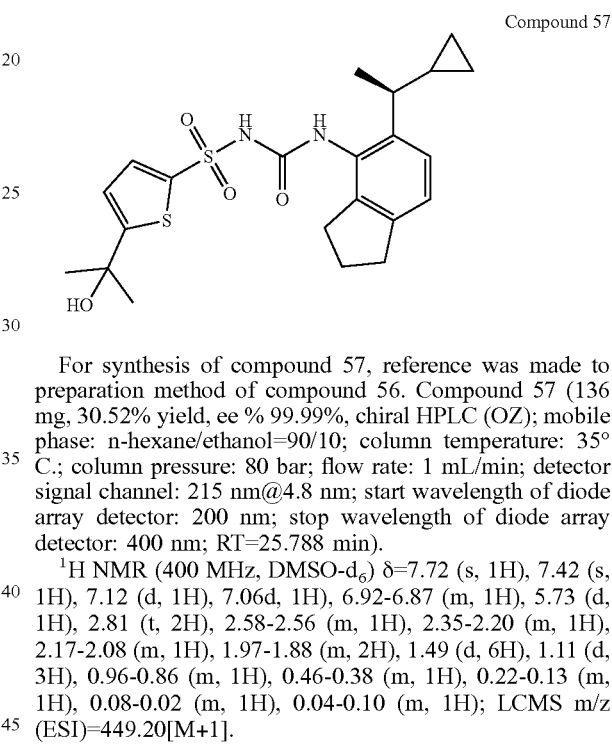

For synthesis of compound 57, reference was made to preparation method of compound 56. Compound 57 (136 mg, 30.52% yield, ee % 99.99%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=25.788 min).

$^1$H NMR (400 MHz, DMSO-$d_6$) δ=7.72 (s, 1H), 7.42 (s, 1H), 7.12 (d, 1H), 7.06d, 1H), 6.92-6.87 (m, 1H), 5.73 (d, 1H), 2.81 (t, 2H), 2.58-2.56 (m, 1H), 2.35-2.20 (m, 1H), 2.17-2.08 (m, 1H), 1.97-1.88 (m, 2H), 1.49 (d, 6H), 1.11 (d, 3H), 0.96-0.86 (m, 1H), 0.46-0.38 (m, 1H), 0.22-0.13 (m, 1H), 0.08-0.02 (m, 1H), 0.04-0.10 (m, 1H); LCMS m/z (ESI)=449.20[M+1].

Example 58

(R)-N-((5-(1-cyclopropylethyl)-2,3-dihydro-1H-inden-4-yl)carbamoyl)-5-(2-hydroxypropan-2-yl)thiophene-2-sulfonamide (Compound 58)

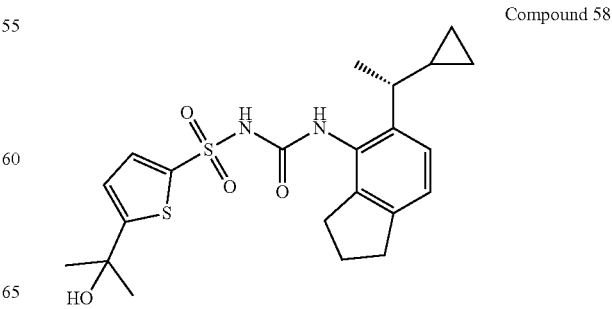

For synthesis of compound 58, reference was made to preparation method of compound 56; compound 58 (120 mg, 26.93% yield, ee %: 99.99%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=24.955 min).

$^1$H NMR (400 MHz, DMSO-d$_6$) δ 7.72 (s, 1H), 7.42 (s, 1H), 7.12 (d, 1H), 7.06 (d, 1H), 6.89 (dd, 1H), 5.73 (d, 1H), 2.81 (t, 2H), 2.72-2.62 (m, 1H), 2.35-2.19 (m, 1H), 2.19-2.09 (m, 1H), 1.98-1.86 (m, 2H), 1.49 (s, 6H), 1.08 (d, 3H), 0.95-0.86 (m, 1H), 0.50-0.39 (m, 1H), 0.22-0.09 (m, 1H), 0.08-0.01 (m, 1H), 0.03-0.11 (m, 1H); LCMS m/z (ESI)=449.20[M+1].

Example 59

(R)-N-((5-(1-cyclopropylethyl)-2,3-dihydro-1H-inden-4-yl)carbamoyl)-4-(1-hydroxycyclopropyl)furan-2-sulfonamide (Compound 59)

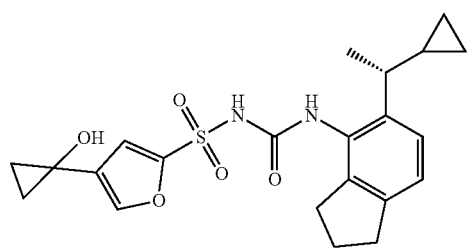

59

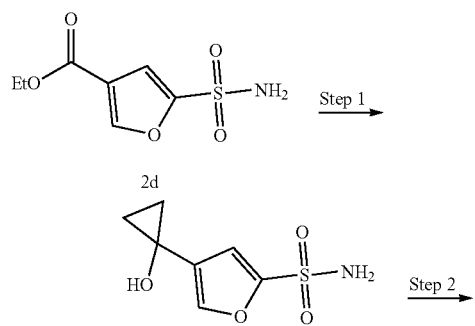

Step 1

4-(1-hydroxycyclopropyl)furan-2-sulfonamide (Compound 59A)

2d (7.0 g, 31.9 mmol), tetraisopropyl titanate (4.48 g, 15.8 mmol), ethylmagnesium bromide (79.8 mL, 1 M, 79.8 mmol) and tetrahydrofuran (150 mL) were added successively into a 100 mL three-necked flask under nitrogen atmosphere, and the reaction system was reacted and then cooled to room temperature after the reaction was completed. The reaction system was then poured into water and extracted with ethyl acetate (150 mL×3). The organic phase was dried over anhydrous sodium sulfate and filtered, and the organic solvent was removed under reduced pressure. The residue was purified by column chromatography (petroleum ether:ethyl acetate=3:1) to give compound 59A in the form of a pale yellow solid (1.4 g, 21.4% yield).

$^1$H NMR (400 MHz, DMSO) δ=7.68 (s, 2H), 7.66 (s, 1H), 6.74 (d, 1H), 6.04 (s, 1H), 1.00-0.97 (m, 2H), 0.82-0.80 (m, 2H); LCMS m/z (ESI)=204.3[M+1].

Step 2

(R)-N-((5-(1-cyclopropylethyl)-2,3-dihydro-1H-inden-4-yl)carbamoyl)-4-(1-hydroxycyclopropyl)furan-2-sulfonamide (Compound 59)

Intermediate 8 (100 mg, 0.497 mmol), triethylamine (60.32 mg, 0.596 mmol) and tetrahydrofuran (20 mL) were added successively into a 100 mL round-bottomed flask under nitrogen atmosphere, and then triphosgene (58.96, 0.2 mmol) was added in an ice bath. The reaction system was warmed to reflux, reacted for 2 h, and then filtered to remove the solids. 59A (220 mg, 0.993 mmol) and sodium hydride (20 mg, 0.833) were added to the filtrate, and the mixture was reacted at 60° C. for 2 h. After the reaction was completed as detected by TLC, EA (50 mL×3) was added for extraction, and preparative medium pressure liquid chromatography was performed to give compound 59 (70 mg, 32.73% yield).

$^1$H NMR (400 MHz, DMSO-d$_6$) δ 7.68 (d, 1H), 7.53 (s, 1H), 7.10 (d, 1H), 7.01 (d, 1H), 6.54 (s, 1H), 5.95 (s, 1H), 2.81 (t, 2H), 2.69-2.57 (m, 2H), 2.28-2.16 (m, 1H), 1.97-1.86 (m, 2H), 1.16-1.05 (m, 3H), 1.00-0.90 (m, 3H), 0.78-0.70 (m, 2H), 0.48-0.38 (m, 1H), 0.25-0.16 (m, 1H), 0.12-0.04 (m, 1H), 0.04-0.01 (m, 1H); LCMS m/z (ESI)=431.20 [M+1].

Example 60

(S)-N-((5-(1-cyclopropylethyl)-2,3-dihydro-1H-inden-4-yl)carbamoyl)-4-(1-hydroxycyclopropyl)furan-2-sulfonamide (Compound 60)

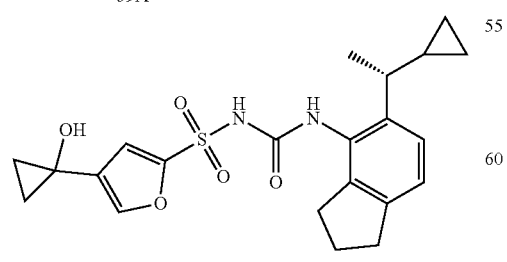

59

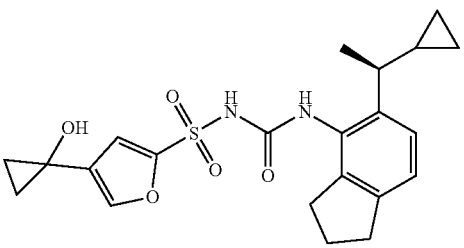

Compound 60

For synthesis of compound 60, reference was made to preparation method of compound 59; compound 60 (80 mg, 37.41% yield).

¹H NMR (400 MHz, DMSO-d₆) δ 7.41 (s, 1H), 7.14 (d, 1H), 7.07 (d, 1H), 6.97 (d, 1H), 6.36 (s, 1H), 5.90 (s, 1H), 2.80 (t, 2H), 2.65 (t, 2H), 2.35-2.22 (m, 1H), 1.97-1.85 (m, 2H), 1.16-1.06 (m, 3H), 1.01-0.83 (m, 3H), 0.75-0.69 (m, 2H), 0.49-0.39 (m, 1H), 0.25-0.15 (m, 1H), 0.12-0.02 (m, 2H); LCMS m/z (ESI)=431.20[M+1].

Example 61

N-((5-(cyclobutylmethyl)-2,3-dihydro-1H-inden-4-yl)carbamoyl)-4-(1-hydroxycyclopropyl)furan-2-sulfonamide (Compound 61)

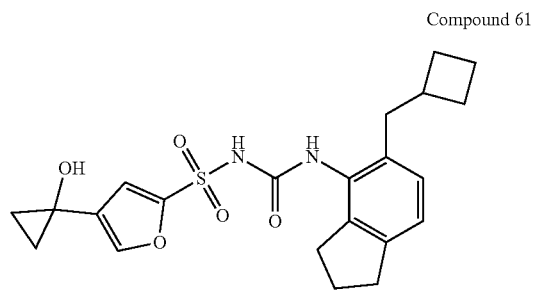 [SMILES: O=C(Nc1c(CC2CCC2)ccc2c1CCC2)NS(=O)(=O)c1cc(C2(O)CC2)co1]

Compound 61

For synthesis of compound 61, reference was made to preparation method of compound 59. Compound 61 (70 mg, 32.73% yield).

¹H NMR (400 MHz, DMSO-d₆) δ=7.47 (s, 1H), 7.39 (s, 1H), 7.08-6.95 (m, 1H), 6.82 (d, 1H), 6.87 (d, 1H), 6.33 (s, 1H), 5.88 (s, 1H), 2.79 (t, 2H), 2.67 (t, 2H), 2.58 (d, 2H), 2.48-2.43 (m, 1H), 1.97-1.85 (m, 4H), 1.82-1.72 (m, 2H), 1.67-1.57 (m, 2H), 0.99-0.91 (m, 2H), 0.75-0.68 (m, 2H); LCMS m/z (ESI)=431.20[M+1].

Example 62

(R)-3-cyano-N-((5-(1-cyclopropylethyl)-2,3-dihydro-1H-inden-4-yl)carbamoyl)-5-(2-hydroxypropan-2-yl)thiophene-2-sulfonamide (Compound 62)

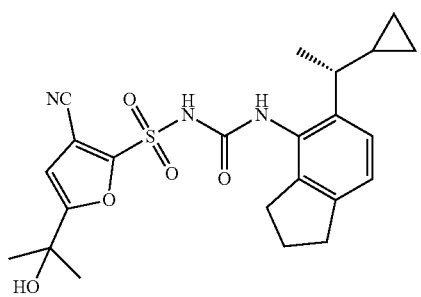

Compound 62

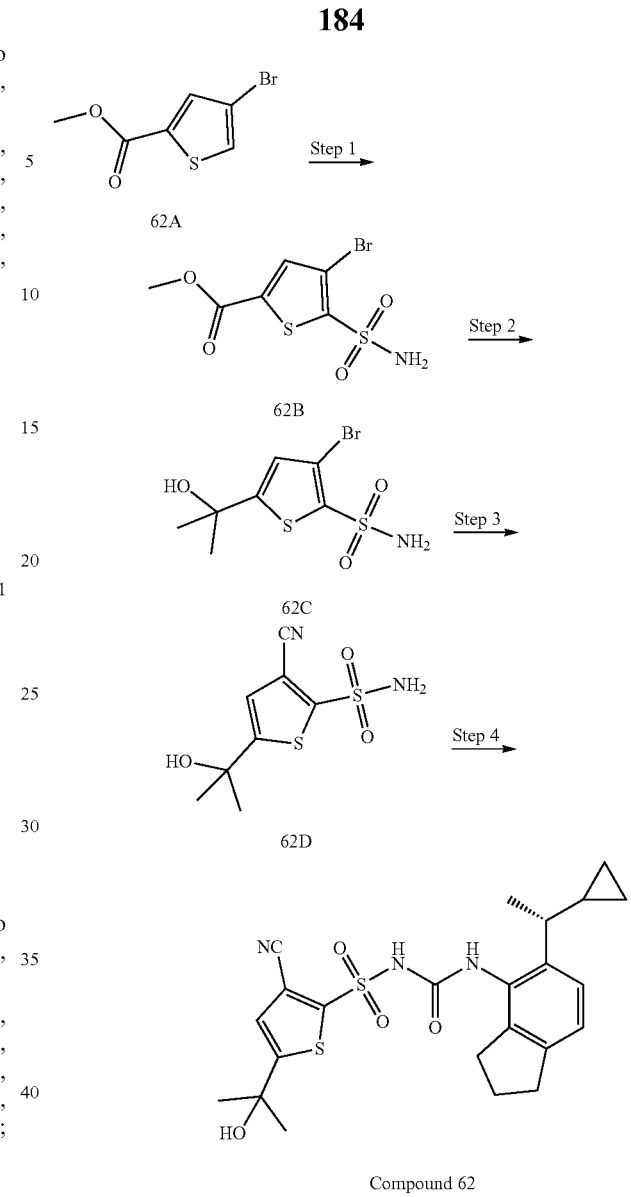

Compound 62

Step 1

Methyl 4-bromo-5-sulfamoylthiophene-2-carboxylate (62B)

A mixture of 62A (30.0 g, 135.70 mmol) in chlorosulfonic acid (44.67 mL, 678.52 mmol) and thionyl chloride (14.78 mL, 203.56 mmol) was added in batches at 0° C. The reaction system was stirred at 0° C. for 20 min and then reacted at 50° C. for 1 h. After the reaction was completed, the reaction system was cooled to room temperature, and a solution of aqueous ammonium bicarbonate and acetone (400 mL, 1:1) was added dropwise at 0° C. The reaction system was stirred overnight. After the reaction was completed as detected by TLC, the reaction system was filtered, and the solids were washed with ethyl acetate (100 mL), and the aqueous phase was extracted with ethyl acetate (200 mL). The organic phases were combined and concentrated to give a dark-colored oil, which was purified by slurrying with dichloromethane (200 mL) to give compound 62B in the form of a pale yellow solid (28.0 g, 68.74% yield).

LC-MS m/z (ESI)=300.03[M+1].

Step 2

3-bromo-5-(2-hydroxypropan-2-yl)thiophene-2-sulfonamide (62C)

Compound 62B (28.0 g, 93.29 mol) was dissolved in dry THF (500 mL) at room temperature, and then the solution was cooled to −15° C. in an ice salt bath. Methylmagnesium bromide (155.48 mL, 466.45 mol) was added dropwise slowly while maintaining the temperature to be not higher than 0° C. After the dropwise addition was completed, the reaction system was reacted for 4 h at room temperature. After the reaction was completed as detected by TLC, the reaction system was poured into ice water (200 mL) to quench the reaction, and then extracted with EA (200 mL×3). The organic phases were combined, washed with saturated brine (100 mL), dried over anhydrous sodium sulfate, and concentrated under reduced pressure to remove the solvent, and the residue was purified by column chromatography (ethyl acetate:petroleum ether=1: 20-1:10) to give compound 62C in the form of a white solid powder (18 g, 64.28% yield).

$^1$H NMR (400 MHz, DMSO-d6) δ=7.79 (s, 2H), 7.07 (s, 1H), 5.87 (s, 1H), 1.48 (s, 6H); LC-MS m/z (ESI)=300.03 [M+1].

Step 3

3-cyano-5-(2-hydroxypropan-2-yl)thiophene-2-sulfonamide (62D)

Compound 62C (4.0 g, 13.33 mmol) and cuprous cyanide (1.4 g, 15.99 mmol) were dissolved in N,N-dimethylformamide (40 mL) in a 50 mL round-bottomed flask under nitrogen atmosphere, and the reaction system was reacted at 150° C. for 4 h. After the reaction was completed as detected by TLC, the reaction system was poured into saturated sodium bicarbonate solution (100 mL), and ethyl acetate (50 mL×10) was added for extraction. The organic phase was dried over anhydrous sodium sulfate and filtered, and the organic solvent was removed under reduced pressure. The residue was purified by column chromatography (petroleum ether:ethyl acetate=10:1-1:5) to give 62D in the form of a white solid (1.0 g, 30.47% yield).

$^1$H NMR (400 MHz, DMSO-d6) δ=8.85 (d, 2H), 7.23 (s, 1H), 6.02 (s, 1H), 1.52 (s, 6H); LC-MS m/z (ESI)=247.03 [M+1].

Step 4

(R)-3-cyano-N-((5-(1-cyclopropylethyl)-2,3-dihydro-1H-inden-4-yl)carbamoyl)-5-(2-hydroxypropan-2-yl)thiophene-2-sulfonamide (Compound 62)

Intermediate 8 (100 mg, 0.497 mmol), triethylamine (60.32 mg, 0.596 mmol) and tetrahydrofuran (20 mL) were added successively into a 100 mL round-bottomed flask under nitrogen atmosphere, and then triphosgene (58.96 mg, 0.2 mmol) was added in an ice bath. The reaction system was warmed to reflux, reacted for 2 h, and then filtered to remove the solids. 62D (123 mg, 0.497 mmol) and sodium hydride (20 mg, 0.833) were added to the filtrate, and the mixture was reacted at 60° C. for 2 h. After the reaction was completed as detected by TLC, EA (50 mL×3) was added for extraction, and preparative medium pressure liquid chromatography was performed to give compound 62 (70 mg, 30.8% yield).

$^1$H NMR (400 MHz, DMSO-d6) δ=11.63 (s, 1H), 9.53 (s, 1H), 7.55 (s, 1H), 7.23 (d, 1H), 7.18 (d, 1H), 6.12 (s, 1H), 2.89 (t, 2H), 2.78 (t, 2H), 2.32 (m, 1H), 2.01 (m, 2H), 1.54 (s, 6H), 1.22 (d, 3H), 1.08-0.97 (m, 1H), 0.54-0.46 (m, 1H), 0.34-0.26 (m, 1H), 0.16-0.08 (m, 1H), 0.07-0.01 (m, 1H); LCMS m/z (ESI)=474.1[M+1].

Example 63

(S)-3-cyano-N-((5-(1-cyclopropylethyl)-2,3-dihydro-1H-inden-4-yl)carbamoyl)-5-(2-hydroxypropan-2-yl)thiophene-2-sulfonamide (Compound 63)

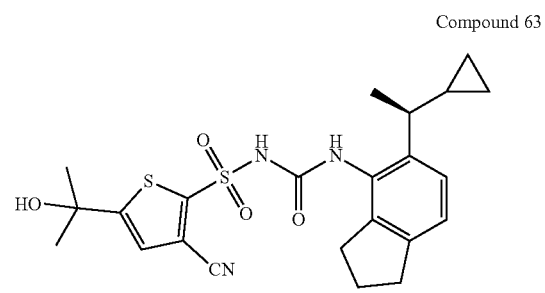 [SMILES: C[C@H](c1ccc2c(c1NC(=O)NS(=O)(=O)c1sc(C(C)(C)O)cc1C#N)CCC2)C1CC1]

Compound 63

For synthesis of compound 63, reference was made to synthesis method of compound 62.

$^1$H NMR (400 MHz, DMSO) δ=11.63 (s, 1H), 9.52 (s, 1H), 7.54 (s, 1H), 7.23 (d, 1H), 7.18 (d, 1H), 6.12 (s, 1H), 2.89 (t, 2H), 2.78 (t, 2H), 2.37-2.26 (m, 1H), 2.07-1.92 (m, 2H), 1.54 (s, 6H), 1.22 (d, 3H), 1.07-0.95 (m, 1H), 0.56-0.44 (m, 1H), 0.36-0.23 (m, 1H), 0.17-0.09 (m, 1H), 0.08-0.02 (m, 1H); LCMS m/z (ESI)=474.1[M+1].

Example 64

(R)-N-((5-(1-cyclopropylethyl)-2,3-dihydro-1H-inden-4-yl)carbamoyl)-3-fluoro-5-(2-hydroxypropan-2-yl)thiophene-2-sulfonamide (Compound 64)

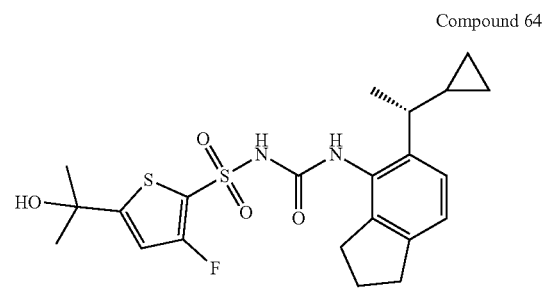 [SMILES: C[C@@H](c1ccc2c(c1NC(=O)NS(=O)(=O)c1sc(C(C)(C)O)cc1F)CCC2)C1CC1]

Compound 64

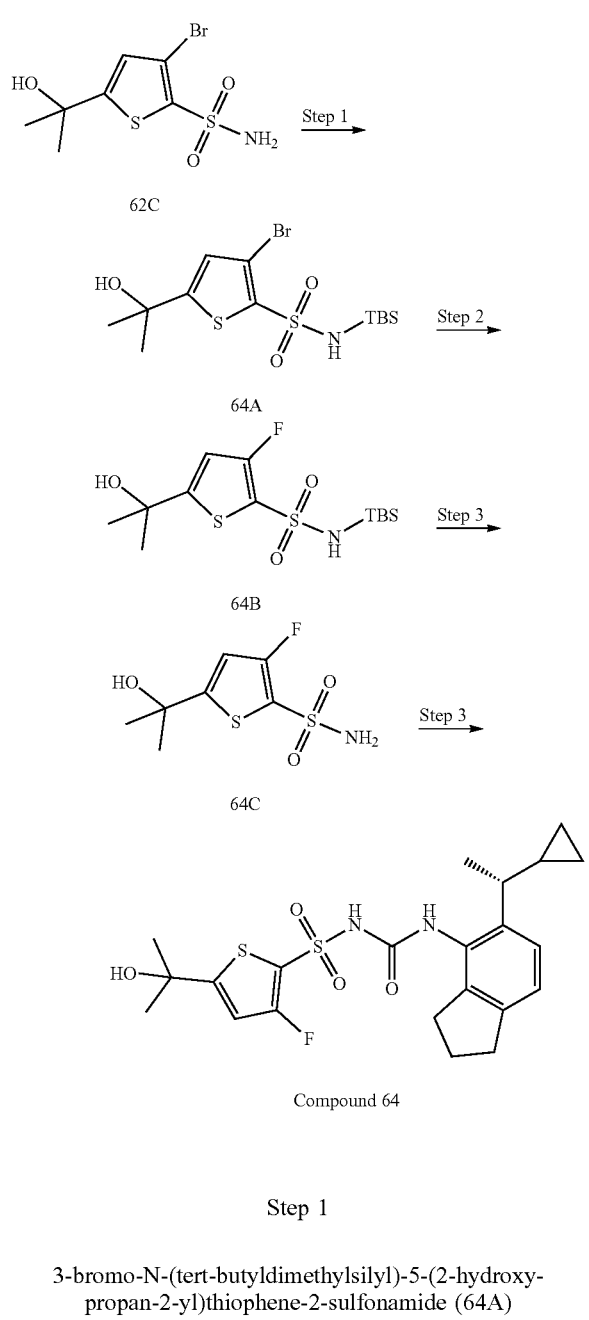

62C

64A

64B

64C

Compound 64

Step 1

3-bromo-N-(tert-butyldimethylsilyl)-5-(2-hydroxy-propan-2-yl)thiophene-2-sulfonamide (64A)

Compound 62C (4.0 g, 13.33 mmol) was dissolved in dry THF (40 mL) at room temperature, and then the solution was cooled to −10° C. in an ice salt bath. Sodium hydride (1.6 g, 39.98 mmol) was added slowly while controlling the temperature to be below −10° C., and then a solution of tert-butyldimethylchlorosilane (2.41 g, 15.99 mmol) in THF (20 mL) was added. The reaction system was reacted at room temperature for 12 h. After the reaction was completed as detected by TLC, the reaction system was poured into ice water (20 mL) to quench the reaction, and then extracted with EA (50 mL×3). The organic phases were combined, washed with saturated brine (50 mL), dried over anhydrous sodium sulfate, and concentrated under reduced pressure to remove the solvent, and the residue was slurried with ethyl acetate:petroleum ether (1:10-1:5) to give compound 64A in the form of a white solid (3.0 g, 54.32%).

$^1$H NMR (400 MHz, DMSO) δ=8.05 (s, 1H), 7.06 (s, 1H), 5.88 (s, 1H), 1.48 (s, 6H), 0.89 (s, 9H), 0.15 (s, 6H); LCMS m/z=414.02[M+1].

Step 2

N-(tert-butyldimethylsilyl)-3-fluoro-5-(2-hydroxy-propan-2-yl)thiophene-2-sulfonamide (64B)

Compound 64A (2.0 g, 4.83 mol) was dissolved in dry THF (20 mL), and the solution was cooled to −78° C. in a dry ice-acetone bath. n-butyllithium (6.76 mL, 16.89 mmol, 2.5 M) was added dropwise slowly while maintaining the temperature to be not higher than −50° C. After the dropwise addition was completed, the temperature was maintained, and the reaction system was reacted for 1 h. N-fluoro-N-(phenylsulfonyl)benzenesulfonamide (1.98 g, 6.27 mmol) was added, the temperature was maintained, and the reaction system was reacted for 1 h. After the reaction was completed as detected by TLC, the reaction system was added dropwise slowly into ice water (100 mL) to quench the reaction, and then extracted with EA (100 mL×3). The organic phases were combined, washed with saturated brine (100 mL), dried over anhydrous sodium sulfate, and concentrated under reduced pressure to remove the solvent, and the residue was separated by column chromatography (ethyl acetate:dichloromethane=1:100-1:10) to give compound 64B in the form of a dark-colored oil (240 mg, 14.07% yield).

$^1$H NMR (400 MHz, DMSO-d6) δ=7.87 (s, 1H), 6.80 (d, 1H), 5.69 (s, 1H), 1.31 (s, 6H), 0.73 (s, 9H), 0.00 (s, 6H); LC-MS m/z (ESI)=354.02[M+1].

Step 3

5-(3-hydroxyoxetan-3-yl)thiophene-2-sulfonamide (64C)

64B (240 mg, 0.679 mmol) and THF (10 mL) were added successively into a 100 mL round-bottomed flask under nitrogen atmosphere, and then the reaction system was cooled to 0° C. in an ice bath. Tetrabutylammonium fluoride (1.4 mL, 1 M/THF, 1.35 mmol) was then added dropwise slowly, and the reaction system was warmed to room temperature and reacted for 2 h after the dropwise addition was completed. After the reaction was completed, water was added to quench the reaction, and EA (30 mL×3) was added for extraction. The organic phase was dried over anhydrous sodium sulfate and filtered, and the solvent was removed under reduced pressure. The residue was purified by column chromatography (petroleum ether:ethyl acetate=1:1) to give 64C in the form of a pale yellow solid (120 mg, 73.6% yield).

LCMS m/z=240.1[M+1].

Step 4

(R)-N-((5-(1-cyclopropylethyl)-2,3-dihydro-1H-inden-4-yl)carbamoyl)-3-fluoro-5-(2-hydroxypro-pan-2-yl)thiophene-2-sulfonamide (Compound 64)

Intermediate 8 (100 mg, 0.497 mmol), triethylamine (60.32 mg, 0.596 mmol) and tetrahydrofuran (20 mL) were added successively into a 100 mL round-bottomed flask under nitrogen atmosphere, and then triphosgene (58.96 mg, 0.2 mmol) was added in an ice bath. The reaction system was warmed to reflux, reacted for 2 h, and then filtered to remove the solids. 64C (119 mg, 0.497 mmol) and sodium hydride (20 mg, 0.833) were added to the filtrate, and the mixture was reacted at 60° C. for 2 h. After the reaction was completed as detected by TLC, EA (50 mL×3) was added for extraction, and the organic phase was dried over anhydrous sodium sulfate. The residue was separated by preparative medium pressure liquid chromatography to give compound 64 (73 mg, 31.2% yield).

$^1$H NMR (400 MHz, DMSO-d6) δ=7.60 (s, 1H), 7.11 (d, 1H), 7.03 (d, 1H), 6.86 (s, 1H), 5.74 (s, 1H), 2.81 (t, 2H), 2.61 (t, 2H), 2.20-2.15 (m, 1H), 1.93-1.86 (m, 2H), 1.44 (s, 6H), 1.09 (d, 3H), 0.94-0.88 (m, 1H), 0.46-0.39 (m, 1H), 0.21-0.16 (m, 1H), 0.09-0.04 (m, 1H), 0.03-0.01 (m, 1H); LC-MS m/z (ESI)=467.2[M+1].

Example 65

N-((5-((S)-1-cyclopropylethyl)-2,3-dihydro-1H-inden-4-yl)carbamoyl)-5-(3-hydroxyoxetan-3-yl)thiophene-2-sulfonimidamide (Compounds 65-1 and 65-2)

Compounds 65-1 and 65-2

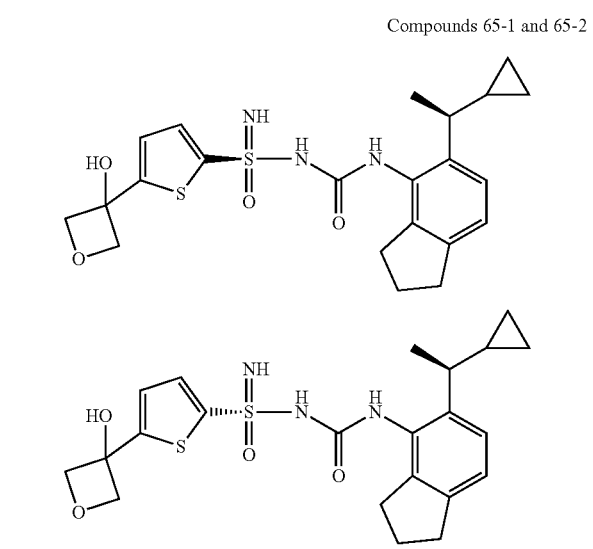

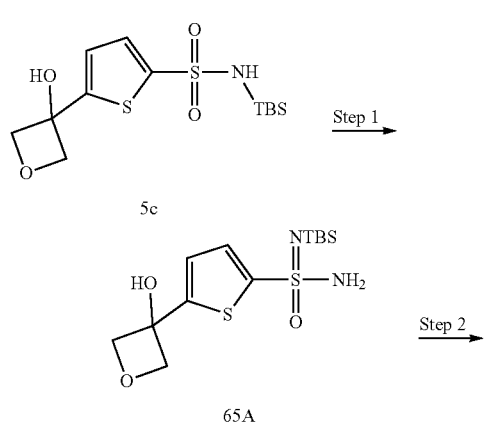

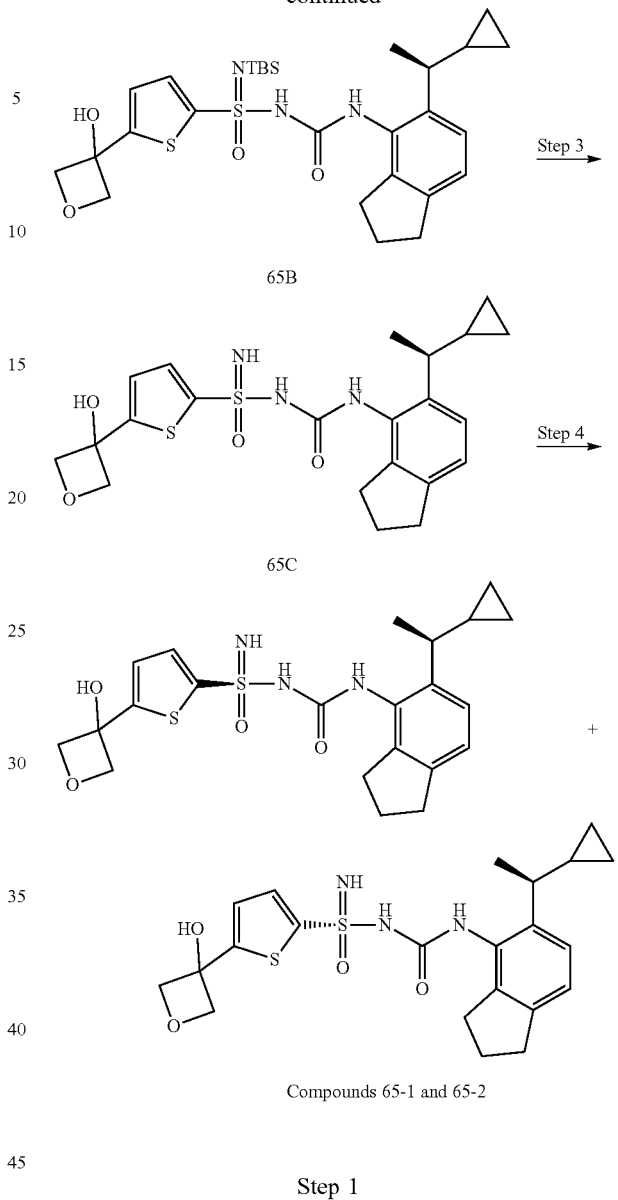

Step 1

N'-(tert-butyldimethylsilyl)-5-(3-hydroxyoxetan-3-yl)thiophene-2-sulfonimidamide (65A)

Triphenylphosphine (3.64 g, 13.84 mmol) and hexachloroethane (3.88 g, 16.36 mmol) were dissolved in chloroform in a 250 mL three-necked flask under nitrogen atmosphere, and then the reaction system was warmed to reflux and reacted for 2 h. The reaction system was then cooled to −10° C. in an ice bath, and diisopropylethylamine (2.6 g, 20.14 mmol) was added dropwise slowly. After the dropwise addition was completed, the reaction system was reacted for 30 min at this temperature. The reaction system was then cooled to −10° C., and a solution of 5c (4.4 g, 12.58 mmol) in chloroform (100 mL) was added. After the addition was completed, the temperature was maintained at −10° C. and the reaction system was reacted for 30 min. Ammonia gas was introduced into the reaction system for 30 min, and then the reaction system was warmed to room temperature and reacted for 2 h. After the reaction was completed as detected by TLC, the reaction system was concentrated under reduced pressure to remove the solvent, and the crude product was purified by column chromatography (petroleum ether:ethyl acetate=3:1) to give 65A in the form of a pale yellow solid (2.7 g, 61% yield).

LCMS m/z=349.1[M+1].

Step 2

N'-(tert-butyldimethylsilyl)-N-((5-((S)-1-cyclopropylethyl)-2,3-dihydro-1H-inden-4-yl)carbamoyl)-5-(3-hydroxyoxetan-3-yl)thiophene-2-sulfonimidamide (65B)

Intermediate 9 (288 mg, 1.44 mmol), triethylamine (174 mg, 1.772 mmol) and tetrahydrofuran (20 mL) were added successively into a 100 mL round-bottomed flask under nitrogen atmosphere, and then triphosgene (171 mg, 0.57 mmol) was added in an ice bath. The reaction system was warmed to reflux, reacted for 2 h, and then filtered to remove the solids. 65A (500 mg, 1.44 mmol) and sodium hydride (115 mg, 2.87 mmol) were added to the filtrate, and the mixture was reacted at room temperature for 12 h. After the reaction was completed as detected by TLC, compound 65B was obtained and was directly used in the next step without purification.

LCMS m/z (ESI)=576.2[M+1].

Step 3

N-((5-((S)-1-cyclopropylethyl)-2,3-dihydro-1H-inden-4-yl)carbamoyl)-5-(3-hydroxyoxetan-3-yl)thiophene-2-sulfonimidamide (65C)

Tetrabutylammonium fluoride (6 mL, 6 mmol, 1 M) was added to the reaction system from the previous step, and the resulting reaction system was reacted overnight at room temperature. After the reaction was completed as detected by TLC, the reaction system was poured into water and extracted with ethyl acetate (100 mL×3). The organic phases were combined, washed once with 1 M diluted HCl, dried over anhydrous sodium sulfate and filtered, and the organic solvent was removed under reduced pressure. The residue was purified by preparative medium pressure liquid chromatography (acetonitrile/water=50%) to give 65C in the form of a transparent solid (220 mg, two-step yield: 32.8%).

LCMS m/z (ESI)=462.1[M+1].

Step 4

(R$_S$, S$_C$)- and (S$_S$, S$_C$)-N-((5-((S)-1-cyclopropylethyl)-2,3-dihydro-1H-inden-4-yl)carbamoyl)-5-(3-hydroxyoxetan-3-yl)thiophene-2-sulfonimidamide (Compounds 65-1 and 65-2)

65C was resolved by SFC to give compound 65-1 (106 mg, 48.2% yield, ee %: 99.99%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=19.784 min) and compound 65-2 (95 mg, 43.2% yield, ee %: 99.99%, chiral HPLC (OZ); mobile phase: n-hexane/ethanol=90/10; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm; RT=21.782 min).

Compound 65-1: $^1$H NMR (400 MHz, DMSO) δ=8.21 (s, 1H), 7.66 (s, 1H), 7.49 (s, 1H), 7.26 (d, 1H), 7.12 (d, 1H), 7.04 (d, 1H), 7.02 (s, 1H), 4.77 (d, 2H), 4.67 (d, 2H), 2.82 (t, 2H), 2.74-2.62 (m, 2H), 2.33 (s, 1H), 2.29-2.18 (m, 1H), 1.98-1.84 (m, 2H), 1.06 (d, 3H), 1.00-0.88 (m, 1H), 0.48-0.37 (m, 1H), 0.25-0.16 (m, 1H), 0.12-0.05 (m, 1H), 0.05-0.01 (m, 1H).

Compound 65-2: $^1$H NMR (400 MHz, DMSO-d6) δ=8.17 (s, 1H), 7.59 (s, 1H), 7.48 (d, 1H), 7.25 (d, 1H), 7.12 (d, 1H), 7.04 (d, 2H), 4.78 (s, 1H), 4.77 (s, 1H), 4.69 (d, 1H), 4.67 (d, 1H), 2.83 (t, 2H), 2.77-2.61 (m, 2H), 2.30-2.17 (m, 1H), 2.02-1.83 (m, 2H), 1.19-1.03 (m, 3H), 0.98-0.85 (m, 1H), 0.48-0.35 (m, 1H), 0.23-0.12 (m, 1H), 0.11-0.02 (m, 1H), 0.00-0.07 (m, 1H).

Example 66

N-((5-((R)-1-cyclopropylethyl)-2,3-dihydro-1H-inden-4-yl)carbamoyl)-5-(3-hydroxytetrahydrofuran-3-yl)thiophene-2-sulfonamide (Compound 66)

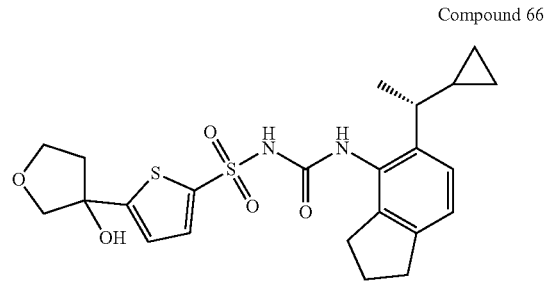 [SMILES: C[C@@H](c1ccc2c(c1NC(=O)NS(=O)(=O)c1ccc(C3(O)CCOC3)s1)CCC2)C1CC1]

Compound 66

For synthesis of compound 66, reference was made to preparation method of compound 59. Compound 66 was in the form of a yellow solid (190 mg, 24.5% yield).

$^1$H NMR (400 MHz, DMSO-d6) δ=7.60 (s, 1H), 7.49 (s, 1H), 7.10-7.00 (m, 4H), 6.26 (s, 1H), 4.18 (d, 1H), 4.10-4.06 (m, 3H), 2.77-2.73 (m, 2H), 2.66-2.60 (m, 2H), 2.39 (d, 1H), 2.31-2.26 (m, 2H), 1.92-1.88 (m, 2H), 1.07 (d, 3H), 0.93-0.88 (m, 1H), 0.43-0.39 (m, 1H), 0.20-0.16 (m, 1H), 0.08-0.04 (m, 1H), 0.03-0.00 (m, 1H); LCMS m/z (ESI)=477.1 [M+1].

| Compound Structures | ¹H NMR | LCMS m/z(ESI) |
|---|---|---|
| 67 | ¹H NMR (400 MHz, DMSO-d6) δ = 7.60(s, 1H), 7.49(s, 1H), 7.08 – 7.03(m, 4H), 6.26(s, 1H), 4.18(d, 1H), 4.10 – 4.06(m, 3H), 2.78 – 2.73(m, 2H), 2.66 – 2.60(m, 2H), 2.39(d, 1H), 2.29 – 2.24(m, 2H), 1.94 – 1.88(m, 2H), 1.07(d, 3H), 0.93 – 0.88(m, 1H), 0.43 – 0.40(m, 1H), 0.20 – 0.16(m, 1H), 0.09 – 0.04(m, 1H), 0.03 – 0.00(m, 1H) | 477.1 [M + 1] |
| 68 | ¹H NMR (400 MHz, DMSO-d6) δ = 10.90(s, 1H), 7.77(s, 1H), 7.49(s, 1H), 7.13(d, 1H), 7.07(d, 1H), 6.99(d, 1H), 5.87(s, 1H), 3.72 – 3.68(m, 4H), 2.82(t, 2H), 2.56(t, 2H), 2.15 – 2.10(m, 1H), 1.96 – 1.90(m, 4H), 1.68(d, 2H), 1.08(d, 3H), 0.93 – 0.87(m, 1H), 0.45 – 0.40(m, 1H), 0.20 – 0.16(m, 1H), 0.09 – 0.06(m, 1H), 0.03 – 0.01(m, 1H) | 491.2 [M + 1] |
| 69 | ¹H NMR (400 MHz, DMSO-d6) δ = 10.90(s, 1H), 7.55(s, 1H), 7.33(s, 1H), 7.10(d, 1H), 7.01(d, 1H), 6.89(d, 1H), 5.72(s, 1H), 3.72 – 3.68(m, 4H), 2.82(t, 2H), 2.60(t, 2H), 2.23 – 2.18(m, 1H), 1.96 – 1.90(m, 4H), 1.68(d, 2H), 1.08(d, 3H), 0.93 – 0.89(m, 1H), 0.46 – 0.40(m, 1H), 0.20 – 0.16(m, 1H), 0.09 – 0.06(m, 1H), 0.03 – 0.01(m, 1H) | 491.2 [M + 1] |

Example 70

$R_S$- and $S_S$-N-((2-(cyclobutylmethyl)-6-isopropylphenyl)carbamoyl)-4-(2-hydroxypropan-2-yl)furan-2-sulfonimidamide (Compounds 70-1 and 70-2)

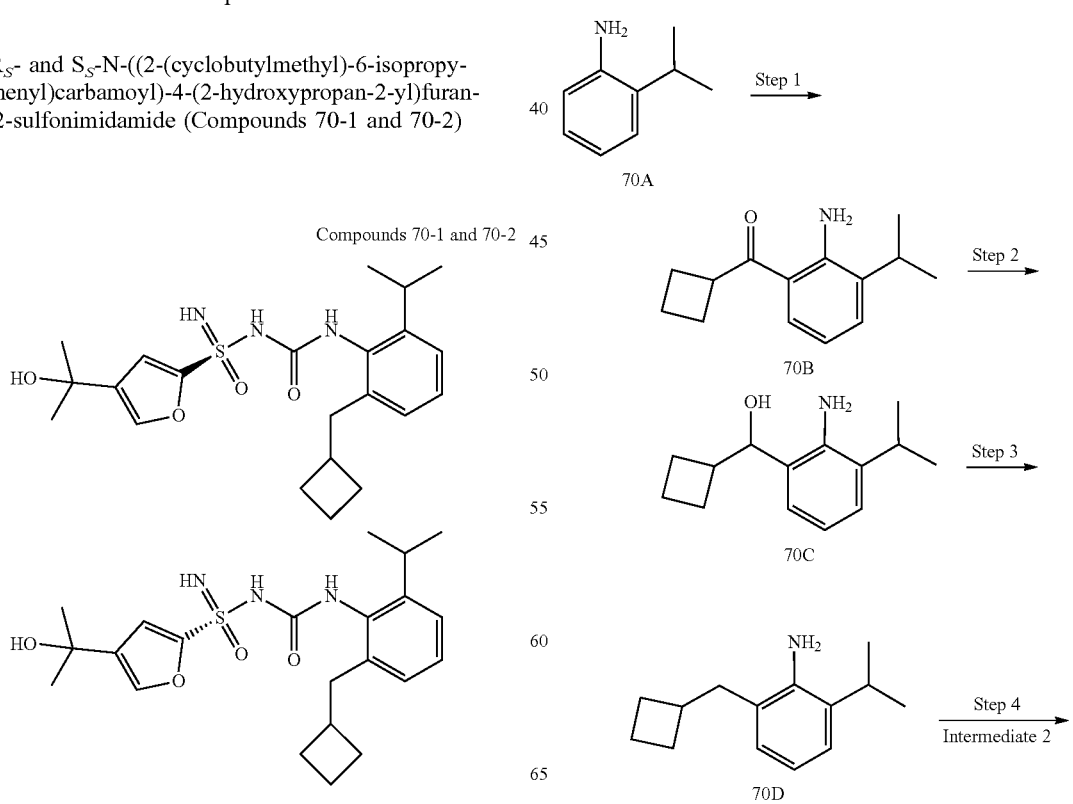

195
-continued

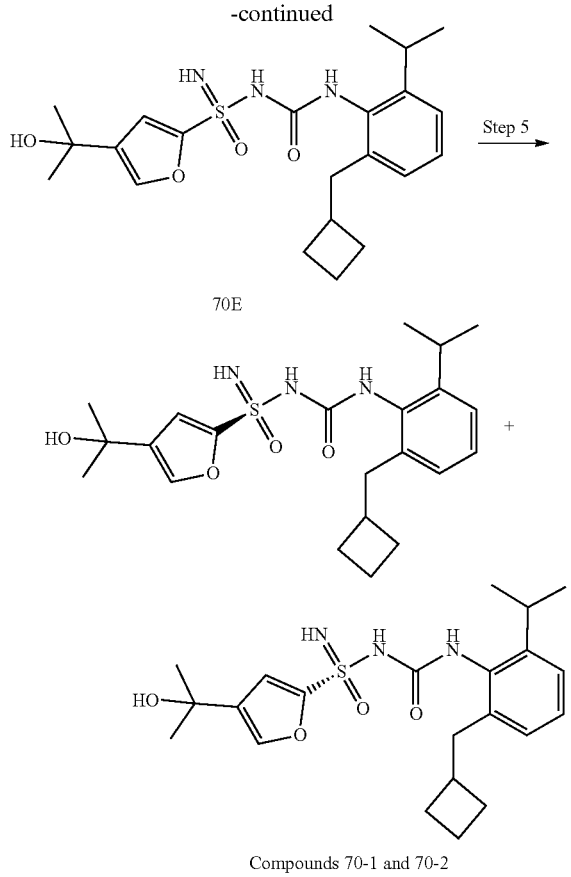

Compounds 70-1 and 70-2

Step 1

(2-amino-3-isopropylphenyl)(cyclobutyl)methanone (70B)

70A (5.2 g, 38.5 mmol) and dichloroethane (100 mL) were added successively into a 500 mL three-necked flask, and the reaction system was placed in an ice water bath after it was clarified. A solution of boron trichloride in toluene (46 mL, 1 M) was added dropwise slowly under nitrogen atmosphere, and anhydrous aluminum trichloride (6.1 g, 10 mmol) was added 10 min later. Cyclobutyl cyanide (5.8 mL, 12.6 mmol) was then added dropwise slowly. After the dropwise addition was completed, the reaction system was reacted at 90° C. for 7 h and then cooled to room temperature. Diluted hydrochloric acid solution (10 mL, 2 N) was added, and the reaction system warmed to reflux, and reacted for 30 min. The organic phase was separated out, washed with saturated sodium bicarbonate (20 mL) to weak acidity, and extracted with dichloromethane (20 mL×3). The organic phase was dried over anhydrous sodium sulfate and filtered, and the organic solvent was removed under reduced pressure. The crude product was purified by column chromatography (petroleum ether:ethyl acetate=10:1) to give compound 70B in the form of a brown oil (1.2 g, 13% yield).

$^1$H NMR (400 MHz, CDCl$_3$) δ=7.50 (d, 1H), 7.27 (d, 1H), 6.65 (t, 1H), 4.01 (p, 1H), 2.90 (dt, 1H), 2.52-2.36 (m, 2H), 2.33-2.19 (m, 2H), 2.12-1.98 (m, 1H), 1.87 (ddd, 1H), 1.27 (d, 6H).

Step 2

(2-amino-3-isopropylphenyl)(cyclobutyl)methanol (70C)

70B (1.1 g, 5 mmol), absolute methanol (10 mL) and sodium borohydride (227 mg, 6 mmol) were added successively into a 50 mL round-bottomed flask, and the reaction system was reacted at room temperature for 2 h. After the reaction was completed as detected by TLC, water (20 mL) was added dropwise slowly to quench the reaction, and dichloromethane (20 mL×3) was added for extraction. The organic phase was dried over anhydrous sodium sulfate and filtered, and the organic solvent was removed under reduced pressure. The crude product was purified by column chromatography (petroleum ether:ethyl acetate=5:1) to give 70C in the form of a brown oil (1.1 g, 99% yield).

$^1$H NMR (400 MHz, DMSO) δ=6.92 (d, 1H), 6.80 (d, 1H), 6.50 (t, 1H), 5.19 (d, 1H), 4.86 (s, 2H), 4.44 (dd, 1H), 2.98 (dt, 1H), 2.78 (dd, 1H), 1.98-1.86 (m, 2H), 1.83-1.62 (m, 4H), 1.14 (d, 6H).

Step 3

2-(cyclobutylmethyl)-6-isopropylaniline (70D)

70C (1.1 g, 5 mmol), dichloromethane (20 mL), triethylsilane (2.4 mL, 15 mmol) and trifluoroacetic acid (1.8 mL, 15 mmol) were added successively into a 50 mL round-bottomed flask, and the reaction system was reacted at room temperature for 2 h. After the reaction was completed as detected by TLC, saturated sodium bicarbonate solution (20 mL) was added dropwise slowly to quench the reaction, and dichloromethane (20 mL×3) was added for extraction. The organic phase was dried over anhydrous sodium sulfate and filtered, and the organic solvent was removed under reduced pressure. The crude product was purified by column chromatography (petroleum ether:ethyl acetate=10:1) to give 70D in the form of a brown oil (820 mg, 78% yield).

$^1$H NMR (400 MHz, DMSO) δ=6.88 (dd, 1H), 6.72 (dd, 1H), 6.50 (t, 1H), 4.46 (s, 2H), 3.00 (dt, 1H), 2.69-2.58 (m, 1H), 2.56 (d, 1H), 2.51-2.48 (m, 1H), 2.06-1.98 (m, 2H), 1.89-1.76 (m, 2H), 1.72-1.63 (m, 2H), 1.14 (d, 6H).

Step 4

N-((2-(cyclobutylmethyl)-6-isopropylphenyl)carbamoyl)-4-(2-hydroxypropan-2-yl)furan-2-sulfonimidamide (70E)

70D (500 mg, 2.46 mmol), tetrahydrofuran (10 mL), N,N-diisopropylethylamine (815 μL, 5 mmol) and 2,2,2-trichloroethyl chloroformate (508 μL, 3.6 mmol) were added successively into a 50 mL round-bottomed flask under nitrogen atmosphere, and the reaction system was reacted at room temperature for 1 h. Water (10 mL) was added to quench the reaction, and ethyl acetate (20 mL×3) was added for extraction. The organic phase was dried over anhydrous sodium sulfate and filtered, and the organic solvent was removed under reduced pressure. The residue was dissolved in tetrahydrofuran (20 mL), and 2e (625 mg, 2 mmol) and sodium hydride (118 mg, 3 mmol) were added. The mixture was reacted at room temperature for 2 h. A solution of tetrabutylammonium fluoride in tetrahydrofuran (4 mL, 1 M) was added, and the resulting mixture was reacted at room temperature for 5 h. After the reaction was completed as detected by TLC, water (20 mL) was added to quench the reaction, and ethyl acetate (30 mL×3) was added for extraction. The organic phase was dried over anhydrous sodium sulfate and filtered, and the organic solvent was removed. The crude product was purified by column chromatography (petroleum ether:ethyl acetate=1:1) to give compound 70E in the form of a pale yellow oil (380 mg, 36% yield).

Step 5

$R_S$- and $S_S$-N-((2-(cyclobutylmethyl)-6-isopropylphenyl)carbamoyl)-4-(2-hydroxypropan-2-yl)furan-2-sulfonimidamide (Compounds 70-1 and 70-2)

70E was resolved by SFC to give compound 70-1 (40 mg, RT=2.989 min, ee %: 99.99%) and compound 70-2 (40 mg, RT=5.033 min, ee %: 96.76%). Chiral HPLC (OX-3), mobile phase: methanol; column temperature: 35° C.; column pressure: 80 bar; flow rate: 2 mL/min; detector signal channel: 215 nm@4.8 nm; start wavelength of diode array detector: 200 nm; stop wavelength of diode array detector: 400 nm.

Compound 70-1: $^1$H NMR (400 MHz, DMSO-$d_6$) δ=8.17 (s, 1H), 7.74-7.62 (m, 3H), 7.13-7.04 (m, 2H), 6.98 (d, 1H), 6.95-6.91 (m, 1H), 5.07 (s, 1H), 3.09 (q, 1H), 2.57 (d, 2H), 2.00-1.93 (m, 2H), 1.83-1.75 (m, 2H), 1.65 (q, 2H), 1.38 (s, 6H), 1.28-1.15 (m, 1H), 1.07 (dd, 6H); LCMS m/z=434.2 [M+1].

Compound 70-2: $^1$H NMR (400 MHz, DMSO-$d_6$) δ=8.17 (s, 1H), 7.74-7.62 (m, 3H), 7.17-7.04 (m, 2H), 6.98 (d, 1H), 6.93 (dd, 1H), 5.07 (s, 1H), 3.18-3.05 (m, 1H), 2.57 (d, 2H), 1.98-1.94 (m, 2H), 1.85-1.75 (m, 2H), 1.72-1.55 (m, 2H), 1.38 (s, 6H), 1.26-1.15 (m, 1H), 1.07 (dd, 6H); LCMS m/z=434.2[M+1].

Example 71

(S)-N-((2-(1-cyclopropylethyl)-6-isopropylphenyl)carbamoyl)-4-(2-hydroxypropan-2-yl)furan-2-sulfonamide (Compound 71)

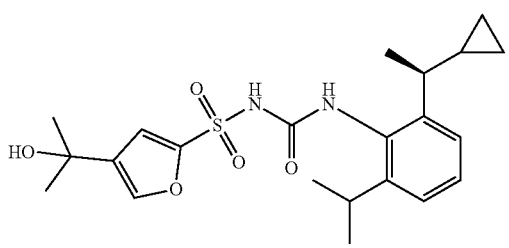

Compound 71

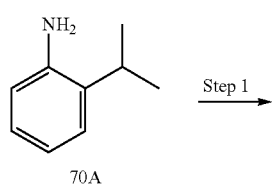

Step 1

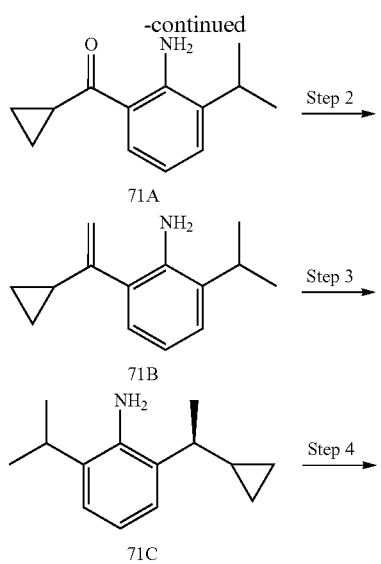

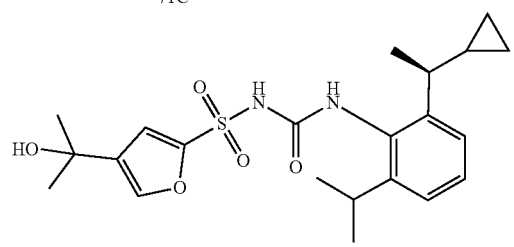

Compound 71

Step 1

(2-amino-3-isopropylphenyl)(cyclopropyl)methanone (71A)

70A (20 g, 148 mmol) and dichloroethane (200 mL) were added successively into a 500 mL three-necked flask, and the reaction system was placed in an ice water bath after it was clarified. A solution of boron trichloride in toluene (175 mL, 1 M) was added dropwise slowly under nitrogen atmosphere, and anhydrous aluminum trichloride (22 g, 177 mmol) was added 10 min later. Cyclobutyl cyanide (16.5 mL, 222 mmol) was then added dropwise slowly. After the dropwise addition was completed, the reaction system was reacted at 90° C. for 7 h and then cooled to room temperature. Diluted hydrochloric acid solution (50 mL, 2 N) and water (50 mL) were added, and the reaction system was warmed to reflux, and reacted for 30 min. The organic phase was separated out, washed with saturated sodium bicarbonate (10 mL) to weak acidity, and extracted with dichloromethane (10 mL×3). The organic phase was dried over anhydrous sodium sulfate and filtered, and the organic solvent was removed under reduced pressure. The crude product was purified by column chromatography (petroleum ether:ethyl acetate=10:1) to give compound 71A in the form of a brown oil (7.2 g, 24% yield).

$^1$H NMR (400 MHz, CDCl$_3$) δ=7.89 (dd, 1H), 7.33-7.28 (m, 1H), 6.73 (t, 1H), 2.90 (dt, 1H), 2.73-2.59 (m, 1H), 1.27 (d, 6H), 1.20-1.14 (m, 2H), 0.96 (dq, 2H).

Step 2

2-(1-cyclopropylvinyl)-6-isopropylaniline (71B)

Methyl triphenyl phosphonium bromide (15.7 g, 44 mmol) and anhydrous tetrahydrofuran (20 mL) were added successively into a 50 mL three-necked flask, and the reaction system was placed in an ice water bath after it was clarified. Potassium tert-butoxide (5.0 g, 44 mmol) was added under nitrogen atmosphere, and a solution of 71A (3.0 g, 15 mmol) in tetrahydrofuran (10 mL) was added 40 min later. 10 min later, the reaction system was reacted at room temperature for 2 h, and then water (10 mL) was added to quench the reaction and ethyl acetate (20 mL×3) was added for extraction. The organic phase was dried over anhydrous sodium sulfate and filtered, and the organic solvent was removed under reduced pressure. The crude product was purified by column chromatography (petroleum ether:ethyl acetate=10:1) to give 71B in the form of a brown oil (2.1 g, 69% yield).

$^1$H NMR (400 MHz, CDCl$_3$) δ=7.07 (dd, 1H), 6.83 (dd, 1H), 6.73 (t, 1H), 5.22 (d, 1H), 4.94 (d, 1H), 2.90 (dt, 1H), 1.65 (tt, 1H), 1.26 (d, 6H), 0.76-0.66 (m, 2H), 0.51-0.39 (m, 2H).

Step 3

(S)-2-(1-cyclopropylethyl)-6-isopropylaniline (71C)

71B (1.0 g, 5 mmol) and dichloromethane (100 mL) were added into a 500 mL autoclave, and then a catalyst ruthenium [(S)-2,2'-bis(diphenylphosphino)-1,11-binaphthyl]diacetate (209 mg, 0.25 mmol) was added. After the addition was completed, the autoclave was tightly closed and sealed, and purged with hydrogen 3 times. The hydrogen was introduced until the pressure gauge on the autoclave showed 12 atm, and then the reaction system was reacted for 5 h at room temperature. The reaction system was concentrated under reduced pressure to remove the solvent, and the crude product was purified by column chromatography (petroleum ether:ethyl acetate=10:1) to give 71C in the form of a pale yellow oil (600 mg, 59% yield).

$^1$H NMR (400 MHz, CDCl$_3$) δ 7.15 (d, 1H), 7.10-7.02 (m, 1H), 6.83 (t, 1H), 3.03-2.89 (m, 1H), 2.44-2.28 (m, 1H), 1.30 (d, 3H), 1.27 (d, 6H), 1.14-1.03 (m, 1H), 0.60-0.51 (m, 1H), 0.48-0.41 (m, 1H), 0.17-0.08 (m, 2H).

Step 4

(S)-N-((2-(1-cyclopropylethyl)-6-isopropylphenyl)carbamoyl)-4-(2-hydroxypropan-2-yl)furan-2-sulfonamide (Compound 71)

71C (100 mg, 0.5 mmol), tetrahydrofuran (10 mL), N,N-diisopropylethylamine (165 μL, 1.0 mmol) and 2,2,2-trichloroethyl chloroformate (103 μL, 0.75 mmol) were added successively into a 50 mL round-bottomed flask under nitrogen atmosphere, and the reaction system was reacted at room temperature for 1 h. Water (10 mL) was added to quench the reaction, and ethyl acetate (20 mL×3) was added for extraction. The organic phase was dried over anhydrous sodium sulfate and filtered, and the organic solvent was removed under reduced pressure. The residue was dissolved in tetrahydrofuran (10 mL), and 2e (82 mg, 0.4 mmol) and sodium hydride (24 mg, 0.6 mmol) were added. The mixture was reacted at room temperature for 2 h. After the reaction was completed as detected by TLC, water (20 mL) was added to quench the reaction, and ethyl acetate (30 mL×3) was added for extraction. The organic phase was dried over anhydrous sodium sulfate and filtered, and the organic solvent was removed. The crude product was purified by preparative medium pressure liquid chromatography to give compound 71 in the form of a yellow solid (46 mg, 21% yield, UPLC: 94.06%, ee %: 98.28%, chiral HPLC (OX-3); mobile phase: methanol; column temperature: 35° C.; column pressure: 80 bar; flow rate: 2 mL/min; detector signal channel: 215 nm@4.8 nm; start wavelength of diode array detector: 200 nm; stop wavelength of diode array detector: 400 nm; RT=14.317 min).

$^1$H NMR (400 MHz, DMSO) δ=11.11 (s, 1H), 7.74 (s, 1H), 7.68 (s, 1H), 7.22 (s, 1H), 7.21 (s, 1H), 7.13-7.06 (m, 1H), 7.02 (s, 1H), 5.05 (s, 1H), 3.06-2.90 (m, 1H), 2.11 (s, 1H), 1.37 (d, 6H), 1.06 (s, 10H), 0.98-0.88 (m, 1H), 0.45 (s, 1H), 0.19 (s, 1H), 0.06 (s, 1H); LCMS m/z=435.2[M+1].

Example 72

N-((2-((R)-1-cyclopropylethyl)-6-isopropylphenyl)carbamoyl)-4-(2-hydroxypropan-2-yl)furan-2-sulfonimidamide (Compound 72)

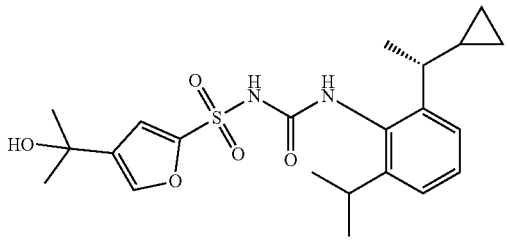

Compound 72

For synthesis of compound 72, reference was made to preparation method of compound 71; compound 72, off-white solid, (60 mg, 28% yield, UPLC: 98.65%, ee %: 95.52%, chiral HPLC (OX-3); mobile phase: methanol; column temperature: 35° C.; column pressure: 80 bar; flow rate: 2 mL/min; detector signal channel: 215 nm@4.8 nm; start wavelength of diode array detector: 200 nm; stop wavelength of diode array detector: 400 nm; RT=12.329 min).

$^1$H NMR (400 MHz, DMSO) δ=11.13 (s, 1H), 7.67 (s, 1H), 7.62 (s, 1H), 7.20 (s, 1H), 7.20 (s, 1H), 7.09 (d, 1H), 6.95 (s, 1H), 5.02 (s, 1H), 3.01 (s, 1H), 2.15 (s, 1H), 1.36 (s, 6H), 1.07 (d, 10H), 0.99-0.89 (m, 1H), 0.45 (s, 1H), 0.19 (s, 1H), 0.06 (s, 1H); LCMS m/z=435.2[M+1].

Example 73

($R_S$, $S_C$) and ($S_S$, $S_C$)-N-((2-(1-cyclopropylethyl)-6-isopropylphenyl)carbamoyl)-4-(2-hydroxypropan-2-yl)furan-2-sulfonimidamide (Compounds 73-1 and 73-2)

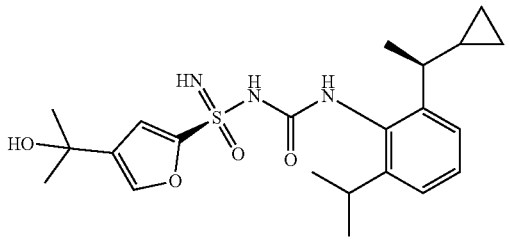

Compounds 73-1 and 73-2

-continued

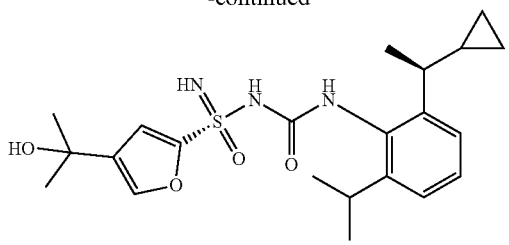

For synthesis of compounds 73-1 and 73-2, reference was made to preparation method of compounds 70-1 and 70-2. Compound 73-1 (90 mg, RT=8.684 min, ee %: 99.44%) and compound 73-2 (70 mg, RT=11.936 min, ee %: 99.99%). Chiral HPLC (OX-3), mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm.

Compound 73-1: $^1$H NMR (400 MHz, DMSO) δ 8.16 (s, 1H), 7.66 (s, 1H), 7.62 (s, 1H), 7.22-7.15 (m, 2H), 7.07 (d, 1H), 6.96 (s, 1H), 5.08 (d, 1H), 3.10 (s, 1H), 2.35-2.21 (m, 1H), 1.37 (s, 6H), 1.27-0.91 (m, 10H), 0.48-0.44 (m, 1H), 0.27-0.18 (m, 1H), 0.13-0.06 (m, 2H); LCMS m/z (ESI)=434.1[M+1].

Compound 73-2: $^1$H NMR (400 MHz, DMSO) δ 8.17 (s, 1H), 7.67 (s, 1H), 7.64 (d, 2H), 7.24-7.13 (m, 2H), 7.11-7.03 (m, 1H), 6.96 (s, 1H), 5.08 (s, 1H), 3.09 (s, 1H), 2.29-2.15 (m, 1H), 1.37 (s, 6H), 1.24-0.93 (m, 10H), 0.49-0.45 (m, 1H), 0.24-0.22 (m, 1H), 0.10-0.05 (m, 2H); LCMS m/z (ESI)=434.1[M+1].

Example 74

($R_S$, $R_C$)- and ($S_S$, $R_C$)-N-((2-(1-cyclopropylethyl)-6-isopropylphenyl)carbamoyl)-4-(2-hydroxypropan-2-yl)furan-2-sulfonimidamide (Compound 74-1 and Compound 74-2)

Compounds 74-1 and 74-2

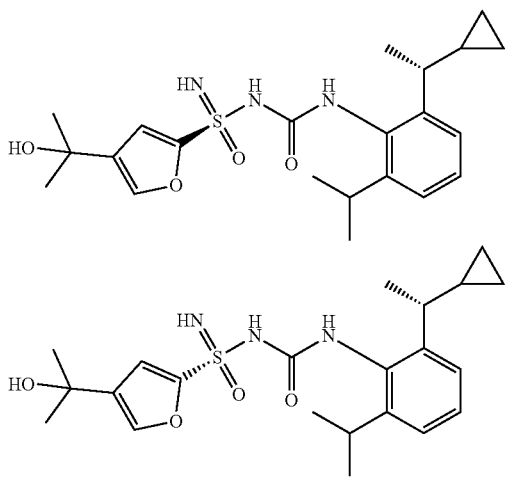

For synthesis of compound 74-1 and compound 74-2, reference was made to preparation method of compounds 70-1 and 70-2; compound 74-1 (30 mg, RT=8.586 min, ee %: 99.18%) and compound 74-2 (30 mg, RT=11.413 min, ee %: 99.99%). Chiral HPLC (OX-3); mobile phase: methanol; column temperature: 35° C.; column pressure: 80 bar; flow rate: 1 mL/min; detector signal channel: 215 nm@4.8 nm; start wavelength of diode array detector: 200 nm; stop wavelength of diode array detector: 400 nm.

Compound 74-1: $^1$H NMR (400 MHz, DMSO-d6) δ 8.17 (s, 1H), 7.67 (d, 1H), 7.63 (s, 1H), 7.25-7.15 (m, 2H), 7.07 (dd, 1H), 6.96 (s, 1H), 5.08 (s, 1H), 3.10 (s, 1H), 2.29-2.14 (m, 1H), 1.37 (s, 6H), 1.23-0.92 (m, 10H), 0.48-0.44 (m, 1H), 0.27-0.18 (m, 1H), 0.13-0.06 (m, 2H); LCMS m/z (ESI)=434.1[M+1].

Compound 74-2: $^1$H NMR (400 MHz, DMSO-$d_6$) δ 8.16 (s, 1H), 7.64 (d, 3H), 7.24-7.14 (m, 2H), 7.07 (dd, 1H), 6.96 (d, 1H), 5.08 (d, 1H), 3.10 (s, 1H), 2.33-2.08 (m, 1H), 1.37 (s, 6H), 1.21 (dd, 1H), 1.18-0.92 (m, 9H), 0.49-0.45 (m, 1H), 0.24-0.22 (m, 1H), 0.10-0.05 (m, 2H); LCMS m/z (ESI)=434.1[M+1].

Example 75

N-((2-(2-cyanopyridin-4-yl)-6-(cyclobutylmethyl)-4-fluorophenyl)carbamoyl)-4-(2-hydroxypropan-2-yl)furan-2-sulfonimidamide (Compound 75)

Compound 75

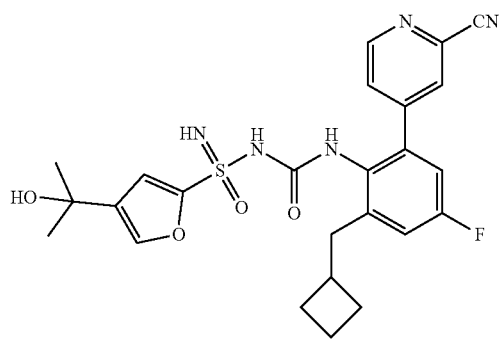

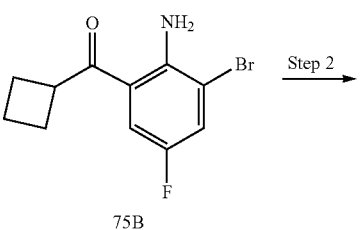

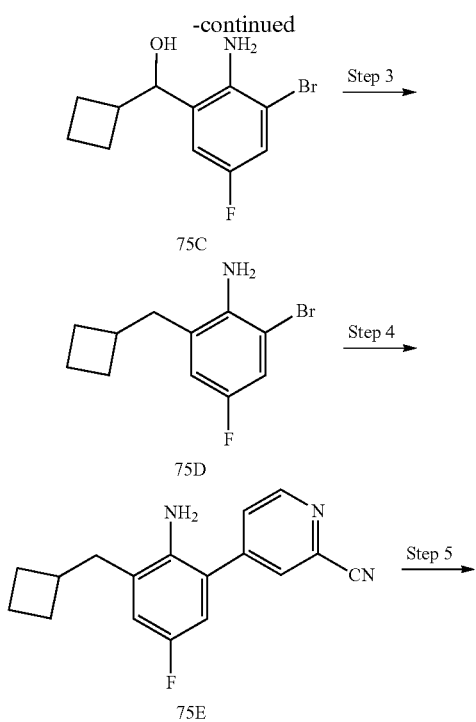

Step 1

(2-amino-3-bromo-5-fluorophenyl)(cyclobutyl) methanone (75B)

75A (40 g, 210.4 mmol) and dichloroethane (500 mL) were added successively into a 1 L three-necked flask, and the reaction system was placed in an ice water bath after it was clarified. A solution of boron trichloride in toluene (252.8 mL, 1 M) was added dropwise slowly under nitrogen atmosphere, and anhydrous aluminum trichloride (33.6 g, 252 mmol) was added 10 min later. Cyclobutyl cyanide (59.2 mL, 632 mmol) was then added dropwise slowly. After the dropwise addition was completed, the reaction system was reacted at 90° C. for 24 h and then cooled to room temperature. Diluted hydrochloric acid solution (30 mL, 2 N) was added, and the reaction system was warmed to reflux, and reacted for 30 min. The organic phase was separated out, washed with saturated sodium bicarbonate (50 mL) to weak acidity, and extracted with dichloromethane (50 mL×3). The organic phase was dried over anhydrous sodium sulfate and filtered, and the organic solvent was removed under reduced pressure to give the crude product 75B in the form of a pale yellow oil (4.8 g, 8.8% yield).

$^1$H NMR (400 MHz DMSO) δ=7.27 (dd, 1H), 6.79 (dd, 1H), 5.17 (d, 2H), 4.14-4.10 (m, 1H), 2.06-2.86 (m, 5H), 1.82-1.68 (m, 1H).

Step 2

(2-amino-3-bromo-5-fluorophenyl)(cyclobutyl) methanol (75C)

75B (4.8 g, 17.3 mmol), absolute methanol (20 mL) and sodium borohydride (2.0 g, 51.9 mmol) were added successively into a 250 mL round-bottomed flask, and the reaction system was reacted at room temperature for 2 h. After the reaction was completed as detected by TLC, water (20 mL) was added dropwise slowly to quench the reaction, and dichloromethane (20 mL×3) was added for extraction. The organic phase was dried over anhydrous sodium sulfate and filtered, and the organic solvent was removed under reduced pressure. The crude product was purified by column chromatography (petroleum ether:ethyl acetate=30:1) to give 75C in the form of a white powder (2.6 g, 54% yield).

$^1$H NMR (400 MHz DMSO) δ=7.21 (dd, 1H), 6.94 (dd, 1H), 5.48 (d, 1H), 5.03 (s, 2H), 4.54 (dd, 1H), 2.74-2.62 (m, 2H), 1.98-1.68 (m, 6H).

Step 3

2-bromo-6-(cyclobutylmethyl)-4-fluoroaniline (75D)

75C (850 mg, 3 mmol), dichloromethane (20 mL), triethylsilane (1.4 mL, 9 mmol) and trifluoroacetic acid (1 mL, 9 mmol) were added successively into a 50 mL round-bottomed flask, and the reaction system was reacted at room temperature for 2 h. After the reaction was completed as detected by TLC, saturated sodium bicarbonate solution (20 mL) was added dropwise slowly to quench the reaction, and dichloromethane (20 mL×3) was added for extraction. The organic phase was dried over anhydrous sodium sulfate and filtered, and the organic solvent was removed under reduced pressure. The crude product was purified by column chromatography (petroleum ether:ethyl acetate=10:1) to give 75D in the form of a brown oil (530 mg, 69% yield).

$^1$H NMR (400 MHz, Chloroform-d) δ 7.06 (dd, 1H), 6.70 (dd, 1H), 3.36 (s, 2H), 2.65 (dq, 1H), 2.58 (d, 2H), 2.22-2.07 (m, 2H), 1.98-1.81 (m, 2H), 1.83-1.63 (m, 2H).

Step 4

4-(2-amino-3-(cyclobutylmethyl)-5-fluorophenyl) picolinonitrile (75E)

75D (100 mg, 0.4 mmol), dioxane (20 mL) and sodium carbonate (103 mg, 1 mmol) were added successively into a 50 mL round-bottomed flask, and bis(triphenylphosphine) palladium(II) chloride (29 mg, 0.04 mmol) and 2-cyanopyridine-4-boronic acid pinacol ester (105 mg, 0.46 mmol) were added under nitrogen atmosphere. The reaction system was reacted at 80° C. for 24 h. After the reaction was completed as detected by TLC, the reaction system was concentrated under reduced pressure to remove the solvent, and the crude product was purified by column chromatography (petroleum ether:ethyl acetate=5:1) to give 75E in the form of a brown oil (50 mg, 45% yield).

LCMS m/z (ESI)=282.1[M+1].

Step 5

N-((2-(2-cyanopyridin-4-yl)-6-(cyclobutylmethyl)-4-fluorophenyl)carbamoyl)-4-(2-hydroxypropan-2-yl)furan-2-sulfonimidamide (Compound 75)

Compound 75F (50 mg, 0.18 mmol), triethylamine (60 μL, 0.43 mmol) and tetrahydrofuran (10 mL) were added successively into a 100 mL round-bottomed flask under nitrogen atmosphere, and then triphosgene (30 mg, 0.1 mmol) was added in an ice bath. The reaction system was reacted at room temperature for 2 h and then filtered to remove the solids.

Intermediate 2 (55 mg, 0.17 mmol) and sodium methoxide (10 mg, 0.18 mmol) were added to the filtrate, and the mixture was refluxed, and reacted for 1 h. After the reaction was completed as detected by TLC, water (10 mL) was added to quench the reaction, and dichloromethane (10 mL×3) was added for extraction. The organic phase was dried over anhydrous sodium sulfate and filtered, and the organic solvent was removed. The crude product was purified by column chromatography to give compound 75 in the form of a white solid (40 mg, 43%, UPLC: 97.73%).

$^1$H NMR (400 MHz, DMSO-d$_6$) δ=8.76 (d, 1H), 8.42 (s, 1H), 8.00 (s, 1H), 7.68-7.52 (m, 4H), 7.21-7.12 (m, 2H), 6.91 (s, 1H), 5.08 (s, 1H), 2.67 (d, 2H), 2.60-2.54 (m, 1H), 2.03-1.95 (m, 2H), 1.87-1.76 (m, 2H), 1.76-1.60 (m, 2H), 1.38 (d, 6H); LCMS m/z=512.1[M+1].

Example 76

N-((2-(cyclobutylmethyl)-4-fluoro-6-(2-methoxypyridin-4-yl)phenyl)carbamoyl)-4-(2-hydroxypropan-2-yl)furan-2-sulfonimidamide (Compound 76)

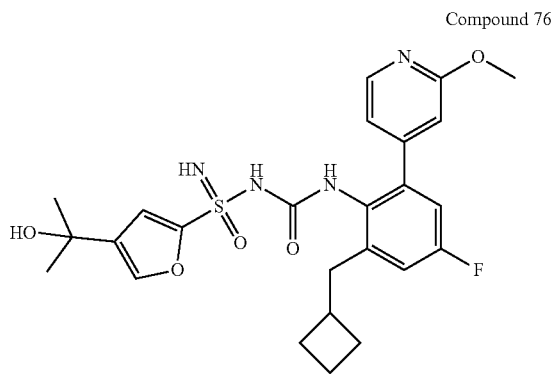 [SMILES: COc1cc(-c2cc(F)cc(CC3CCC3)c2NC(=O)NS(=N)(=O)c2cc(C(C)(C)O)co2)ccn1]

Compound 76

For synthesis of compound 76, reference was made to preparation method of compound 75. Compound 76 was in the form of a white solid (70 mg, 30% yield).

$^1$H NMR (400 MHz, DMSO-d$_6$) δ=8.26 (s, 1H), 8.16 (d, 1H), 7.71-7.53 (m, 4H), 7.08-7.00 (m, 2H), 6.94 (s, 1H), 6.79 (s, 1H), 5.11 (s, 1H), 3.89 (s, 3H), 2.80-2.56 (m, 3H), 2.00 (t, 2H), 1.81 (q, 2H), 1.75-1.60 (m, 2H), 1.40 (s, 6H); LCMS m/z=517.2[M+1].

Example 77

(R)- and (S)-N-((5-(cyclobutylmethyl)-2,3-dihydro-1H-inden-4-yl)carbamoyl)-5-(3-hydroxyoxetan-3-yl)thiophene-2-sulfonimidamide Compounds 77-1 and 77-2

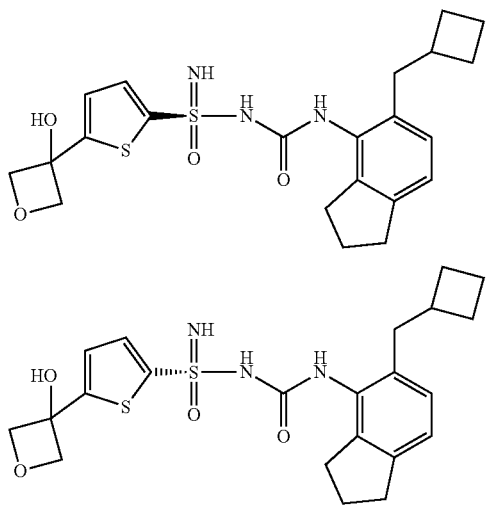

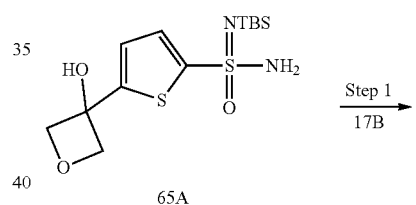

65A

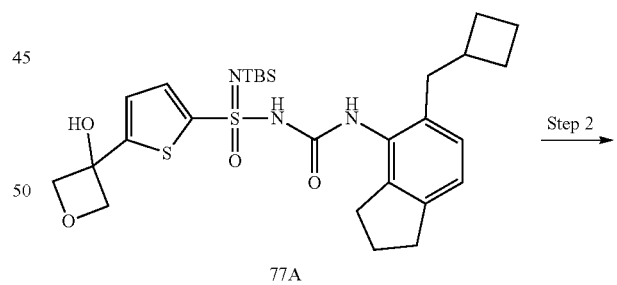

77A

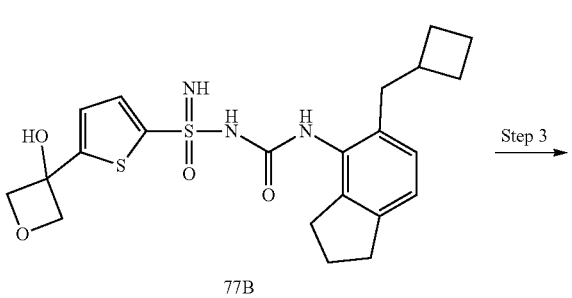

77B

207

-continued

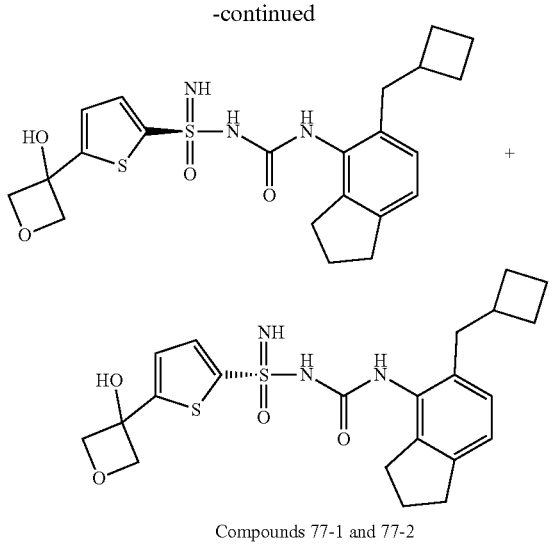

Compounds 77-1 and 77-2

Step 1

N'-(tert-butyldimethylsilyl)-N-((5-(((S)-1-cyclopropylethyl)-2,3-dihydro-1H-inden-4-yl)carbamoyl)-5-(3-hydroxyoxetan-3-yl)thiophene-2-sulfonimidamide (77A)

17B (288 mg, 1.44 mmol), triethylamine (174 mg, 1.772 mmol) and tetrahydrofuran (20 mL) were added successively into a 100 mL round-bottomed flask under nitrogen atmosphere, and then triphosgene (171 mg, 0.57 mmol) was added in an ice bath. The reaction system was warmed to reflux, reacted for 2 h, and then filtered to remove the solids. Compound 65A (500 mg, 1.44 mmol) and sodium hydride (115 mg, 2.87 mmol) were added to the filtrate, and the mixture was reacted at room temperature for 12 h. After the reaction was completed as detected by TLC, 77A was obtained and was directly used in the next step without purification.

LCMS m/z (ESI)=576.2[M+1].

Step 2

N-((5-(cyclobutylmethyl)-2,3-dihydro-1H-inden-4-yl)carbamoyl)-5-(3-hydroxyoxetan-3-yl)thiophene-2-sulfonimidamide (77B)

Tetrabutylammonium fluoride (6 mL, 6 mmol, 1 M/THF) was added to the reaction system from the previous step, and the resulting reaction system was reacted overnight at room temperature. After the reaction was completed as detected by TLC, the reaction system was poured into water and extracted with ethyl acetate (100 mL×3). The organic phases were combined, washed once with 1 M diluted HCl, dried over anhydrous sodium sulfate and filtered, and the organic solvent was removed under reduced pressure. The residue was purified by preparative medium pressure liquid chromatography (acetonitrile/water=50%) to give 77B in the form of a transparent solid (231 mg, 34.9%).

LCMS m/z (ESI)=462.1[M+1].

208

Step 3

(R)- and (S)-N-((5-(cyclobutylmethyl)-2,3-dihydro-1H-inden-4-yl)carbamoyl)-5-(3-hydroxyoxetan-3-yl)thiophene-2-sulfonimidamide (Compounds 77-1 and 77-2)

77B was resolved by SFC to give compound 77-1 (89 mg, 38.5% yield, RT=19.784 min, ee %: 99.99%) and compound 77-2 (83 mg, 35.9% yield, RT=21.782 min, ee %: 99.99%). Chiral HPLC (OZ) mobile phase: n-hexane/ethanol=90/10; column temperature: 35° C.; column pressure: 80 bar; flow rate: 1 mL/min; detector signal channel: 215 nm@4.8 nm; start/stop wavelength of diode array detector: 200-400 nm.

Compound 77-1: $^1$H NMR (400 MHz, DMSO-d6) δ=8.27 (s, 1H), 7.69 (s, 2H), 7.52 (s, 1H), 7.28 (d, 1H), 7.05 (s, 1H), 6.95 (d, 1H), 6.86 (d, 1H), 4.77 (d, 2H), 4.68 (d, 2H), 2.81 (t, 2H), 2.68 (s, 2H), 2.58 (d, 2H), 2.03-1.84 (m, 4H), 1.75 (dd, 2H), 1.65-1.54 (m, 2H), 1.28-1.21 (m, 1H); LCMS m/z=462.1[M+1].

Compound 77-2: $^1$H NMR (400 MHz, DMSO-d6) δ=8.28 (s, 1H), 7.65 (s, 2H), 7.53 (d, 1H), 7.28 (d, 1H), 7.05 (s, 1H), 6.95 (d, 1H), 6.86 (d, 1H), 4.78 (d, 2H), 4.68 (d, 2H), 2.81 (t, 2H), 2.68 (s, 2H), 2.58 (d, 2H), 1.99-1.84 (m, 4H), 1.81-1.70 (m, 2H), 1.66-1.55 (m, 2H), 1.28-1.19 (m, 1H); LCMS m/z=462.1[M+1].

Example 78

($R_S$, $S_C$) or ($S_S$, $S_C$)-N-((5-((S)-1-cyclopropylethyl)-2,3-dihydro-1H-inden-4-yl)carbamoyl)-4-(prop-1-en-2-yl)furan-2-sulfonimidamide (Compound 78)

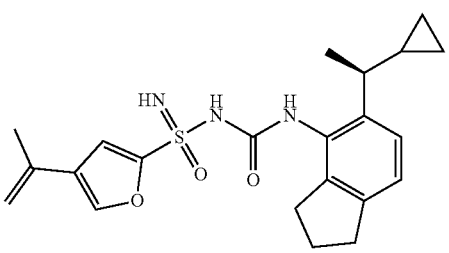

Compound 78

Compound 6-1 → Step 1

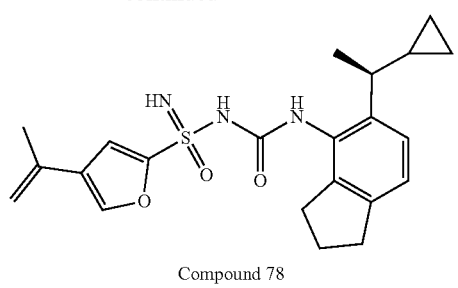

Compound 78

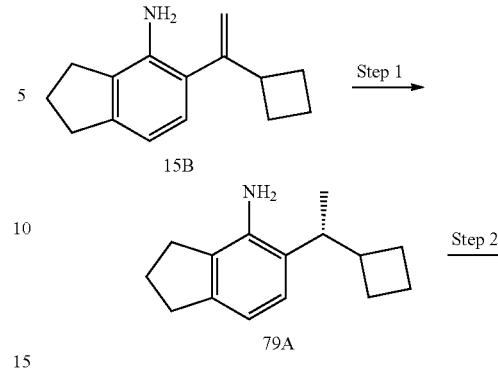

Step 1

Compound 6-1 (435 mg, 1.01 mmol) was dissolved in dry THF (10 mL) in a 100 mL round-bottomed flask, and Burgess reagent (481 mg, 2.02 mmol) was added in an ice bath. The reaction system was reacted overnight at room temperature. After the reaction was completed, water was added to quench the reaction, and ethyl acetate was added for extraction. The organic phase was dried over anhydrous sodium sulfate and filtered, and the organic solvent was removed under reduced pressure. The crude product was purified by column chromatography to give compound 78 in the form of a white solid (121 mg, 32.1% yield, chiral HPLC (OZ); mobile phase: methanol; column temperature: 35° C.; column pressure: 80 bar; flow rate: 2 mL/min; detector signal channel: 215 nm@4.8 nm; start wavelength of diode array detector: 200 nm; stop wavelength of diode array detector: 400 nm; RT=11.721 min).

Compound 78: $^1$H NMR (400 MHz, DMSO) δ=8.27 (s, 1H), 8.00 (s, 1H), 7.69 (s, 2H), 7.23 (s, 1H), 7.12 (d, 1H), 7.04 (d, 1H), 5.37 (s, 1H), 5.00 (s, 1H), 2.81 (t, 2H), 2.71-2.61 (m, 2H), 2.26-2.19 (m, 1H), 1.98 (s, 3H), 1.94-1.84 (m, 2H), 1.06 (d, 3H), 0.98-0.91 (m, 1H), 0.52-0.39 (m, 1H), 0.23-0.18 (m, 1H), 0.14-0.08 (m, 1H), 0.05-0.01 (m, 1H); LCMS m/z (ESI)=374.1[M+1].

Example 79

(R)-N-((5-(1-cyclobutylethyl)-2,3-dihydro-1H-inden-4-yl)carbamoyl)-4-(2-hydroxypropan-2-yl)furan-2-sulfonamide (Compound 79)

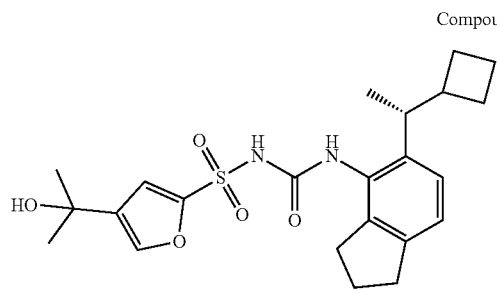

Compound 79

Step 1

(R)-5-(1-cyclobutylethyl)-2,3-dihydro-1H-inden-4-amine (Compound 79A)

Compound 15B (2 g, 9.4 mmol) was added to DCM (20 mL) in an autoclave, and then a catalyst ruthenium [(R)-2,2'-bis(diphenylphosphino)-1,11-binaphthyl]diacetate (316 mg, 0.38 mmol) was added. After the addition was completed and purge with hydrogen was performed three times, the autoclave was tightly closed and sealed. Purge with hydrogen was performed 3 times, the hydrogen was introduced until the pressure gauge on the autoclave showed 12 atm, and then the reaction system was reacted overnight at room temperature. The reaction system was concentrated, and the residue was purified by column chromatography (ethyl acetate/petroleum ether=15:1) to give 79A in the form of a brownish yellow liquid (1.4 g, 70% yield).
LCMS m/z (ESI)=216.2[M+1].

Step 2

(R)-N-((5-(1-cyclobutylethyl)-2,3-dihydro-1H-inden-4-yl)carbamoyl)-4-(2-hydroxypropan-2-yl)furan-2-sulfonamide (Compound 79)

Compound 79A (100 mg, 0.47 mmol) was added to THF (10 mL) under nitrogen atmosphere, and then triethylamine (63.6 mg, 0.58 mmol) was added. Triphosgene (69 mg, 0.19 mmol) was added in an ice bath, and the reaction system was warmed to reflux at 70° C., reacted for 1 h, and then filtered to remove the solids. 2e (76 mg, 0.47 mmol) and sodium methoxide (50 mg, 0.94 mmol) were added to the filtrate, and the mixture was reacted at 70° C. for 1 h. After the reaction was completed as detected by TLC, water (50 mL) was added, and EA (40 mL) was added for extraction. The organic phase was washed with saturated brine, dried over anhydrous sodium sulfate and concentrated to give the crude product, which was subjected to preparative chromatography and lyophilized to give 79 in the form of a white solid (35 mg, 98.98% purity, 16.9% yield, ee %: 99.99%, chiral HPLC (OZ); mobile phase: methanol; column temperature: 35° C.; column pressure: 80 bar; flow rate: 2 mL/min; detector signal channel: 215 nm@4.8 nm; start wavelength of diode array detector: 200 nm; stop wavelength of diode array detector: 400 nm; RT=12.817 min).

$^1$H NMR (400 MHz, DMSO) δ=7.87 (s, 1H), 7.67 (d, 1H), 7.02 (s, 1H), 7.01 (s, 1H), 6.91 (d, 1H), 5.05 (s, 1H), 2.81 (dd, 3H), 2.63-2.54 (m, 2H), 2.46-2.37 (m, 1H), 2.10-1.98 (m, 1H), 1.96-1.85 (m, 2H), 1.75-1.54 (m, 4H), 1.38 (s, 1H), 1.37-1.29 (m, 6H), 0.93 (d, 3H); LCMS m/z (ESI)=447.2 [M+1].

Example 80

(R$_S$)- and (S$_S$)-N-((5-((R)-1-cyclobutylethyl)-2,3-dihydro-1H-inden-4-yl)carbamoyl)-4-(2-hydroxy-propan-2-yl)furan-2-sulfonimidamide (Compounds 80-1 and 80-2)

Example 81

(S)-N-((5-(1-cyclobutylethyl)-2,3-dihydro-1H-inden-4-yl)carbamoyl)-4-(2-hydroxypropan-2-yl)furan-2-sulfonamide (Compound 81)

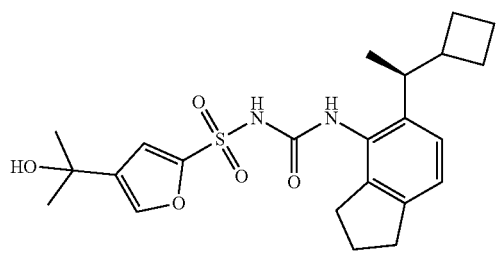

Compound 81

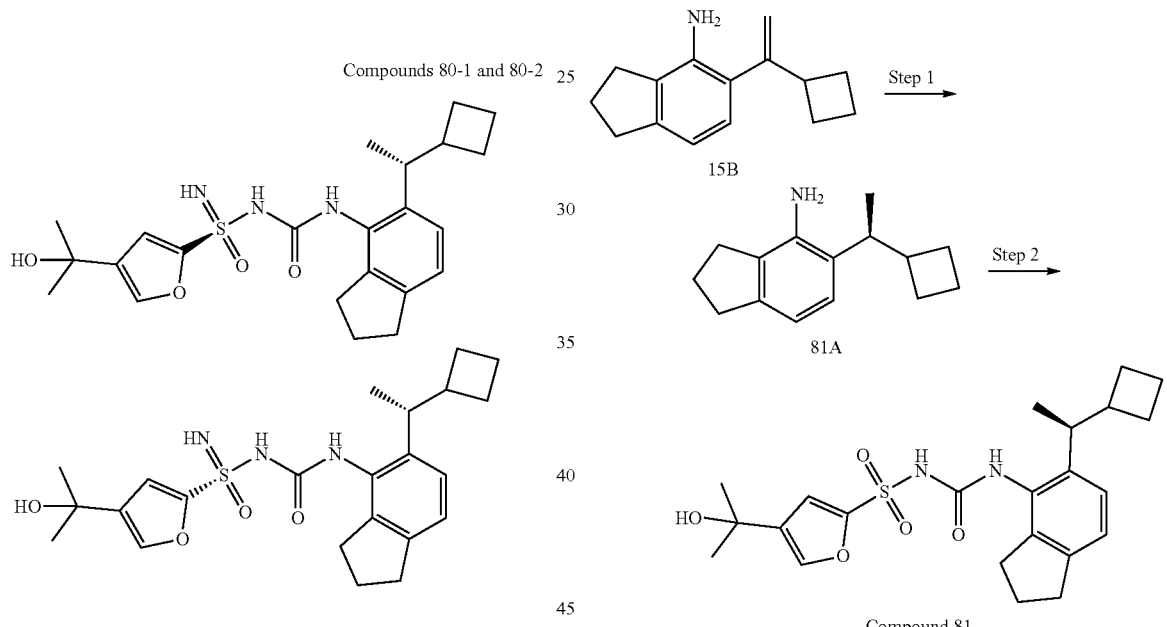

For synthesis of compounds 80-1 and 80-2, reference was made to preparation method of compounds 21-1 and 21-2; compound 80-1 (110 mg, RT=12.702 min, ee %: 99.47%) and compound 80-2 (106 mg, RT=15.822 min, ee %: 99.40%). Chiral HPLC (OZ) mobile phase: methanol; column temperature: 35° C.; column pressure: 80 bar; flow rate: 2 mL/min; detector signal channel: 215 nm@4.8 nm; start wavelength of diode array detector: 200 nm; stop wavelength of diode array detector: 400 nm.

Compound 80-1: $^1$H NMR (400 MHz, DMSO) 8.32 (s, 1H), 7.68 (d, 1H), 7.66 (s, 1H), 6.99 (d, 2H), 6.88 (d, 1H), 5.08 (s, 1H), 2.88 (d, 1H), 2.80 (t, 2H), 2.68 (m, 2H), 2.44-2.35 (m, 1H), 2.12-1.97 (m, 1H), 1.98-1.85 (m, 2H), 1.73-1.61 (m, 3H), 1.57 (t, 1H), 1.46 (s, 1H), 1.37 (s, 6H), 0.94 (d, 3H); LCMS m/z=446.2[M+1].

Compound 80-2: $^1$H NMR (400 MHz, DMSO) 8.34 (s, 1H), 7.68 (d, 1H), 7.66 (s, 1H), 6.99 (d, 2H), 6.88 (d, 1H), 5.09 (s, 1H), 2.90 d, 1H), 2.80 (t, 2H), 2.66 (s, 2H), 2.43 (s, 1H), 2.11-2.00 (m, 1H), 1.98-1.85 (m, 2H), 1.75-1.63 (m, 3H), 1.58 (t, 1H), 1.45 (dd, 1H), 1.38 (s, 6H), 0.95-0.87 (m, 3H); LCMS m/z (ESI)=446.2[M+1].

Step 1

(R)-5-(1-cyclobutylethyl)-2,3-dihydro-1H-inden-4-amine (Compound 81A)

Compound 15B (3.3 g, 15.5 mmol) was added to DCM (20 mL) in an autoclave, and then a catalyst ruthenium [(S)-2,2'-bis(diphenylphosphino)-1,11-binaphthyl]diacetate (521 mg, 0.62 mmol) was added. After the addition was completed and purge with H$_2$ was performed three times, the autoclave was tightly closed and sealed. Purge with hydrogen was performed 3 times, the hydrogen was introduced until the pressure gauge on the autoclave showed 12 atm, and then the reaction system was reacted overnight at room temperature. The reaction system was concentrated, and the residue was mixed with silica gel. Column chromatography (PE/EA=6%) was performed to give compound 81A in the form of a brownish yellow liquid (1.6 g, 99.0% purity, 53% yield).

LCMS m/z (ESI)=216.2[M+1].

Step 2

(S)-N-((5-(1-cyclobutylethyl)-2,3-dihydro-1H-inden-4-yl)carbamoyl)-4-(2-hydroxypropan-2-yl)furan-2-sulfonamide (Compound 81)

Compound 81A (100 mg, 0.47 mmol) was added to THF (10 mL) under nitrogen atmosphere, and then triethylamine (63.6 mg, 0.58 mmol) was added. Triphosgene (69 mg, 0.19 mmol) was added in an ice bath, and the reaction system was warmed to reflux at 70° C., reacted for 1 h, and then filtered to remove the solids. 2e (76 mg, 0.47 mmol) and sodium methoxide (50 mg, 0.94 mmol) were added to the filtrate, and the mixture was reacted at 70° C. for 1 h. After the reaction was completed as detected by TLC, water (50 mL) was added, and ethyl acetate (40 mL) was added for extraction. The organic phase was washed with saturated brine, dried over anhydrous sodium sulfate and concentrated to give the crude product, which was subjected to, preparative chromatography and lyophilized to give 81 in the form of a white solid (74 mg, 97.50% purity, 35.7% yield, ee %: 95.0%, chiral HPLC (OZ); mobile phase: methanol; column temperature: 35° C.; column pressure: 80 bar; flow rate: 2 mL/min; detector signal channel: 215 nm@4.8 nm; start wavelength of diode array detector: 200 nm; stop wavelength of diode array detector: 400 nm; RT=11.801 min).

$^1$H NMR (400 MHz, DMSO) δ=7.87 (s, 1H), 7.67 (d, 1H), 7.02 (s, 1H), 7.01 (s, 1H), 6.91 (d, 1H), 5.05 (s, 1H), 2.80 (t, 3H), 2.59 (dd, 2H), 2.42 (dd, 1H), 2.10-1.98 (m, 1H), 1.96-1.85 (m, 2H), 1.75-1.54 (m, 4H), 1.38 (s, 1H), 1.36 (s, 6H), 0.93 (d, 3H); LCMS m/z (ESI)=447.2[M+1].

Example 82

($R_S$, $S_C$)- and ($S_S$, $S_C$)-N-((5-(1-cyclobutylethyl)-2,3-dihydro-1H-inden-4-yl)carbamoyl)-4-(2-hydroxypropan-2-yl)furan-2-sulfonimidamide (Compound 82)

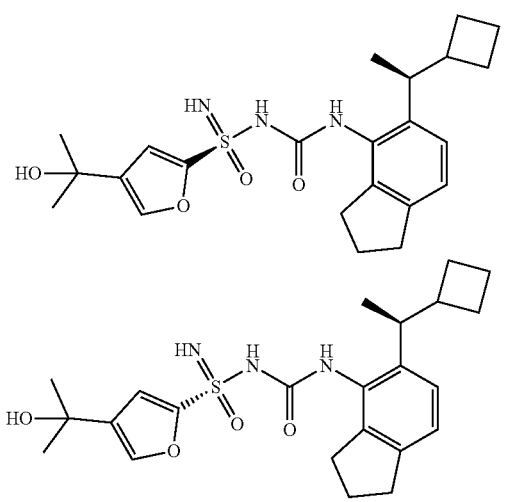

Compounds 82-1 and 82-2

For synthesis of compounds 82-1 and 82-2, reference was made to preparation method of compounds 21-1 and 21-2.

Compound 82-1 (103 mg, RT=12.68 min, ee %: 99.39%) and compound 82-2 (106 mg, RT=16.028 min, ee %: 99.99%). Chiral HPLC (OZ) mobile phase: methanol; column temperature: 35° C.; column pressure: 80 bar; flow rate: 2 mL/min; detector signal channel: 215 nm@4.8 nm; start/stop wavelength of diode array detector: 200-400 nm.

Compound 82-1: $^1$H NMR (400 MHz, DMSO) δ=8.32 (s, 1H), 7.68 (d, 1H), 7.66 (s, 1H), 6.99 (d, 2H), 6.88 (d, 1H), 5.08 (s, 1H), 2.89 (d, 1H), 2.80 (t, 2H), 2.68 (m, 2H), 2.44-2.35 (m, 1H), 2.12-1.97 (m, 1H), 1.98-1.85 (m, 2H), 1.69 (dd, 3H), 1.57 (t, 1H), 1.43 (t, 1H), 1.37 (s, 6H), 0.94 (d, 3H); LCMS m/z (ESI)=446.1[M+1].

Compound 82-2: $^1$H NMR (400 MHz, DMSO) δ=8.34 (s, 1H), 7.68 (d, 1H), 7.66 (s, 1H), 6.99 (d, 2H), 6.88 (d, 1H), 5.09 (s, 1H), 2.92 (d, 1H), 2.80 (t, 2H), 2.66 (s, 2H), 2.44 (d, 1H), 2.11-2.00 (m, 1H), 1.98-1.85 (m, 2H), 1.75-1.63 (m, 3H), 1.62 (s, 1H), 1.51-1.40 (m, 1H), 1.38 (s, 6H), 0.95-0.87 (m, 3H); LCMS m/z (ESI)=446.1[M+1].

Example 83

($R_S$)- and ($S_S$)-N-((5-(cyclobutylmethyl)-2,3-dihydro-1H-inden-4-yl)carbamoyl)-4-(2-hydroxypropan-2-yl)thiophene-2-sulfonimidamide (83A)

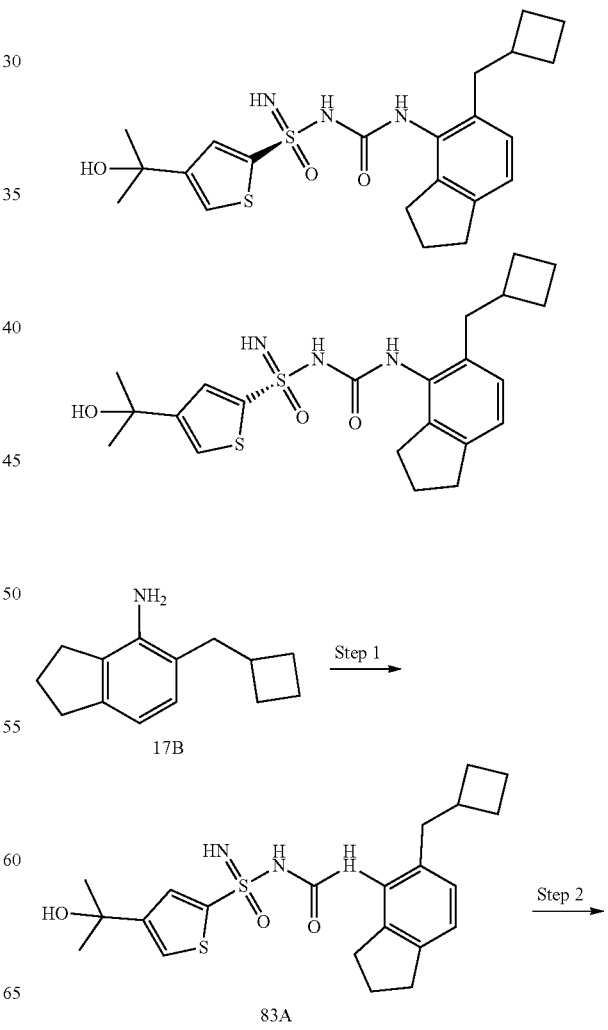

Compounds 83-1 and 83-2

-continued

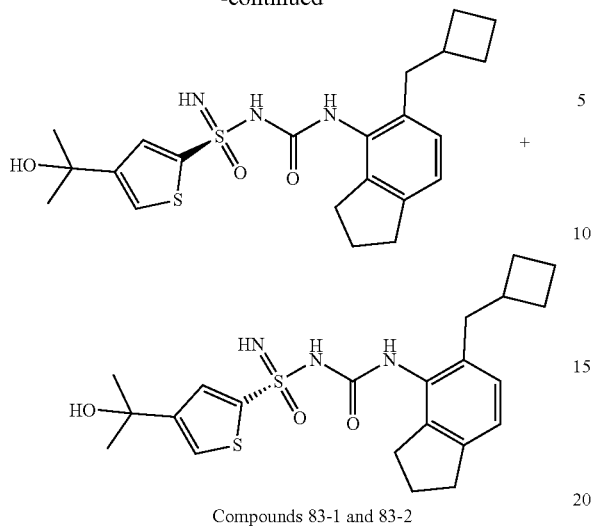

Compounds 83-1 and 83-2

Step 1

N-((5-(cyclobutylmethyl)-2,3-dihydro-1H-inden-4-yl)carbamoyl)-4-(2-hydroxypropan-2-yl)thiophene-2-sulfonimidamide (83A)

17B (400 mg, 1.99 mmol), triethylamine (242 mg, 2.39 mmol) and tetrahydrofuran (20 mL) were added successively into a 100 mL round-bottomed flask under nitrogen atmosphere, and then triphosgene (237 mg, 0.796 mmol) was added in an ice bath. The reaction system was warmed to reflux, reacted for 2 h, and then filtered to remove the solids. Intermediate 4 (665 mg, 1.99 mmol) and NaH (239 mg, 3.98 mmol) were added to the filtrate, and the mixture was reacted at room temperature for 12 h. Tetrabutylammonium fluoride (4 mL, 4.0 mmol, 1 M/THF) was added 12 h later, and the resulting reaction system was reacted overnight at room temperature. After the reaction was completed as detected by TLC, the reaction system was poured into water and extracted with ethyl acetate (100 mL×3). The organic phases were combined, washed once with 1 M diluted HCl, dried over anhydrous sodium sulfate and filtered, and the organic solvent was removed under reduced pressure. The residue was purified by preparative medium pressure liquid chromatography (acetonitrile/water=50%) to give 83A in the form of a transparent solid (352 mg, two-step yield: 41.3%).

Step 2

($R_S$)- and ($S_S$)-N-((5-(cyclobutylmethyl)-2,3-dihydro-1H-inden-4-yl)carbamoyl)-4-(2-hydroxypropan-2-yl)thiophene-2-sulfonimidamide (83A)

83A was resolved by SFC to give compound 83-1 (122 mg, 48.2% yield, RT=7.322 min, ee %: 99.99%) and compound 83-2 (138 mg, 43.2% yield, RT=7.978 min, ee %: 99.99%). Chiral HPLC (OZ) mobile phase: n-hexane/ethanol=90/10; column temperature: 35° C.; column pressure: 80 bar; flow rate: 1 mL/min; detector signal channel: 215 nm@4.8 nm; start/stop wavelength of diode array detector: 200-400 nm.

Compound 83-1: $^1$H NMR (400 MHz, DMSO) δ 8.26 (s, 1H), 7.67 (s, 2H), 7.61 (s, 1H), 7.57 (s, 1H), 6.95 (d, 1H), 6.86 (d, 1H), 5.20 (s, 1H), 2.80 (t, 2H), 2.76-2.63 (m, 2H), 2.59 (d, 2H), 1.97-1.85 (m, 4H), 1.81-1.70 (m, 2H), 1.66-1.56 (m, 2H), 1.41 (d, 6H).

Compound 83-2: $^1$H NMR (400 MHz, DMSO) δ 8.26 (s, 1H), 7.67 (s, 2H), 7.61 (s, 1H), 7.57 (s, 1H), 6.95 (d, 1H), 6.86 (d, 1H), 5.20 (s, 1H), 2.80 (t, 2H), 2.73-2.63 (m, 2H), 2.59 (d, 2H), 2.33 (s, 1H), 1.98-1.82 (m, 4H), 1.81-1.69 (m, 2H), 1.68-1.55 (m, 2H), 1.41 (d, 6H).

Example 84

(R)-N-((5-(1-cyclopropylethyl)-2,3-dihydro-1H-inden-4-yl)carbamoyl)-5-(3-hydroxyoxetan-3-yl)thiophene-2-sulfonamide (Compound 84)

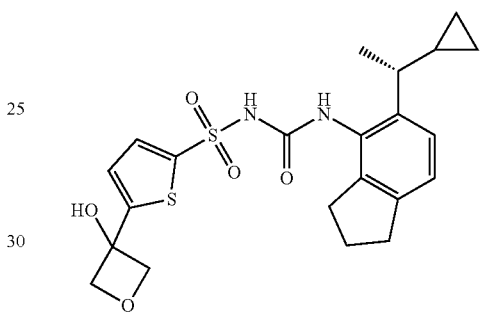

Compound 84

For synthesis of compound 84, reference was made to preparation method of compound 59. Compound 84 (42 mg, 19.0% yield).

$^1$H NMR (400 MHz, DMSO) δ=7.90 (s, 1H), 7.81 (s, 1H), 7.21 (s, 1H), 7.15 (d, 1H), 7.11 (d, 1H), 7.04 (d, 1H), 6.97 (s, 1H), 4.92 (d, 2H), 4.67 (d, 2H), 2.80 (t, 2H), 2.59 (d, 2H), 2.07 (d, 1H), 1.97-1.80 (m, 2H), 1.05 (d, 3H), 0.96-0.82 (m, 1H), 0.47-0.35 (m, 1H), 0.20-0.10 (m, 1H), 0.09-0.00 (m, 1H), 0.00-0.10 (m, 1H). LCMS m/z (ESI)=463.1[M+1].

Example 85

N-((5-(cyclobutylmethyl)-2,3-dihydro-1H-inden-4-yl)carbamoyl)-4-(2-hydroxypropan-2-yl)-5-methylfuran-2-sulfonamide (Compound 85)

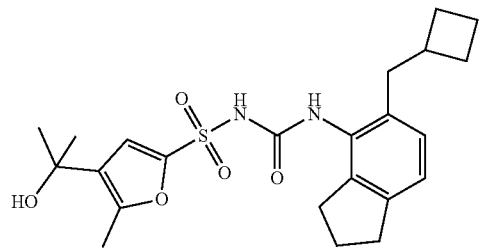

Compound 85

For synthesis of compound 85, reference was made to preparation method of compound 84. Compound 85 (444 mg, RT=14.133 min, 19.3% yield, ee %: 99.40%). Chiral HPLC (OZ) mobile phase: n-hexane/ethanol=90/10; column temperature: 35° C.; column pressure: 80 bar; flow rate: 1 mL/min; detector signal channel: 215 nm@4.8 nm; start/stop wavelength of diode array detector: 200-400 nm.

$^1$H NMR (400 MHz, DMSO) δ=7.84 (s, 1H), 7.56 (s, 1H), 6.99 (d, 1H), 6.94 (s, 1H), 6.90 (d, 1H), 5.00 (s, 1H), 2.81 (t, 2H), 2.73 (t, 1H), 2.81 (m, 4H), 2.40 (s, 3H), 2.00-1.84 (m, 4H), 1.76 (dd, 2H), 1.61 (dd, 2H), 1.37 (s, 6H); LCMS m/z=447.2[M+1].

Example 86

N-((5-(dicyclopropylmethyl)-2,3-dihydro-1H-inden-4-yl)carbamoyl)-4-(2-hydroxypropan-2-yl)furan-2-sulfonamide (Compound 86)

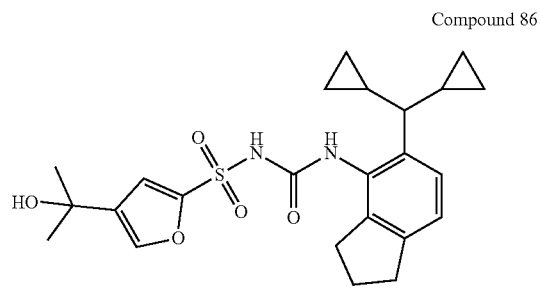 [SMILES: CC(C)(O)c1coc(S(=O)(=O)NC(=O)Nc2c(C(C3CC3)C3CC3)ccc3c2CCC3)c1]

Compound 86

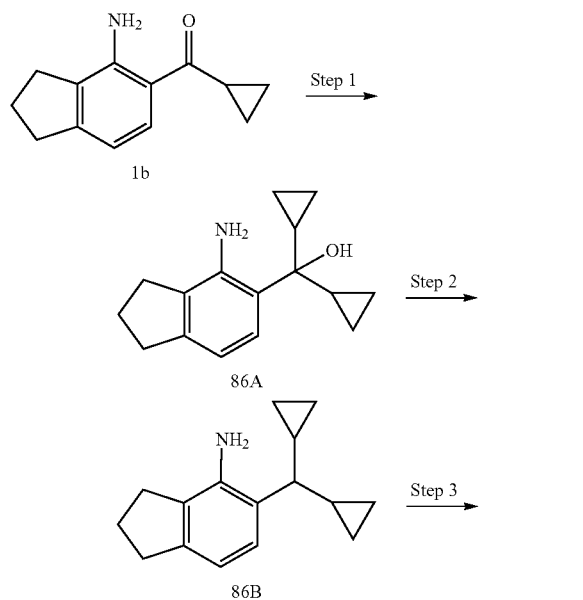

Step 1

(4-amino-2,3-dihydro-1H-inden-5-yl)dicyclopropylmethanol (86A)

Compound 1b (5.0 g, 24.84 mmol) was added into a 250 mL three-necked flask under nitrogen atmosphere, and then dry tetrahydrofuran (25 mL) was added under nitrogen atmosphere. The reaction system was stirred until it was clarified, and then cooled to 0° C. in an ice salt bath. A solution of cyclopropylmagnesium bromide in tetrahydrofuran (75 mL, 1 M, 75 mmol) was added dropwise slowly, and after the dropwise addition was completed, the reaction system was warmed to room temperature and stirred for 1 h. After the reaction was completed, saturated aqueous ammonium chloride solution (100 mL) was added to quench the reaction, and ethyl acetate (80 mL×3) was added for extraction. The ethyl acetate layers were combined, dried over anhydrous sodium sulfate and filtered, and the organic solvent was removed under reduced pressure. The residue was purified by column chromatography (petroleum ether: ethyl acetate=20:1) to give compound 86A in the form of a white cream (4.5 g, 74.4% yield).

LC-MS m/z (ESI)=226.3[M−17].

Step 2

5-(dicyclopropylmethyl)-2,3-dihydro-1H-inden-4-amine (86B)

Compound 86A (2.0 g, 8.2 mmol) was dissolved in DCM (30 mL) in a 100 mL three-necked flask under nitrogen atmosphere, and the solution was cooled to 0° C. in an ice salt bath. Trifluoroacetic acid (9.4 g, 82.2 mmol) was added slowly, and the temperature was maintained and the reaction system was reacted for 30 min. Triethylsilane (4.8 g, 41.1 mmol) was added, and the resulting reaction system was reacted at room temperature for 4 h. After the reaction was completed, water was added to quench the reaction, and DCM (30 mL×3) was added for extraction. The organic phase was dried over anhydrous sodium sulfate and filtered, and the organic solvent was removed under reduced pressure. The residue was purified by column chromatography (petroleum ether:ethyl acetate=30:1) to give compound 86B in the form of an off-white solid (320 mg, 17.3%).

LC-MS m/z (ESI)=228.1[M+1].

Step 3

N-((5-(dicyclopropylmethyl)-2,3-dihydro-1H-inden-4-yl)carbamoyl)-4-(2-hydroxypropan-2-yl)furan-2-sulfonamide (Compound 86)

For synthesis of compound 86, reference was made to preparation method of compound 85. Compound 86 (42 mg, 19.0%).

$^1$H NMR (400 MHz, DMSO) δ=7.70-7.56 (m, 1H), 7.51 (s, 1H), 7.11 (d, 2H), 6.98 (dd, 1H), 6.79 (s, 1H), 4.99 (s, 1H), 2.81 (t, 2H), 2.62 (s, 2H), 1.99-1.83 (m, 2H), 1.72 (s, 1H), 1.36 (s, 6H), 1.07-0.92 (m, 2H), 0.49-0.36 (m, 2H), 0.23-0.08 (m, 4H), 0.01 (s, 2H); LCMS m/z (ESI)=459.2 [M+1].

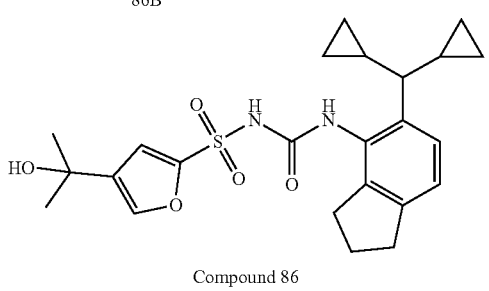

Compound 86

Example 87

(R)-N-((5-(1-cyclopropylethyl)-2,3-dihydro-1H-inden-4-yl)carbamoyl)-2-(2-hydroxypropan-2-yl)thiazole-5-sulfonamide (Compound 87)

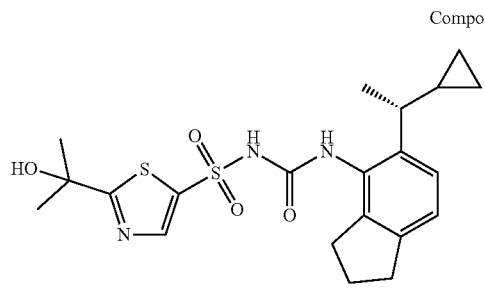

Compound 87

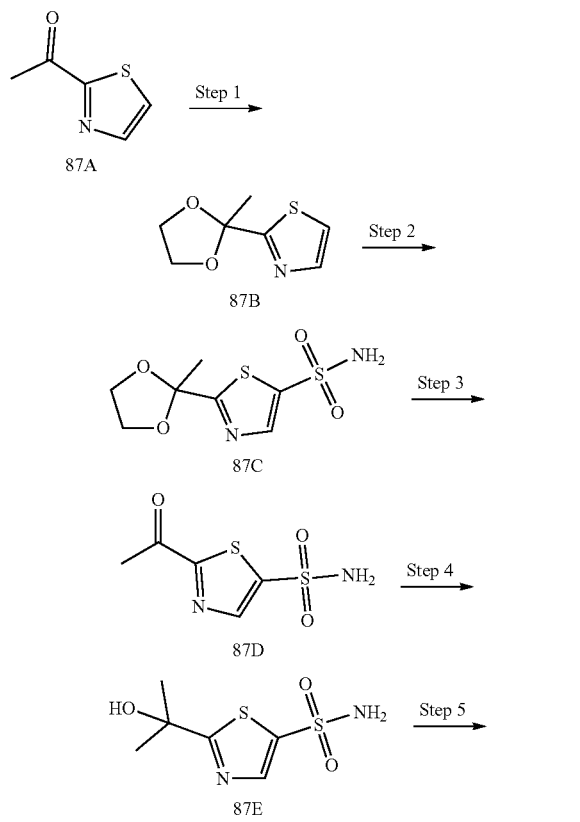

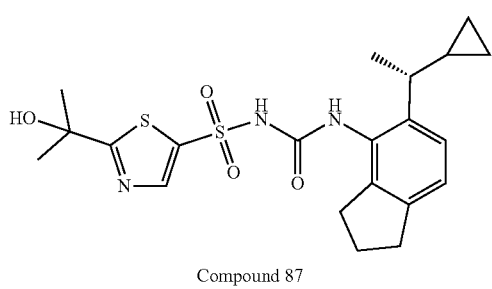

Compound 87

Step 1

2-(2-methyl-1,3-dioxolan-2-yl)thiazole (87B)

Compound 87A (50.0 g, 393.7 mmol) was dissolved in toluene (600 mL) in a 1 L three-necked flask under nitrogen atmosphere, and p-toluenesulfonic acid monohydrate (7.48 g, 39.3 mmol) and ethylene glycol (50 mL) were added at room temperature. The reaction system was warmed to reflux, and reacted for 16 h. After the reaction was completed, the reaction system was cooled to room temperature, washed with water (200 mL), and extracted with ethyl acetate (100 mL×3). The organic phases were combined, dried over anhydrous sodium sulfate and filtered, and the organic solvent was removed under reduced pressure to give compound 87B in the form of a pale yellow liquid (62 g, 92%).

$^1$H NMR (400 MHz, CD$_3$CN) δ=7.78 (d, 1H), 7.47 (d, 1H), 4.09-4.05 (m, 2H), 4.01-3.97 (m, 2H), 1.76 (s, 3H); LC-MS m/z (ESI)=172.0[M+1].

Step 2

2-(2-methyl-1,3-dioxolan-2-yl)thiazole-5-sulfonamide (87C)

Compound 87B (10.0 g, 58.48 mmol) was dissolved in tetrahydrofuran (100 mL) in a 1 L three-necked flask under nitrogen atmosphere, and the solution was cooled to −70° C. in a dry ice-ethanol bath. n-butyllithium (2.5 M in THF, 26 mL, 64.33 mmol) was added dropwise slowly. The reaction system was reacted at −70° C. for 30 min. Triethylene diamine-bis(sulfur dioxide) (14.1 g, 58.48 mmol) was then added, and the reaction system was slowly warmed to room temperature and reacted for 1 h after the addition was completed. The reaction system was then cooled to 0° C., and NCS (23.4 g, 175.4 mmol) was added slowly. The reaction system was reacted at room temperature for 4 h and then cooled to −10° C. or lower, and ammonia gas was introduced slowly and continuously for 1 h. After the reaction was completed, the reaction system was warmed to room temperature, washed with water (100 mL) and extracted with DCM (100 mL×3). The organic phases were combined, dried over anhydrous sodium sulfate and filtered, and the organic solvent was removed under reduced pressure. The crude product was purified by column chromatography (petroleum ether:ethyl acetate=4:1) to give compound 87C in the form of a yellow solid powder (6.0 g, 41%).

$^1$H NMR (400 MHz, DMSO-d6) δ=8.14 (s, 1H), 7.94 (s, 2H), 4.10-4.07 (m, 2H), 3.99-3.96 (m, 2H), 1.72 (s, 3H); LC-MS m/z (ESI)=251.0[M+1].

Step 3

2-acetylthiazole-5-sulfonamide (87D)

Compound 7c (6 g, 24.00 mmol) was dissolved in tetrahydrofuran (50 mL) in a 250 mL three-necked flask under nitrogen atmosphere, concentrated hydrochloric acid (2 mL) was added with stirring, and the reaction system was warmed to reflux, and reacted for 4 h in an oil bath. After the reaction was completed, the reaction system was cooled to room temperature. Aqueous sodium bicarbonate solution (60 mL) was added slowly to quench the reaction, and ethyl acetate (50 mL×3) was added for extraction. The organic phases were combined, dried over anhydrous sodium sulfate and filtered, and the organic solvent was removed under reduced pressure to give compound 87D in the form of a pale yellow solid powder (4.4 g, 90% yield).

¹H NMR (400 MHz, DMSO-d6) δ=8.41 (s, 1H), 8.17 (s, 2H), 2.65 (s, 3H); LC-MS m/z (ESI)=207.0[M+1].

Step 4

2-(2-hydroxypropan-2-yl)thiazole-5-sulfonamide (87E)

Compound 87D (4.4 g, 21.35 mmol) was dissolved in tetrahydrofuran (50 mL) in a 100 mL three-necked flask under nitrogen atmosphere, and the solution was cooled to −15° C. in an ice salt bath. Methylmagnesium bromide (21 mL, 3 M, 64.08 mmol) was added dropwise slowly. After the dropwise addition was completed, the reaction system was warmed to room temperature and reacted overnight. After the reaction was completed, saturated aqueous ammonium chloride solution (50 mL) was added to quench the reaction, and ethyl acetate (40 mL×3) was added for extraction. The organic phases were combined, dried over anhydrous sodium sulfate and filtered, and the organic solvent was removed under reduced pressure. The crude product was purified by column chromatography (petroleum ether:ethyl acetate=1:2) to give 87E in the form of a white solid powder (4 g, 85% yield).

¹H NMR (400 MHz, DMSO-d6) δ=8.00 (s, 1H), 7.83 (s, 2H), 6.30 (s, 1H), 1.50 (s, 6H); LC-MS m/z (ESI)=223.0 [M+1].

Step 5

(R)-N-((5-(1-cyclopropylethyl)-2,3-dihydro-1H-inden-4-yl)carbamoyl)-2-(2-hydroxypropan-2-yl)thiazole-5-sulfonamide (Compound 87)

Intermediate 8 (90 mg, 0.447 mmol), triethylamine (63 mg, 0.627 mmol) and tetrahydrofuran (10 mL) were added successively into a 100 mL round-bottomed flask under nitrogen atmosphere, and then triphosgene (44 mg, 0.149 mmol) was added in an ice bath. The reaction system was warmed to reflux, reacted for 2 h, and then filtered to remove the solids. Compound 87E (90 mg, 0.405 mmol) and sodium methoxide (43.78 mg, 0.81 mmol) were added to the filtrate, and the mixture was reacted at room temperature for 12 h. After the reaction was completed as detected by TLC, water (10 mL) was added to quench the reaction, and DCM (30 mL×3) was added for extraction. The organic phase was dried over anhydrous sodium sulfate and filtered, and the organic solvent was removed. The crude product was purified by preparative medium pressure liquid chromatography to give compound 87 in the form of a white solid powder (90 mg, 50% yield, ee %: 99.99%, chiral HPLC (OX-3); mobile phase: methanol; column temperature: 35° C.; column pressure: 80 bar; flow rate: 2 mL/min; detector signal channel: 215 nm@4.8 nm; start wavelength of diode array detector: 200 nm; stop wavelength of diode array detector: 400 nm; RT=29.459 min).

¹H NMR (400 MHz, DMSO-d6) δ=7.74 (s, 1H), 7.11 (br, 2H), 7.07 (d, 1H), 6.97 (d, 1H), 5.97 (s, 1H), 2.80 (t, 2H), 2.64 (t, 2H), 2.29-2.25 (m, 1H), 1.89 (m, 2H), 1.47 (s, 6H), 1.07 (d, 3H), 0.93-0.88 (m, 1H), 0.43-0.38 (m, 1H), 0.19-0.13 (m, 1H), 0.06-0.00 (m, 2H); LCMS m/z=450.0[M+1].

Example 88

(S)-N-((5-(1-cyclopropylethyl)-2,3-dihydro-1H-inden-4-yl)carbamoyl)-2-(2-hydroxypropan-2-yl)thiazole-5-sulfonamide (Compound 88)

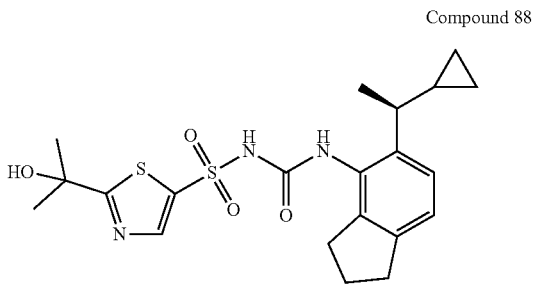 [SMILES: C[C@H](c1ccc2c(c1NC(=O)NS(=O)(=O)c1cnc(C(C)(C)O)s1)CCC2)C1CC1]

Compound 88

For synthesis of compound 88, reference was made to preparation method of compound 87. Compound 88 was in the form of a white solid powder (100 mg, 55% yield, RT=31.834 min, ee %: 96.42%). Chiral HPLC (OX-3) mobile phase: methanol; column temperature: 35° C.; column pressure: 80 bar; flow rate: 2 mL/min; detector signal channel: 215 nm@4.8 nm; start/stop wavelength of diode array detector: 200-400 nm.

¹H NMR (400 MHz, DMSO-d6) δ=7.76 (s, 1H), 7.11 (br, 2H), 7.07 (d, 1H), 6.97 (d, 1H), 5.99 (s, 1H), 2.80 (t, 2H), 2.64 (t, 2H), 2.29-2.23 (m, 1H), 1.96-1.90 (m, 2H), 1.47 (s, 6H), 1.07 (d, 3H), 0.93-0.88 (m, 1H), 0.43-0.38 (m, 1H), 0.19-0.13 (m, 1H), 0.06-0.00 (m, 2H); LCMS m/z=450.0 [M+1].

Example 89

N-((2-(1-cyclopropylvinyl)-4-fluoro-6-(2-methoxypyridin-4-yl)phenyl)carbamoyl)-4-(2-hydroxypropan-2-yl)furan-2-sulfonamide (Compound 89)

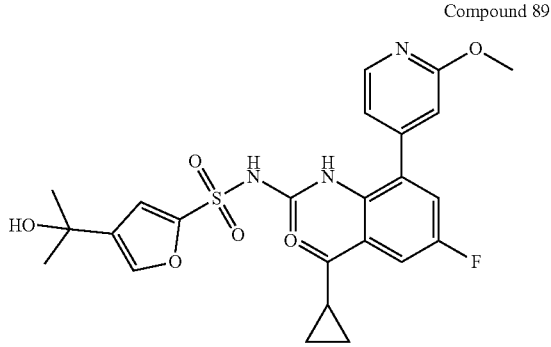

Compound 89

223

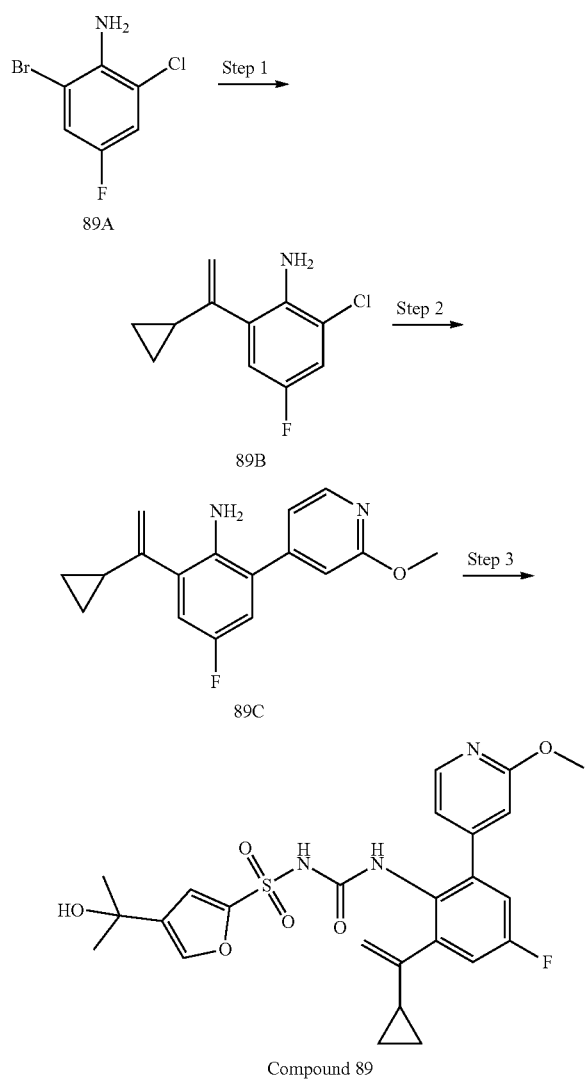

89A

89B

89C

Compound 89

Step 1

2-chloro-6-(1-cyclopropylvinyl)-4-fluoroaniline (89B)

89A (8.66 g, 38.56 mmol), 2-(1-cyclopropylvinyl)-4,4,5,5-tetramethyl-1,3,2-dioxaborolane (9.73 g, 50.13 mmol), potassium phosphate (10.61 g, 77.12 mmol), bis(triphenylphosphine)palladium(II) chloride (4.23 g, 5.784 mmol) and 1,4-dioxane/water (120/40 mL) were added successively into a 250 mL three-necked flask under nitrogen atmosphere, and then the reaction system was warmed to 100° C. and reacted for 6 h. Water was added to quench the reaction, and EA (100 mL×3) was added for extraction. The organic phase was dried over anhydrous sodium sulfate and filtered, and the organic solvent was removed under reduced pressure. The crude product was purified by column chromatography to give 89B in the form of a pale yellow oil (5.4 g, 66%).

LCMS m/z (ESI)=212.0[M+1].

224

Step 2

2-(1-cyclopropylvinyl)-4-fluoro-6-(2-methoxypyridin-4-yl)aniline (89C)

89B (500 mg, 2.37 mmol), (2-methoxypyridin-4-yl)boronic acid (544 mg, 3.55 mmol), potassium phosphate (1.51 g, 7.10 mmol), bis(triphenylphosphine)palladium(II) chloride (260 mg, 0.355 mmol) and DMF (15 mL) were added successively into a 250 mL three-necked flask under nitrogen atmosphere, and then the reaction system was warmed to 110° C. and reacted for 6 h. Water was added to quench the reaction, and EA (100 mL×3) was added for extraction. The organic phase was dried over anhydrous sodium sulfate and filtered, and the organic solvent was removed under reduced pressure. The crude product was purified by column chromatography to give 89C in the form of a pale yellow oil (180 mg, 12%).

LCMS m/z=285.1[M+1].

Step 3

N-((2-(1-cyclopropylvinyl)-4-fluoro-6-(2-methoxypyridin-4-yl)phenyl)carbamoyl)-4-(2-hydroxypropan-2-yl)furan-2-sulfonamide (Compound 89)

89C (180 mg, 0.633 mmol), triethylamine (77 mg, 0.76 mmol) and tetrahydrofuran (10 mL) were added successively into a 100 mL round-bottomed flask under nitrogen atmosphere, and then triphosgene (75 mg, 0.253 mmol) was added in an ice bath. The reaction system was warmed to reflux, reacted for 2 h, and then filtered to remove the solids. Compound 2e (130 mg, 0.633 mmol) and sodium methoxide (69 mg, 1.27 mmol) were added to the filtrate, and the mixture was reacted at room temperature for 12 h. After the reaction was completed as detected by TLC, water (10 mL) was added to quench the reaction, and DCM (30 mL×3) was added for extraction. The organic phase was dried over anhydrous sodium sulfate and filtered, and the organic solvent was removed. The crude product was purified by preparative medium pressure liquid chromatography to give compound 89 in the form of a white solid powder (92 mg, 27.6%).

$^1$H NMR (400 MHz, DMSO) δ=11.27 (s, 1H), 8.12 (d, 1H), 8.03 (s, 1H), 7.79 (d, 1H), 7.45 (dd, 1H), 7.20 (d, 1H), 7.06 (dd, 1H), 6.82 (dd, 1H), 6.75 (s, 1H), 6.40-6.31 (m, 1H), 5.95 (dd, 1H), 5.76 (s, 1H), 3.88 (s, 3H), 1.54 (tt, 1H), 1.37 (d, 6H), 0.88-0.77 (m, 2H), 0.59-0.48 (m, 2H); LCMS m/z (ESI)=516.2[M+1].

Example 90

(R)-N-((5-(1-cyclopropylethyl)-6-methyl-2,3-dihydro-1H-inden-4-yl)carbamoyl)-4-(2-hydroxypropan-2-yl)furan-2-sulfonamide (Compound 90)

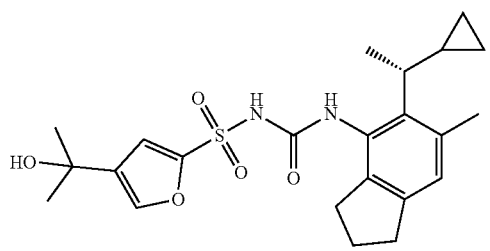

Compound 90

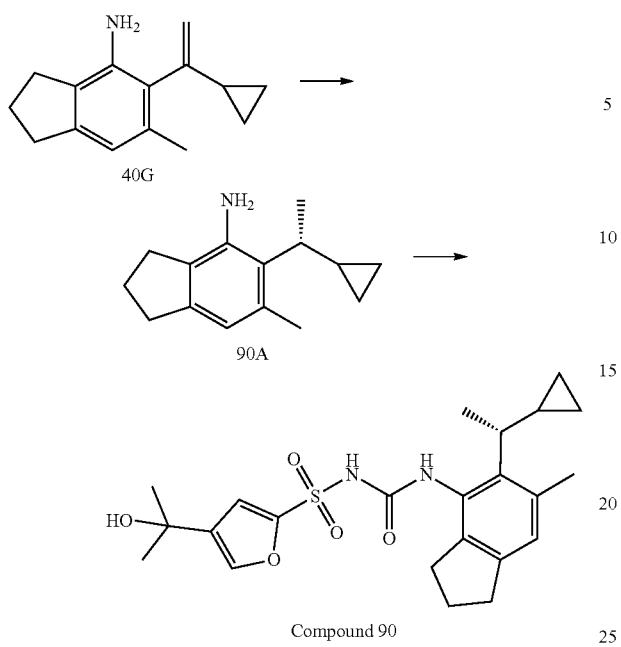

For synthesis of compound 90, reference was made to preparation method of compound 81; compound 90 was in the form of an off-white solid (8.3 mg, 12.3% yield).

¹H NMR (400 MHz, DMSO-d6) δ=7.80 (s, 1H), 7.55 (s, 1H), 7.14 (d, 1H), 7.07 (d, 1H) 4.99 (d, 1H), 2.82 (t, 2H), 2.59 (t, 2H), 2.40 (s, 3H), 2.18-2.13 (m, 1H), 1.96-1.90 (m, 2H), 1.37 (s, 6H), 1.11 (d, 3H), 0.96-0.90 (m, 1H), 0.50-0.41 (m, 1H), 0.23-0.18 (m, 1H), 0.10-0.06 (m, 1H), 0.06-0.01 (m, 1H); LCMS m/z=447.2 [M+1].

Example 91

(S)-N-((5-(1-cyclopropylethyl)-6-methyl-2,3-di-hydro-1H-inden-4-yl)carbamoyl)-4-(2-hydroxypro-pan-2-yl)furan-2-sulfonamide (Compound 91)

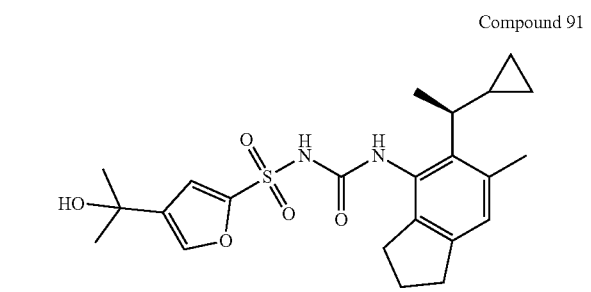 [SMILES: Cc1cc2c(c(NC(=O)NS(=O)(=O)c3cc(C(C)(C)O)co3)c1[C@@H](C)C1CC1)CCC2]

Compound 91

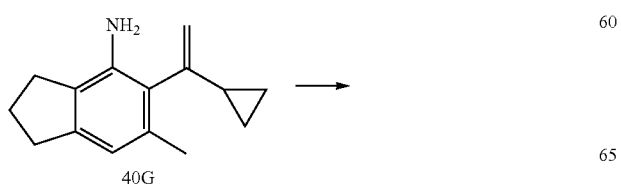

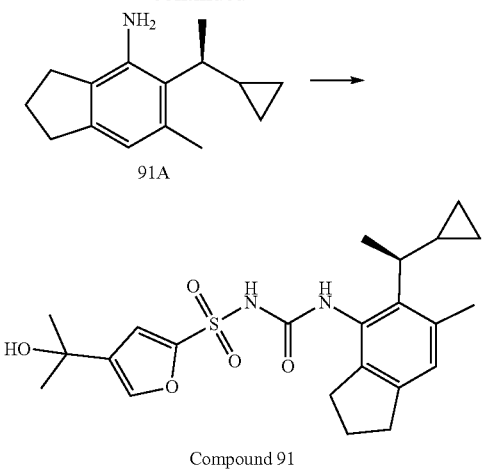

For synthesis of compound 91, reference was made to preparation method of compound 81; compound 91 was in the form of an off-white solid (11.7 mg, 12.7% yield).

¹H NMR (400 MHz, DMSO-d6) δ=7.84 (s, 1H), 7.56 (s, 1H), 7.15 (d, 1H), 7.08 (d, 1H) 5.00 (d, 1H), 2.82 (t, 2H), 2.59 (t, 2H), 2.40 (s, 3H), 2.18-2.13 (m, 1H), 1.96-1.90 (m, 2H), 1.37 (s, 6H), 1.11 (d, 3H), 0.96-0.90 (m, 1H), 0.50-0.41 (m, 1H), 0.23-0.18 (m, 1H), 0.10-0.06 (m, 1H), 0.06-0.01 (m, 1H); LCMS m/z=447.2 [M+1].

Reference Example 1

$R_S$- and $S_S$-N-((2,6-diisopropylphenyl)carbamoyl)-4-methylbenzenesulfonimidamide (Compounds 92-1 and 92-2)

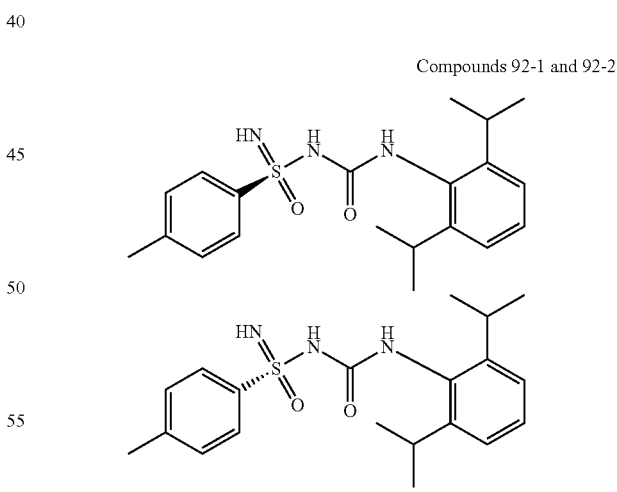

Compounds 92-1 and 92-2

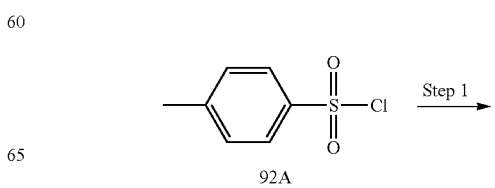

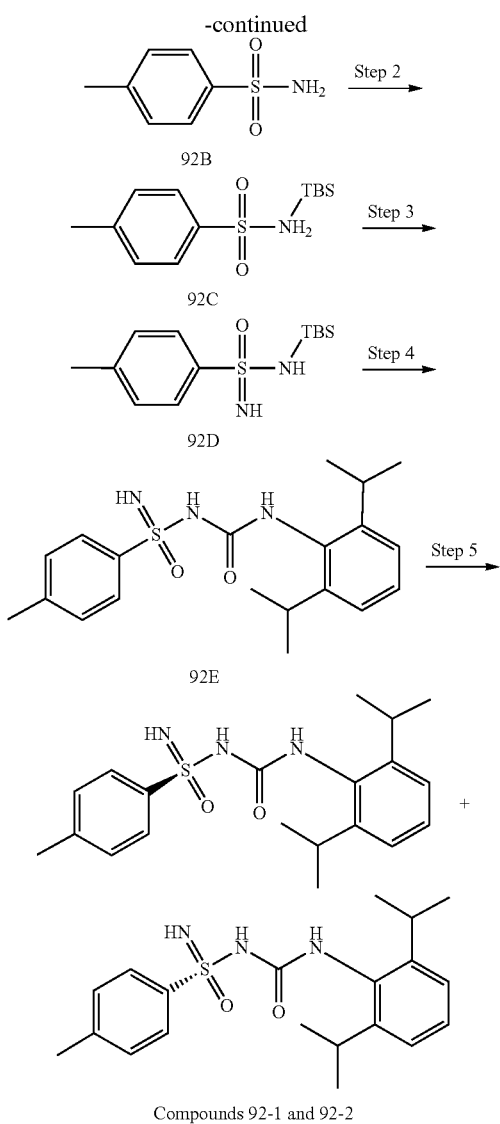

Compounds 92-1 and 92-2

Step 1

4-methylbenzenesulfonamide (92B)

Compound 92A (10.0 g, 52.4 mmol) and acetone (100 mL) were added successively into a 250 mL round-bottomed flask under nitrogen atmosphere, and saturated aqueous ammonium bicarbonate (16.6 g, 209.8 mmol) solution was added dropwise slowly at room temperature. The reaction system was reacted at room temperature for 3 h. After the reaction was completed as detected by TLC, the reaction system was concentrated to remove part of the acetone, and then extracted with ethyl acetate (100 mL×3). The organic phases were combined, dried over anhydrous sodium sulfate and filtered, and the organic solvent was removed under reduced pressure to give crude product 92B in the form of a white solid (12.2 g, purity: 70%, 95.1% yield).

$^1$H NMR (400 MHz, DMSO-d6) δ=7.70 (d, 2H), 7.37 (d, 2H), 7.27 (s, 2H), 2.37 (s, 3H); LCMS m/z (ESI)=172.2[M+1].

Step 2

N-(tert-butyldimethylsilyl)-4-methylbenzenesulfonamide (92C)

Compound 92B (12.2 g, 71.2 mmol) and dry tetrahydrofuran (200 mL) were added successively into a 500 mL round-bottomed flask under nitrogen atmosphere, and sodium hydride (3.93 g, 163.9 mmol) was added slowly in an ice bath. The reaction system was stirred for 0.5 h, and then a solution of tert-butyldimethylchlorosilane (16.1 g, 106.9 mmol) in dry tetrahydrofuran (40 mL) was added dropwise slowly in an ice bath. The reaction system was stirred for 10 min, warmed to room temperature and reacted for 2 h. After the reaction was completed as detected by LC-MS, ice water (200 mL) was added to quench the reaction, and the reaction system was concentrated to remove part of the tetrahydrofuran, and then extracted with ethyl acetate (100 mL×3). The organic phases were combined, dried over anhydrous sodium sulfate and filtered, and the organic solvent was removed under reduced pressure to give 92C in the form of a white solid (15.0 g, 73.7% yield).

$^1$H NMR (400 MHz, DMSO-d6) δ=7.68 (d, 2H), 7.58 (s, 1H), 7.36 (d, 2H), 2.37 (s, 3H), 0.85 (s, 9H), 0.08 (s, 6H); LCMS m/z (ESI)=286.4[M+1].

Step 3

N-(tert-butyldimethylsilyl)-4-methylbenzenesulfonimidamide (92D)

Triphenylphosphine (15.1 g, 57.8 mmol), hexachloroethane (16.1 g, 68.3 mmol) and trichloromethane (300 mL) were added successively into a 500 mL round-bottomed flask under nitrogen atmosphere, and the reaction system was warmed to reflux, and reacted at 85° C. for 1.0 h and then cooled to room temperature. N,N-diisopropylethylamine (10.8 g, 84.0 mmol) was added dropwise slowly in an ice bath. The reaction system was stirred for 10 min, and a solution of compound 92C (15 g, 52.5 mmol) in trichloromethane (50 mL) was added dropwise slowly in an ice bath. The reaction system was stirred for 0.5 h, and ammonia gas was introduced in an ice bath for 1 h. The reaction system was then reacted overnight at room temperature. After the reaction was completed as detected by TLC, the reaction system was poured into water, and the organic phase was extracted out, and then extraction was performed with ethyl acetate (100 mL×3). The organic phases were combined, dried over anhydrous sodium sulfate and filtered, and the organic solvent was removed under reduced pressure. The crude product was purified by column chromatography (petroleum ether:ethyl acetate=3:1) to give 92D in the form of a white solid (13.0 g, 86.9% yield).

LCMS m/z (ESI)=285.5[M+1].

Step 4

N-((2,6-diisopropylphenyl)carbamoyl)-4-methylbenzenesulfonimidamide (92E)

Compound 92D (7 g, 24.6 mmol) and dry tetrahydrofuran 300 mL were added successively into a 1000 mL round-bottomed flask under nitrogen atmosphere, and sodium hydride (1.4 g, 56.5 mmol) was added in an ice bath. The reaction system was reacted for 1 h, and a solution of 2-isocyanato-1,3-diisopropylbenzene (5.0 g, 24.6 mmol) in tetrahydrofuran (50 mL) was added dropwise slowly in an ice bath. The reaction system was reacted at room temperature for 1 h. After the reaction was completed as detected by LC-MS, tetrabutylammonium fluoride (49 mL, 49.2 mmol, 1 M/THF) was added dropwise slowly. The reaction system was reacted overnight at room temperature. After the reaction was completed as detected by TLC, the reaction system was poured into water, and ethyl acetate (200 mL) was added. The organic phase was filtered, the filtrate was slurried once (petroleum ether/ethyl acetate=10/1) and then filtered, and the filter cake was washed once with methanol to give 92E in the form of a white solid (5.0 g, 54.4% yield).

Step 5

$R_S$- and $S_S$-N-((2,6-diisopropylphenyl)carbamoyl)-4-methylbenzenesulfonimidamide (Compounds 92-1 and 92-2)

92E was resolved by SFC to give compound 92-1 (190 mg, 47.5% yield, RT=8.037 min, ee %: 100.00%) and compound 92-2 (182 mg, 45.5% yield, RT=11.043 min, ee %: 99.53%). Chiral HPLC (OZ) mobile phase: n-hexane/ethanol=90/10; column temperature: 35° C.; column pressure: 80 bar; flow rate: 1 mL/min; detector signal channel: 215 nm@4.8 nm; start/stop wavelength of diode array detector: 200-400 nm.

Compound 92-1: $^1$H NMR (400 MHz, DMSO) δ 8.13-8.08 (m, 1H), 7.76 (d, 2H), 7.36 (s, 1H), 7.34 (s, 3H), 7.15 (t, 1H), 7.03 (d, 2H), 3.06 (s, 2H), 2.36 (s, 3H), 1.07 (d, 12H); LCMS m/z (ESI)=374.5[M+1].

Compound 92-2: $^1$H NMR (400 MHz, DMSO) δ 8.09 (s, 1H), 7.76 (d, 2H), 7.36 (s, 1H), 7.34 (s, 3H), 7.14 (t, 1H), 7.04 (s, 1H), 7.02 (s, 1H), 3.12-2.98 (m, 2H), 2.36 (s, 3H), 1.09 (t, 12H); LCMS m/z (ESI)=374.5[M+1].

Biological Test Examples

1. Culturing of THP-1 Cells

Human monocyte cell line THP-1 (ATCC® TB-202TM) was cultured in RPMI-1640 culture medium containing 1000 FBS, 1 mM pyruvic acid, 0.05 mM β-mercaptoethanol and 10% double antibody under the culture conditions of 37° C. and 500 $CO_2$.

2. Detection of THP-1 Cell Pyroptosis

Cell counting was performed, THP-1 cells were seeded into a 96-well plate at 50000 per well, and 20 nM PMA was added for inducing at 37° C./5% $CO_2$ for 48 h. The culture medium was then discarded, and 100 μL of serum-free RPMI-1640 medium containing 1 μg/mL LPS was added. 5 μL of compound or solvent control was added and 3-fold diluted in gradient from a maximum concentration of 10 μM, and 10 gradient concentrations were set. The mixtures were incubated at 37° C./5% $CO_2$ for 3 h. After the incubation, the mixtures were centrifuged at 300 g for 5 min, and the culture medium was discarded. Pyroptosis assay was performed according to specific steps described in instructions of Caspase-Glo® 1 Inflammasome Assay kit. $IC_{50}$ was calculated using GraphPad Prism7.0 software. The results are shown in Table 1.

TABLE 1

| Compound | $IC_{50}$ | Compound | $IC_{50}$ |
|---|---|---|---|
| 1 | B | 2 | A |
| 3 | B | 4 | B |
| 5 | A | 6-1 | A |

TABLE 1-continued

| Compound | $IC_{50}$ | Compound | $IC_{50}$ |
|---|---|---|---|
| 6-2 | B | 7 | A |
| 8-1 | A | 8-2 | C |
| 15 | B | 16 | A |
| 17 | B | 18-1 | C |
| 18-2 | A | 19-1 | D |
| 19-2 | B | 20-2 | B |
| 21-1 | A | 22 | A |
| 23 | B | 24-1 | B |
| 24-2 | A | 25-1 | A |
| 25-2 | B | 26 | D |
| 28 | C | 29 | B |
| 30 | D | 31-1 | B |
| 31-2 | A | 32-1 | D |
| 32-2 | A | 33 | B |
| 34-1 | E | 34-2 | A |
| 35 | D | 36-1 | A |
| 36-2 | D | 37 | B |
| 38-1 | A | 38-2 | D |
| 39-1 | A | 39-2 | D |
| 40 | D | 41 | A |
| 42-1 | B | 42-2 | A |
| 43 | C | 44-2 | A |
| 45 | B | 46-1 | B |
| 46-2 | B | 47 | C |
| 48-1 | B | 48-2 | D |
| 49-1 | B | 50-1 | C |
| 51-2 | E | 52-1 | D |
| 53-2 | B | 54-1 | D |
| 54-2 | B | 55-1 | B |
| 57 | D | 58 | D |
| 59 | C | 60 | B |
| 61 | D | 62 | A |
| 63 | B | 64 | B |
| 65C | B | 68 | B |
| 70-1 | A | 70-2 | D |
| 71 | B | 72 | B |
| 73-1 | A | 73-2 | D |
| 74-1 | A | 74-2 | D |
| 79 | B | 80-1 | B |
| 80-2 | A | 81 | D |
| 82-1 | B | 82-2 | D |
| 83A | A | 86 | C |
| 87 | A | 88 | B |
| 90 | B | 92-1 (control 1) | F |
| 92-2 (control 2) | F | | |

Note:
A ≤ 0.1 μM; 0.1 μM < B ≤ 0.5 μM; 0.5 μM < C ≤ 1 μM; 1 μM < D ≤ 5 μM; 5 μM < E ≤ 10 μM; F > 10 μM The results show that the compounds disclosed herein can effectively inhibit the pyroptosis of human monocyte cell line THP-1.

3. Assay of IL-1β Release in Human PBMCs 5 mL of human venous whole blood from a healthy donor was placed in a Li-heparin tube. PBMCs were isolated and incubated in a culture medium containing 10 ng/mL LPS at 37° C./5% $CO_2$ for 3 h. Cells were plated in a 96-well plate at 50 μL per well. 25 μL of compound or solvent control was added to each well and 3-fold diluted in gradient from a maximum concentration of 10 μM, and 8 gradient concentrations were set. The mixtures were incubated for 0.5 h. 25 μL of ATP at a final concentration of 5 mM was added to each well, and the resulting mixtures were incubated for 1 h. After the incubation, the mixtures were centrifuged at 1500 rpm for 20 min, and the supernatant was collected to detect the expression level of IL-103 by ELISA (BD, Human IL-1β ELISA Set II, Cat #557953). $IC_{50}$ was calculated using GraphPad Prism7.0 software. The results are shown in Table 2, which indicate that: the compounds disclosed herein down-regulate release of mature IL-1β by inhibiting the activity of Caspase-1, and the $IC_{50}$ is <50 nM.

TABLE 2

| Compound | IC$_{50}$, nM | Compound | IC$_{50}$, nM |
|---|---|---|---|
| 7 | 41.1 | 8-1 | 26.3 |
| 9 | 25.6 | 18-2 | 11.2 |
| 21-1 | 26.2 | 23 | 5 |
| 24-2 | 17.4 | 29 | 18.5 |
| 31-2 | 25 | 32-2 | 28.9 |
| 39-1 | 31.7 | 41 | 5 |
| 42-1 | 18.5 | 42-2 | 3.2 |
| 43 | 11.6 | 44-2 | 16.3 |
| 80-2 | 14.8 | 82-1 | 5.2 |
| 87 | 40.36 | | | administration group and intragastric administration group. The tail vein administration group was subjected to blood collection of 0.1 mL from orbital venous plexus before the administration and 5 min, 15 min, 0.5 h, 1 h, 2 h, 4 h, 8 h, 12 h and 24 h after the administration, and plasma was separated out by centrifugation at 4° C. for 5 min and stored at −20° C. for test. The intragastric administration group was subjected to blood collection of 0.1 mL from orbital venous plexus before the administration and 5 min, 15 min, 0.5 h, 1 h, 2 h, 4 h, 8 h, 12 h and 24 h after the administration, and the subsequent treatment procedures were the same as those of the tail vein injection group. The concentration of parent drug in the plasma was determined by LC-MS/MS. The results are shown in Table 3.

TABLE 3

| Example | Route of administration | Dosage (mg/kg) | $C_{max}$ (ng/mL) | AUC (ng·h/mL) | $t_{1/2}$ (h) | Cl (mL/min/kg) | $V_{ss}$ (mL/kg) | F % |
|---|---|---|---|---|---|---|---|---|
| Control | iv | 1 | — | 1395 | 0.46 | 14.2 | 402 | — |
| 3 | po | 10 | 1927 | 5079 | 2.1 | — | — | 36.4 |
| 8-1 | iv | 1 | — | 2557 | 0.74 | 6.8 | 296 | — |
| | po | 10 | 6397 | 14367 | 2.4 | — | — | 56.2 |
| 8-2 | iv | 1 | — | 2170 | 2.0 | 7.8 | 656 | — |
| | po | 10 | 6190 | 14484 | 3.4 | — | — | 66.7 |
| 6-1 | iv | 1 | — | 6312 | 1.6 | 2.7 | 260 | — |
| | po | 10 | 13900 | 41521 | 2.5 | — | — | 65.8 |
| 6-2 | iv | 1 | — | 1657 | 1.5 | 10.2 | 781 | — |
| | po | 10 | 4073 | 10920 | 2.8 | — | — | 65.9 |
| 18-1 | iv | 1 | — | 2226 | 2.2 | 7.59 | 845 | — |
| | po | 10 | 9867 | 20153 | 2.9 | — | — | 90.5 |
| 18-2 | iv | 1 | — | 3691 | 0.86 | 5.6 | 346 | — |
| | po | 10 | 16600 | 28427 | 3.1 | — | — | 77.6 |
| 21-1 | iv | 1 | — | 2404 | 0.65 | 7.4 | 371 | — |
| | po | 10 | 12717 | 37246 | 2.3 | — | — | 155 |
| 42-2 | iv | 1 | — | 1984 | 0.79 | 8.6 | 503 | — |
| | po | 10 | 8497 | 17301 | 2.1 | — | — | 87.2 |
| 44-2 | iv | 1 | — | 1622 | 0.93 | 10.5 | 537 | — |
| | po | 10 | 6377 | 14460 | 2.4 | — | — | 89.1 |
| 82-1 | iv | 1 | — | 2228 | 0.70 | 11.2 | 379 | — |
| | po | 10 | 5883 | 16478 | 2.3 | — | — | 74.0 |
| 36-1 | iv | 1 | — | 14614 | 3.9 | 1.3 | 220 | — |
| | po | 10 | 33467 | 143938 | 2.9 | — | — | 98.5 |
| 38-1 | iv | 1 | — | 2112 | 2.2 | 8.2 | 679 | — |
| | po | 10 | 13267 | 38823 | 3.1 | — | — | 184 |

4. Assay of TNF Releaseα, in Human PBMCs 5 mL of human venous whole blood from a healthy donor was placed in a Li-heparin tube. PBMCs were isolated and plated in a 96-well plate at 50 μL per well. 25 μL of compound or solvent control was added to each well and 5-fold diluted in gradient from a maximum concentration of 10 μM, and 9 gradient concentrations were set. The mixtures were incubated at 37° C./5% CO$_2$ for 24 h. 25 μL of LPS at a final concentration of 100 ng/mL was added to each well. 25 μL of ATP at a final concentration of 5 mM was added to each well, and the resulting mixtures were incubated for 1.5 h. After the incubation, the mixtures were centrifuged at 1500 rpm for 20 min, and the supernatant was collected to detect the expression level of αTNF by ELISA (BD, Human TNFα ELISA Set II, Cat #555212). IC$_{50}$ was calculated using GraphPad Prism7.0 software. The results show that the compounds disclosed herein have no down-regulation effect on TNF expression in PBMCs induced by LPS, and the IC$_{50}$ is >10 μM.

5. Pharmacokinetic Analysis of Compounds in Rats

Healthy adult SD rats weighing 180-220 g were fasted (free access to water) overnight and divided into tail vein Control 3 was 1-(1,2,3,5,6,7-hexahydro-s-indacen-4-yl)-3-[4-(1-hydroxy-1-methyl-ethyl)-furan-2-sulfonyl]urea prepared by referring to the method for preparing compound 1 described in SYNTHETIC COMMUNICATIONS, Vol. 33, No. 12, pp. 2029-2043, 2003.

The results show that the compounds disclosed herein are superior to the control compounds in terms of pharmacokinetic characteristics.

6. Rat Dorsal Air Pouch Pharmacodynamic Models

Healthy adult male SD rats weighing 180-220 g were purchased, and rat dorsal air pouch models were constructed after adaptive feeding of the rats. On day 1, day 4 and day 7 of modeling, 20 mL of sterile air was injected subcutaneously into the back of rats by means of injection needles, and the air pouch was maintained at an inflated state. On day 8, 50 mg/kg compound or vehicle control was administered intragastrically. 5 mL of 1% sodium urate suspension was injected into the dorsal air pouch, and air pouch exudate was collected 5 h later. 40 μL of the exudate was taken for leukocyte counting. The remaining exudate was centrifuged at 1500 rpm for 20 min, and the supernatant was collected to detect the expression level of IL-1β by ELISA (BD, Human IL-1β ELISA Set II, Cat #557953). The results are shown in Table 4.

TABLE 4

| Group | Leukocyte concentration ($10^6$/mL) | IL-1β concentration in exudate (pg/mL) |
|---|---|---|
| Normal control | 1.77 ± 0.3 | 153.8 ± 26.2 |
| Model | 6.43 ± 1.3 | 3382.9 ± 742.9 |
| Colchicine (30 mg/kg) | 3.40 ± 0.7 | 1190.9 ± 463.6 |
| 6-1 | 1.99 ± 0.4 | 895.7 ± 266.4 |
| 8-1 | 2.25 ± 0.5 | 1522.5 ± 313.2 |
| 18-2 | 1.72 ± 0.3 | 795.5 ± 232.8 |

The results show that compared with colchicine, the compounds disclosed herein can significantly reduce the infiltration quantity of leucocytes and the release of inflammatory factor IL-1β induced by sodium urate.

While specific embodiments of the present invention have been described in detail in the specification, it will be understood by those skilled in the art that the embodiments described above are illustrative and are not to be construed as limiting the present invention, and that various changes and modifications can be made to the present invention without departing from the principles of the present invention, and the technical schemes resulting from these changes and modifications also fall within the protection scope of the appended claims.

The invention claimed is:

1. A compound shown as general formula (I) or a stereoisomer, solvate, prodrug, deuteride, pharmaceutically acceptable salt or cocrystal thereof:

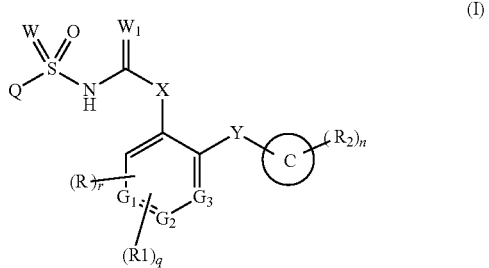

(I)

wherein,

Q is selected from 6-10 membered aryl and 5-10 membered heteroaryl, wherein the heteroaryl contains 1 to 3 heteroatoms selected from N, O and S, and the aryl or heteroaryl is optionally substituted with 0 to 4 $R^{q0}$;

$R^{q0}$ are the same or different and are each independently selected from $C_{1-6}$ alkyl, $C_{1-6}$ alkoxy, $C_{2-6}$ alkenyl, $C_{2-6}$ alkynyl, halogen, OH, cyano, nitro, —$NH_2$, $C_{3-8}$ cycloalkyl, $C_{3-8}$ heterocycloalkyl, $C_{6-10}$ aryl, $C_{5-10}$ heteroaryl, —C(=O)$C_{1-6}$ alkyl, —C(=O)O$C_{1-6}$ alkyl, —OC(=O)$C_{1-6}$ alkyl, —C(=O)O$C_{3-8}$ cycloalkyl, —OC(=O)$C_{3-8}$ cycloalkyl, —OC(=O)$C_{3-8}$ heterocycloalkyl, —C(=O)O$C_{3-8}$ heterocycloalkyl, —C(=O)$C_{6-10}$ aryl, —C(=O)O$C_{6-10}$ aryl, —OC(=O)$C_{6-10}$ aryl, —C(=O)$C_{5-10}$ heteroaryl, —C(=O)O$C_{5-10}$ heteroaryl, —OC(=O)$C_{5-10}$ heteroaryl, —$NHC_{1-6}$ alkyl, —N($C_{1-6}$ alkyl)$_2$, —NHC(=O)$C_{1-6}$ alkyl, —NHC(=O)($C_{1-6}$ alkyl)$_2$, —NHC(=O)$C_{6-10}$ aryl, —NHC(=O)$C_{5-10}$ heteroaryl, —NHC(=O)$C_{3-8}$ heterocycloalkyl, —NHC(=O)$C_{3-8}$ cycloalkyl, —NHC(=O)$C_{2-6}$ alkynyl, —NHC(=O)$C_{2-6}$ alkenyl, —NH(C=N$R^{q1}$)N$R^{q2}R^{q3}$, —C(=O)N$R^{q4}R^{q5}$, —SH, —SC$_{1-6}$ alkyl, —S(=O)$C_{1-6}$ alkyl, —S(=O)$_2$C$_{1-6}$ alkyl and —S(=O)$_2$N$R^{q2}R^{q3}$, wherein the heterocycloalkyl or heteroaryl contains 1 to 3 heteroatoms selected from N, O and S, and the alkyl, alkoxy, —$NH_2$, alkenyl, alkynyl, heterocycloalkyl, cycloalkyl, aryl or heteroaryl is optionally further substituted with 1 or more substituents selected from deuterium, OH, halogen, cyano, =O, $C_{1-6}$ alkyl, $C_{1-6}$ alkoxy, $C_{2-6}$ alkenyl, $C_{2-6}$ alkynyl, —N$R^{q4}R^{q5}$, =N$R^{q6}$, —C(=O)O$C_{1-6}$ alkyl, —OC(=O)$C_{1-6}$ alkyl, —C(=O)N$R^{q4}R^{q5}$, $C_{3-8}$ cycloalkyl, $C_{3-8}$ heterocycloalkyl, $C_{6-10}$ aryl, $C_{5-10}$ heteroaryl, —C(=O)O$C_{6-10}$ aryl, —OC(=O)$C_{6-10}$ aryl, —OC(=O)$C_{5-10}$ heteroaryl, —C(=O)O$C_{5-10}$ heteroaryl, —OC(=O)$C_{3-8}$ heterocycloalkyl, —C(=O)O$C_{3-8}$ heterocycloalkyl, —OC(=O)$C_{3-8}$ cycloalkyl, —C(=O)O$C_{3-8}$ cycloalkyl, —NHC(=O)$C_{3-8}$ heterocycloalkyl, —NHC(=O)$C_{6-10}$ aryl, —NHC(=O)$C_{5-10}$ heteroaryl, —NHC(=O)$C_{3-8}$ cycloalkyl, —NHC(=O)$C_{3-8}$ heterocycloalkyl, —NHC(=O)$C_{1-6}$ alkyl, —NHC(=O)$C_{2-6}$ alkenyl and —NHC(=O)$C_{2-6}$ alkynyl, wherein the substituent $C_{1-6}$ alkyl, $C_{1-6}$ alkoxy, $C_{2-6}$ alkenyl, $C_{2-6}$ alkynyl, $C_{3-8}$ cycloalkyl, $C_{3-8}$ heterocycloalkyl, $C_{6-10}$ aryl, $C_{5-10}$ heteroaryl, —NHC(=O)$C_{6-10}$ aryl, —NHC(=O)$C_{5-10}$ heteroaryl, —NHC(=O)$C_{3-8}$ heterocycloalkyl or —NHC(=O)$C_{3-8}$ cycloalkyl is optionally further substituted with 1 to 3 substituents selected from OH, halogen, $C_{1-6}$ alkyl, $C_{1-6}$ alkoxy, —N$R^{q4}R^{q5}$ and =O; or at least one pair of $R^{q0}$ and an atom to which they are attached form a 4-10 membered carbocycle or a 5-10 membered heterocycle, wherein the heterocycle contains 1 to 2 heteroatoms selected from N, O and S, the carbocycle or the heterocycle is optionally further substituted with 1 or more substituents selected from OH, halogen, $C_{1-6}$ alkyl, $C_{1-6}$ alkoxy, $C_{2-6}$ alkenyl, $C_{2-6}$ alkynyl, —N$R^{q4}R^{q5}$, =N$R^{q6}$, —C(=O)O$C_{1-6}$ alkyl and —C(=O)N$R^{q4}R^{q5}$, and the substituent $C_{1-6}$ alkyl or $C_{1-6}$ alkoxy is optionally further substituted with a substituent selected from OH, halogen, =O, —N$R^{q4}R^{q5}$, =N$R^{q6}$, —C(=O)O$C_{1-6}$ alkyl, $C_{3-8}$ cycloalkyl, $C_{3-8}$ heterocycloalkyl, $C_{6-10}$ aryl, $C_{5-10}$ heteroaryl and —C(=O)N$R^{q4}R^{q5}$;

$R^{q1}$ is selected from $C_{1-6}$ alkyl, $C_{1-6}$ alkoxy and $C_{6-10}$ aryl;

$R^{q2}$ and $R^{q3}$ are selected from H and $C_{1-6}$ alkyl;

$R^{q4}$ and $R^{q5}$ are selected from H, $C_{1-6}$ alkyl, —NH(C=N$R^{q1}$)N$R^{q2}R^{q3}$, —S(=O)$_2$N$R^{q2}R^{q3}$, —C(=O)$R^{q1}$ and —C(=O)N$R^{q2}R^{q3}$, wherein the $C_{1-6}$ alkyl is optionally further substituted with 1 or more substituents selected from OH, halogen, $C_{1-6}$ alkyl, $C_{1-6}$ alkoxy, $C_{6-10}$ aryl, $C_{5-10}$ heteroaryl, $C_{3-8}$ cycloalkyl and $C_{3-8}$ heterocycloalkyl; or $R^{q4}$ and $R^{q5}$ form a 3-8 membered heterocycle with an N atom, the heterocycle containing 1 to 3 heteroatoms selected from N, O and S;

$R^{q6}$ is $C_{1-6}$ alkyl;

W is selected from O and NH;

$W_1$ is O;

X is NH;

Y is $CR_bR_c$;

$R_b$ and $R_c$ are each independently selected from H, $C_{1-6}$ alkyl and 3-10 membered carbocyclyl, wherein the $C_{1-6}$ alkyl is optionally further substituted with 1 to 4 substituents selected from F, Cl, Br, I, $C_{1-6}$ alkyl, $C_{1-6}$ alkoxy, 3-10 membered carbocyclyl and 3-10 membered heterocyclyl, the heterocyclyl optionally containing 1 to 3 heteroatoms selected from N, O and S; or

235

$R_b$ and $R_c$ form a double bond;

R and $R_1$ are each independently selected from deuterium, H, F, Cl, Br, I, CN, $NH_2$, OH, $C_{1-6}$ alkyl, $C_{1-6}$ alkoxy, $C_{2-6}$ alkenyl, $C_{2-6}$ alkynyl, —(C=O)—$C_{1-6}$ alkyl, —(C=O)O—$C_{1-6}$ alkyl, —O(C=O)—$C_{1-6}$ alkyl, —O(C=O)-3-10 membered carbocyclyl, —O(C=O)-3-10 membered heterocyclyl, —(C=O)O-3-10 membered carbocyclyl, —O(C=O)O—$C_{1-6}$ alkyl, 3-10 membered carbocyclyl, 4-10 membered heterocyclyl, —NH$C_{1-6}$ alkyl, —N($C_{1-6}$ alkyl)$_2$ and (C=O)N$R_{a1}R_{a2}$, wherein the heterocyclyl contains 1 to 3 heteroatoms selected from N, O and S, and the alkyl, alkenyl, alkoxy, carbocycle or heterocycle is optionally further substituted with 1 to 4 substituents selected from OH, F, Cl, Br, I, CN, N$R_{a1}R_{a2}$, =O, $C_{1-6}$ alkyl, $C_{1-6}$ alkoxy, $C_{1-6}$ haloalkyl, $C_{1-6}$ haloalkoxy, —(C=O)—$C_{1-6}$ alkyl, —(C=O)O—$C_{1-6}$ alkyl, —O(C=O)—$C_{1-6}$ alkyl, —(C=O)O-3-10 membered carbocyclyl, —O(C=O)-3-10 membered carbocyclyl, —O(C=O)-3-10 membered heterocyclyl, —O(C=O)O—$C_{1-6}$ alkyl, 3-10 membered carbocyclyl, 5-10-membered heterocyclyl, —NHCO$C_{1-6}$ alkyl, —NH(C=O)-3-10 membered carbocyclyl, —NH(C=O)-3-10 membered heterocyclyl and —(C=O)N$R_{a1}R_{a2}$; or R and $R_1$, together with an atom to which they are attached, form a 4-8 membered ring, wherein the 4-8 membered ring contains 0 to 4 heteroatoms selected from N, O and S, and is optionally further substituted with 0 to 4 substituents selected from H, F, Cl, Br, I, OH, —N$R_{a1}R_{a2}$, =O, $C_{1-6}$ alkyl, $C_{1-6}$ alkoxy, $C_{2-6}$ alkenyl, $C_{2-6}$ alkynyl, —(C=O)O$C_{1-6}$ alkyl, 3-10 membered carbocyclyl and 5-10 membered heterocyclyl;

C is 3-10 membered cycloalkyl;

$R_2$ is selected from H, F, Cl, Br, I, OH, —N$R_{a1}R_{a2}$, $C_{1-6}$ alkyl, $C_{2-6}$ alkenyl, $C_{2-6}$ alkynyl and $C_{1-6}$ alkoxy;

G1, G2 and G3 are each independently selected from N and CH;

q and r are selected from 0, 1 and 2;

n is selected from 0, 1, 2 and 3.

2. The compound or the stereoisomer, solvate, deuteride, prodrug, pharmaceutically acceptable salt or cocrystal thereof according to claim 1, wherein the compound is selected from compounds shown as formulas (II) and (II-1):

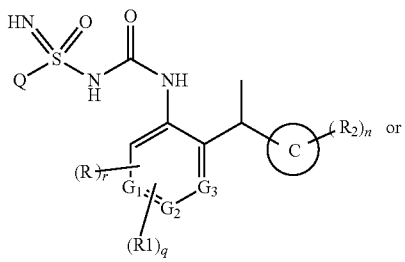

(II)

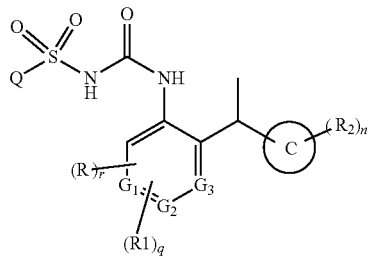

(II-1)

236 wherein,

Q, R, $R_1$, $R_2$, C, G1, G2, G3, r, q and n are defined in the same way as in general formula (I).

3. The compound or the stereoisomer, solvate, deuteride, prodrug, pharmaceutically acceptable salt or cocrystal thereof according to claim 1, wherein the compound is selected from a compound shown as formula (II-2):

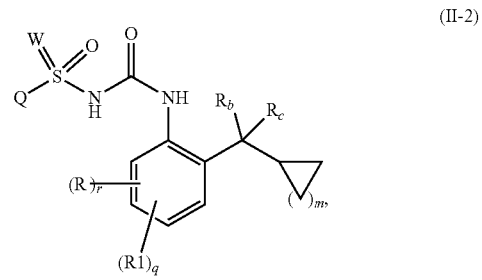

(II-2)

wherein, Q, W, R, $R_1$, $R_b$, $R_c$, r and q are defined in the same way as in general formula (I);

m is selected from 1, 2 and 3.

4. The compound or the stereoisomer, solvate, deuteride, prodrug, pharmaceutically acceptable salt or cocrystal thereof according to claim 2, wherein the compound is selected from compounds shown as formulas (III) and (III-1):

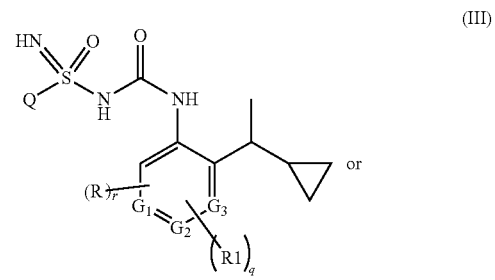

(III)

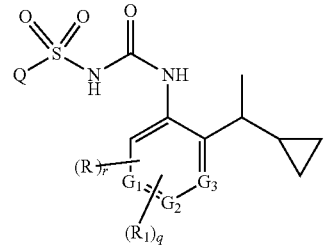

(III-1)

wherein, Q, R, $R_1$, G1, G2, G3, r and q are defined in the same way as in general formula (I).

5. The compound or the stereoisomer, solvate, deuteride, prodrug, pharmaceutically acceptable salt or cocrystal thereof according to claim 4, wherein:

Q is selected from 5 membered heteroaryl, wherein the heteroaryl contains 1 to 3 heteroatoms selected from N, O and S, and the aryl or heteroaryl is optionally substituted with 0 to 4 $R^{q0}$;

$R^{q0}$ are the same or different and are each independently selected from $C_{1-4}$ alkyl, halogen, OH, cyano, —$NH_2$, $C_{2-4}$ alkenyl, $C_{3-6}$ cycloalkyl, $C_{3-6}$ heterocycloalkyl, —NH$C_{1-4}$ alkyl and —N($C_{1-4}$ alkyl)$_2$, wherein the heterocycloalkyl contains 1 to 3 heteroatoms selected from N and O, and the alkyl, heterocycloalkyl and cycloalkyl are optionally further substituted with 1 or more substituents selected from deuterium, OH, halogen, cyano, $C_{1-4}$ alkyl and $—NR^{q4}R^{q5}$;

$R^{q4}$ and $R^{q5}$ are selected from H and $C_{1-4}$ alkyl;

R and $R_1$ are each independently selected from deuterium, H, F, CN, OH, $C_{1-6}$ alkyl and 4-6 membered heterocyclyl, wherein the heterocyclyl contains 1 to 3 heteroatoms selected from N and O, and the alkyl or heterocycle is optionally further substituted with 1 to 4 substituents selected from OH, F, CN and $C_{1-6}$ alkoxy; or R and $R_1$, together with an atom to which they are attached, form a 4-5 membered ring;

G1, G2 and G3 are each independently selected from CH;

q and r are selected from 0, 1 and 2.

6. The compound or the stereoisomer, solvate, deuteride, prodrug, pharmaceutically acceptable salt or cocrystal thereof according to claim 3, wherein the compound is selected from a compound shown as formula (IV):

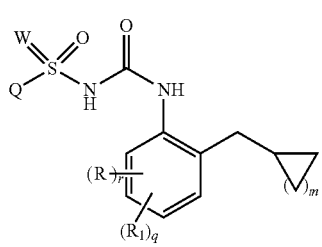

(IV)

wherein, Q, W, R, $R_1$, r and q are defined in the same way as in general formula (I);

m is selected from 1, 2 and 3.

7. The compound or the stereoisomer, solvate, deuteride, prodrug, pharmaceutically acceptable salt or cocrystal thereof according to claim 6, wherein:

Q is selected from 5 membered heteroaryl, wherein the heteroaryl contains 1 to 3 heteroatoms selected from N, O and S, and the aryl or heteroaryl is optionally substituted with 0 to 4 $R^{q0}$;

$R^{q0}$ are the same or different and are each independently selected from $C_{1-4}$ alkyl, halogen, OH, cyano, $—NH_2$, $C_{2-4}$ alkenyl, $C_{3-6}$ cycloalkyl, $C_{3-6}$ heterocycloalkyl, $—NHC_{1-4}$ alkyl and $—N(C_{1-4}$ alkyl$)_2$, wherein the heterocycloalkyl contains 1 to 3 heteroatoms selected from N and O, and the alkyl, heterocycloalkyl and cycloalkyl are optionally further substituted with 1 or more substituents selected from deuterium, OH, halogen, cyano, $C_{1-4}$ alkyl, $—NR^{q4}R^{q5}$, $C_{3-6}$ cycloalkyl and $C_{3-6}$ heterocycloalkyl;

$R^{q4}$ and $R^{q5}$ are selected from H and $C_{1-4}$ alkyl;

W is selected from O and NH;

R and $R_1$ are each independently selected from deuterium, H, F, CN, OH, $C_{1-6}$ alkyl and 4-6 membered heterocyclyl, wherein the heterocyclyl contains 1 to 3 heteroatoms selected from N and O, and the alkyl or heterocycle is optionally further substituted with 1 to 4 substituents selected from OH, F, CN and $C_{1-6}$ alkoxy; or R and $R_1$, together with an atom to which they are attached, form a 4-5 membered ring;

q and r are selected from 0, 1 and 2;

m is selected from 1, 2 and 3.

8. The compound or the stereoisomer, solvate, deuteride, prodrug, pharmaceutically acceptable salt or cocrystal thereof according to claim 3, wherein the compound is selected from a compound shown as formula (V):

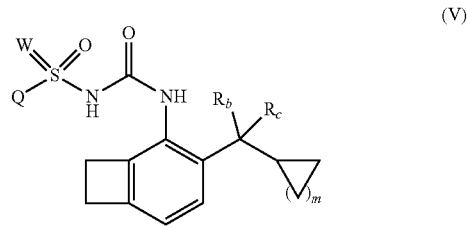

(V)

wherein, Q, W, $R_b$ and $R_c$ are defined in the same way as in general formula (I);

m is selected from 1, 2 and 3.

9. The compound or the stereoisomer, solvate, deuteride, prodrug, pharmaceutically acceptable salt or cocrystal thereof according to claim 8, wherein:

Q is selected from 5 membered heteroaryl, wherein the heteroaryl contains 1 to 3 heteroatoms selected from N, O and S, and the aryl or heteroaryl is optionally substituted with 0 to 4 $R^{q0}$;

$R^{q0}$ are the same or different and are each independently selected from $C_{1-4}$ alkyl, halogen, OH, cyano, $—NH_2$, $C_{2-4}$ alkenyl, $C_{3-6}$ cycloalkyl, $C_{3-6}$ heterocycloalkyl, $—NHC_{1-4}$ alkyl and $—N(C_{1-4}$ alkyl$)_2$, wherein the heterocycloalkyl contains 1 to 3 heteroatoms selected from N and O, and the alkyl, heterocycloalkyl and cycloalkyl are optionally further substituted with 1 or more substituents selected from deuterium, OH, halogen, cyano, $C_{1-4}$ alkyl and $—NR^{q4}R^{q5}$;

$R^{q4}$ and $R^{q5}$ are selected from H and $C_{1-4}$ alkyl;

W is selected from O and NH;

$R_b$ and $R_c$ are each independently selected from H, $C_{1-4}$ alkyl and 3-5 membered carbocyclyl, or $R_b$ and $R_c$ form a double bond;

q and r are selected from 0, 1 and 2;

m is selected from 1, 2 and 3.

10. The compound or the stereoisomer, solvate, deuteride, prodrug, pharmaceutically acceptable salt or cocrystal thereof according to claim 3, wherein the compound is selected from a compound shown as formula (VI):

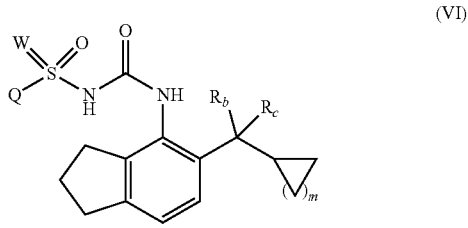

(VI)

wherein, Q, W, $R_b$ and $R_c$ are defined in the same way as in general formula (I);

m is selected from 1, 2 and 3.

11. The compound or the stereoisomer, solvate, deuteride, prodrug, pharmaceutically acceptable salt or cocrystal thereof according to claim 10, wherein:

Q is selected from 5 membered heteroaryl, wherein the heteroaryl contains 1 to 3 heteroatoms selected from N, O and S, and the aryl or heteroaryl is optionally substituted with 0 to 4 $R^{q0}$;

$R^{q0}$ are the same or different and are each independently selected from $C_{1-4}$ alkyl, halogen, OH, cyano, —$NH_2$, $C_{2-4}$ alkenyl, $C_{3-6}$ cycloalkyl, $C_{3-6}$ heterocycloalkyl, —$NHC_{1-4}$ alkyl and —$N(C_{1-4}$ alkyl$)_2$, wherein the heterocycloalkyl contains 1 to 3 heteroatoms selected from N and O, and the alkyl, heterocycloalkyl and cycloalkyl are optionally further substituted with 1 or more substituents selected from deuterium, OH, halogen, cyano, $C_{1-4}$ alkyl and —$NR^{q4}R^{q5}$;

$R^{q4}$ and $R^{q5}$ are selected from H and $C_{1-4}$ alkyl;

W is selected from O and NH;

$R_b$ and $R_c$ are each independently selected from H, $C_{1-4}$ alkyl and 3-5 membered carbocyclyl;

q and r are selected from 0, 1 and 2;

m is selected from 1, 2 and 3.

12. The compound or the stereoisomer, solvate, deuteride, prodrug, pharmaceutically acceptable salt or cocrystal thereof according to claim 1, wherein:

Q is selected from

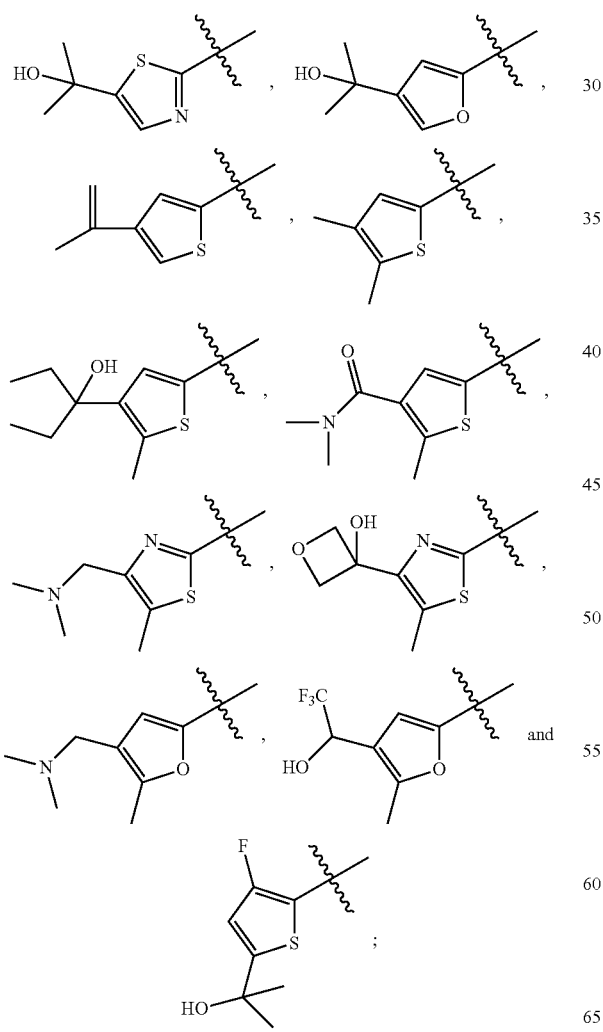

is selected from

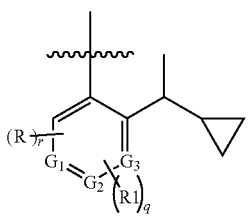

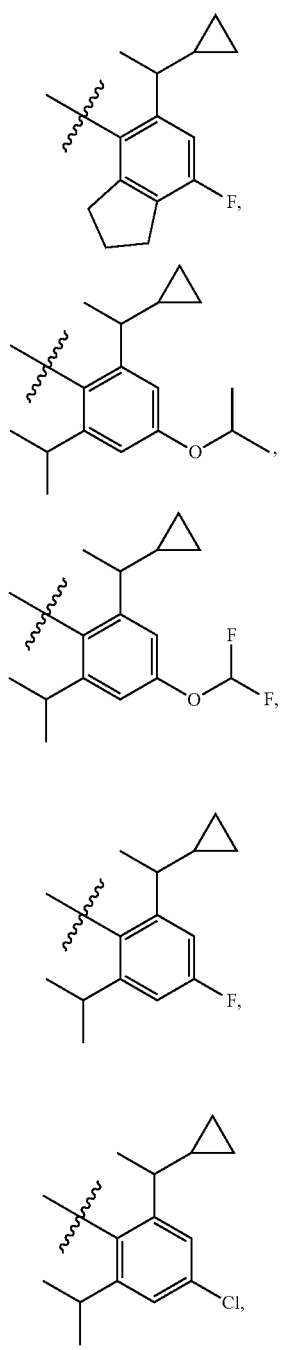

241
-continued
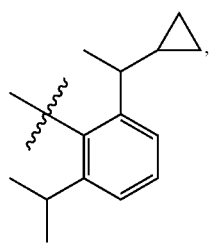
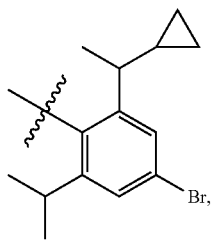
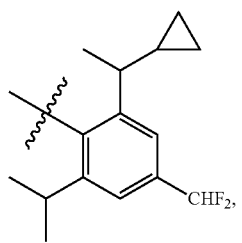
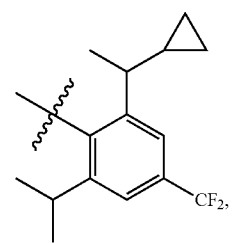
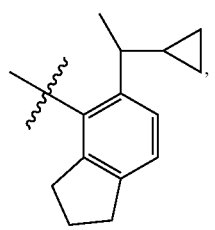
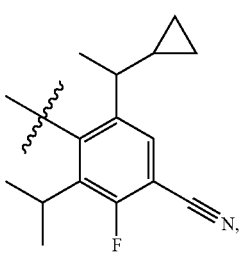
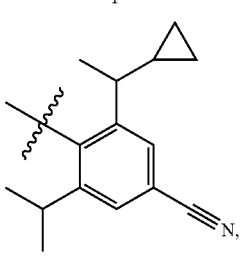
242
-continued
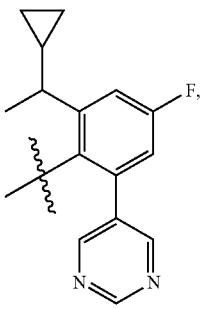
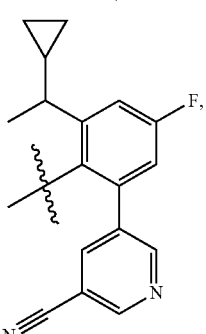
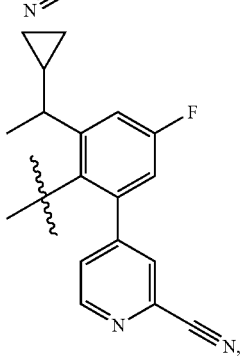
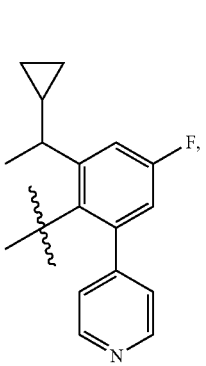
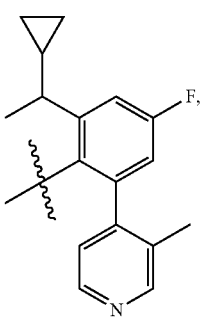

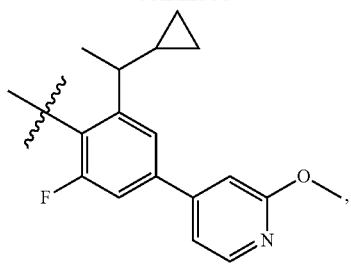
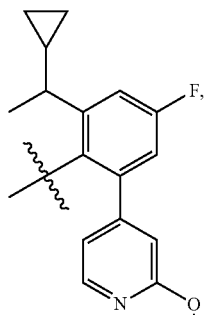
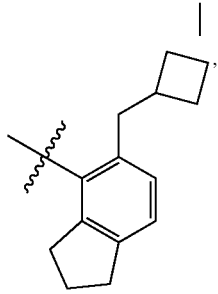
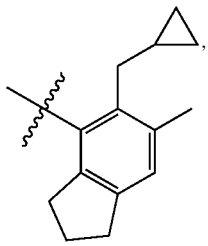
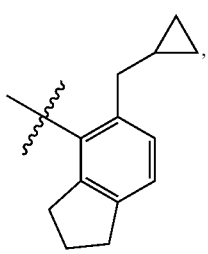
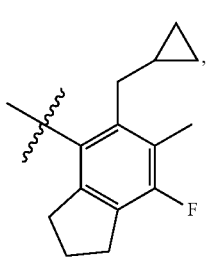
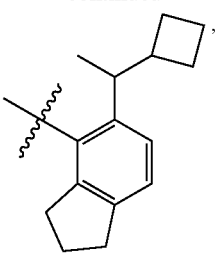
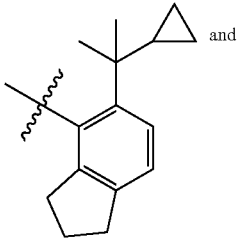
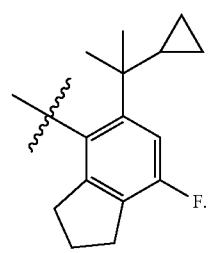
13. The compound or the stereoisomer, solvate, deuteride, prodrug, pharmaceutically acceptable salt or cocrystal thereof according to claim 1, wherein the compound is selected from one of the following structures:
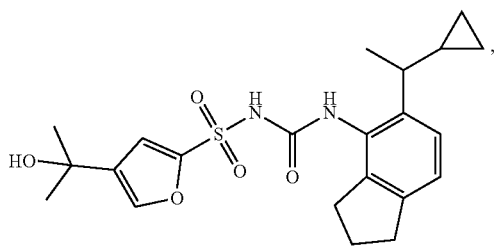
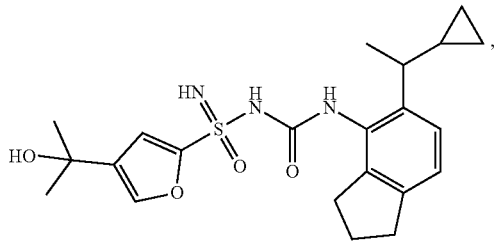
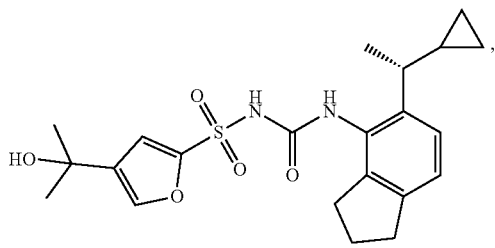

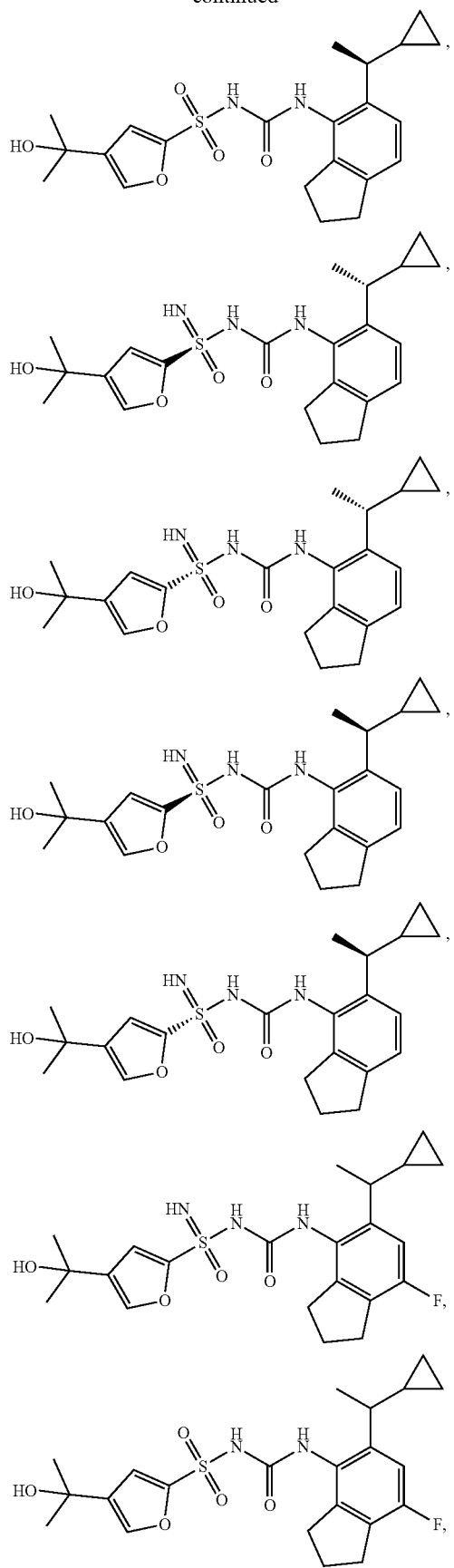
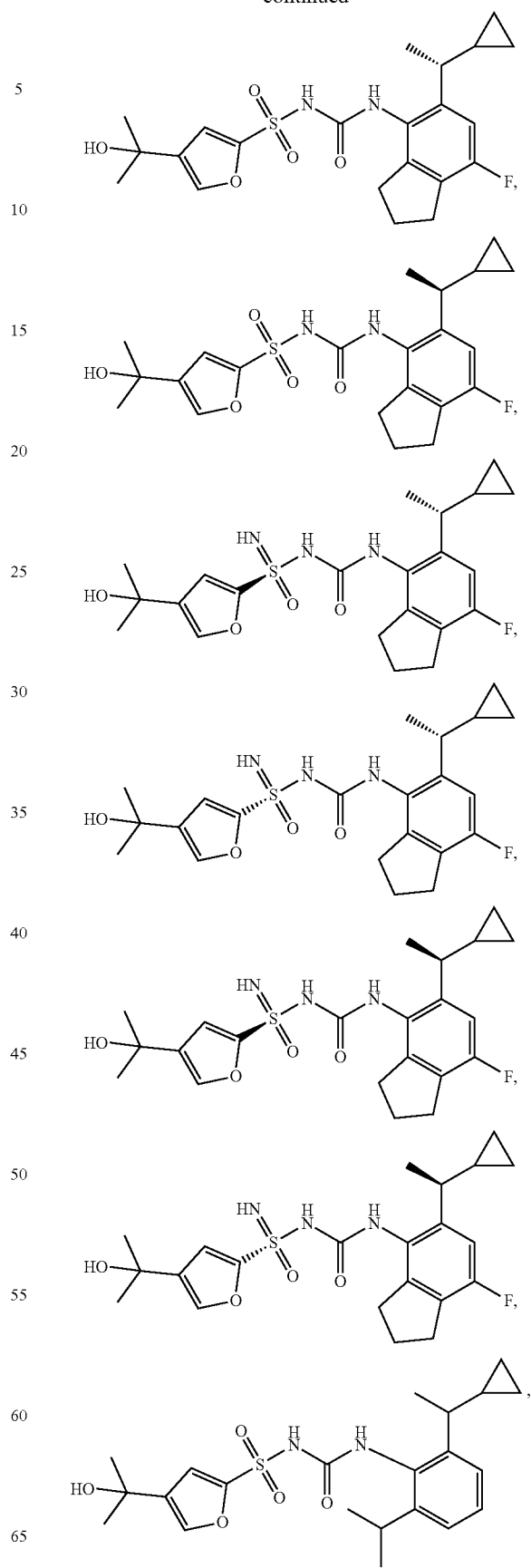

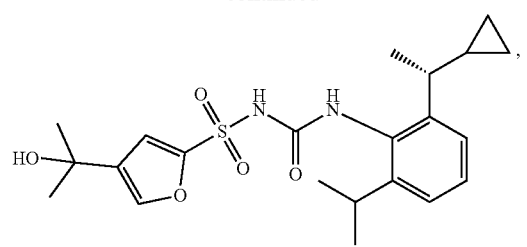
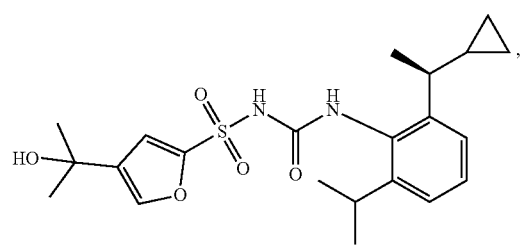
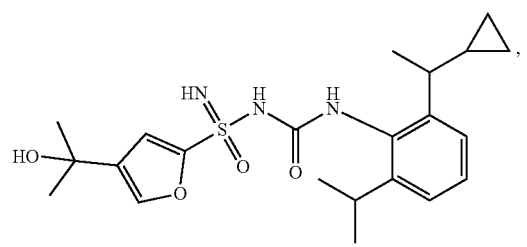
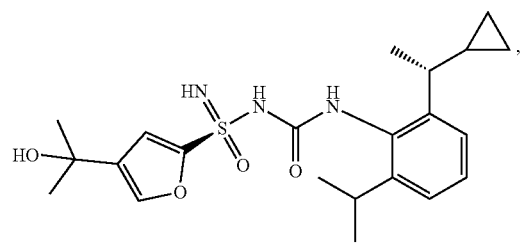
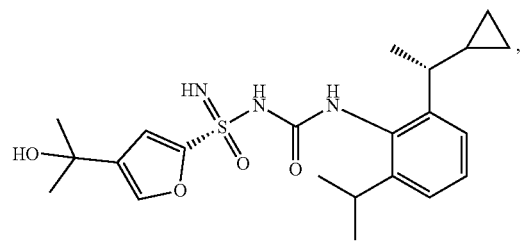
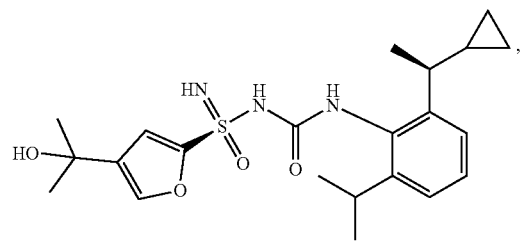
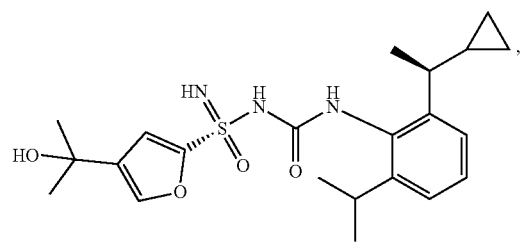
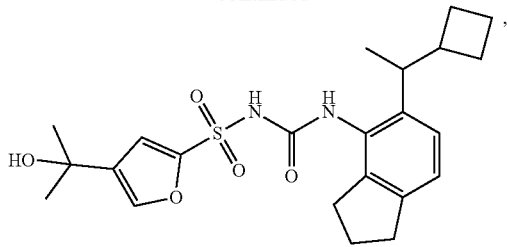
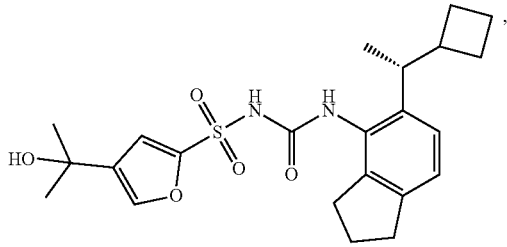
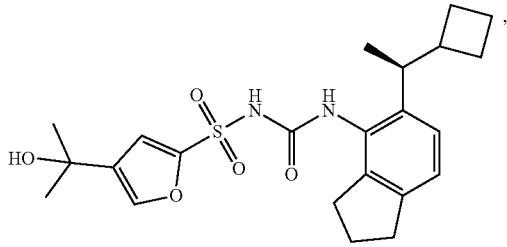
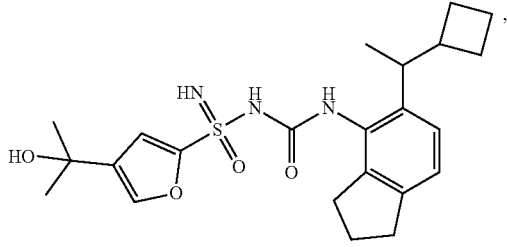
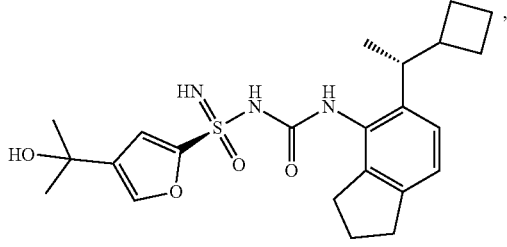
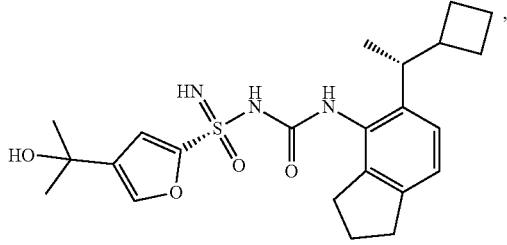
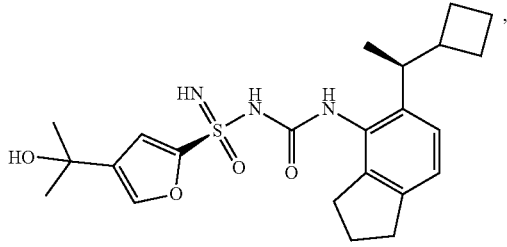

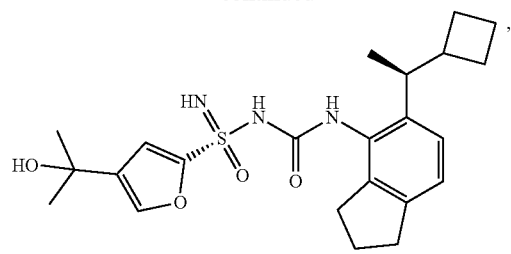
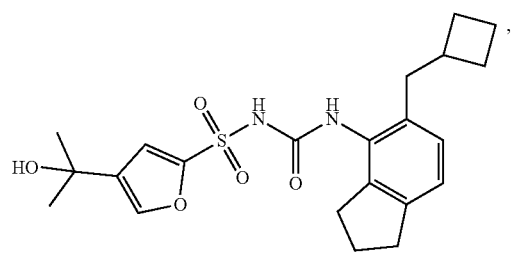
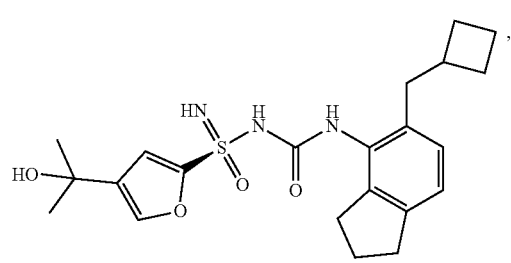
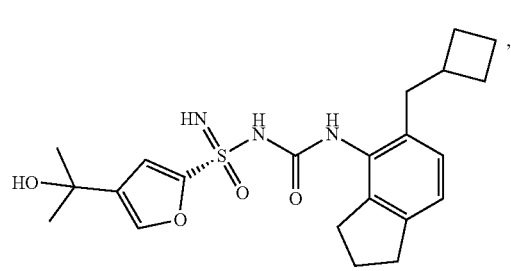
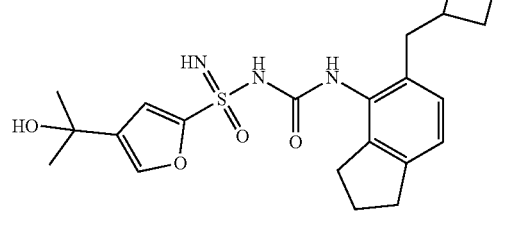
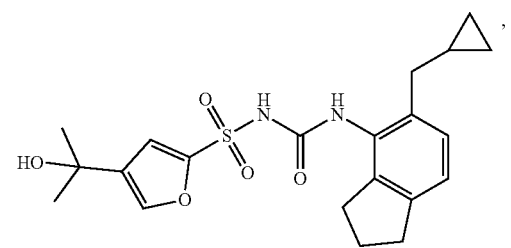
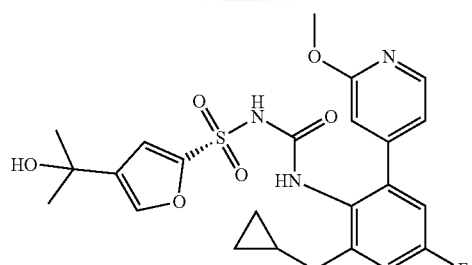
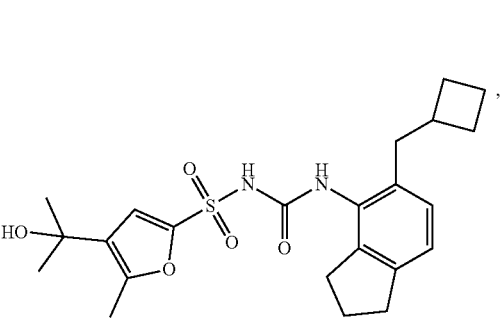
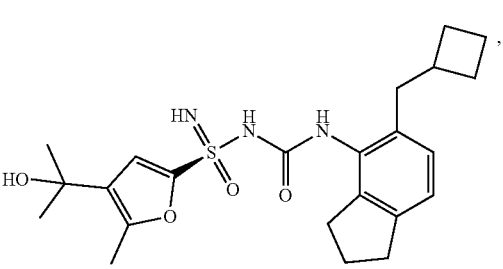
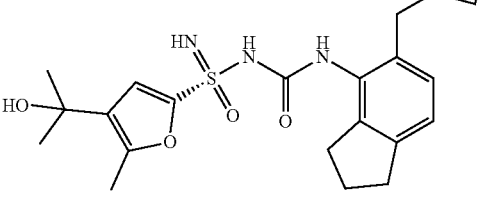
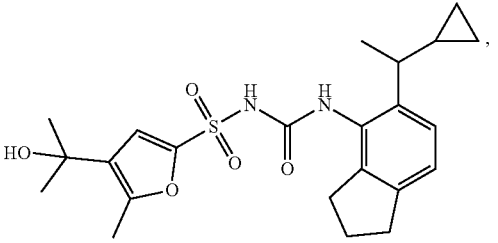
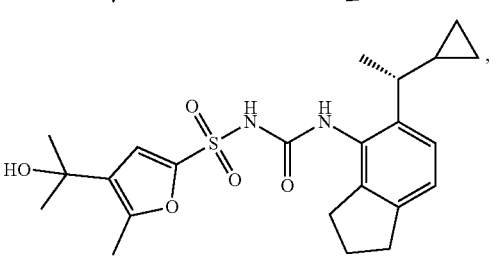

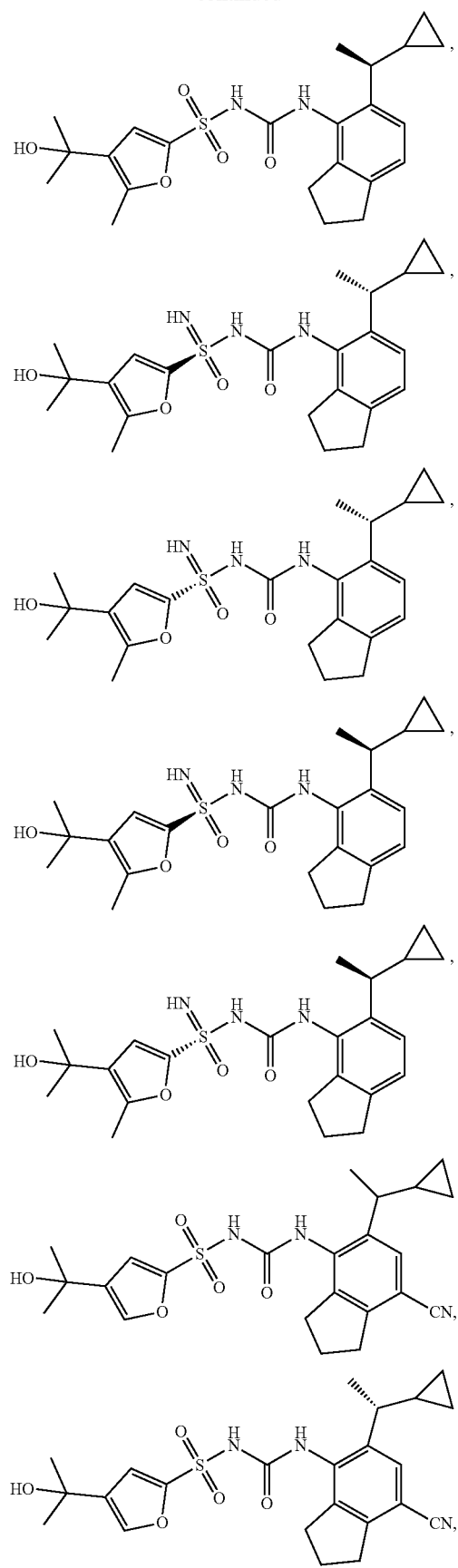
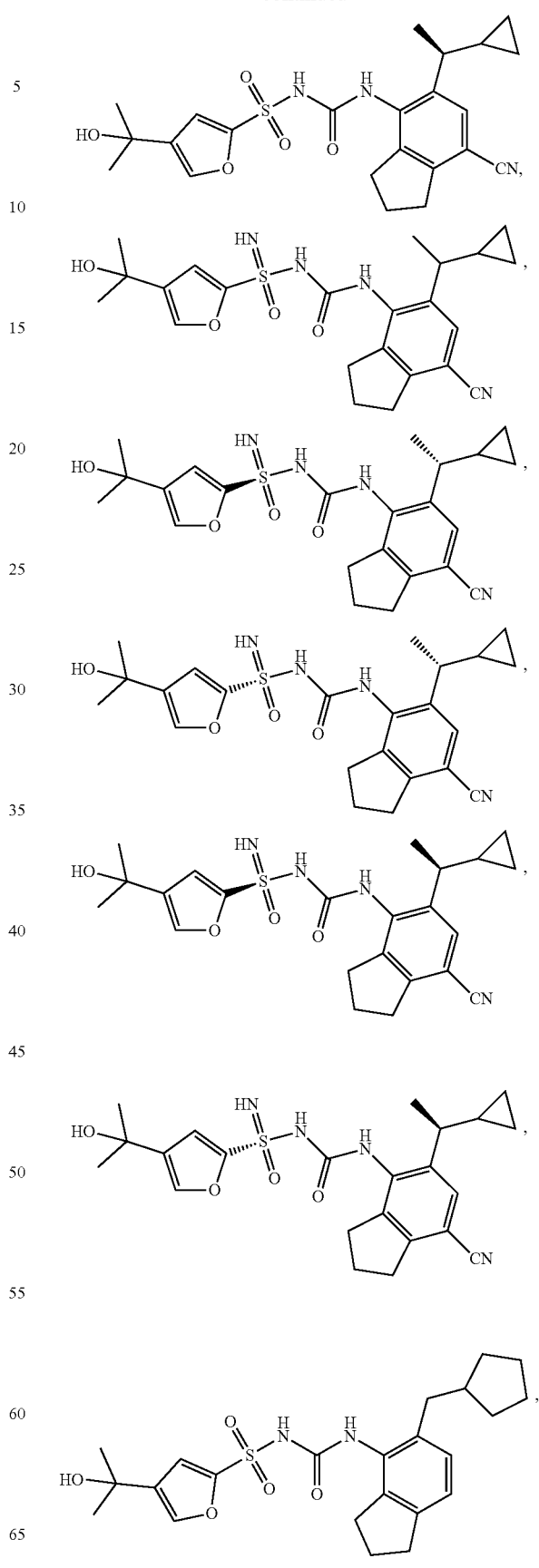

253
-continued
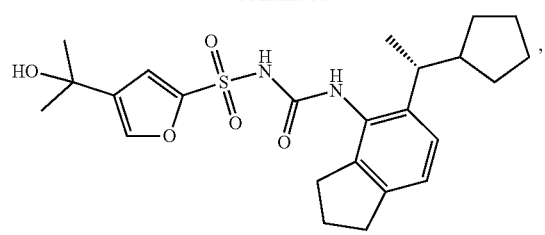
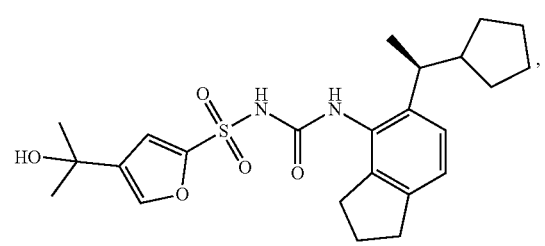
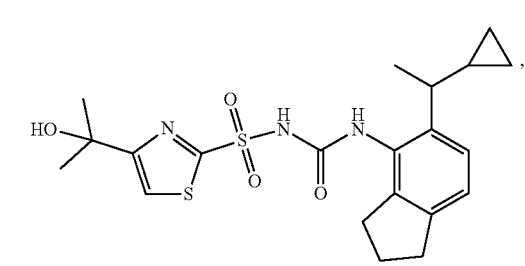
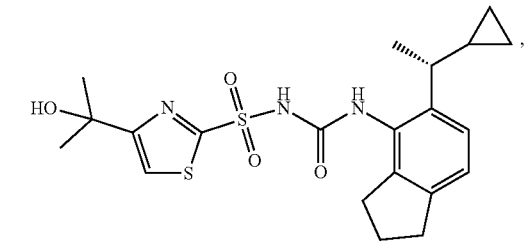
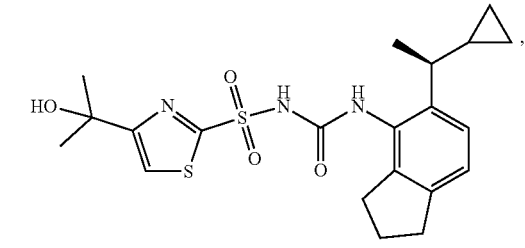
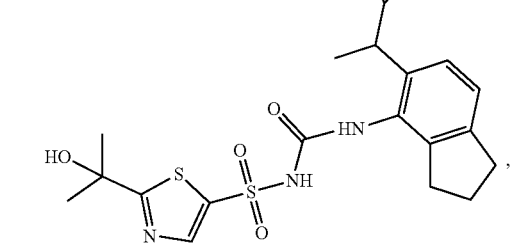
254
-continued
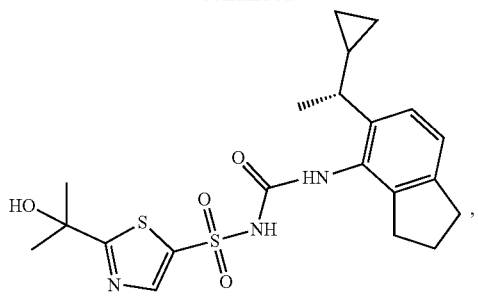
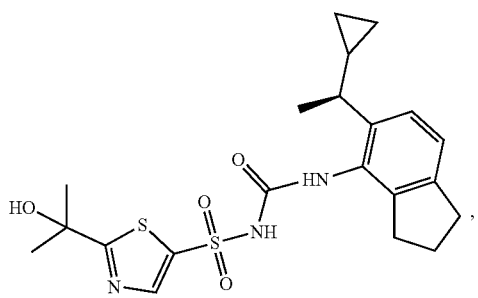
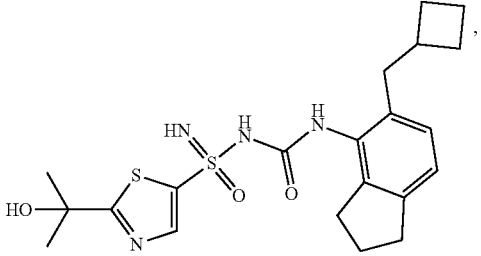
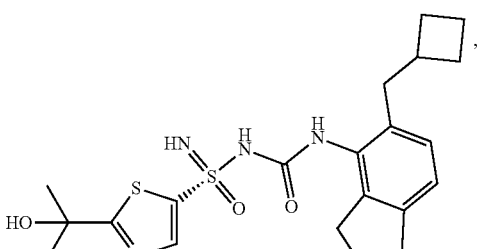
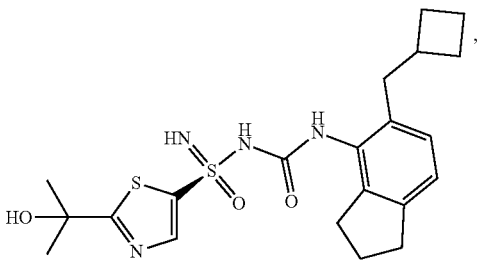
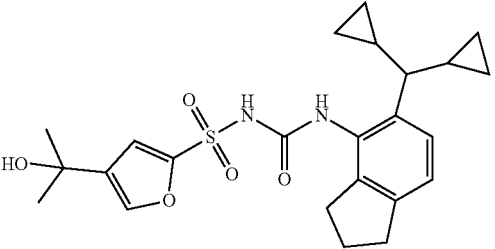

255
-continued

256
-continued

257
-continued
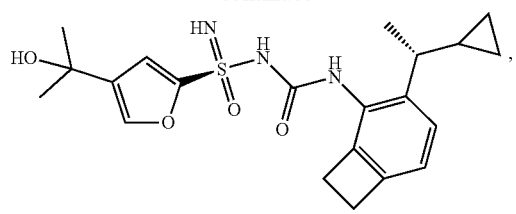
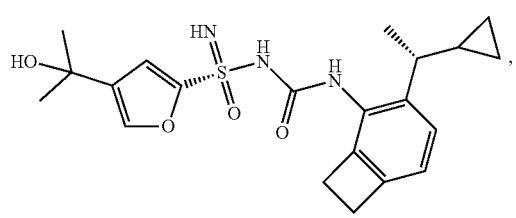
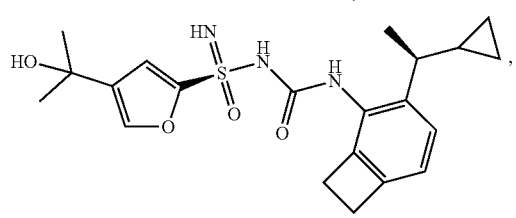
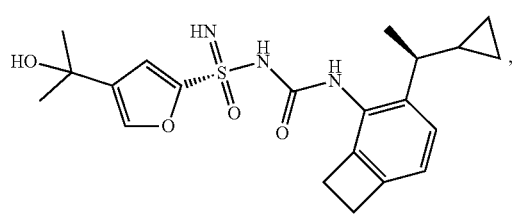
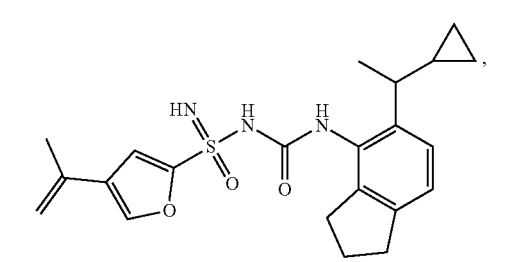
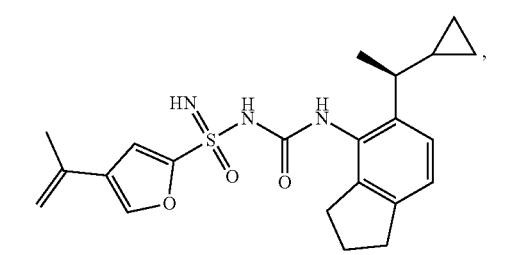
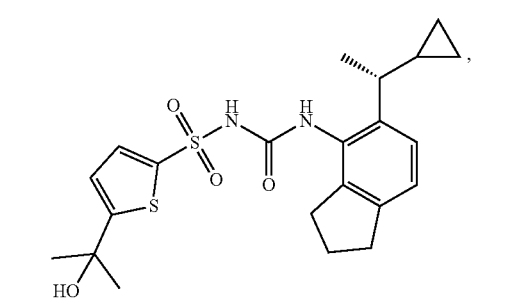
258
-continued
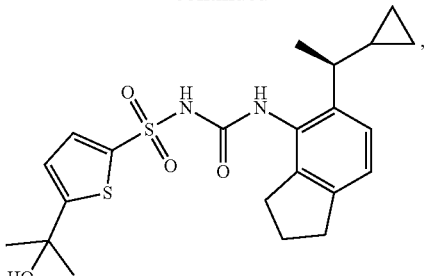
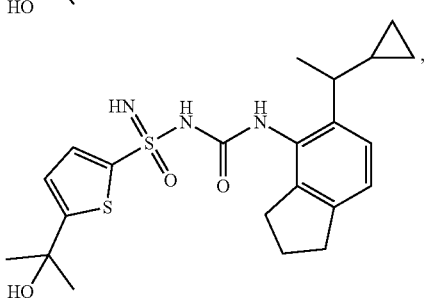
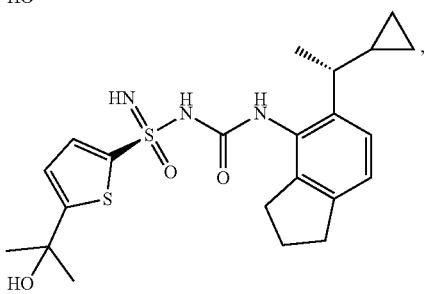
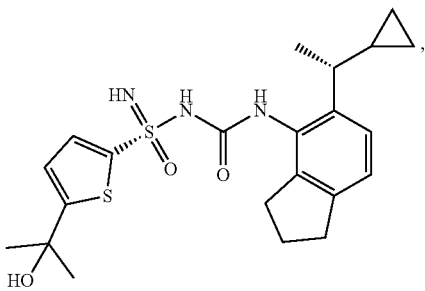
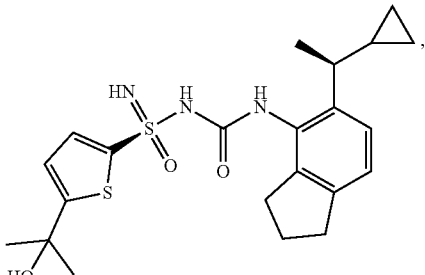
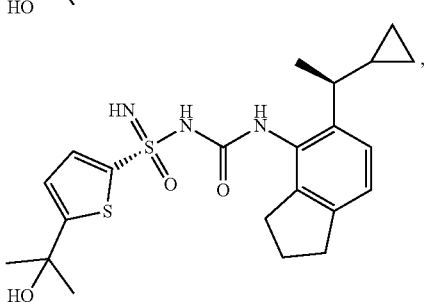

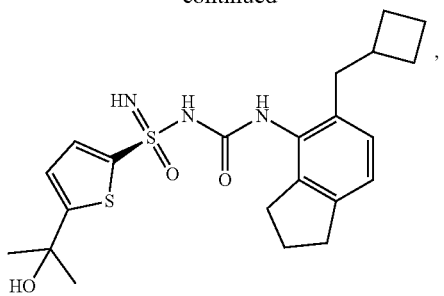
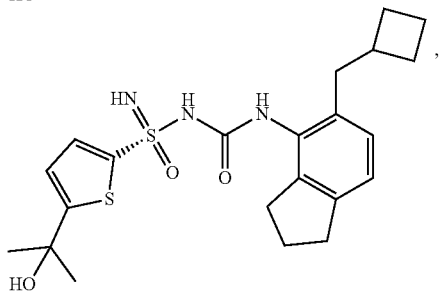
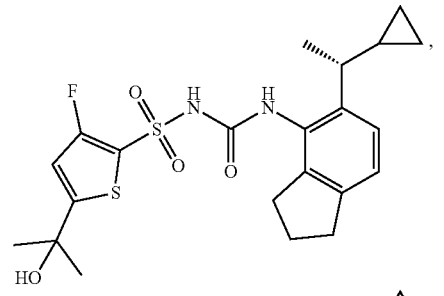
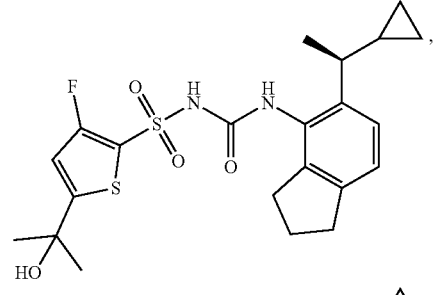
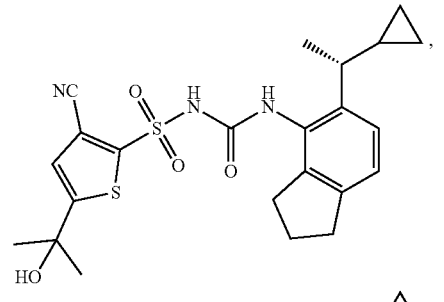
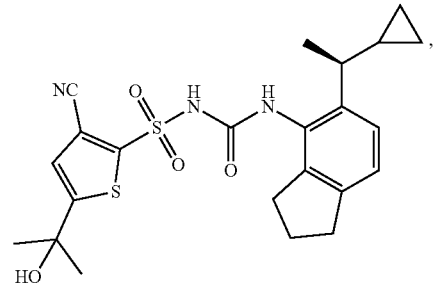
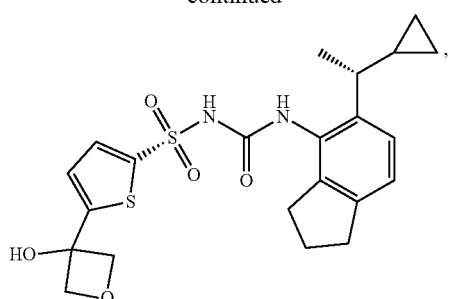
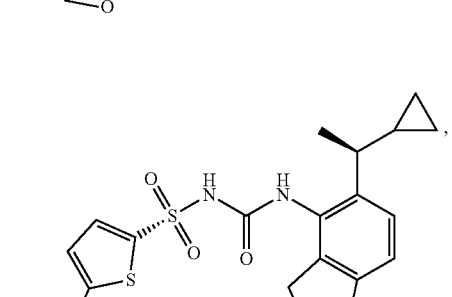
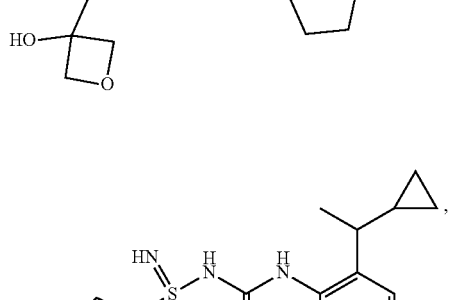
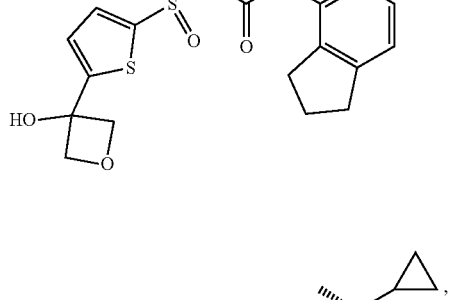
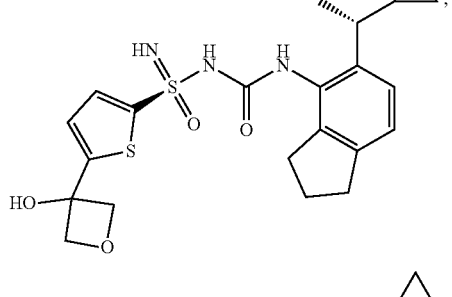
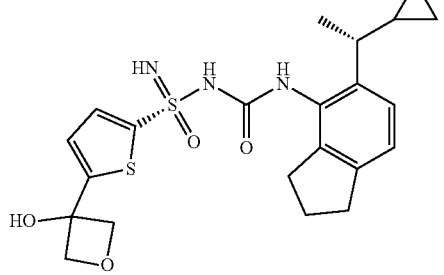

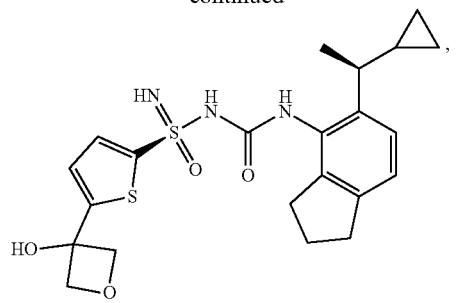
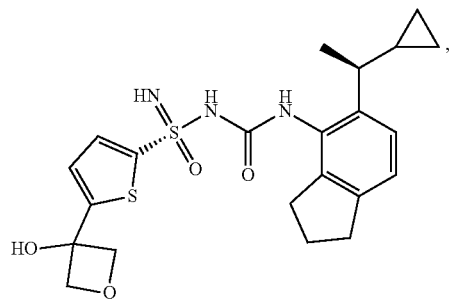
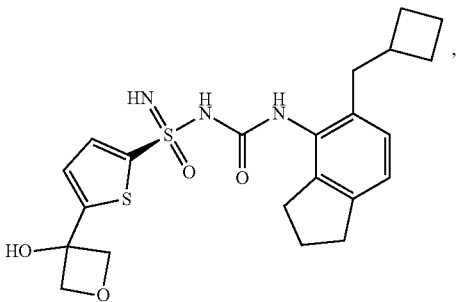
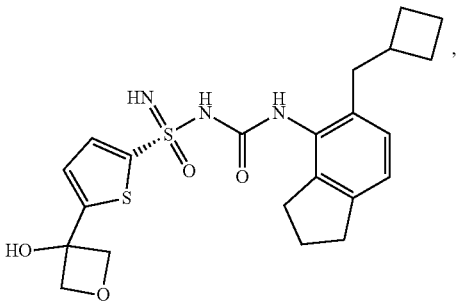
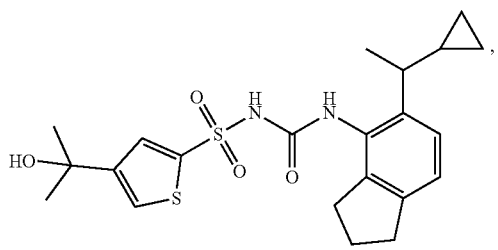
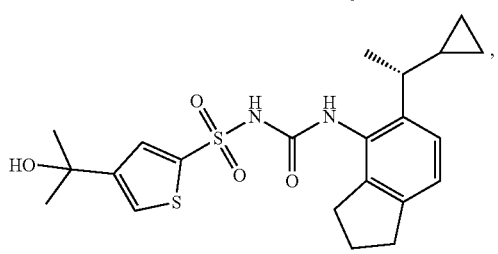
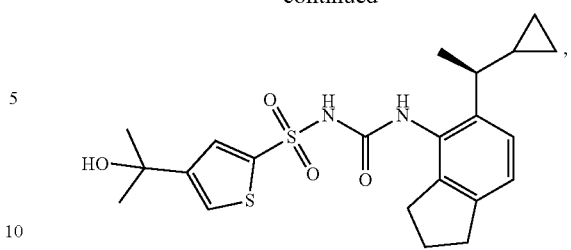
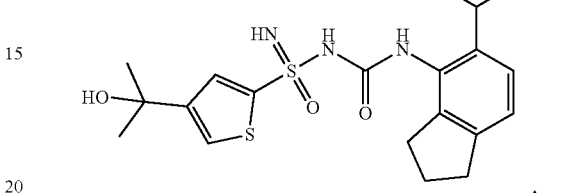
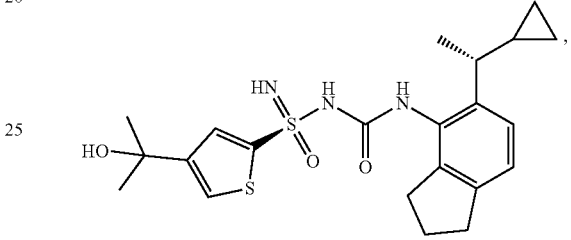
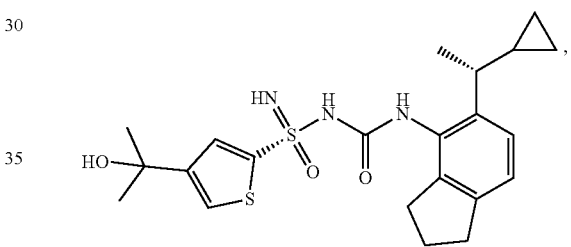
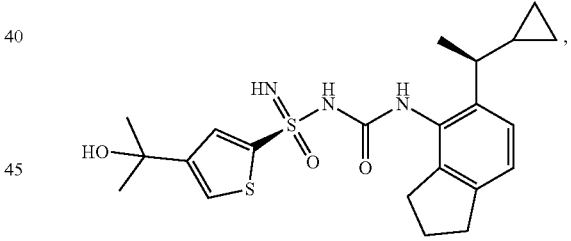
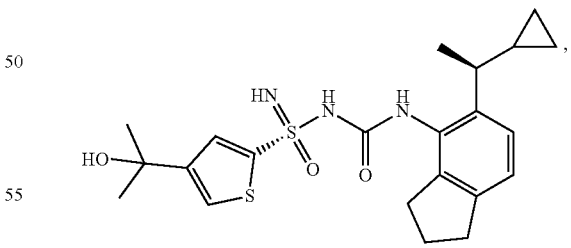
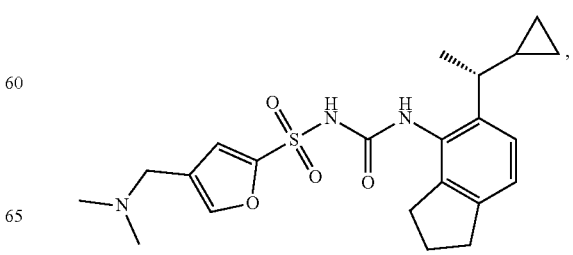

263
-continued
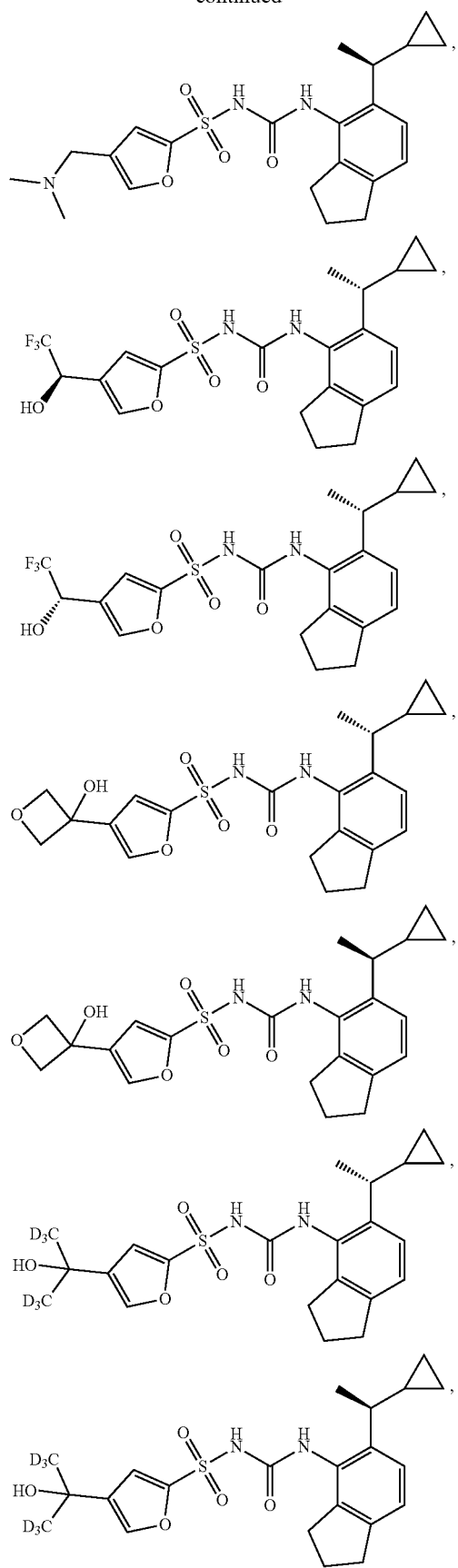
264
-continued
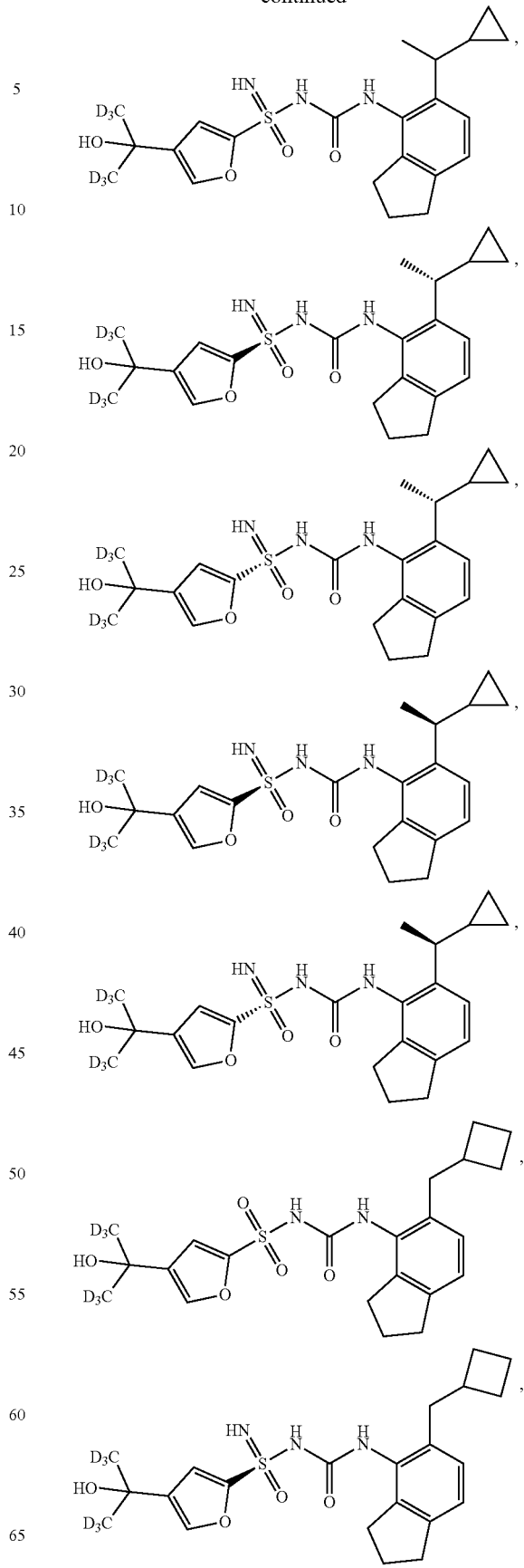

265
-continued
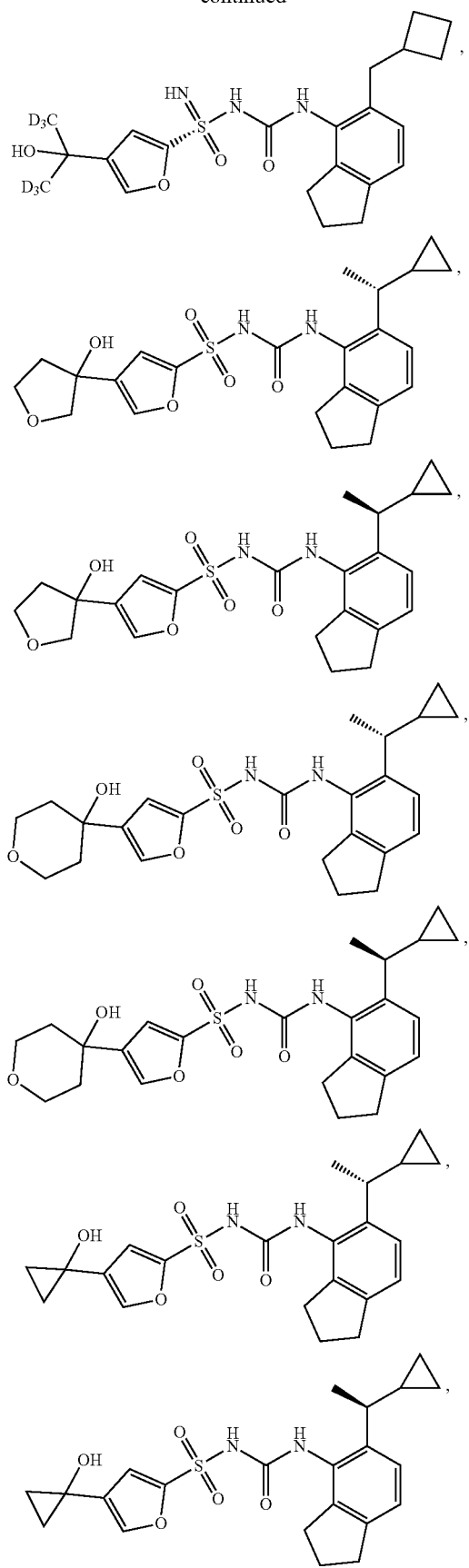
266
-continued
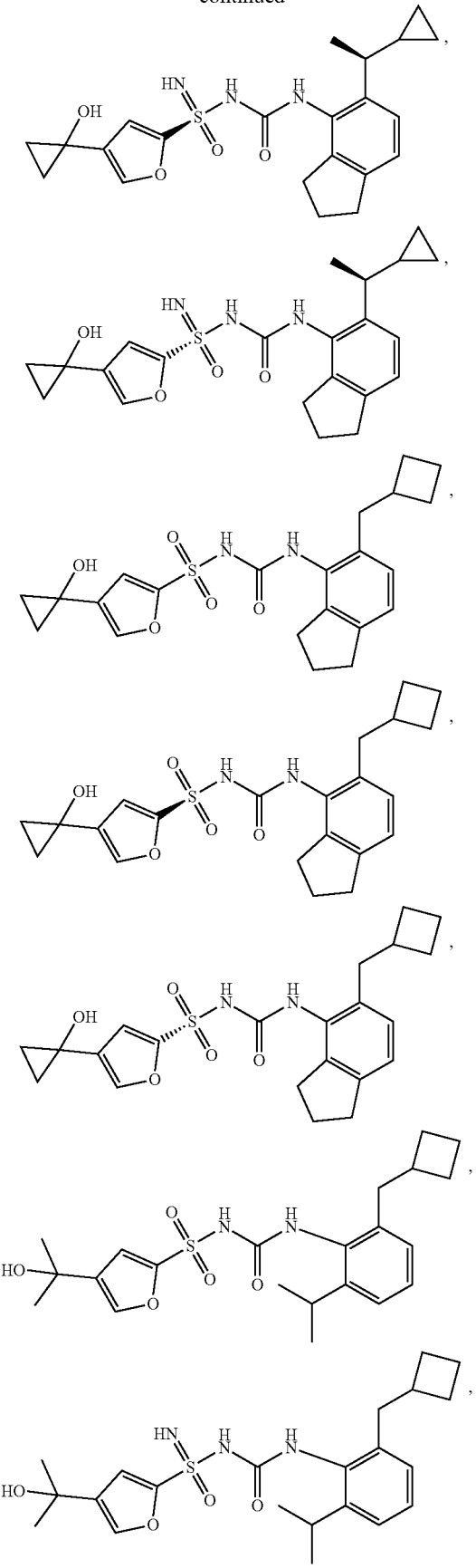

267
-continued
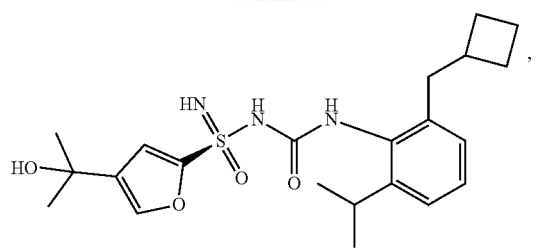
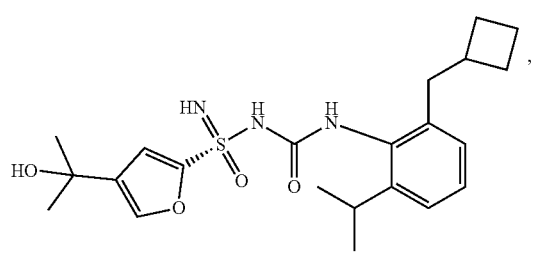
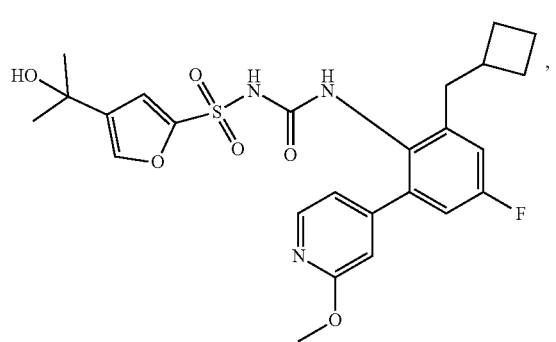
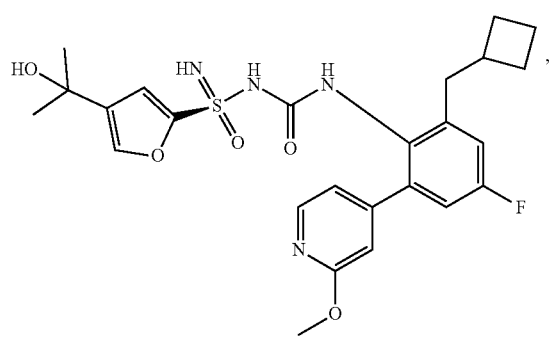
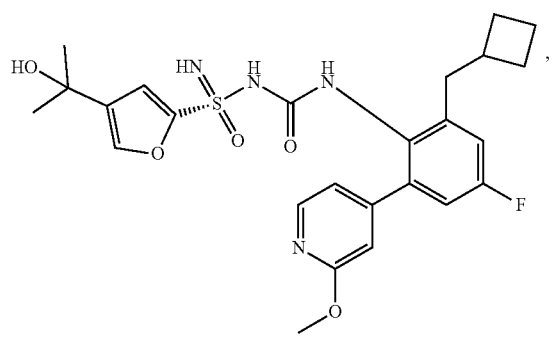
268
-continued
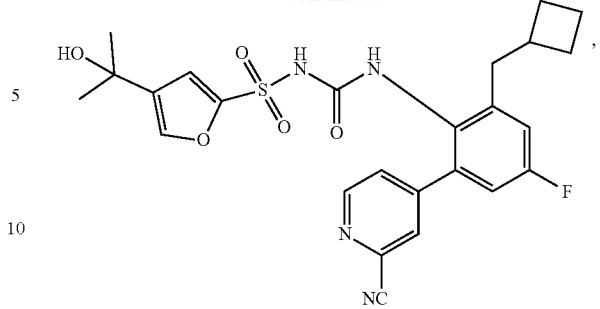
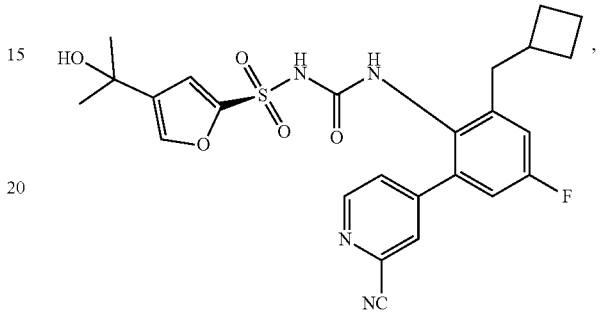
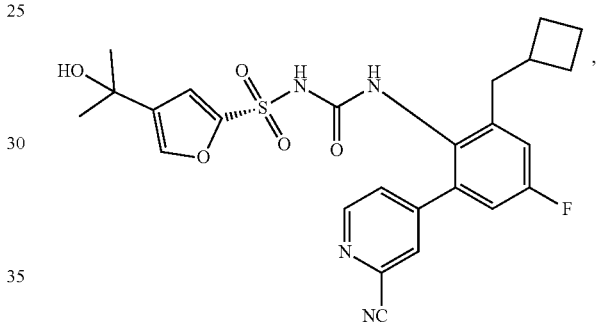
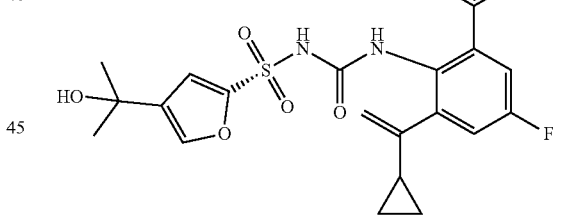
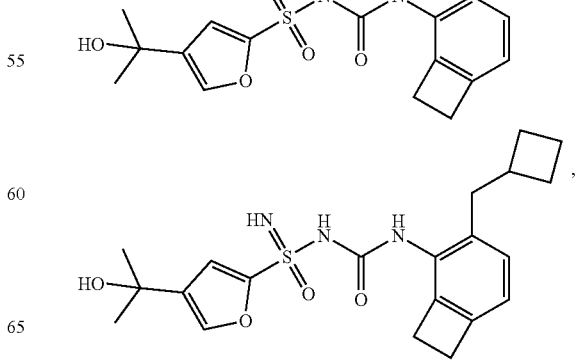

269
-continued
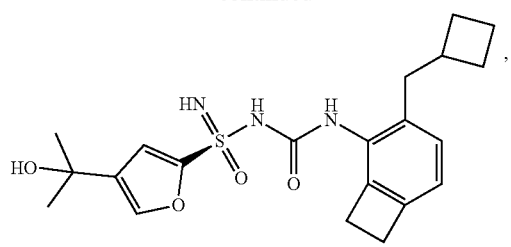
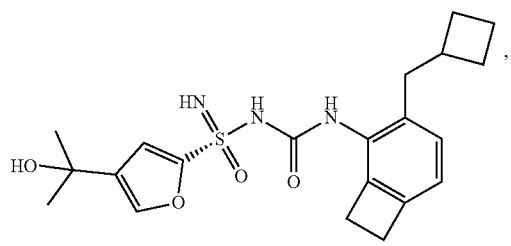
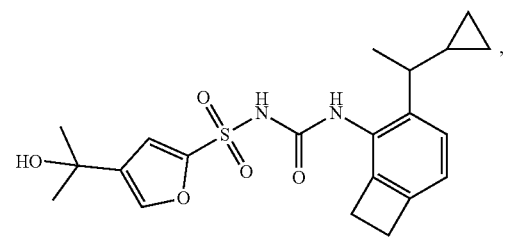
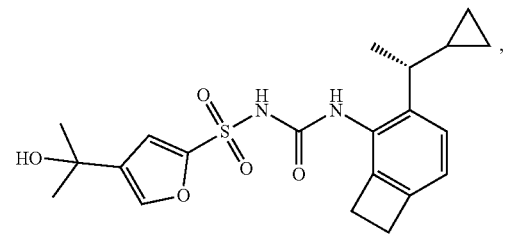
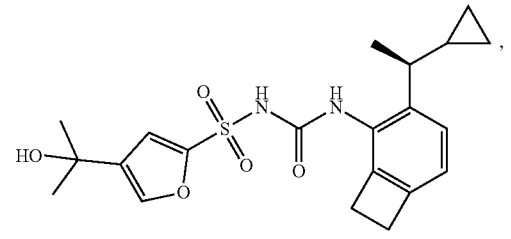
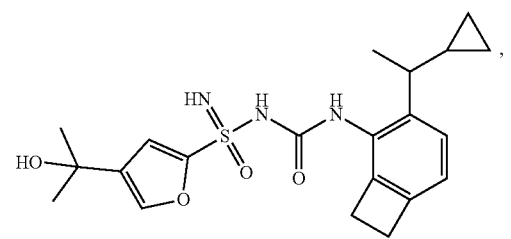
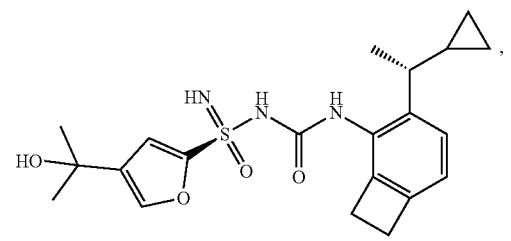
270
-continued
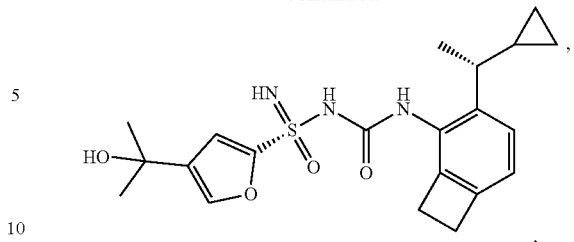
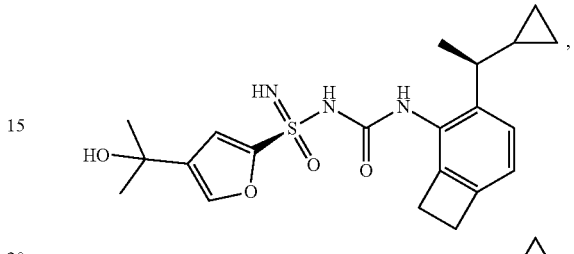
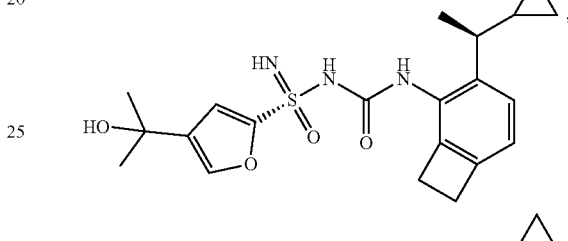
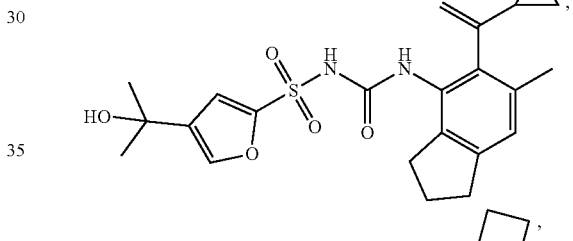
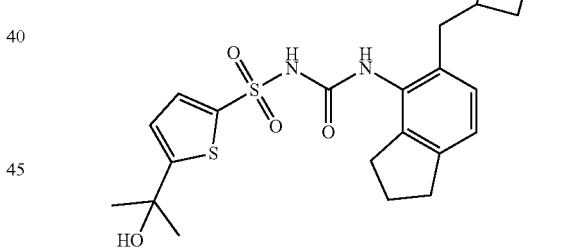
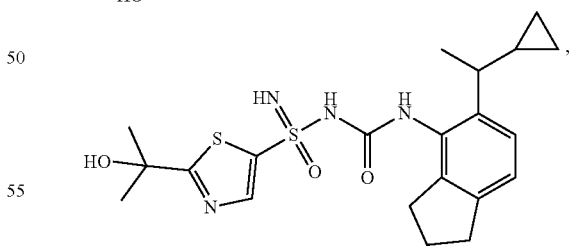
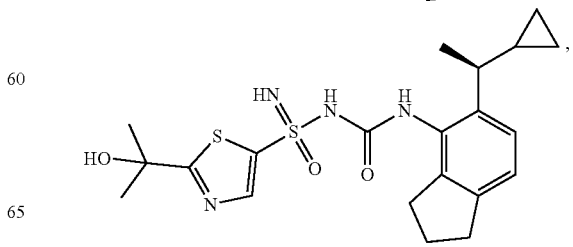

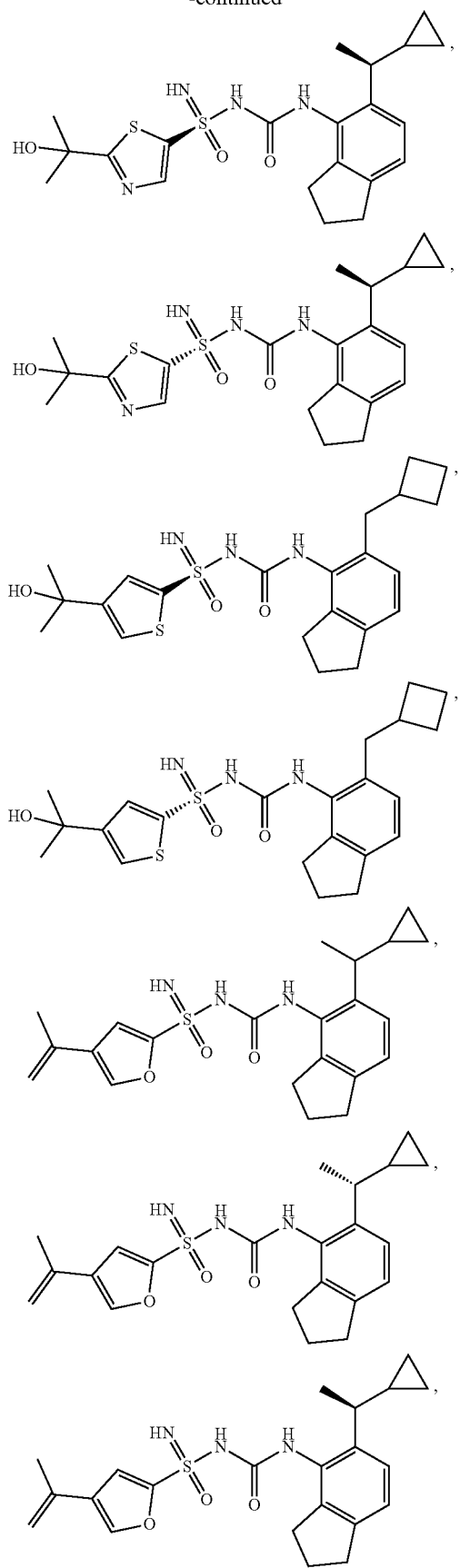
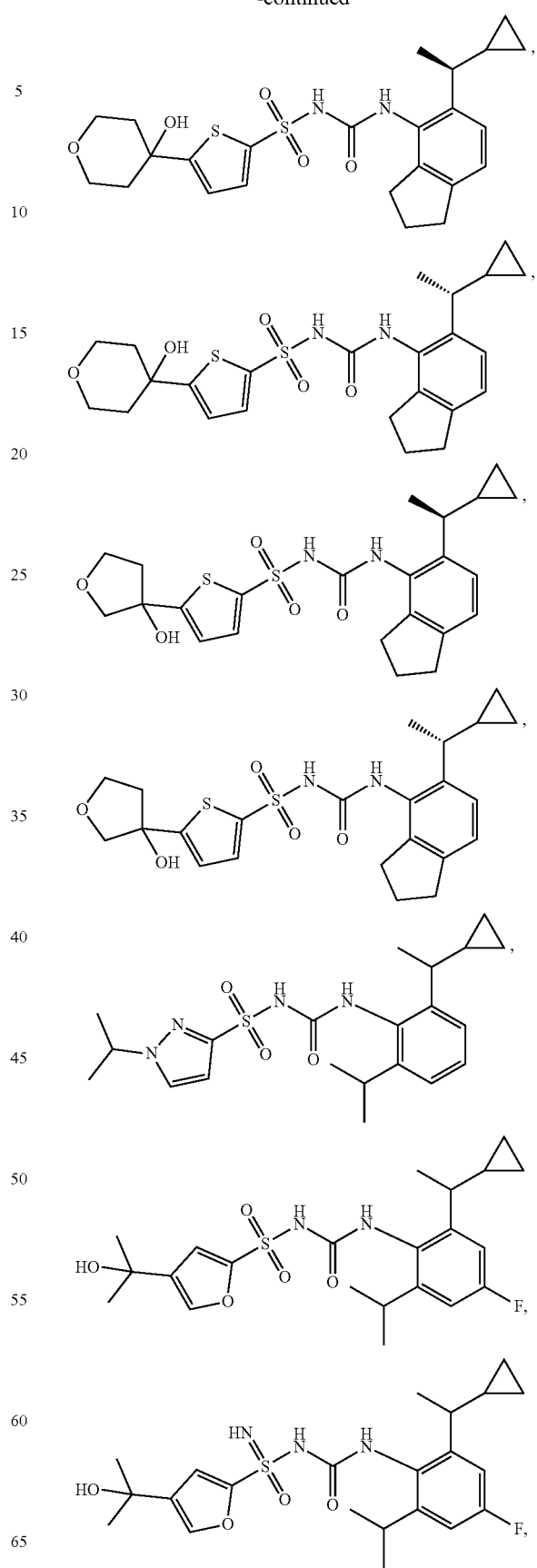

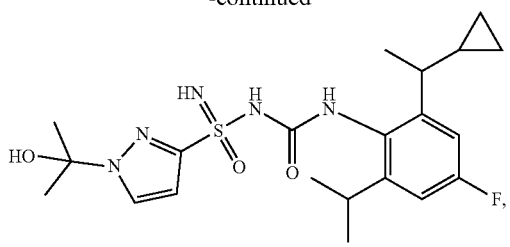
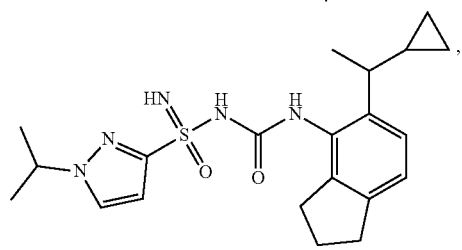
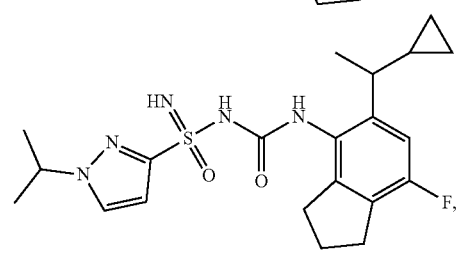
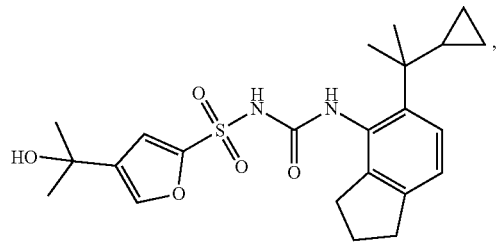
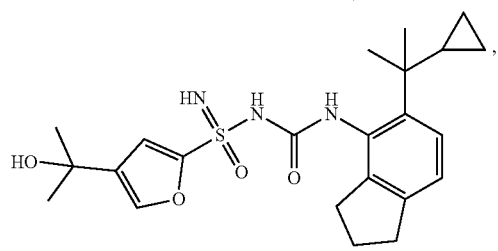
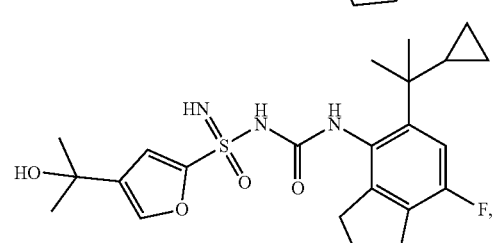
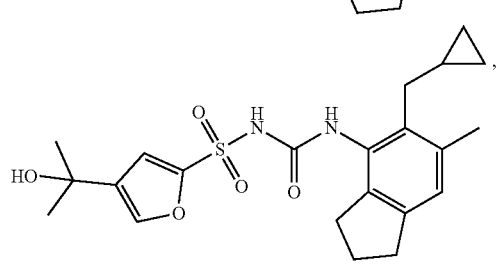
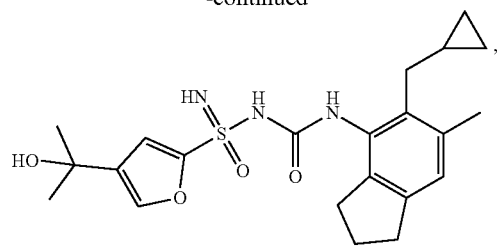
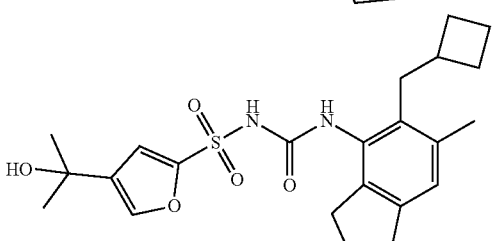
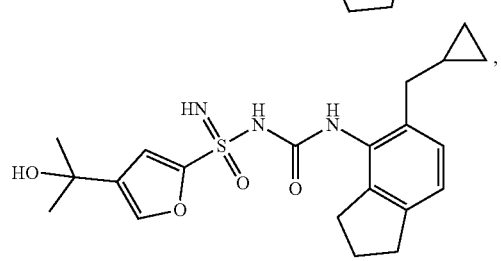
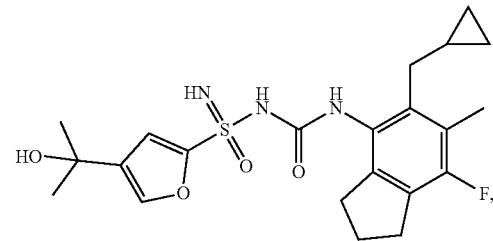
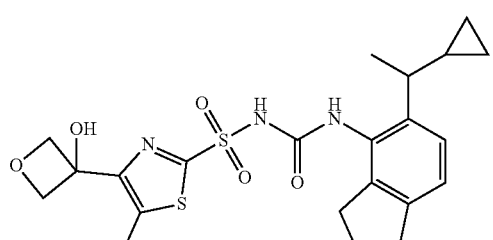
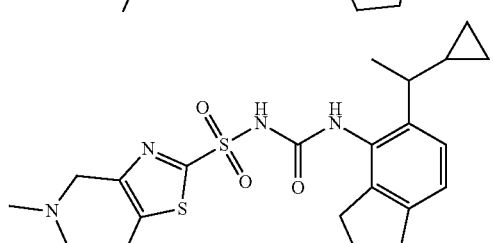
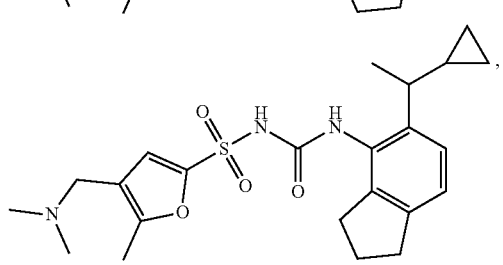

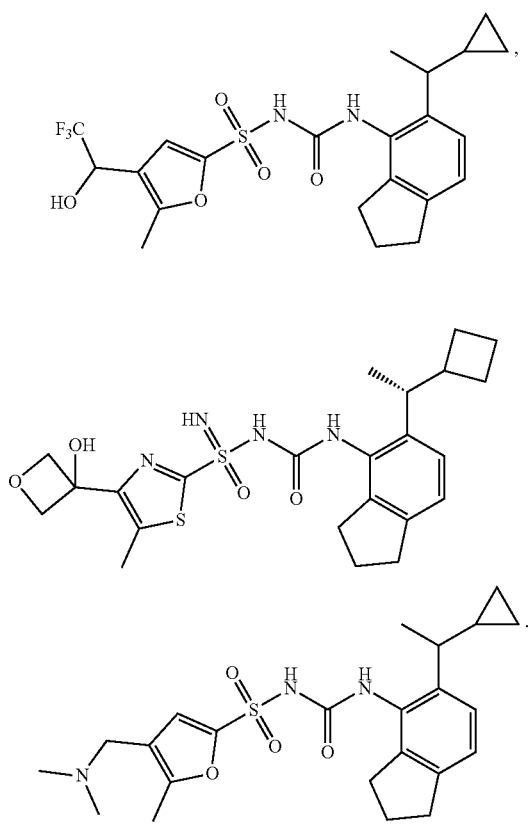
14. An intermediate for preparing the compound according to claim 1, wherein the intermediate is selected from one of the following structures:
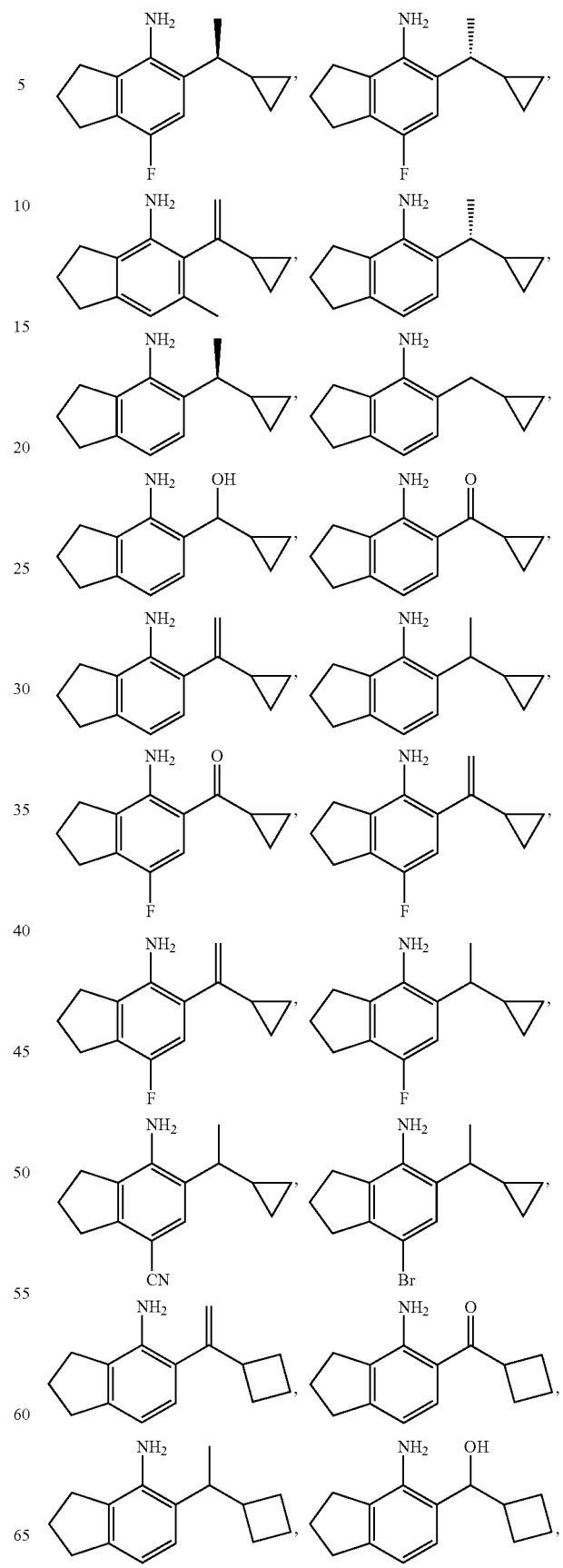

277
-continued
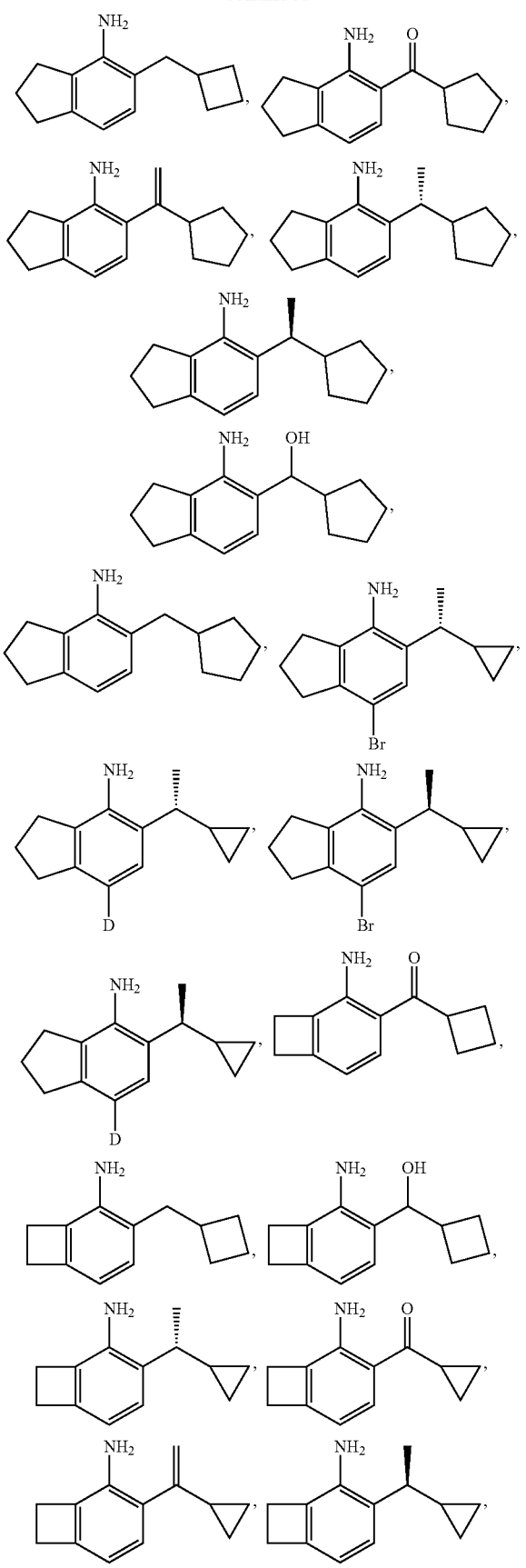
278
-continued
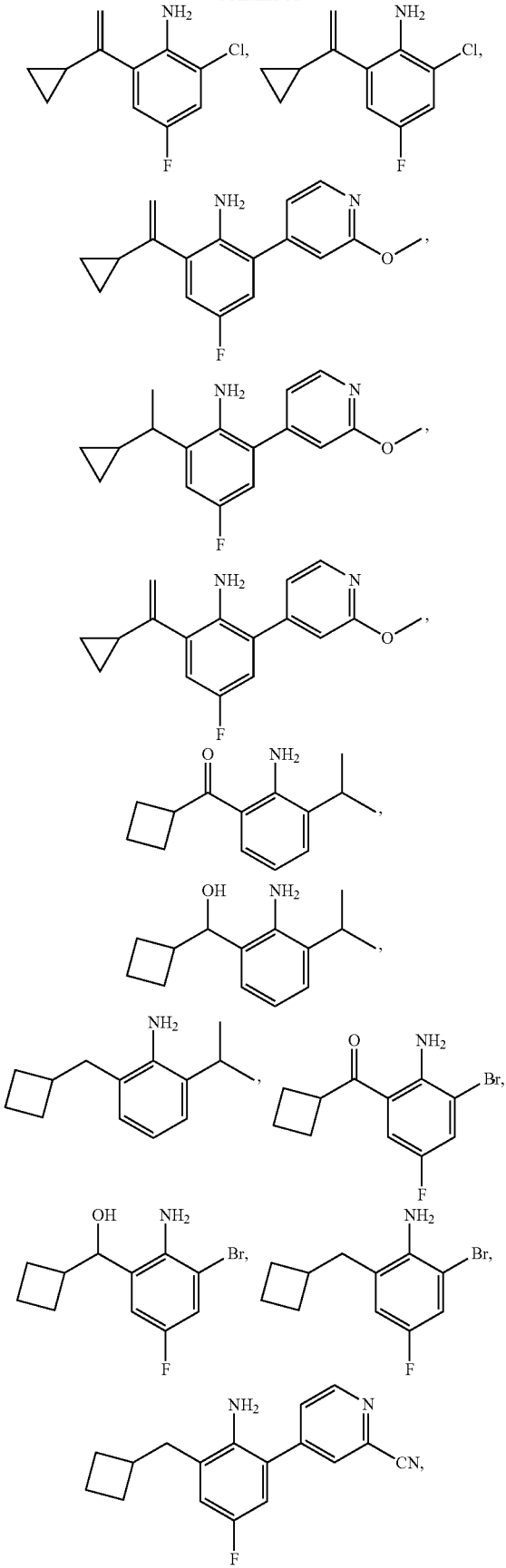

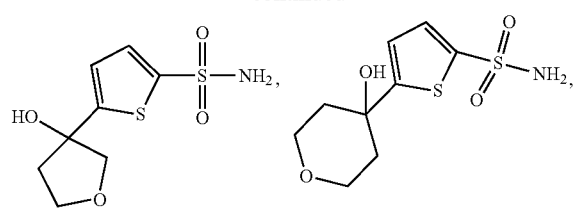
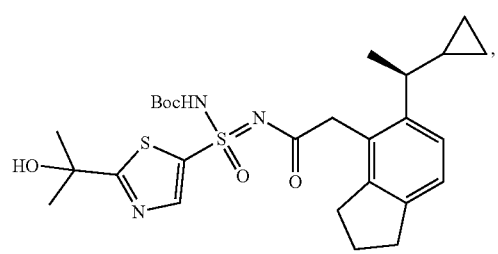
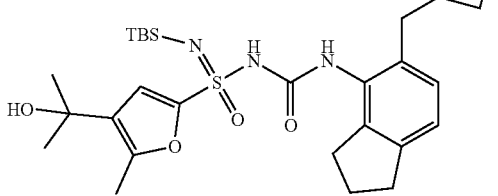
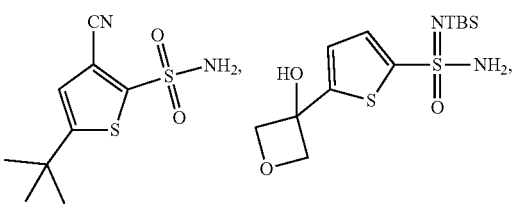
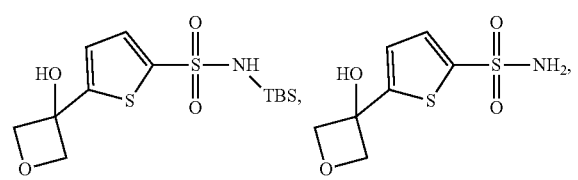
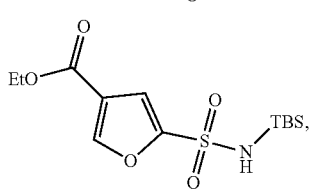
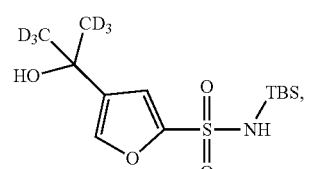
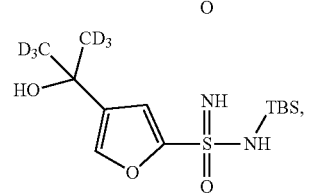
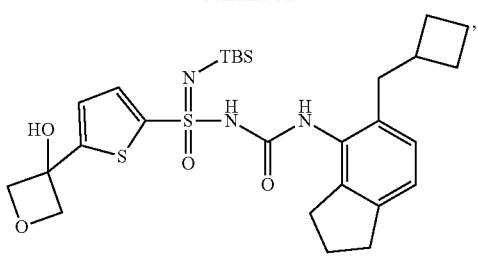
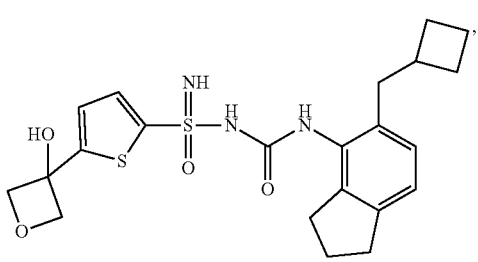
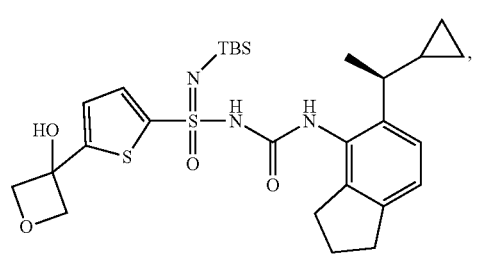
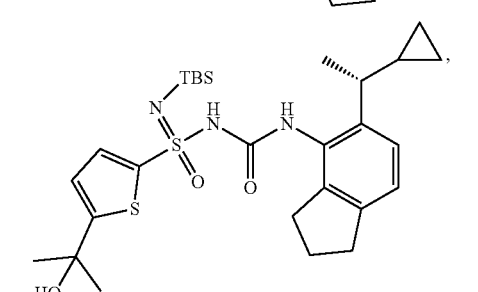
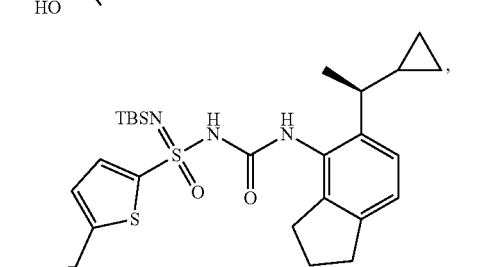
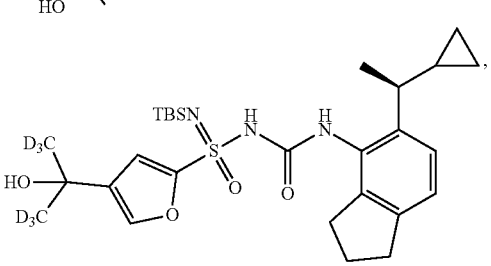

281
-continued

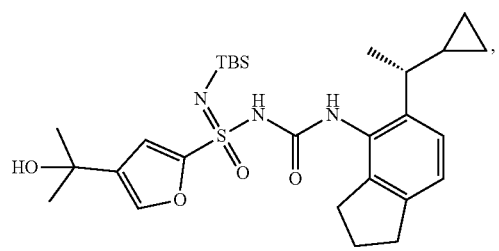

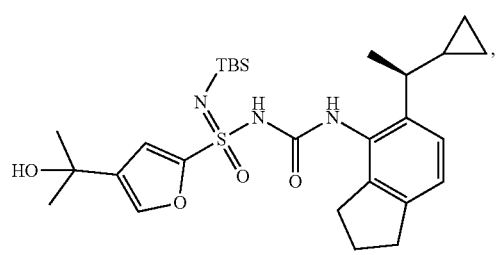

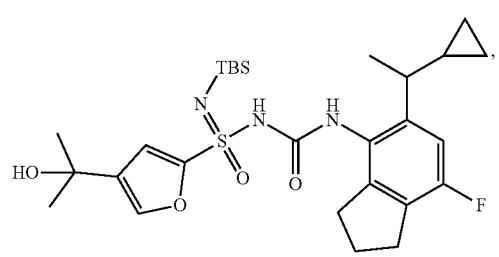

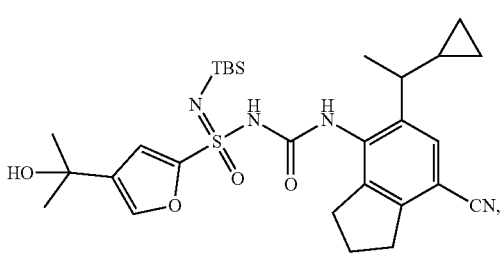

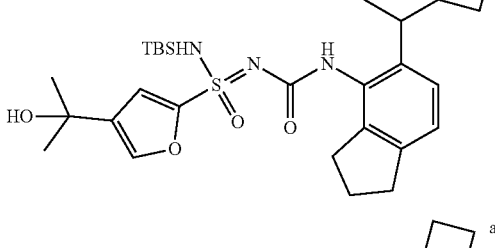

and

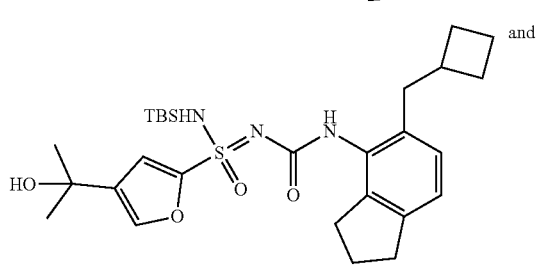

282
-continued

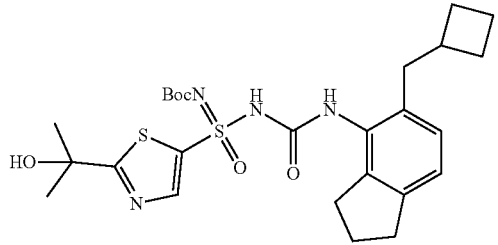

15. A pharmaceutical composition, comprising the compound or the stereoisomer, solvate, deuteride, pharmaceutically acceptable salt, cocrystal or prodrug thereof according to claim 1, and one or more pharmaceutically acceptable carriers and/or excipients.

16. A method for inhibiting NLRP3 or treating a disease associated with NLRP3, which comprises:
contacting a pharmaceutical composition having one or more pharmaceutically acceptable carriers and/or excipients or a compound or a stereoisomer, solvate, deuteride, pharmaceutically acceptable salt, cocrystal or prodrug thereof, with a subject in need thereof or administering to a subject in need thereof the pharmaceutical composition or the compound or the stereoisomer, solvate, deuteride, pharmaceutically acceptable salt, cocrystal or prodrug thereof; and
wherein the composition shown as general formula (I) or a stereoisomer, solvate, prodrug, deuteride, pharmaceutically acceptable salt or cocrystal thereof:

(I)

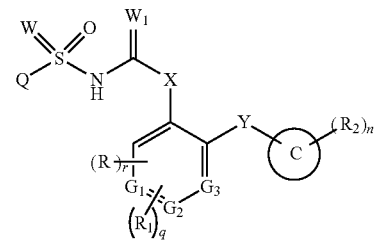

wherein,
Q is selected from 6-10 membered aryl and 5-10 membered heteroaryl, wherein the heteroaryl contains 1 to 3 heteroatoms selected from N, O and S, and the aryl or heteroaryl is optionally substituted with 0 to 4 $R^{q0}$;
$R^{q0}$ are the same or different and are each independently selected from $C_{1-6}$ alkyl, $C_{1-6}$ alkoxy, $C_{2-6}$ alkenyl, $C_{2-6}$ alkynyl, halogen, OH, cyano, nitro, —$NH_2$, $C_{3-8}$ cycloalkyl, $C_{3-8}$ heterocycloalkyl, $C_{6-10}$ aryl, $C_{5-10}$ heteroaryl, —C(=O)$C_{1-6}$ alkyl, —C(=O)O$C_{1-6}$ alkyl, —OC(=O)$C_{1-6}$ alkyl, —C(=O)O$C_{3-8}$ cycloalkyl, —OC(=O)$C_{3-8}$ cycloalkyl, —OC(=O)$C_{3-8}$ heterocycloalkyl, —C(=O)O$C_{3-8}$ heterocycloalkyl, —C(=O)$C_{6-10}$ aryl, —C(=O)O$C_{6-10}$ aryl, —OC(=O)$C_{6-10}$ aryl, —C(=O)$C_{5-10}$ heteroaryl, —C(=O)O$C_{5-10}$ heteroaryl, —OC(=O)$C_{5-10}$ heteroaryl, —NH$C_{1-6}$ alkyl, —N($C_{1-6}$ alkyl)$_2$, —NHC(=O)$C_{1-6}$ alkyl, —NHC(=O)($C_{1-6}$ alkyl)$_2$, —NHC(=O)$C_{6-10}$ aryl, —NHC(=O)$C_{5-10}$ heteroaryl, —NHC(=O)$C_{3-8}$ heterocycloalkyl, —NHC(=O)$C_{3-8}$ cycloalkyl, —NHC(=O)$C_{2-6}$ alkynyl, —NHC(=O)$C_{2-6}$ alkenyl, —NH(C=N$R^{q1}$)N$R^{q2}R^{q3}$, —C(=O)N$R^{q4}R^{q5}$, —SH, —S$C_{1-6}$ alkyl, —S(=O)$C_{1-6}$ alkyl, —S(=O)$_2C_{1-6}$ alkyl and —S(=O)$_2$N$R^{q2}R^{q3}$, wherein the heterocycloalkyl or heteroaryl contains 1 to 3 heteroatoms selected from N, O and S, and the alkyl, alkoxy, —NH$_2$, alkenyl, alkynyl, heterocycloalkyl, cycloalkyl, aryl or heteroaryl is optionally further substituted with 1 or more substituents selected from deuterium, OH, halogen, cyano, =O, C$_{1-6}$ alkyl, C$_{1-6}$ alkoxy, C$_{2-6}$ alkenyl, C$_{2-6}$ alkynyl, —NR$^{q4}$R$^{q5}$, =NR$^{q6}$, —C(=O)OC$_{1-6}$ alkyl, —OC(=O)C$_{1-6}$ alkyl, —C(=O)NR$^{q4}$R$^{q5}$, C$_{3-8}$ cycloalkyl, C$_{3-8}$ heterocycloalkyl, C$_{6-10}$ aryl, C$_{5-10}$ heteroaryl, —C(=O)OC$_{6-10}$ aryl, —OC(=O)C$_{6-10}$ aryl, —OC(=O)C$_{5-10}$ heteroaryl, —C(=O)OC$_{5-10}$ heteroaryl, —OC(=O)C$_{3-8}$ heterocycloalkyl, —C(=O)OC$_{3-8}$ heterocycloalkyl, —OC(=O)C$_{3-8}$ cycloalkyl, —C(=O)OC$_{3-8}$ cycloalkyl, —NHC(=O)C$_{3-8}$ heterocycloalkyl, —NHC(=O)C$_{6-10}$ aryl, —NHC(=O)C$_{5-10}$ heteroaryl, —NHC(=O)C$_{3-8}$ cycloalkyl, —NHC(=O)C$_{3-8}$ heterocycloalkyl, —NHC(=O)C$_{1-6}$ alkyl, —NHC(=O)C$_{2-6}$ alkenyl and —NHC(=O)C$_{2-6}$ alkynyl, wherein the substituent C$_{1-6}$ alkyl, C$_{1-6}$ alkoxy, C$_{2-6}$ alkenyl, C$_{2-6}$ alkynyl, C$_{3-8}$ cycloalkyl, C$_{3-8}$ heterocycloalkyl, C$_{6-10}$ aryl, C$_{5-10}$ heteroaryl, —NHC(=O)C$_{6-10}$ aryl, —NHC(=O)C$_{5-10}$ heteroaryl, —NHC(=O)C$_{3-8}$ heterocycloalkyl or —NHC(=O)C$_{3-8}$ cycloalkyl is optionally further substituted with 1 to 3 substituents selected from OH, halogen, C$_{1-6}$ alkyl, C$_{1-6}$ alkoxy, —NR$^{q4}$R$^{q5}$ and =O; or at least one pair of R$^{q0}$ and an atom to which they are attached form a 4-10 membered carbocycle or a 5-10 membered heterocycle, wherein the heterocycle contains 1 to 2 heteroatoms selected from N, O and S, the carbocycle or the heterocycle is optionally further substituted with 1 or more substituents selected from OH, halogen, C$_{1-6}$ alkyl, C$_{1-6}$ alkoxy, C$_{2-6}$ alkenyl, C$_{2-6}$ alkynyl, —NR$^{q4}$R$^{q5}$, =NR$^{q6}$, —C(=O)OC$_{1-6}$ alkyl and —C(=O)NR$^{q4}$R$^{q5}$, and the substituent C$_{1-6}$ alkyl or C$_{1-6}$ alkoxy is optionally further substituted with a substituent selected from OH, halogen, =O, —NR$^{q4}$R$^{q5}$, =NR$^{q6}$, —C(=O)OC$_{1-6}$ alkyl, C$_{3-8}$ cycloalkyl, C$_{3-8}$ heterocycloalkyl, C$_{6-10}$ aryl, C$_{5-10}$ heteroaryl and —C(=O)NR$^{q4}$R$^{q5}$;

R$^{q1}$ is selected from C$_{1-6}$ alkyl, C$_{1-6}$ alkoxy and C$_{6-10}$ aryl;
R$^{q2}$ and R$^{q3}$ are selected from H and C$_{1-6}$ alkyl;
R$^{q4}$ and R$^{q5}$ are selected from H, C$_{1-6}$ alkyl, —NH(C=NR$^{q1}$)NR$^{q2}$R$^{q3}$, —S(=O)$_2$NR$^{q2}$R$^{q3}$, —C(=O)R$^{q1}$ and —C(=O)NR$^{q2}$R$^{q3}$, wherein the C$_{1-6}$ alkyl is optionally further substituted with 1 or more substituents selected from OH, halogen, C$_{1-6}$ alkyl, C$_{1-6}$ alkoxy, C$_{6-10}$ aryl, C$_{5-10}$ heteroaryl, C$_{3-8}$ cycloalkyl and C$_{3-8}$ heterocycloalkyl; or R$^{q4}$ and R$^{q5}$ form a 3-8 membered heterocycle with an N atom, the heterocycle containing 1 to 3 heteroatoms selected from N, O and S;
R$^{q6}$ is C$_{1-6}$ alkyl;
W is selected from O and NH;
W$_1$ is O;
X is NH;
Y is CR$_b$R$_c$;
R$_b$ and R$_c$ are each independently selected from H, C$_{1-6}$ alkyl and 3-10 membered carbocyclyl, wherein the C$_{1-6}$ alkyl is optionally further substituted with 1 to 4 substituents selected from F, Cl, Br, I, C$_{1-6}$ alkyl, C$_{1-6}$ alkoxy, 3-10 membered carbocyclyl and 3-10 membered heterocyclyl, the heterocyclyl optionally containing 1 to 3 heteroatoms selected from N, O and S; or
R$_b$ and R$_c$ form a double bond;
R and R$_1$ are each independently selected from deuterium, H, F, Cl, Br, I, CN, NH$_2$, OH, C$_{1-6}$ alkyl, C$_{1-6}$ alkoxy, C$_{2-6}$ alkenyl, C$_{2-6}$ alkynyl, —(C=O)—C$_{1-6}$ alkyl, —(C=O)O—C$_{1-6}$ alkyl, —O(C=O)—C$_{1-6}$ alkyl, —O(C=O)-3-10 membered carbocyclyl, —O(C=O)-3-10 membered heterocyclyl, —(C=O)O-3-10 membered carbocyclyl, —O(C=O) O—C$_{1-6}$ alkyl, 3-10 membered carbocyclyl, 4-10 membered heterocyclyl, —NHC$_{1-6}$ alkyl, —N(C$_{1-6}$ alkyl)$_2$ and (C=O)NR$_{a1}$R$_{a2}$, wherein the heterocyclyl contains 1 to 3 heteroatoms selected from N, O and S, and the alkyl, alkenyl, alkoxy, carbocycle or heterocycle is optionally further substituted with 1 to 4 substituents selected from OH, F, Cl, Br, I, CN, NR$_{a1}$R$_{a2}$, =O, C$_{1-6}$ alkyl, C$_{1-6}$ alkoxy, C$_{1-6}$ haloalkyl, C$_{1-6}$ haloalkoxy, —(C=O)—C$_{1-6}$ alkyl, —(C=O)O—C$_{1-6}$ alkyl, —O(C=O)—C$_{1-6}$ alkyl, —(C=O)O-3-10 membered carbocyclyl, —O(C=O)-3-10 membered carbocyclyl, —O(C=O)-3-10 membered heterocyclyl, —O(C=O)O—C$_{1-6}$ alkyl, 3-10 membered carbocyclyl, 5-10-membered heterocyclyl, —NHCOC$_{1-6}$ alkyl, —NH(C=O)-3-10 membered carbocyclyl, —NH(C=O)-3-10 membered heterocyclyl and —(C=O)NR$_{a1}$R$_{a2}$; or R and R$_1$, together with an atom to which they are attached, form a 4-8 membered ring, wherein the 4-8 membered ring contains 0 to 4 heteroatoms selected from N, O and S, and is optionally further substituted with 0 to 4 substituents selected from H, F, Cl, Br, I, OH, —NR$_{a1}$R$_{a2}$, =O, C$_{1-6}$ alkyl, C$_{1-6}$ alkoxy, C$_{2-6}$ alkenyl, C$_{2-6}$ alkynyl, —(C=O)OC$_{1-6}$ alkyl, 3-10 membered carbocyclyl and 5-10 membered heterocyclyl;

C is 3-10 membered cycloalkyl;

R$_2$ is selected from H, F, Cl, Br, I, OH, —NR$_{a1}$R$_{a2}$, C$_{1-6}$ alkyl, C$_{2-6}$ alkenyl, C$_{2-6}$ alkynyl and C$_{1-6}$ alkoxy;

G1, G2 and G3 are each independently selected from N and CH;

q and r are selected from 0, 1 and 2;

n is selected from 0, 1, 2 and 3.

17. The method according to claim 16, wherein the disease associated with NLRP3 is inflammatory diseases, autoimmune diseases, cardiovascular system diseases, cancers, renal system diseases, gastrointestinal diseases, respiratory system diseases, endocrine system diseases and central nervous system diseases.

18. The method according to claim 17, wherein the disease associated with NLRP3 is cryopyrin-associated periodic syndrome (CAPS), Muckle-Wells syndrome (MWS), familial cold autoinflammatory syndrome (FCAS), neonatal-onset multisystem inflammatory disease (NOMID), familial Mediterranean fever (FMF), non-alcoholic steatohepatitis, alcoholic liver disease, graft-versus-host disease, multiple sclerosis (MS), rheumatoid arthritis, type I diabetes, type II diabetes, psoriasis, Alzheimer's disease, atherosclerosis, gout and chronic kidney disease.

19. The compound or the stereoisomer, solvate, deuteride, prodrug, pharmaceutically acceptable salt or cocrystal thereof according to claim 3, wherein the compound is selected from compounds shown as formulas (III) and (III-1):

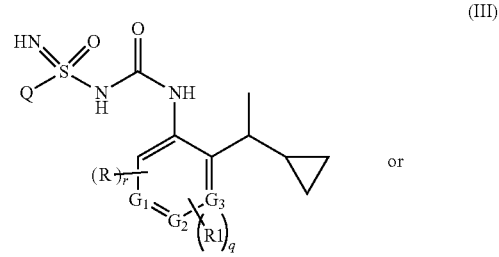

(III)

or

-continued

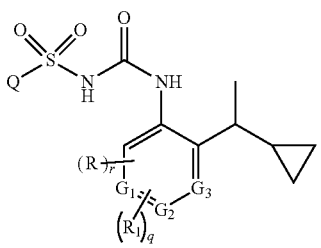

(III-1)

wherein, Q, R, R₁, G1, G2, G3, r and q are defined in the same way as in general formula (I).

20. The compound or the stereoisomer, solvate, deuteride, prodrug, pharmaceutically acceptable salt or cocrystal thereof according to claim 5, wherein:

Q is selected from 5 membered heteroaryl, wherein the heteroaryl contains 1 to 3 heteroatoms selected from N, O and S, and the aryl or heteroaryl is optionally substituted with 0 to 4 $R^{q0}$;

$R^{q0}$ are the same or different and are each independently selected from $C_{1-4}$ alkyl, halogen, OH, cyano, —NH₂, $C_{2-4}$ alkenyl, $C_{3-6}$ cycloalkyl, $C_{3-6}$ heterocycloalkyl, —NH$C_{1-4}$ alkyl and —N($C_{1-4}$ alkyl)₂, wherein the heterocycloalkyl contains 1 to 3 heteroatoms selected from N and O, and the alkyl, heterocycloalkyl and cycloalkyl are optionally further substituted with 1 or more substituents selected from deuterium, OH, halogen, cyano, $C_{1-4}$ alkyl and —NR$^{q4}$R$^{q5}$;

$R^{q4}$ and $R^{q5}$ are selected from H and $C_{1-4}$ alkyl;

R and R₁ are each independently selected from deuterium, H, F, CN, OH, $C_{1-6}$ alkyl and 4-6 membered heterocyclyl, wherein the heterocyclyl contains 1 to 3 heteroatoms selected from N and O, and the alkyl or heterocycle is optionally further substituted with 1 to 4 substituents selected from OH, F, CN and $C_{1-6}$ alkoxy; or R and R₁, together with an atom to which they are attached, form a 4-5 membered ring;

G1, G2 and G3 are each independently selected from CH;

q and r are selected from 0, 1 and 2.

* * * * *